US010751423B2

(12) United States Patent
Ghoroghchian et al.

(10) Patent No.: US 10,751,423 B2
(45) Date of Patent: Aug. 25, 2020

(54) NANOPARTICLE CONJUGATES OF HIGHLY POTENT TOXINS AND INTRAPERITONEAL ADMINISTRATION OF NANOPARTICLES FOR TREATING OR IMAGING CANCER

(71) Applicant: Massachusetts Institute of Technology, Cambridge, MA (US)

(72) Inventors: Paiman Peter Ghoroghchian, Boston, MA (US); Ruogu Qi, Houston, TX (US); Angela M. Belcher, Lexington, MA (US); Xiangnan Dang, Sharon, MA (US); Zhimin Tao, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/584,516

(22) Filed: May 2, 2017

(65) Prior Publication Data

US 2018/0008687 A1 Jan. 11, 2018

Related U.S. Application Data

(60) Provisional application No. 62/489,111, filed on Apr. 24, 2017, provisional application No. 62/330,684,
(Continued)

(51) Int. Cl.
  *A61K 9/00*  (2006.01)
  *A61K 48/00* (2006.01)
  (Continued)

(52) U.S. Cl.
  CPC .......... *A61K 48/0041* (2013.01); *A61K 9/107* (2013.01); *A61K 31/282* (2013.01);
  (Continued)

(58) Field of Classification Search
  CPC .................................................. A61K 48/0041
  See application file for complete search history.

(56) References Cited

U.S. PATENT DOCUMENTS

| 4,534,881 A | 8/1985 | Sikes et al. |
| 5,877,158 A | 3/1999 | Bosslet et al. |

(Continued)

FOREIGN PATENT DOCUMENTS

| WO | WO-2007/008300 A2 | 1/2007 |
| WO | WO-2008/137733 A2 | 11/2008 |

(Continued)

OTHER PUBLICATIONS

Blencowe et al., "Self-immolative linkers in polymeric delivery systems," Polym Chem, 2:773-790 (2011).

(Continued)

*Primary Examiner* — Paul W Dickinson
(74) *Attorney, Agent, or Firm* — Foley Hoag LLP

(57) ABSTRACT

Disclosed are methods of treating cancer of the intraperitoneal cavity using compositions comprising nanoparticles without targeting agents. In addition, nanoparticles are described that comprise a highly toxic anticancer agent (e.g., an anticancer agent having an $IC_{50}$ less than 1 nM) covalently bound via a linker to a triblock copolymer. Other nanoparticles that comprise Pt(IV) and an anticancer agent are also described. Also disclosed are nanoparticles comprising imaging agents non-covalently associated with a polymer, and methods of imaging cancer of the intraperitoneal cavity using compositions comprising nanoparticles without targeting agents.

16 Claims, 75 Drawing Sheets

Specification includes a Sequence Listing.

Related U.S. Application Data filed on May 2, 2016, provisional application No. 62/330,697, filed on May 2, 2016.

(51) Int. Cl.

| | | |
|---|---|---|
| *A61K 47/60* | (2017.01) | |
| *A61K 47/64* | (2017.01) | |
| *A61K 47/69* | (2017.01) | |
| *A61K 31/555* | (2006.01) | |
| *A61K 33/24* | (2019.01) | |
| *C08G 81/00* | (2006.01) | |
| *C12N 15/11* | (2006.01) | |
| *A61K 9/107* | (2006.01) | |
| *A61K 31/282* | (2006.01) | |
| *A61K 47/34* | (2017.01) | |
| *C07K 2/00* | (2006.01) | |
| *C08G 69/10* | (2006.01) | |
| *C12N 15/90* | (2006.01) | |
| *A61K 39/00* | (2006.01) | |
| *A61K 47/10* | (2017.01) | |
| *C12N 15/09* | (2006.01) | |
| *G01N 21/47* | (2006.01) | |

(52) U.S. Cl.
CPC ............ *A61K 31/555* (2013.01); *A61K 33/24* (2013.01); *A61K 39/0011* (2013.01); *A61K 47/10* (2013.01); *A61K 47/34* (2013.01); *A61K 47/60* (2017.08); *A61K 47/646* (2017.08); *A61K 47/6907* (2017.08); *A61K 47/6935* (2017.08); *A61K 48/005* (2013.01); *C07K 2/00* (2013.01); *C08G 69/10* (2013.01); *C08G 81/00* (2013.01); *C12N 15/11* (2013.01); *C12N 15/90* (2013.01); *A61K 2039/585* (2013.01); *C12N 15/09* (2013.01); *C12N 2310/20* (2017.05); *G01N 21/47* (2013.01)

(56) References Cited

U.S. PATENT DOCUMENTS

| | | | |
|---|---|---|---|
| 6,815,167 B2 | 11/2004 | Crothers et al. | |
| 6,977,153 B2 | 12/2005 | Kumar et al. | |
| 8,575,330 B2 | 11/2013 | Tan | |
| 8,647,604 B2* | 2/2014 | VanVeggel | A61K 41/009 424/9.34 |
| 9,161,993 B2 | 10/2015 | Jolck et al. | |
| 9,227,917 B2 | 1/2016 | Anderson et al. | |
| 9,241,898 B2 | 1/2016 | Saltzman et al. | |
| 9,260,471 B2 | 2/2016 | Cancilla et al. | |
| 9,295,685 B2 | 3/2016 | Gombotz et al. | |
| 9,295,689 B2 | 3/2016 | de Fougerolles et al. | |
| 9,472,694 B2 | 10/2016 | Dionne et al. | |
| 9,555,132 B2 | 1/2017 | Vinogradov et al. | |
| 2012/0009267 A1* | 1/2012 | Cho | A61K 9/5026 424/497 |
| 2014/0308363 A1* | 10/2014 | Zale | A61K 9/5153 424/501 |
| 2017/0362609 A1 | 12/2017 | Ghoroghchian et al. | |
| 2018/0021453 A1* | 1/2018 | Bazzill | A61K 9/1271 424/450 |
| 2018/0078657 A1 | 3/2018 | Ghoroghchian et al. | |

FOREIGN PATENT DOCUMENTS

| | | |
|---|---|---|
| WO | WO-2011/110694 A2 | 9/2011 |
| WO | WO-2013/142969 A1 | 10/2013 |
| WO | WO-2014/066912 A1 | 5/2014 |
| WO | WO-2014/093343 A2 | 6/2014 |
| WO | WO-2014/145749 A1 | 9/2014 |
| WO | WO-2015/051349 A1 | 4/2015 |
| WO | WO-2016/037165 A1 | 3/2016 |
| WO | WO-2017/192512 A2 | 11/2017 |
| WO | WO-2017/192544 A1 | 11/2017 |
| WO | WO-2017/192573 A1 | 11/2017 |

OTHER PUBLICATIONS

Creixell et al., "Co-delivery of siRNA and therapeutic agents using nanocarriers to overcome cancer resistance," Nano Today, 7(4):367-379 (2012).

Emoto et al., "Antitumor effect and pharmacokinetics of intraperitoneal NK105, a nanomicellar paclitaxel formulation for peritoneal dissemination," Cancer Sci, 103(7):1304-1310 (2012).

Gorris et al., "Surface modification and characterization of photon-upconverting nanoparticles for bioanalytical applications," Chem Soc Rev, 44(6): 1526-1560 (2015).

Huynh et al., "Acid degradable cross-linked micelles for the delivery of cisplatin: a comparison with nondegradable cross-linker," Chem Mater, 24(16):3197-3211 (2012).

International Search Report and Written Opinion for International Application No. PCT/US2017/030578 dated Aug. 21, 2017.

Juetten, "Self-immolative linkers for chemical amplification application," Graduate Theses and Dissertations, Iowa State University (2013).

Kren et al., "Nanocapsule-delivered Sleeping Beauty mediates therapeutic Factor VIII expression in liver sinusoidal endothelial cells of hemophilia A mice," J Clin Invest, 119(7):2086-2099 (2009).

Li et al., "Challenges in CRISPR/CAS9 delivery: Potential roles of nonviral vectors," Hum Gene Ther, 26(7): 452-462 (2015).

Liu et al., "A mPEG-PLGA-b-PLL copolymer carrier for adriamycin and siRNA delivery," Biomaterials, 33(17): 4403-4412 (2012).

Liu et al., "Nanoparticle tumor localization, disruption of autophagosomal trafficking, and prolonged drug delivery improve survival in peritoneal mesothelioma," Biomaterials, 102: 175-186 (2016).

Lu et al., "Paclitaxel nanoparticle inhibits growth of ovarian cancer xenografts and enhances lymphatic targeting," Cancer Chemother Pharmacol, 59(2):175-181 (2007).

Miyata et al., Polyplexes from poly(aspartamide) bearing 1,2-diaminoethane side chains induce pH-selective, endosomal membrane destabilization with amplified transfection and negligible cytotoxicity, J Am Chem Soc, 130(48): 16287-16294 (2008).

O'Reilly et al., "Cross-linked block copolymer micelles: functional nanostructures of great potential and versatility," Chem Soc Rev, 35(11): 1068-1083 (2006).

Osada et al., "Polymeric micelles from poly(ethylene glycol)-poly(amino acid) block copolymer for drug and gene delivery," J R Soc Interface, 6(Suppl 3):S325-S339 (2009).

Partial International Search Report for International Application No. PCT/US2017/030618, dated Aug. 16, 2017.

Qi et al., "Biodegradable copolymers with identical cationic segments and their performance in siRNA delivery," J Control Release, 159(2):251-260 (2012).

Riber et al., "Self-immolative linkers literally bridge disulfide chemistry and the realm of thiol-free drugs," Adv Healthc Mater, 4(12): 1887-1890 (2015).

Schumann et al., "Generation of knock-in primary human T cells using Cas9 ribonucleoproteins," Proc Natl Acad Sci U S A, 112(33):10437-10442 (2015).

Shen et al., "Antiproliferative activity of polymer-bound, monoamine-coordinated platinum complexes against LNCaP human metastatic prostate adenocarcinoma cells," J Inorg Organomet Polym, 10(1): 51-60 (2000).

Shen et al., "Co-delivery of platinum drug and siNotch1 with micelleplex for enhanced hepatocellular carcinoma therapy," Biomaterials, 70:71-83 (2015).

Sheng, "Self-immolative chemistry: structural features and applications in designing smart materials," (2014).

Sun et al., "Self-assembled DNA nanoclews for the efficient delivery of CRISPR-Cas9 for genome editing," Angew Chem Int Ed Engl, 54(41):12029-12033 (2015).

(56) References Cited

OTHER PUBLICATIONS

Thevenaz et al., "Luminescent Nanoparticles with Lanthanide-Containing Poly(ethylene glycol-Polycaprolactone) Block Copolymers," Biomacromolecules, 15(11): 3994-4001 (2014).
Weninger et al., "Combinatorial optimization of CRISPR/Cas9 expression enables precision genome engineering in the methylotrophic yeast *Pichia pastoris*," J Biotechnol, 235:139-149 (2016).
Xiao et al., "Biodegradable polymer-cisplatin(IV) conjugate as a pro-drug of cisplatin(II)," Biomaterials, 32(30):7732-7739 (2011).
Xu et al., "Co-delivery of doxorubicin and P-glycoprotein siRNA by multifunctional triblock copolymers for enhanced anticancer efficacy in breast cancer cells," J Mater Chem B, 3(10):2215-2228 (2015).
Xu et al., "Enhancing tumor cell response to chemotherapy through nanoparticle-mediated codelivery of siRNA and cisplatin prodrug," Proc Natl Acad Sci U S A, 110(46): 18638-18643 (2013).
Yin et al., "Therapeutic genome editing by combined viral and non-viral delivery of CRISPR system components in vivo," Nat Biotechnol, 34(3):328-333 (2016).
Zheng et al., "Polypeptide cationic micelles mediated co-delivery of docetaxel and siRNA for synergistic tumor therapy," Biomaterials, 34(13):3431-3438 (2013).
Zhu et al., "Co-delivery of siRNA and paclitaxel into cancer cells by biodegradable cationic micelles based on PDMAEMA-PCL-PDMAEMA triblock copolymers," Biomaterials, 31(8):2408-2416 (2010).
Zuris et al., "Efficient Delivery of Genome-Editing Proteins In Vitro and In Vivo," Nat Biotechnol, 33(1): 73-80 (2015).
International Search Report and Written Opinion for International Application No. PCT/US2017/030618 dated Oct. 17, 2017.
International Search Report and Written Opinion for International Application No. PCT/US2017/030541 dated Nov. 8, 2017.
Xiao et al., "A dual-targeting hybrid platinum(IV) prodrug for enhancing efficacy," Chem Commun, 48:10730-10732 (2012).
Song et al., "Multifunctional Pt(IV) pro-drug and its micellar platform: to kill two birds with one stone," J Mater Chem B, 1:762-772 (2013).
Qi et al., "Design and delivery of camplatin to overcome cisplatin drug resistance," J Mater Chem B, 3:176-179 (2015).
Cao et al., "A novel cationic triblock copolymer as noncovalent coating for the separation of proteins by CE," Electrophoresis, 32(20):2874-2883 (2011).
Cordeiro et al., "Novel cationic triblock copolymer of poly[2-(dimethylamino)ethyl methacrylate]block-poly(β-amino ester)-block-poly[2-(dimethylamino)ethyl methacrylate]: a promising non-viral gene delivery system," Macromol Biosci, 15(2):215-228 (2015).

Gallon et al., "Triblock copolymer nanovesicles for pH-responsive targeted delivery and controlled release of siRNA to cancer cells," Biomacromolecules, 16(7):1924-1937 (2015).
Hinton et al., "Inhibition of influenza virus in vivo by siRNA delivered using ABA triblock copolymer synthesized by reversible addition-fragmentation chain-transfer polymerization," Nanomedicine, 9(8):1141-1154 (2014).
Jansson et al., "Small-angle X-ray scattering, light scattering, and NMR study of PEO-PPO-PEO triblock copolymer/cationic surfactant complexes in aqueous solution," J Phys Chem B, 109:7073-7083 (2005).
Jones et al., "Folate Receptor Targeted Delivery of siRNA and Paclitaxel to Ovarian Cancer Cells via Folate Conjugated Triblock Copolymer to Overcome TLR4 Driven Chemotherapy Resistance," Biomacromolecules, 17(1):76-87 (2016).
Kim et al., "siRNA delivery from triblock copolymer micelles with spatially-ordered compartments of PEG shell, siRNA-loaded intermediate layer, and hydrophobic core," Biomaterials, 35:4548-4556 (2014).
Mao et al., "A biodegradable amphiphilic and cationic triblock copolymer for the delivery of siRNA targeting the acid ceramidase gene for cancer therapy," Biomaterials, 32:3124-3133 (2011).
Qian et al., "Triblock copolymer-encapsulated nanoparticles with outstanding colloidal stability for siRNA delivery," ACS Appl Mater Interfaces, 5:2845-2852 (2013).
Segura et al., "Synthesis and in vitro characterization of an ABC triblock copolymer for siRNA delivery," Bioconjugate Chem, 18:736-745 (2007).
Yang et al., "Thermoresponsive behavior of cationic polyrotaxane composed of multiple pentaethylenehexamine-grafted alpha-cyclodextrins threaded on poly(propylene oxide)-poly(ethylene oxide)-poly(propylene oxide) triblock copolymer," J Phys Chemistry B, 113:682-690 (2009).
Yoncheva et al., "Cationic triblock copolymer micelles enhance antioxidant activity, intracellular uptake and cytotoxicity of curcumin," Int J Pharmaceut, 490:298-307 (2015).
Zhao et al., "Self-assembly nanomicelles based on cationic mPEG-PLA-b-Polyarginine(R15) triblock copolymer for siRNA delivery," Biomaterials, 33:6793-6807 (2012).
International Preliminary Report on Patentability for International Application No. PCT/US2017/030541 dated Nov. 6, 2018.
International Preliminary Report on Patentability for International Application No. PCT/US2017/030578 dated Nov. 6, 2018.
International Preliminary Report on Patentability for International Application No. PCT/US2017/030618 dated Nov. 6, 2018.
U.S. Appl. No. 15/584,496, Pending.
U.S. Appl. No. 15/584,309, Pending.

* cited by examiner

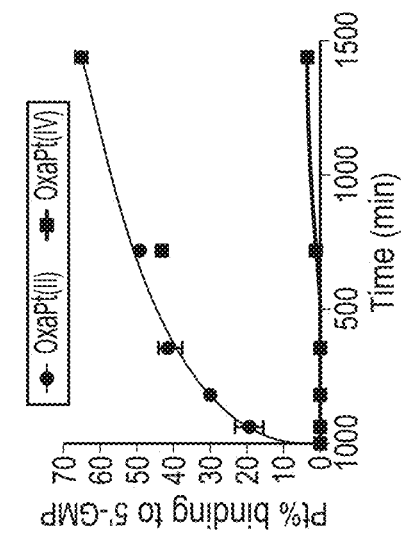
FIG. 4A
FIG. 4B
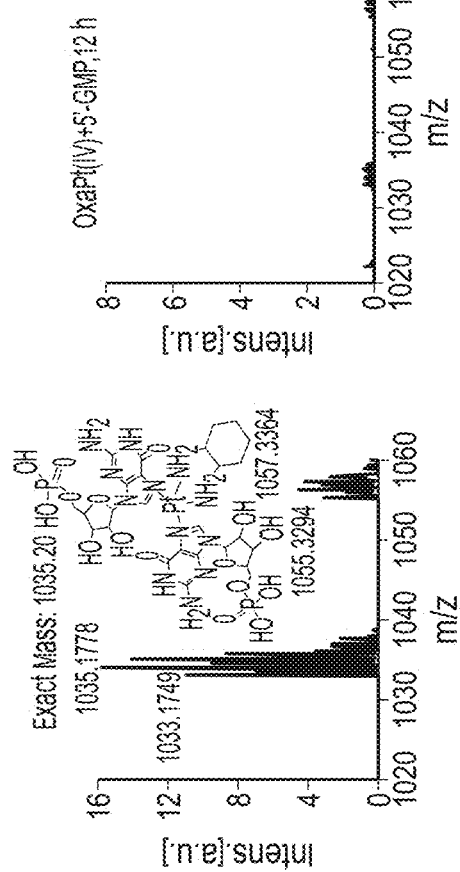
FIG. 4C
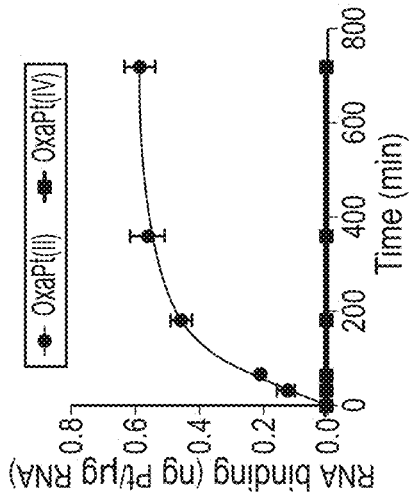
FIG. 4D
FIG. 4E
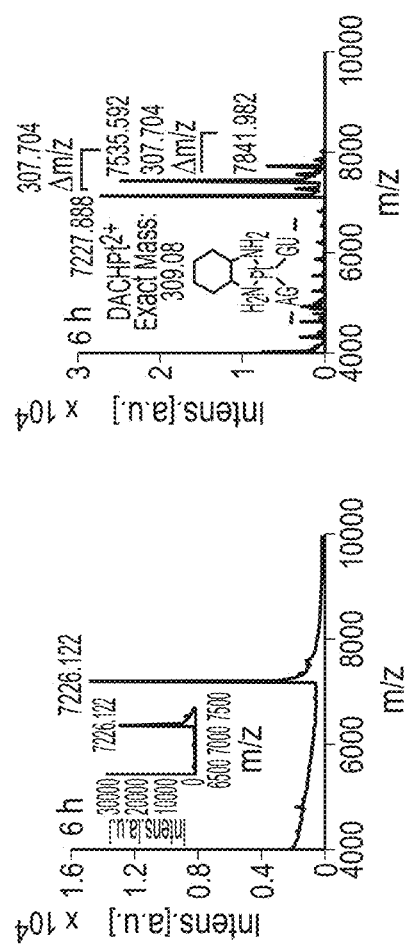
FIG. 4F

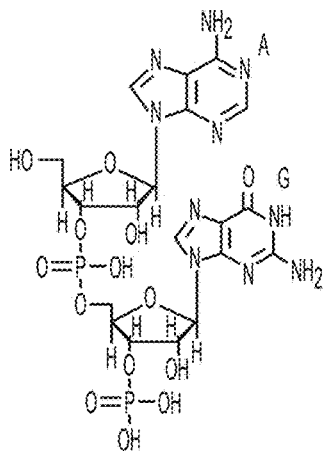
Chemical Formula: $C_{20}H_{26}N_{10}O_{14}P_2$
Exact Mass: 692.11
Molecular Weight: 692.43
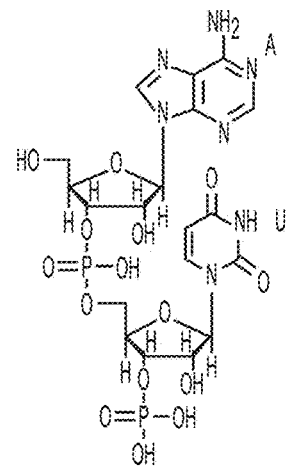
Chemical Formula: $C_{19}H_{25}N_7O_{15}P_2$
Exact Mass: 653.09
Molecular Weight: 653.39
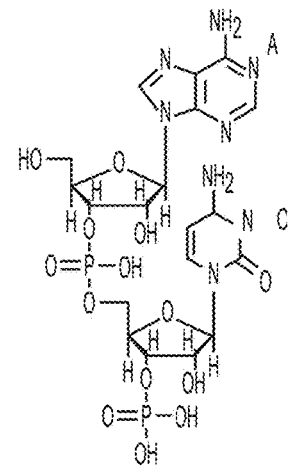
Chemical Formula: $C_{19}H_{26}N_8O_{14}P_2$
Exact Mass: 652.10
Molecular Weight: 652.41
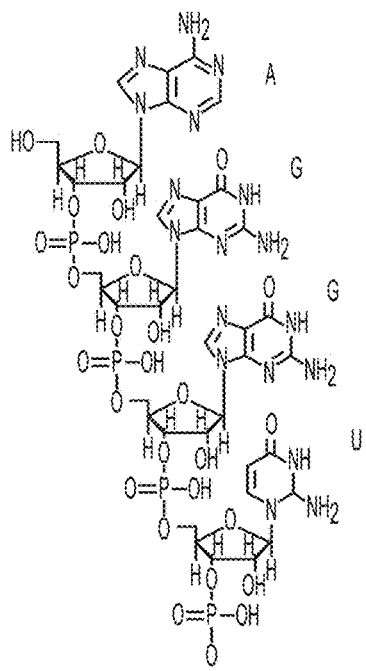
Chemical Formula: $C_{39}H_{49}N_{17}O_{29}P_4$
Exact Mass: 1343.18
Molecular Weight: 1343.81
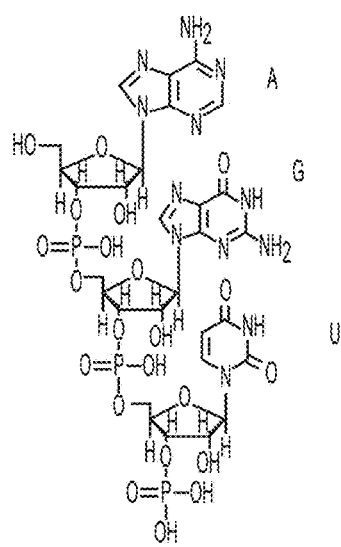
Chemical Formula: $C_{29}H_{37}N_{12}O_{22}P_3$
Exact Mass: 998.14
Molecular Weight: 998.60
FIG. 5C

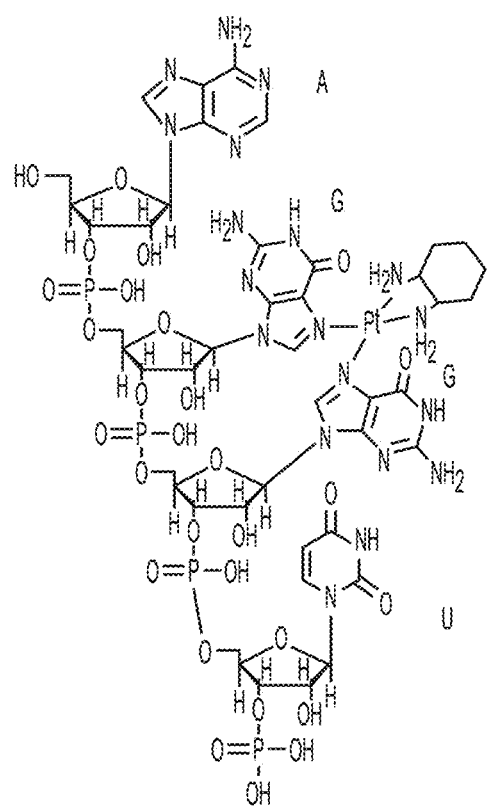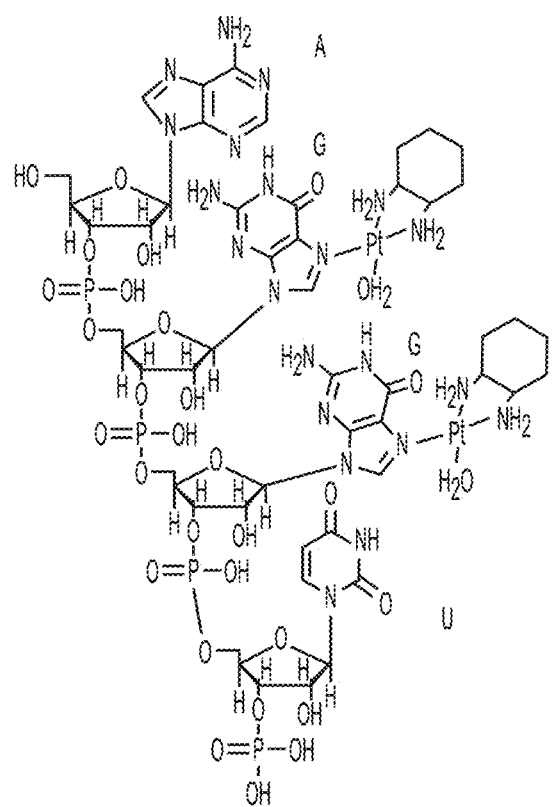
Chemical Formula: $C_{45}H_{63}N_{19}O_{29}P_4Pt$
Exact Mass: 1652.26
Molecular Weight: 1653.08
Chemical Formula: $C_{51}H_{81}N_{21}O_{31}P_4Pt_2$
Exact Mass: 1997.37
Molecular Weight: 1998.39
FIG. 5D

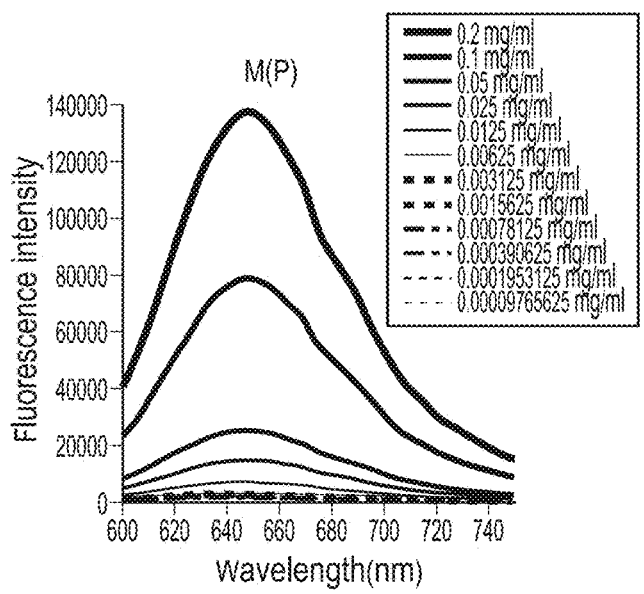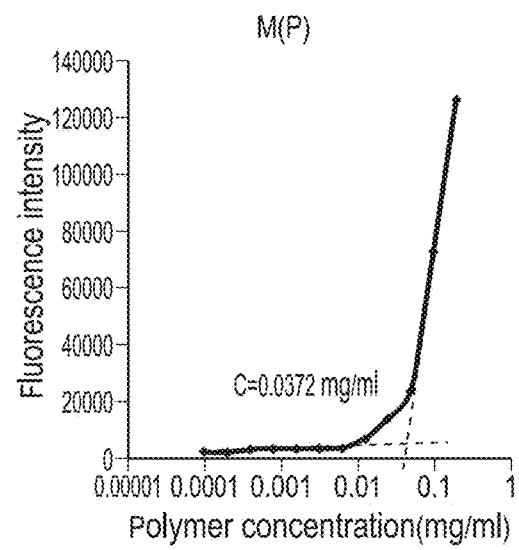
FIG. 10A  FIG. 10B
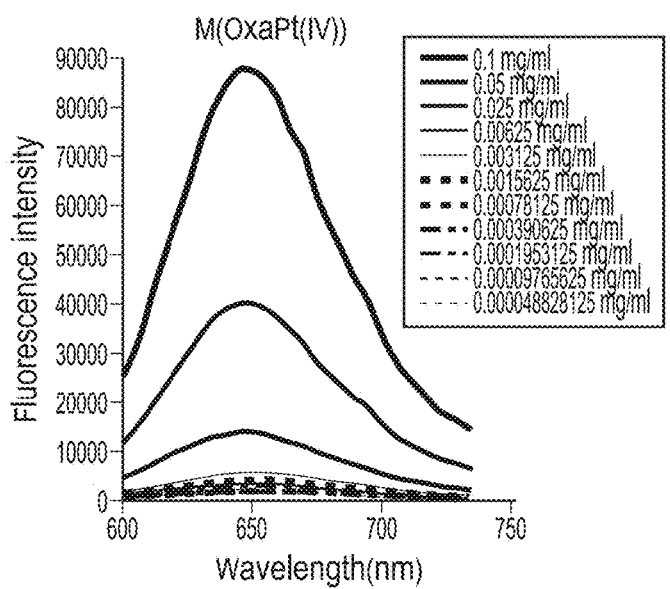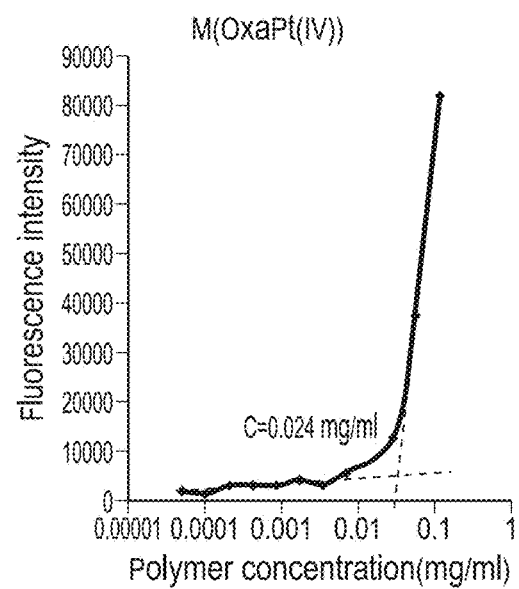
FIG. 10C  FIG. 10D

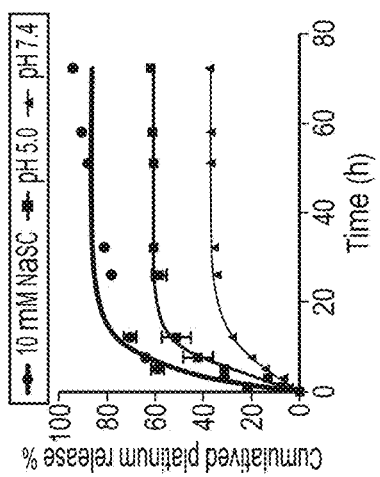
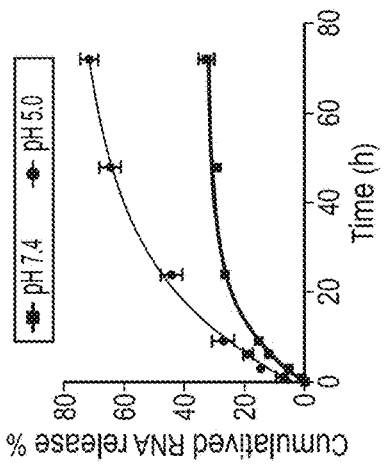
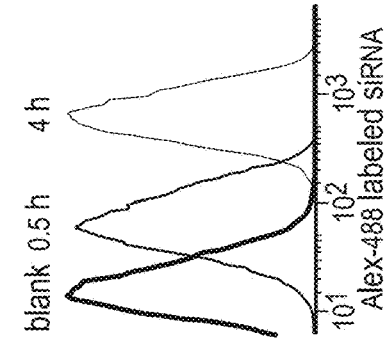
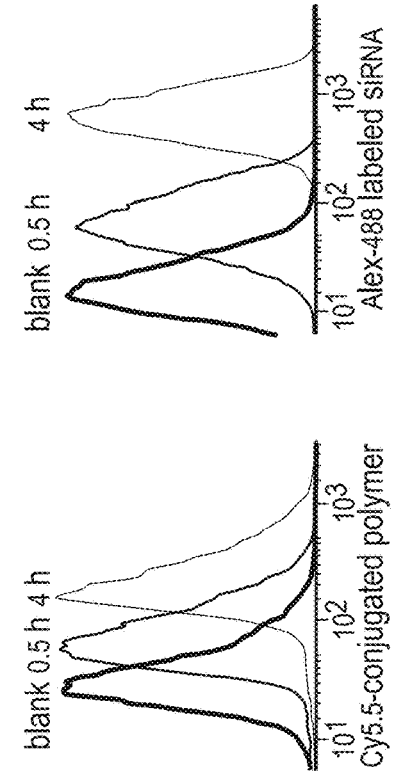
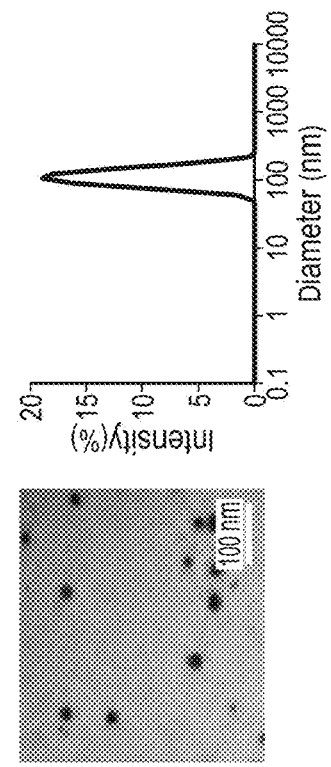
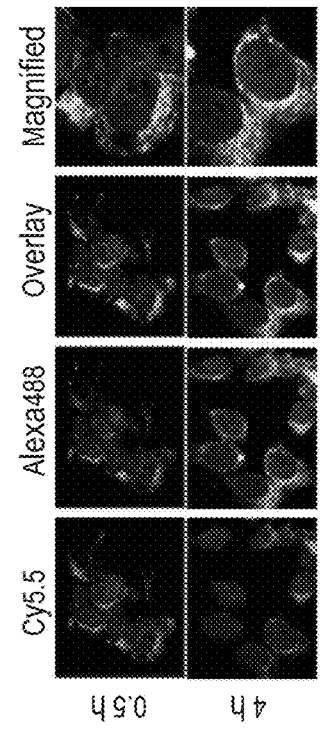
FIG. 12A  FIG. 12B  FIG. 12C  FIG. 12D  FIG. 12E  FIG. 12F  FIG. 12G

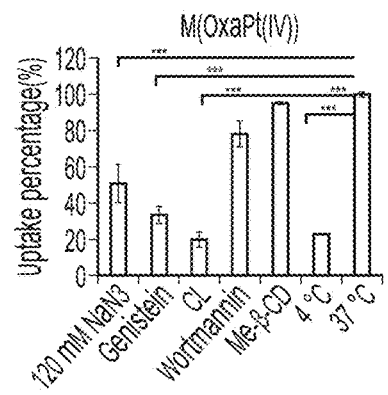 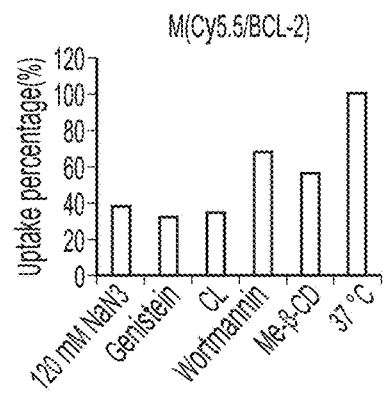 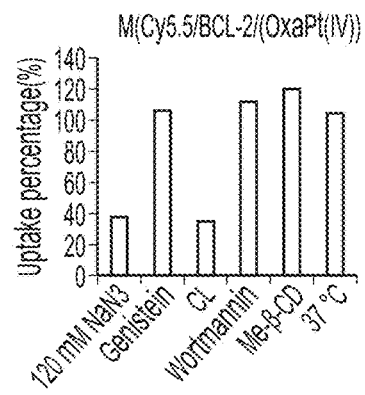
FIG. 17A  FIG. 17B  FIG. 17C
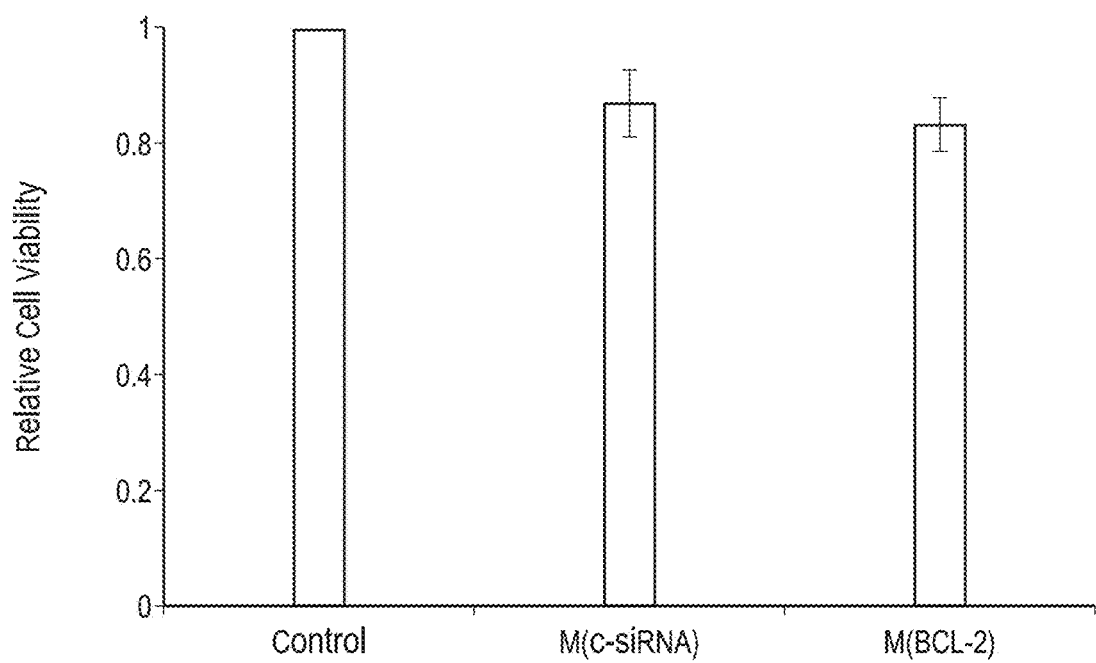
FIG. 18

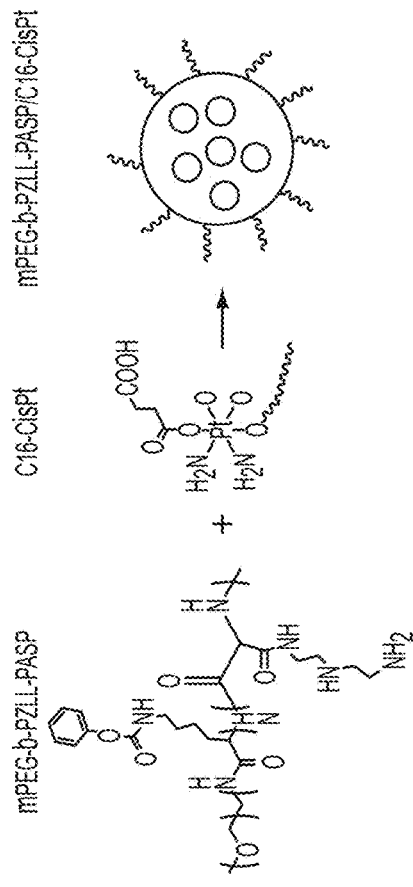
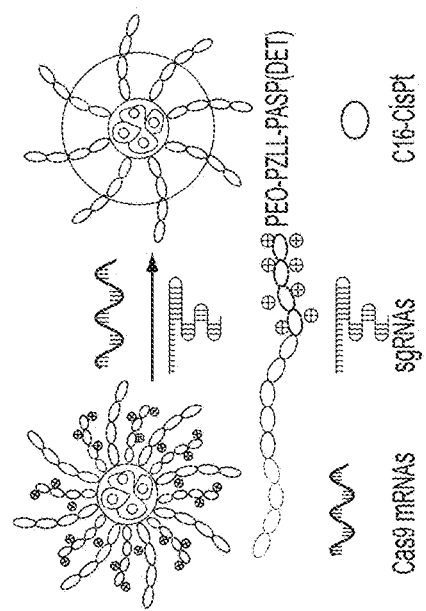
FIG. 28A
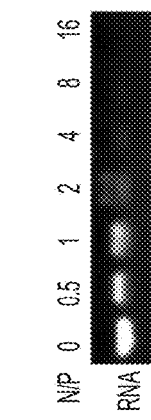
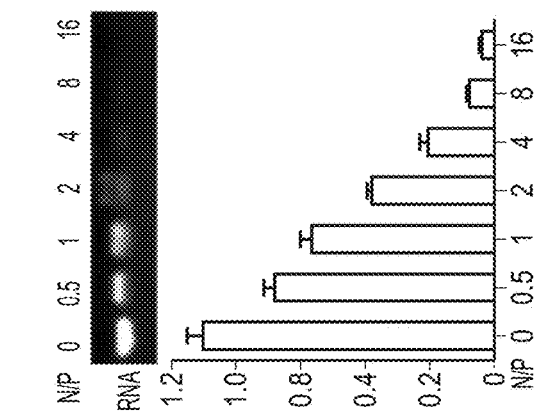
FIG. 28B
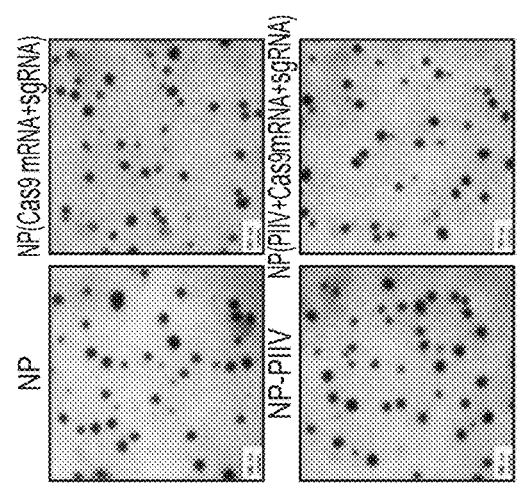
FIG. 28D
FIG. 28C
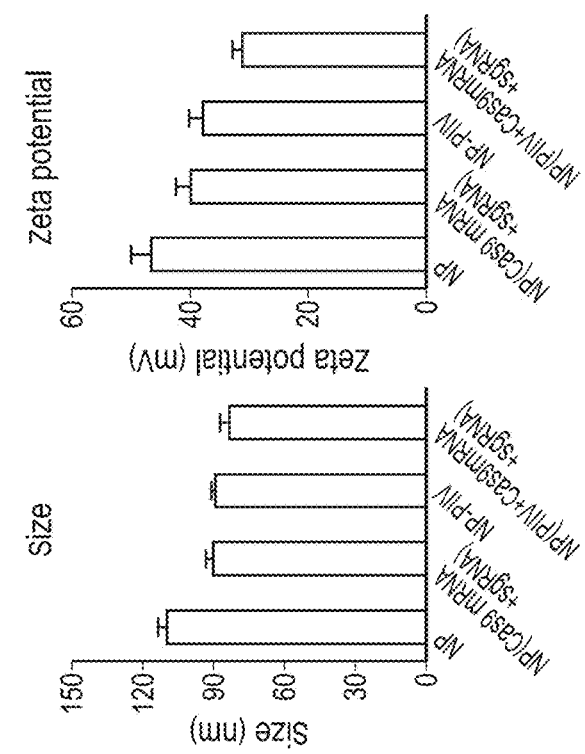
FIG. 28E
FIG. 28F

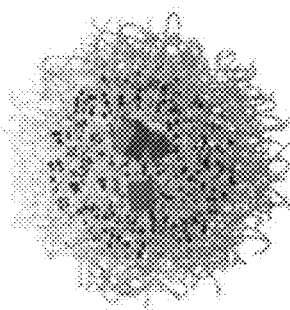 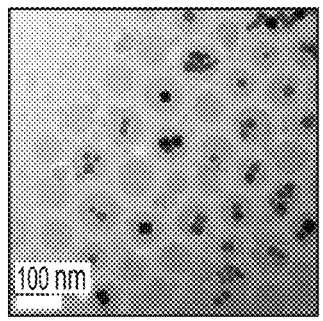 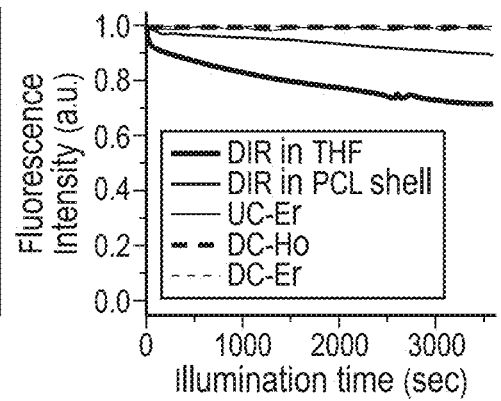
FIG. 31A    FIG. 31B    FIG. 31D
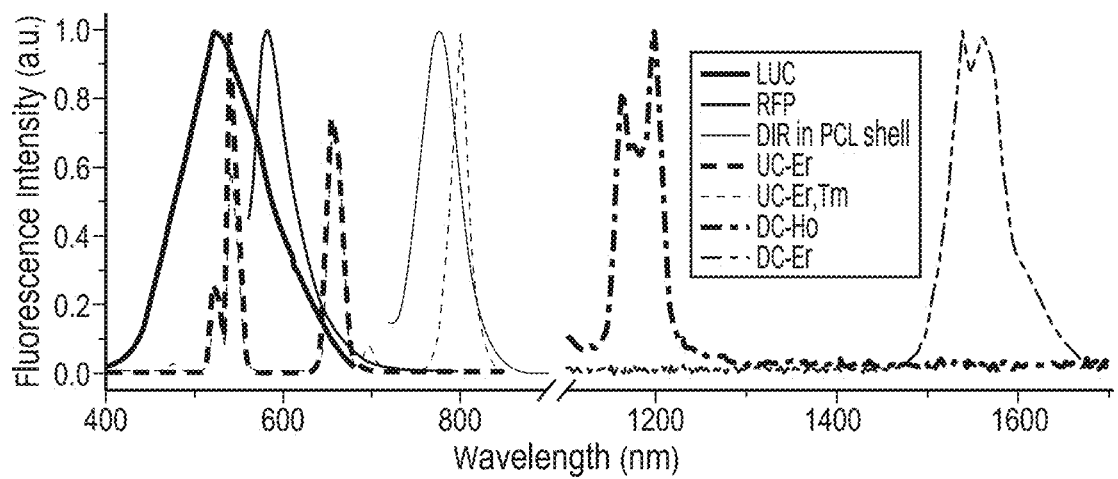
FIG. 31C

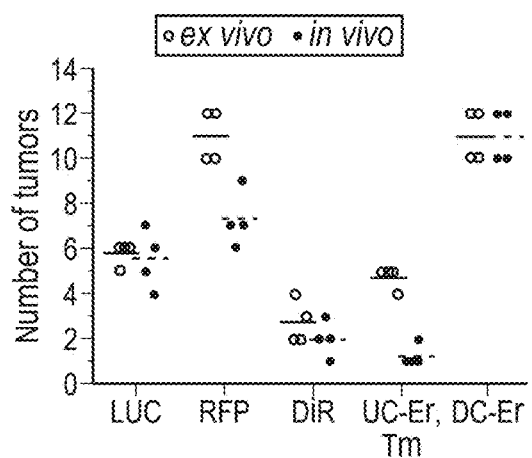
FIG. 33A
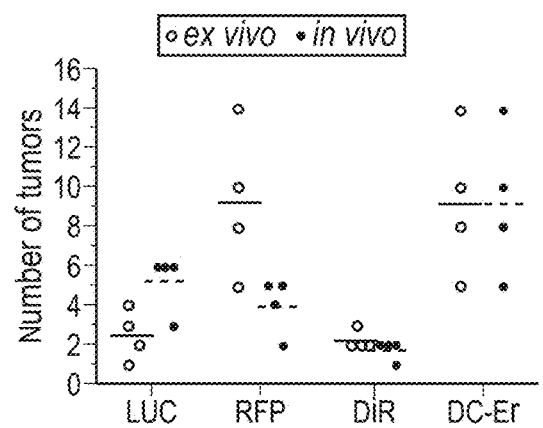
FIG. 33B
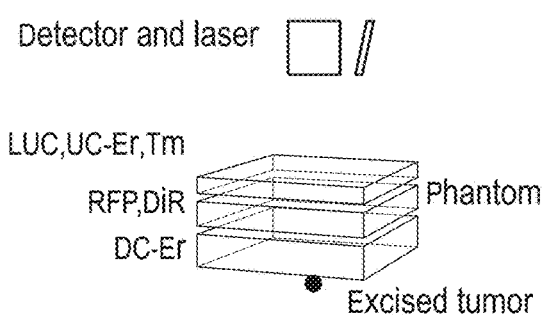
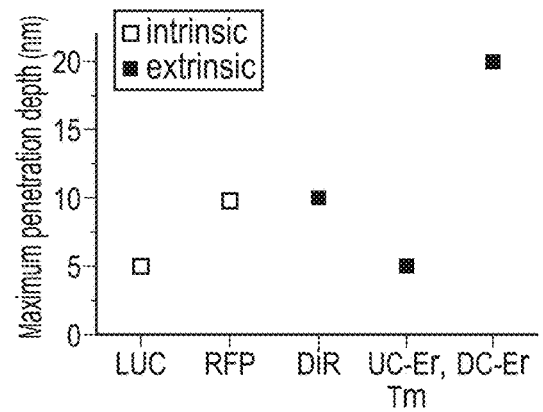
FIG. 33C

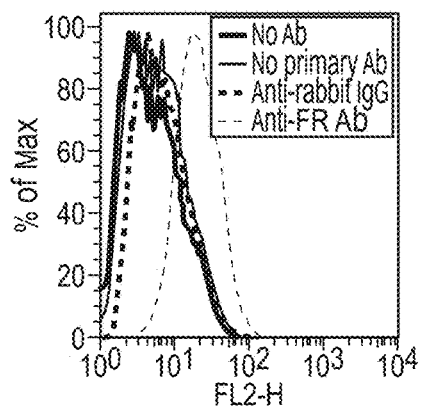 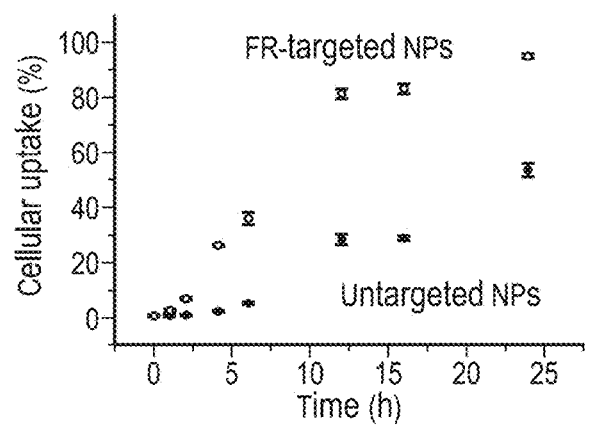
FIG. 34A  FIG. 34B
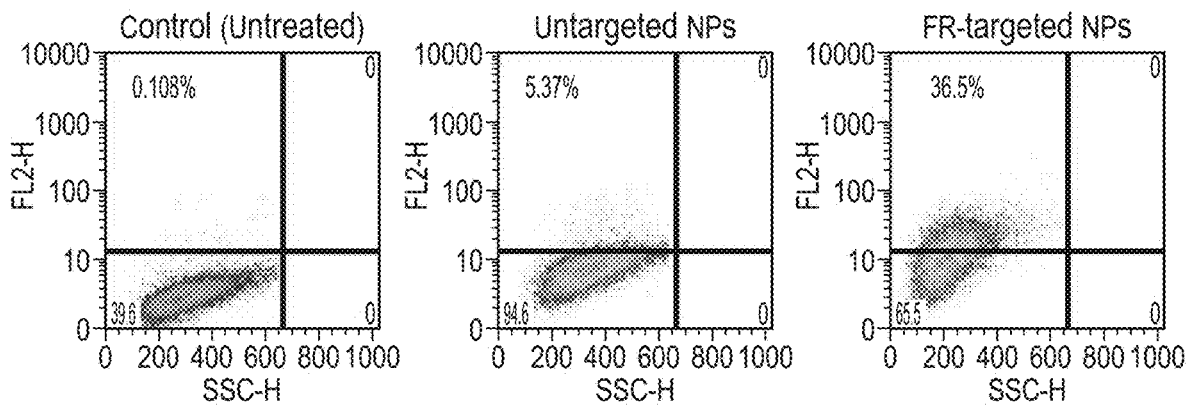
FIG. 34C
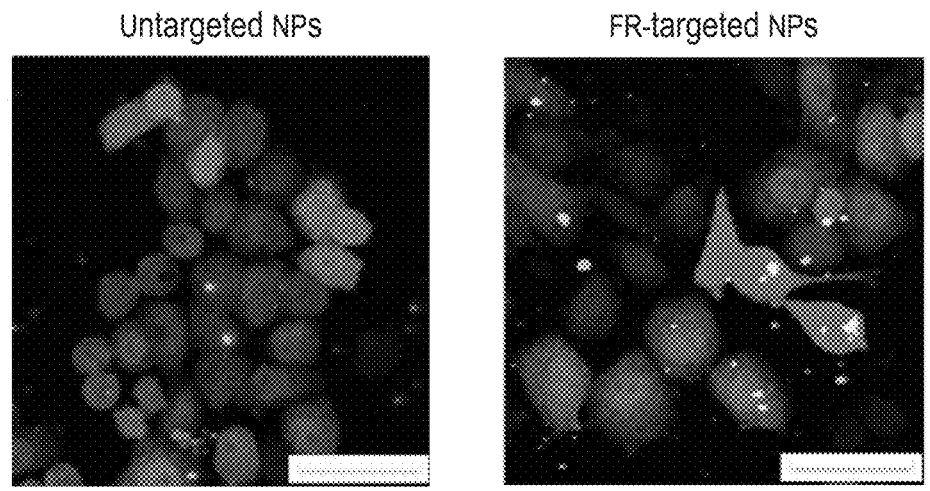
FIG. 34D

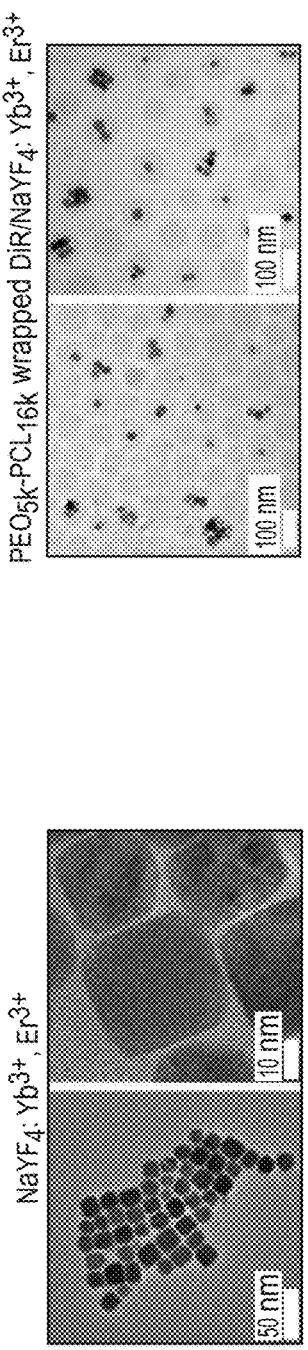
FIG. 41A
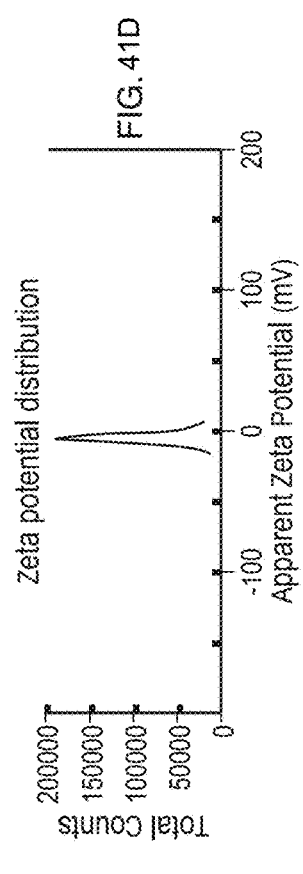
FIG. 41B
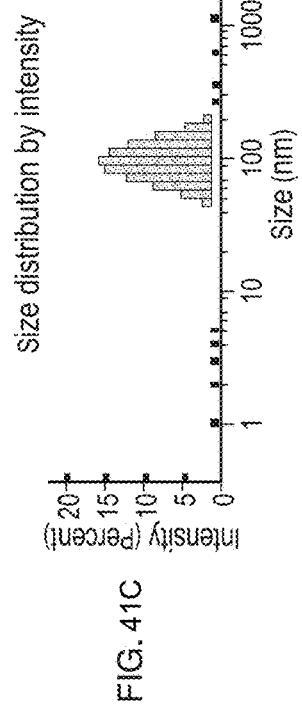
FIG. 41C
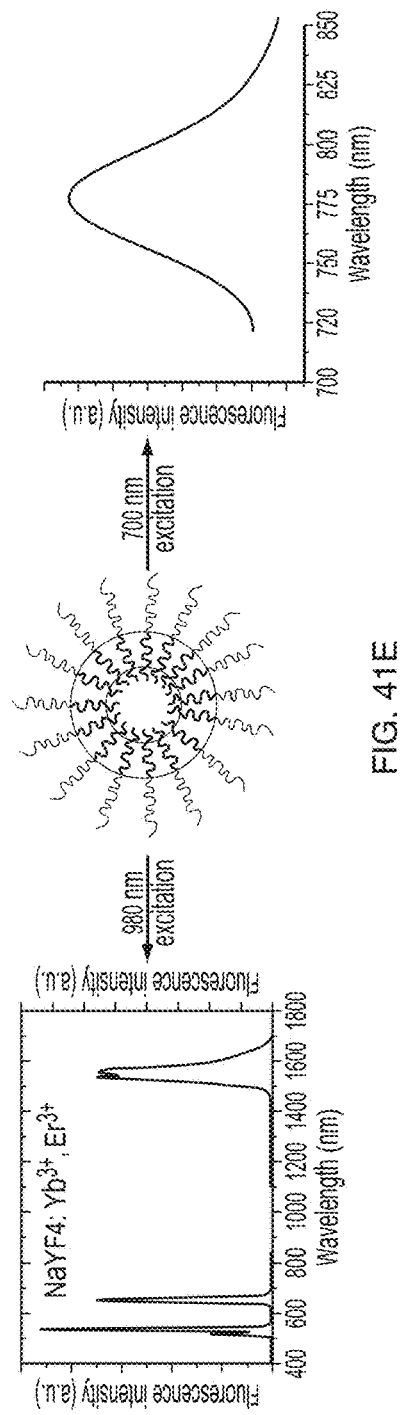
FIG. 41D
FIG. 41E

| Core-Shell Nanoparticle Formulation | Average Size by DLS (nm) | PDI | Zeta Potential (mV) | Yield of LNPs (wt%) | Polymer yield (wt%) | DiR Encapsulation Efficiency (mol%) |
|---|---|---|---|---|---|---|
| DiR-Er,Tm/PEO-PCL ($PEO_{5k}$-$PCL_{16k}$-coated $NaYF_4$:$Yb^{3+}$,$Er^{3+}$,$Tm^{3+}$-based LNPs containing DiR in the PCL shell) | 103.0±3.8 | 0.13±0.02 | -6.5±0.9 | 18.4±1.6 | 56.5±2.8 | 21.7±2.1 |
| Dir-Er,Tm/PEO-PCL ($PEO_{5k}$-$PCL_{16k}$-coated $NaYF_4$:$Yb^{3+}$,$Er^{3+}$-based LNPs containing DiR in the PCL shell) | 95.9±2.5 | 0.13±0.02 | -3.9±1.0 | 15.6±4.8 | 52.7±1.8 | 33.3±10.1 |
| Dir-Ho/Folate-PEO-PCL (1:9 molar ratio of Folate-$PEO_{6k}$-$PCL_{16k}$ to $PEO_{5k}$-$PCL_{16k}$)-coated $NaYF_4$:$Yb^{3+}$,$Ho^{3+}$-based LNPs containing DiR in the PCL shell) | 96.3±2.1 | 0.15±0.03 | -6.1±1.1 | 20.0±5.0 | 51.5±5.0 | 45.4±13.8 |

FIG. 43

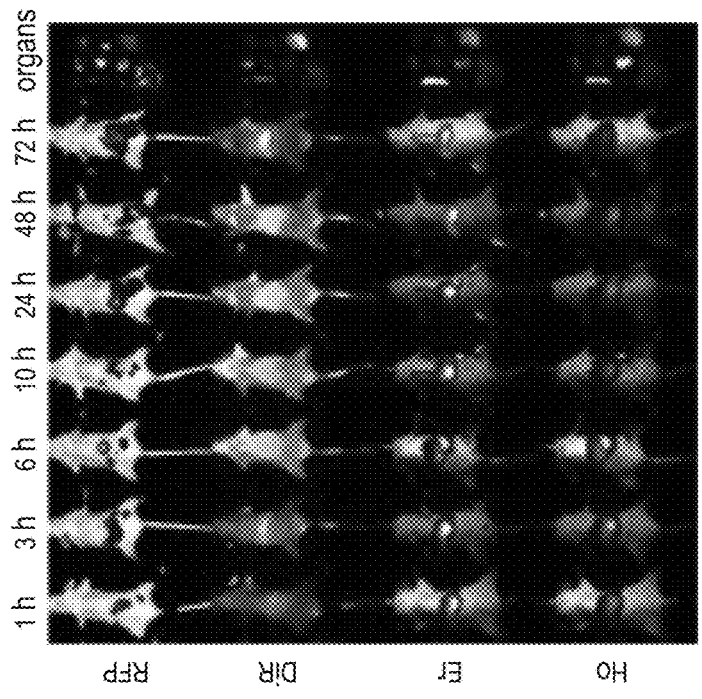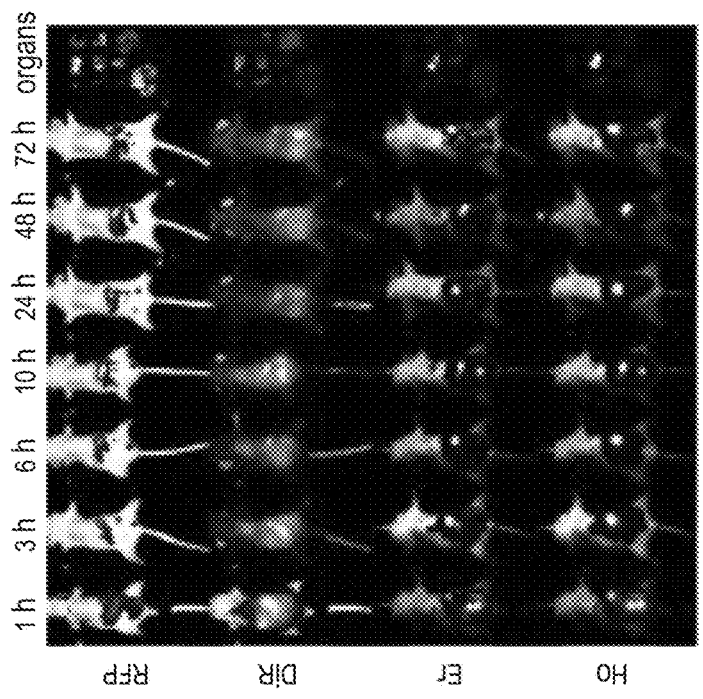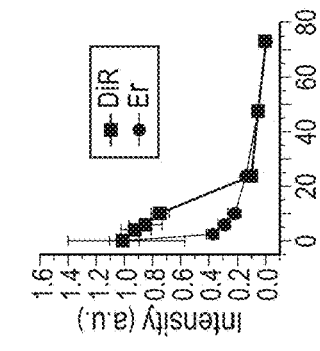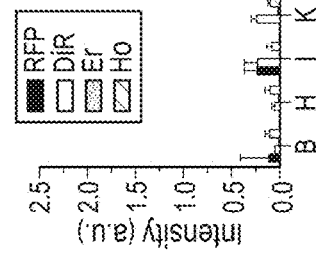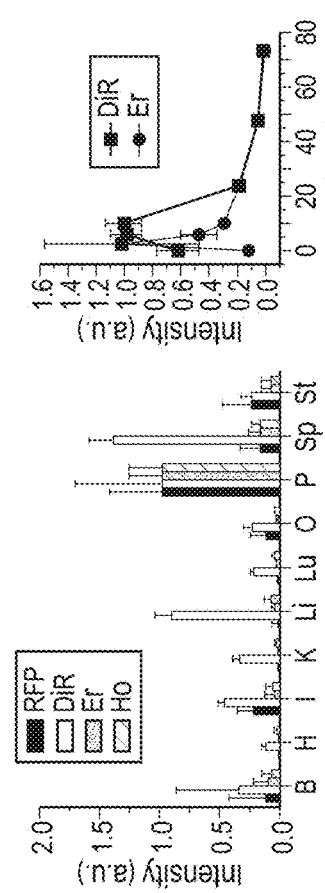
FIG. 50A  FIG. 50B  FIG. 50C  FIG. 50D  FIG. 50E  FIG. 50F

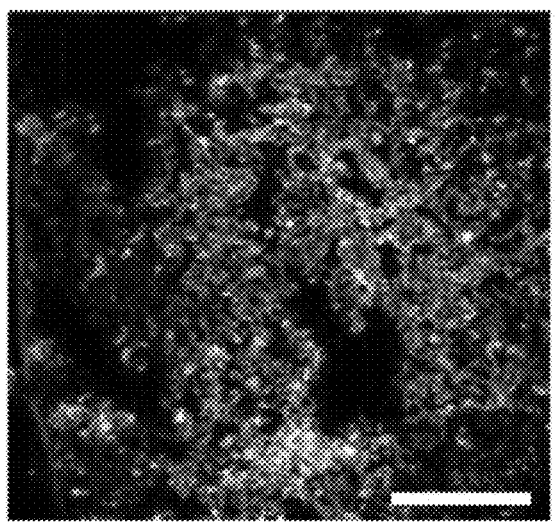 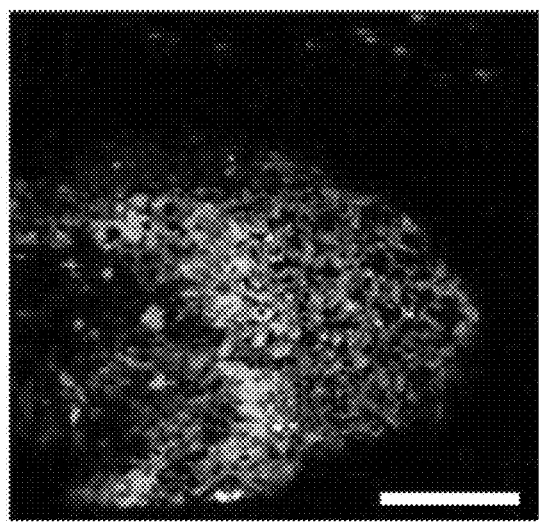
FIG. 54A                    FIG. 54B

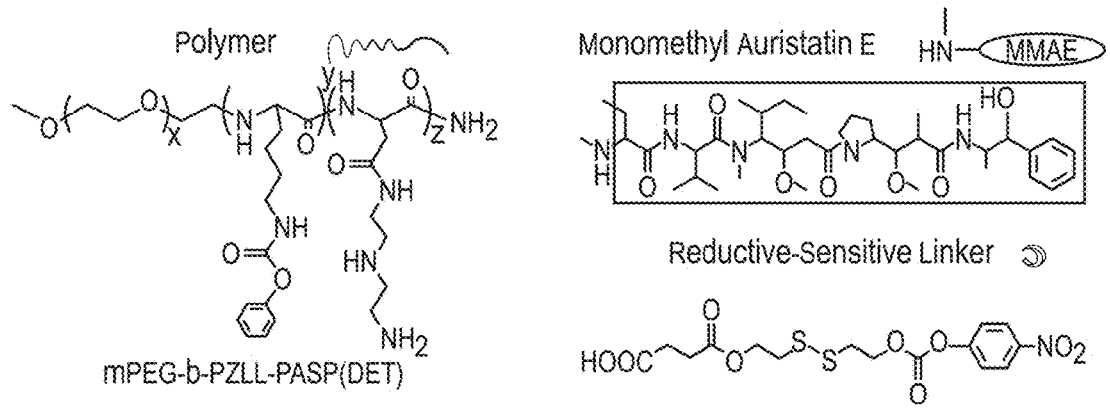
FIG. 55A
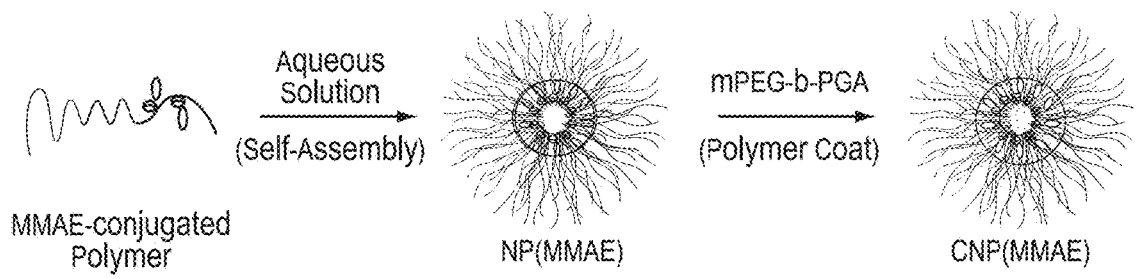
FIG. 55B
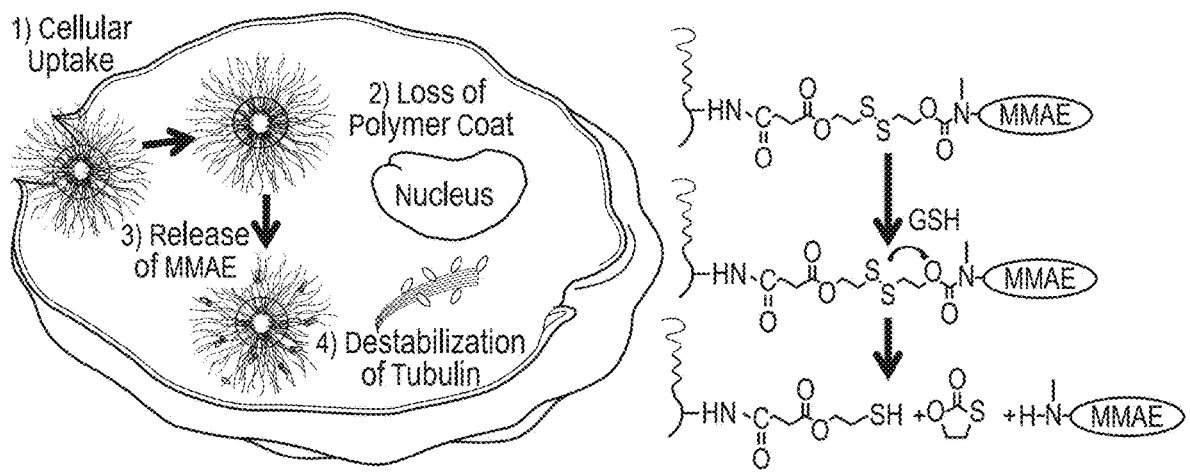
FIG. 55C
FIG. 55D

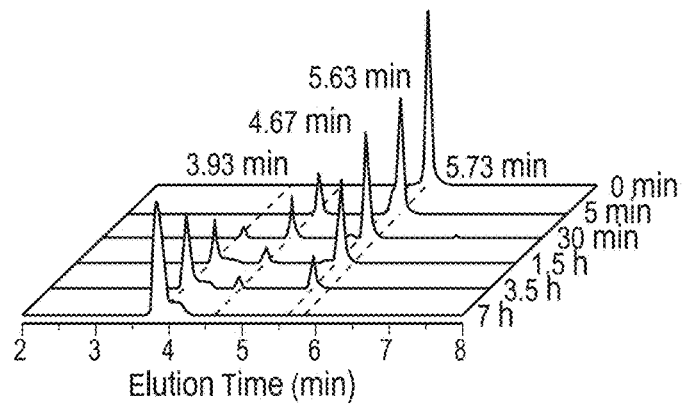
FIG. 56A
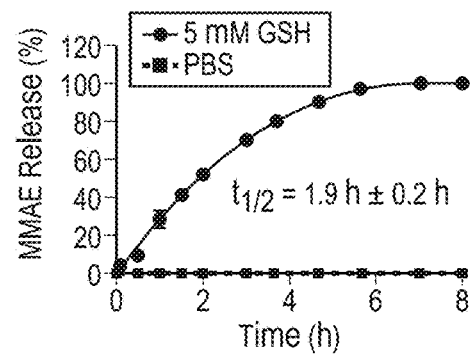
FIG. 56B
| Elution Time (min) | m/z | Postulated Chemical Structure | Mw (g/mol) | Name |
|---|---|---|---|---|
| 5.73 | 998.5 (M+H)+ 499.8 (M+2H)2+ | HOOC—\—C(=O)—O—\—S—S—\—O—C(=O)—N(—)—MMAE | 997.5 | MMAE-Pro |
| 5.63 | 822.5 (M+H)+ | HS—\—O—C(=O)—N(—)—MMAE | 821.5 | MMAE-SH |
| 4.67 | 1127.5 (M+H)+ | GS—S—\—O—C(=O)—N(—)—MMAE | 1126.5 | MMAE-GSH |
| 3.93 | 718.5 (M+H)+ 359.8 (M+2H)2+ 740.5 (M+Na)+ | HN—MMAE | 717.5 | MMAE |
FIG. 56C

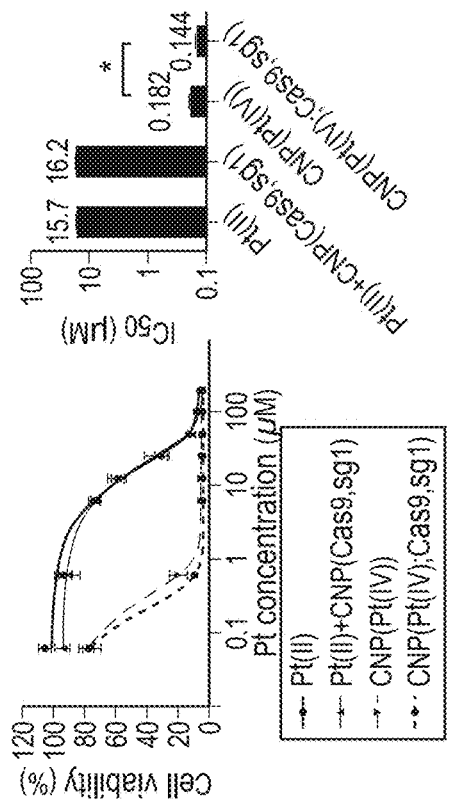
FIG. 62A
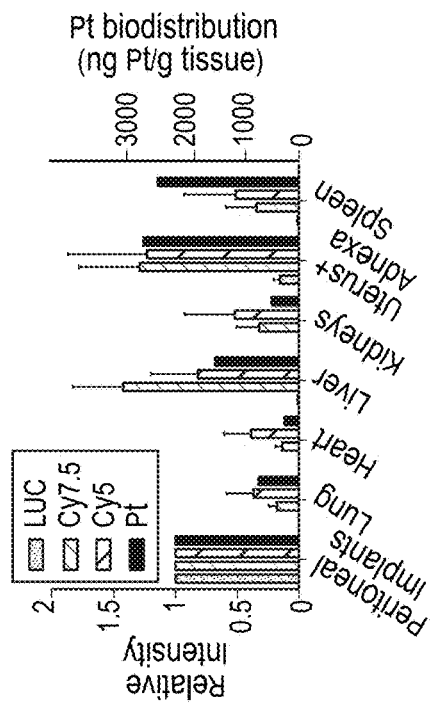
FIG. 62B
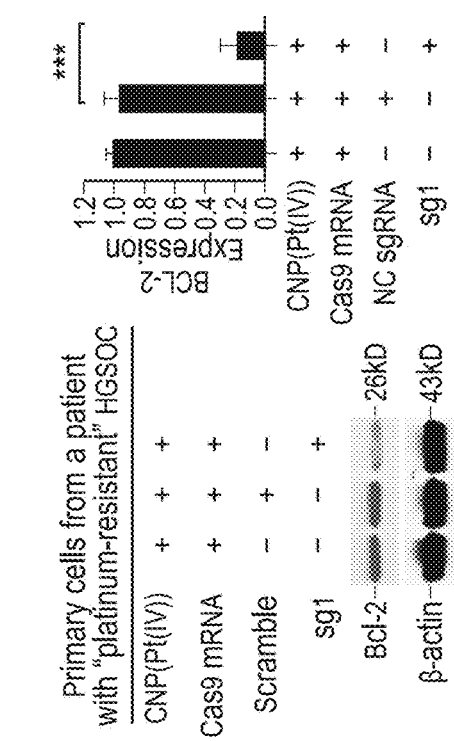
FIG. 62C
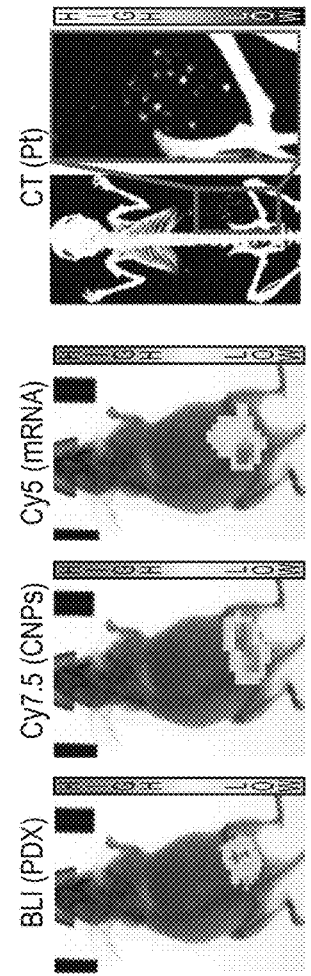
FIG. 62D
FIG. 62E

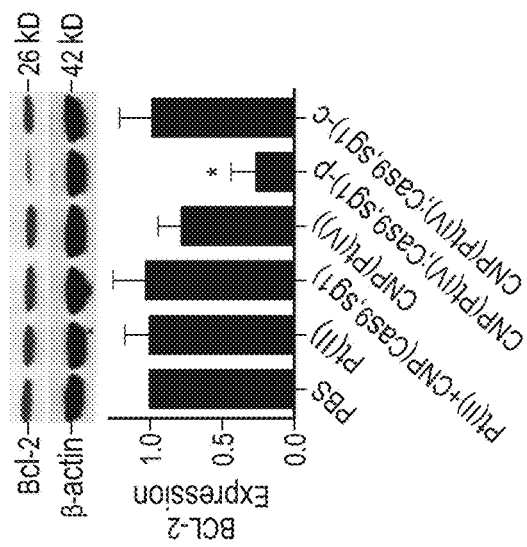
FIG. 62H
FIG. 62I
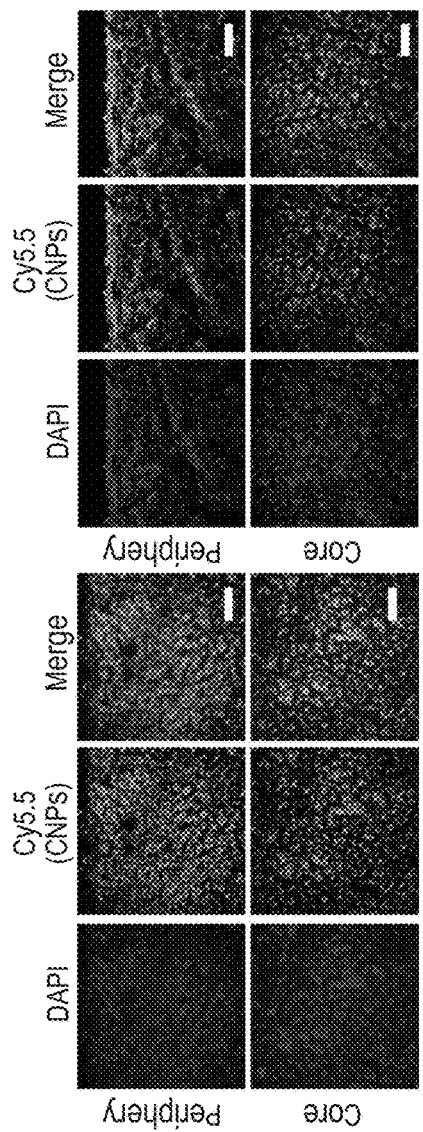
FIG. 62F
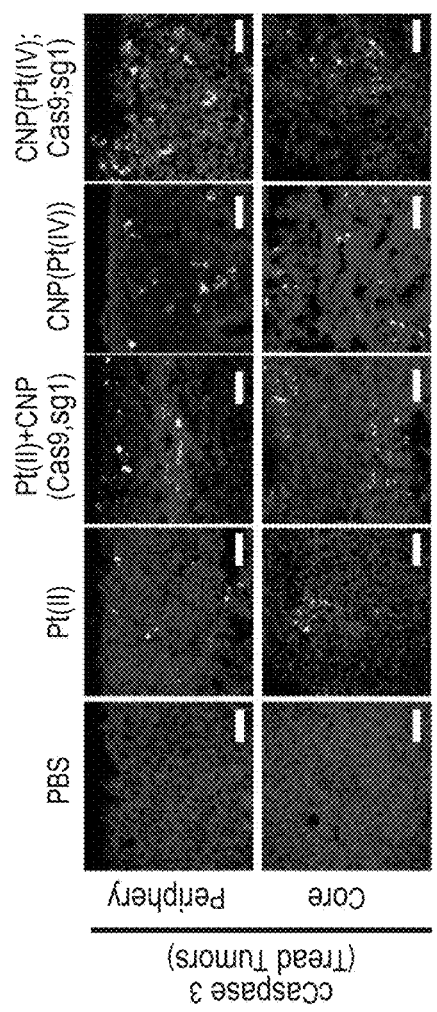
FIG. 62G

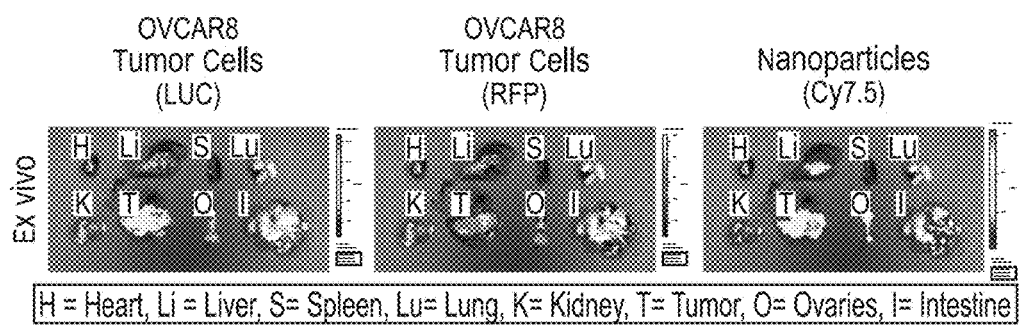
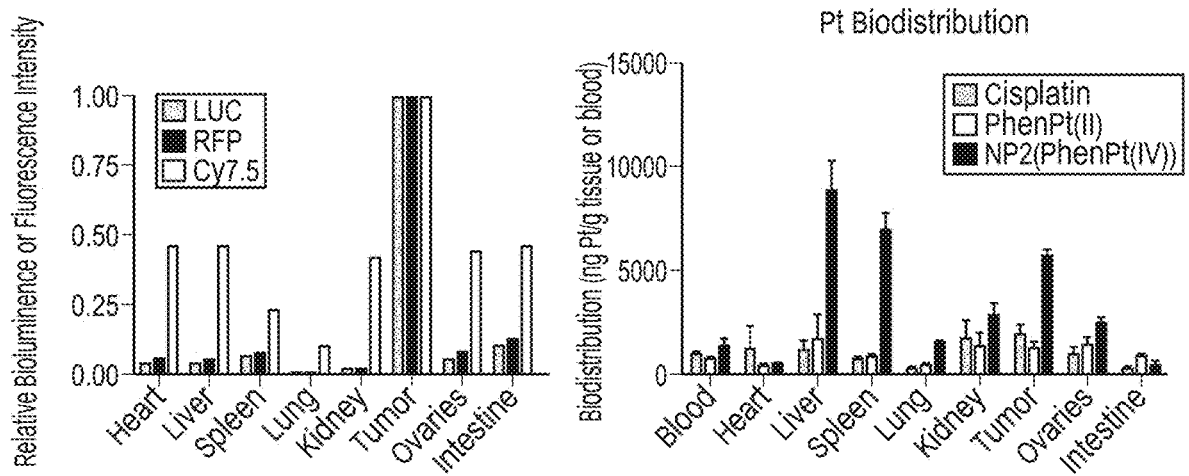
FIG. 65

NANOPARTICLE CONJUGATES OF HIGHLY POTENT TOXINS AND INTRAPERITONEAL ADMINISTRATION OF NANOPARTICLES FOR TREATING OR IMAGING CANCER

RELATED APPLICATIONS

This application claims the benefit of priority to U.S. Patent Application Ser. No. 62/330,684, filed May 2, 2016, U.S. Patent Application Ser. No. 62/330,697, filed May 2, 2016, and U.S. Patent Application Ser. No. 62/489,111, filed Apr. 24, 2017, the contents of each of which are hereby incorporated by reference.

SEQUENCE LISTING

The instant application contains a Sequence Listing which has been submitted electronically in ASCII format and is hereby incorporated by reference in its entirety. Said ASCII copy, created on Jun. 30, 2017, is named MTU-28301_SL.txt and is 2,930 bytes in size.

BACKGROUND

Several strategies have recently been pursued to improve EOC therapy by delivering chemotherapeutic agents in a targeted fashion. These include the attachment of highly potent toxins to antibodies, forming antibody-drug conjugates (ADCs), and, the incorporation of existing small molecule chemotherapies within nanoparticles (NPs). There are currently several ADCs in last stage clinical development for "platinum resistant" EOC (e.g. Mirvetuximab soravtansine (IMGN853); ImmunoGen Inc., Waltham, Mass.). Most of these agents bind 1-4 toxin molecules per antibody, are critically reliant on the properties of their drug-linker, and can suffer from suboptimal tradeoffs between efficacy and therapeutic index; dissociation of the toxin payload is necessary for antitumor activity but the prolonged circulation times of ADCs may lead to premature drug release, which results in persistent and sometimes significant side effects. Similarly, the first-generation of clinically tested NPs have generally failed to improve the therapeutic efficacy of their associated agents. They have typically incorporated drugs with tolerable toxicity profiles such as doxorubicin (e.g. DOXIL® (doxorubicin HCl liposome injection); Johnson & Johnson) and paclitaxel (e.g. Abraxane® (paclitaxel protein-bound; Celgene), displaying modest activity against multiple cancer cell types (i.e. $IC_{50}$s in the tens to hundreds of nanomolar range); additionally, they have generally relied on drug encapsulation as opposed to chemical conjugation. As a result, these NPs have displayed continuous drug release during their intravascular circulation, which has led to persistent off-target side effects with only mild increases in antitumor efficacy.

The development of novel agents and delivery methods with increased antitumor efficacy and limited toxicity is, thus, a critical unmet need.

SUMMARY

In certain embodiments, the invention relates to a method of treating cancer in a human subject in need thereof comprising administering by intraperitoneal injection or infusion to the intraperitoneal cavity a composition comprising a plurality of particles in an aqueous pharmaceutically acceptable carrier, wherein the cancer is a cancer that forms a peritoneal implant on the serosal surface of an organ of the peritoneal cavity;

each particle comprises a biodegradable core having an outer surface and a polymer non-covalently associated with the outer surface of the core;

the polymer comprises a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;

the biodegradable core comprises an anticancer agent; and the characteristic size of the particles, as determined by dynamic light scattering (DLS), is about 20 nm to about 300 nm.

In certain embodiments, the invention relates to any one of the methods described herein, wherein the composition does not comprise a targeting agent. In certain embodiments, the invention relates to any one of the methods described herein, wherein the particle does not comprise a targeting agent.

In certain embodiments, the invention relates to any one of the methods described herein, wherein the biodegradable core comprises a second polymer.

In certain embodiments, the invention relates to any one of the methods described herein, wherein the anticancer agent has an $IC_{50}$ of less than 1 nM.

In certain embodiments, the invention relates to a method of treating cancer in a human subject in need thereof comprising administering by intraperitoneal injection or infusion to the intraperitoneal cavity a composition comprising a plurality of particles in an aqueous pharmaceutically acceptable carrier, wherein the cancer is a cancer that forms a peritoneal implant on the serosal surface of an organ of the peritoneal cavity;

each particle comprises a biodegradable core having an outer surface and a polymer non-covalently associated with the outer surface of the core;

the biodegradable core comprises an agent, wherein the agent is (a) a nuclease selected from the group consisting of Cas9, TALEN, and zinc finger, or (b) a nucleic acid encoding a nuclease selected from the group consisting of Cas9, TALEN, and zinc finger;

an optional DNA editing template; and a block copolymer comprising:

(i) a first block comprising a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;

(ii) a second block comprising a plurality of second monomers, wherein each second monomer is hydrophobic; and (iii) a third block comprising a plurality of third monomers, wherein each third monomer is positively charged at a pH from about 6.8 to about 7.4, wherein the agent is non-covalently associated with the block copolymer; and the DNA editing template, when present, is non-covalently associated with the block copolymer;

the polymer comprises a plurality of first monomers; and
the characteristic size of the particles, as determined by dynamic light scattering (DLS), is about 20 nm to about 300 nm.

In certain embodiments, the invention relates to any one of the methods described herein, wherein the composition does not comprise a targeting agent. In certain embodiments, the invention relates to any one of the methods described herein, wherein the particle does not comprise a targeting agent.

In certain embodiments, the invention relates to a particle comprising a biodegradable core having an outer surface and a polymer non-covalently associated with the outer surface of the core,
wherein
the biodegradable core comprises
an anticancer agent; and
a block copolymer comprising:
(i) a first block comprising a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;
(ii) a second block comprising a plurality of second monomers, wherein each second monomer is selected from the group consisting of 6-hydroxycaproic acid, side-chain N-protected lysine, lactic acid, glycolic acid, hydroxybutyrate, valine, isoleucine, leucine, methionine, phenylalanine, tryptophan, cysteine, alanine, proline, glycine, tyrosine, side-chain carbonyl-protected aspartic acid, side-chain carbonyl-protected glutamic acid, propylene carbonate, butyl acrylate, butyl methacrylate, and benzyl methacrylate; and
(iii) a third block comprising a plurality of third monomers, wherein each third monomer is selected from the group consisting of lysine, side-chain aminoalkyl-functionalized lysine, asparagine, side-chain aminoalkyl-functionalized asparagine, arginine, aspartamide, side-chain aminoalkyl-functionalized aspartamide, and ethyleneimine,
wherein the anticancer agent is covalently bound to the block copolymer;
the polymer comprises a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin; and
the characteristic size of the particle, as determined by dynamic light scattering (DLS), is about 20 nm to about 300 nm.

In certain embodiments, the invention relates to any one of the particles described herein, wherein the particle does not comprise a targeting agent.

In certain embodiments, the invention relates to any one of the particles described herein, wherein the anticancer agent has an $IC_{50}$ of less than 1 nM.

In certain embodiments, the invention relates to a particle comprising a biodegradable core having an outer surface and a polymer non-covalently associated with the outer surface of the core,
wherein
the biodegradable core comprises
an anticancer agent; and
Pt(IV);
the polymer comprises a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin; and
the characteristic size of the particle, as determined by dynamic light scattering (DLS), is about 20 nm to about 300 nm In certain embodiments, the invention relates to any one of the particles described herein, wherein the particle does not comprise a targeting agent.

In certain embodiments, the invention relates to a particle comprising a core and a polymer non-covalently associated with the core, wherein
the polymer comprises a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;
the core comprises an imaging agent; and
the characteristic size of the particle, as determined by DLS, is about 20 nm to about 300 nm.

In certain embodiments, the invention relates to a method of imaging cancer in a human subject in need thereof comprising
administering by intraperitoneal injection or infusion to the intraperitoneal cavity a composition comprising a plurality of particles comprising an imaging agent, as described herein, and an aqueous pharmaceutically acceptable carrier; and
obtaining an image of the cancer,
wherein the cancer is a cancer that forms a peritoneal implant on the serosal surface of an organ of the peritoneal cavity.

Surprisingly, the methods and compositions described herein have been shown to co-localize with intraperitoneal tumors, even in the absence of targeting agent.

BRIEF DESCRIPTION OF THE FIGURES

FIG. 4A is a representative ESI-MS spectrum (intensity (a.u.) vs. m/z) of solutions of 10 mM 5'-GMP at 12 h after incubation with 5 mM OxaPt(II) at 37° C. The presence of the DACHPt(5'-GMP)$_2$ adduct was monitored over time by measuring changes in the relative height of the peak at m/z=1035.1778; the structure and molecular weight of any bis-adducts are shown in the inset. Note: other peaks in the ESI spectra correspond to adducts formed with Na+ and K+.

FIG. 4B is a representative ESI-MS spectrum (intensity (a.u.) vs. m/z) of solutions of 10 mM 5'-GMP at 12 h after incubation with 5 mM OxaPt(IV) at 37° C. The presence of the DACHPt(5'-GMP)$_2$ adduct was monitored over time by measuring changes in the relative height of the peak at m/z=1035.1778; the structure and molecular weight of any bis-adducts are shown in the inset. Note: other peaks in the ESI spectra correspond to adducts formed with Na+ and K+.

FIG. 4C is a plot of % platinum binding to 5'-GMP as a function of time. These data show the kinetics of DACHPt (5'-GMP)$_2$ adduct formation, depicted as the molar percentage of the total 5'-GMP pool in solution, as determined by $^1$HNMR.

FIG. 4D is a representative MALDI-TOF-MS spectrum (intensity (a.u.) vs. m/z) of the products formed after 6 h of incubation of (50 µM) BCL-2 siRNA with 500 µM OxaPt(II) at 37° C. Three major peaks are attributed to unmodified BCL-2 siRNA (m/z=7227.8888), BCL-2 siRNA with one DACHPt$^{2+}$ adduct (m/z=7535.592), and BCL-2 siRNA with two DACHPt$^{2+}$ adducts (m/z=7841.982). Note, the molecular weight of DACHPt is 309.08 and the Am/z upon formation of the siRNA-DACHPt$^{2+}$ mono adduct is 307.704; RNA loses two H$^+$ to keep it at +1 charge state.

FIG. 4E is a representative MALDI-TOF-MS spectrum (intensity (a.u.) vs. m/z) of the products formed after 6 h of incubation of (50 uM) BCL-2 siRNA with 500 uM OxaPt (IV) at 37° C. Three major peaks are attributed to unmodified BCL-2 siRNA (m/z=7227.8888), BCL-2 siRNA with one DACHPt$^{2+}$ adduct (m/z=7535.592), and BCL-2 siRNA with two DACHPt$^{2+}$ adducts (m/z=7841.982). Note, the molecular weight of DACHPt is 309.08 and the Am/z upon formation of the siRNA-DACHPt$^{2+}$ mono adduct is 307.704; RNA loses two H$^+$ to keep it at +1 charge state. Unmodified BCL-siRNA displays a mass peak at m/z=7226.12 (inset).

FIG. 4F is a plot of RNA binding (ng Pt/µg RNA) as a function of time. These data show the binding kinetics of OxaPt(II) and OxaPt(IV) to double-stranded BCL-2 siRNA as measured by AAS. Data are expressed as "ng Pt atoms per µg RNA".

FIG. 5C is the structure, chemical formula, exact mass, and molecular weight of possible reaction products obtained after site specific cleavage of ss-BCL-2 siRNA (anti-sense) by RNase A. Mass peaks of 5'-AU-3', 5'-AGU-3' and 5'-AGGU-3' can be found in the MALDI/TOF-MS spectra in FIG. 4E.

FIG. 5D is the structure, chemical formula, exact mass, and molecular weight of the possible oligo-nucleotide reaction products of platinated ss-BCL-2 siRNA after cleavage by RNase A; note, 5'-AG(Pt)GU-3' and 5'-AG(Pt)G(Pt)U-3' are the potential cleavage products. Note, "Pt" here denotes "DACHPt".

FIG. 10A is a plot of fluorescence intensity as a function of wavelength. These data were detected by Nile Red fluorescence for mPEG-PCL-PLL at various concentrations, which forms M(P) in solution.

FIG. 10B is a plot of fluorescence intensity as a function of polymer concentration (mg/mL). These data were used to determine the critical micelle concentration (CMC) for mPEG-PCL-PLL, which forms M(P) in solution.

FIG. 10C is a plot of fluorescence intensity as a function of wavelength. These data were detected by Nile Red fluorescence for mPEG-PCL-PLL-OxaPt(IV) at various concentrations, which generates M(OxaPt(IV)).

FIG. 10D is a plot of fluorescence intensity as a function of polymer concentration (mg/mL). These data were used to determine the critical micelle concentration (CMC) for represent analogous plots for mPEG-PCL-PLL-OxaPt(IV), which generates M(OxaPt(IV)).

FIG. 12A is a TEM image showing the average size distribution of M(OxaPt(IV)/BCL-2) formed at an amine (monomer unit) to phosphate (nucleic acid) ratio (N/P) of 4. The resultant micelles had a mean particle diameter of 78.9+/−10.4 nm by TEM.

FIG. 12B is a DLS plot (intensity (%) vs. diameter (nm)), which shows the average size distribution of M(OxaPt(IV)/ BCL-2) formed at an amine (monomer unit) to phosphate (nucleic acid) ratio (N/P) of 4. The resultant micelles had a mean particle diameter of 104.9+/−2.1 nm by DLS.

FIG. 12C is a plot of the cumulative RNA release (%) as a function of time (h). These data show that the in situ release of free oxaPt(II) species occurs rapidly in reducing environments while a more controlled release profile is observed dependent upon pH.

FIG. 12D is a plot of the cumulative platinum release (%) as a function of time (h). These data show that the in situ release of Alexa488-labeled siRNA loaded on the same micelles as those used to produce the data shown in FIG. 12C; release is slower but similarly pH-dependent.

FIG. 12E is a series of confocal laser scanning microscopy (CLSM) images visualizing cellular uptake and cytoplasmic delivery of M(Cy5.5/OxaPt(IV)/Alexa-488 siRNA). Images were taken at 30 min (upper panel) or at 4 h after incubation of micelles with MCF-7 cells (lower panel); note, cell nuclei are stained with DAPI. Cy5.5-conjugated PEG-b-PCL-b-PLL polymer and Alexa488-labeled BCL-2 siRNA were simultaneously utilized to independently track polymer and RNA species over time (scale bar=100 µm).

FIG. 12F is a plot of the uptake of Cy5.5-conjugated polymer in MCF-7 cells treated with M(Cy5.5/OxaPt(IV)/ Alexa488 siRNA), as quantified by flow cytometry. Signals generated from the untreated (blank) cells are included for reference. Data shown are expressed as mean values±standard deviation of the mean (n=3 experimental replicates per condition).

FIG. 12G is a plot of the uptake of Alexa488-labeled BCL-2 siRNA in MCF-7 cells treated with M(Cy5.5/OxaPt (IV)/Alexa488 siRNA), as quantified by flow cytometry. Signals generated from the untreated (blank) cells are included for reference. Data shown are expressed as mean values±standard deviation of the mean (n=3 experimental replicates per condition).

FIG. 17A is a bar graph showing the % cellular uptake for various polymeric micelles. MCF-7 cells were seeded in 6-well plates at a density of $1\times10^6$ cells/well. After attachment overnight, the cells were then treated with media containing different small molecule inhibitors of specific endocytosis pathways, including $NaN_3$ (120 mM), genistein (200 µg/mL), chlorpromazine (CL) (20 µg/mL), wortmannin (0.2 µM), or methyl-β-cyclodextrin (Me-β-CD) (200 µM). Note, CL was utilized as an inhibitor of clathrin-dependent (CDE) endocytosis; Me-β-CD and genistein were used as inhibitors of clathrin-independent (CIE) endocytosis; and, wortmannin is a known inhibitor of macropinocytosis. Control cells were similarly plated with fresh media and incubated at either 4 (positive control) or 37° C. (negative control). 1 h after media exchange, cells were treated with M(OxaPt(IV)) at a fixed Pt (10 µM) and Cy5.5 concentrations (1 µg/mL). After 4 h, all cells were washed with (×5) PBS and lysed with $HNO3/H_2O_2$; the concentrations of internalized micelles were determined by either ICP-MS (for quantification of Pt) or by flow cytometry (for quantification of Cy5.5-conjugated polymer) and data were normalized to the average values for the negative control. Data are presented as mean values±the standard deviations of the mean for n=3 technical replicates per condition. Significance is denoted by ***p.<0.001.

FIG. 17B is a bar graph showing the % cellular uptake for various polymeric micelles. MCF-7 cells were seeded in 6-well plates at a density of $1\times10^6$ cells/well. After attachment overnight, the cells were then treated with media containing different small molecule inhibitors of specific endocytosis pathways, including $NaN_3$ (120 mM), genistein (200 µg/mL), chlorpromazine (CL) (20 µg/mL), wortmannin (0.2 µM), or methyl-β-cyclodextrin (Me-β-CD) (200 µM). Note, CL was utilized as an inhibitor of clathrin-dependent (CDE) endocytosis; Me-β-CD and genistein were used as inhibitors of clathrin-independent (CIE) endocytosis; and, wortmannin is a known inhibitor of macropinocytosis. Control cells were similarly plated with fresh media and incubated at either 4 (positive control) or 37° C. (negative control). 1 h after media exchange, cells were treated with M(Cy5.5/BCL-2) at a fixed Pt (10 µM) and Cy5.5 concentrations (1 µg/mL). After 4 h, all cells were washed with (×5) PBS and lysed with $HNO_3/H_2O_2$; the concentrations of internalized micelles were determined by either ICP-MS (for quantification of Pt) or by flow cytometry (for quantification of Cy5.5-conjugated polymer) and data were normalized to the average values for the negative control. Data are presented as mean values±the standard deviations of the mean for n=3 technical replicates per condition. Significance is denoted by ***p.<0.001.

FIG. 17C is a bar graph showing the % cellular uptake for various polymeric micelles. MCF-7 cells were seeded in 6-well plates at a density of $1\times10^6$ cells/well. After attachment overnight, the cells were then treated with media containing different small molecule inhibitors of specific endocytosis pathways, including $NaN_3$ (120 mM), genistein (200 µg/mL), chlorpromazine (CL) (20 µg/mL), wortmannin (0.2 µM), or methyl-β-cyclodextrin (Me-β-CD) (200 µM). Note, CL was utilized as an inhibitor of clathrin-dependent (CDE) endocytosis; Me-β-CD and genistein were used as inhibitors of clathrin-independent (CIE) endocytosis; and, wortmannin is a known inhibitor of macropinocytosis. Control cells were similarly plated with fresh media and incubated at either 4 (positive control) or 37° C. (negative control). 1 h after media exchange, cells were treated with M(Cy5.5/BCL-2/OxaPt(IV)) at a fixed Pt (10 µM) and Cy5.5 concentrations (1 µg/mL). After 4 h, all cells were washed with (×5) PBS and lysed with $HNO_3/H_2O_2$; the concentrations of internalized micelles were determined by either ICP-MS (for quantification of Pt) or by flow cytometry (for quantification of Cy5.5-conjugated polymer) and data were normalized to the average values for the negative control. Data are presented as mean values±the standard deviations of the mean for n=3 technical replicates per condition. Significance is denoted by ***p.<0.001.

FIG. 18 is a bar graph showing relative cell viability of MCF-7 cells treated with various siRNA-containing polymeric micelles. mPEG-b-PCL-b-PLL micelles containing either control siRNA (M(c-siRNA)) or BCL-2 siRNA (M(BCL-2)) were formed at an N/P ratio of 8:1 anionic siRNA to cationic polymer. The treatment concentration of each siRNA species was 100 nM. Fresh media served as a control treatment. Data are presented as mean values±standard deviation of the mean for an n=4 technical replicates per condition.

Only mean values are displayed. In all cases, significance is defined as * p<0.05, p<0.01, and * p<0.001.

Figure 19C:
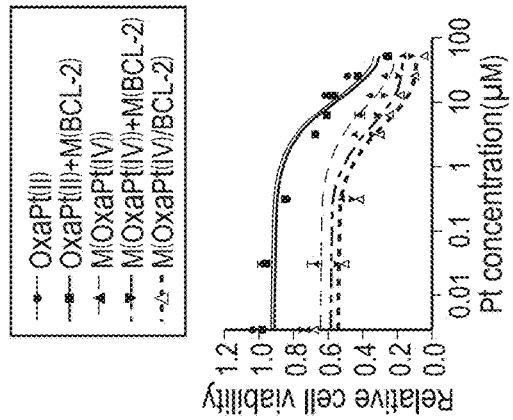
FIG. 19A is a bar graph showing platinum uptake (µg Pt/cell) for various compositions. These data show that co-encapsulation of OxaPt(IV) and BCL-2 siRNA within a single micellar transfection reagent (i.e. M(oxaPt(IV)/BCL-2) quantitatively maximizes the intracellular uptake of oxaliplatin, the numbers of Pt-DNA adducts that are formed, the suppression of BCL-2 mRNA, and cytotoxicity to MCF-7 cells through augmentation of cellular apoptosis. Oxaliplatin uptake into MCF-7 cells after 1 h and 4 h of cellular exposure to various treatments. The platinum concentration was 10 µM and 100 nmol of siRNA was used in each experimental group. Cells were lyzed after treatment and the determination of intracelluar platinum content was conducted by ICP-MS. Experiments were performed in triplicate. Data are displayed as the mean value±standard deviation of the mean. $IC_{50}$ values were derived from three independent experiments each with four technical replicates per condition.
FIG. 19B is a bar graph showing the total number of Pt-DNA adducts (pg Pt/µg DNA) as assessed after 24 h of incubation with each treatment group, as defined in the description of FIG. 19A. DNA was isolated after cellular lysis and the content of DNA-bound Pt was determined by ICP-MS. Experiments were performed in triplicate. Data are displayed as the mean value±standard deviation of the mean. $IC_{50}$ values were derived from three independent experiments each with four technical replicates per condition.
Figure 19F:
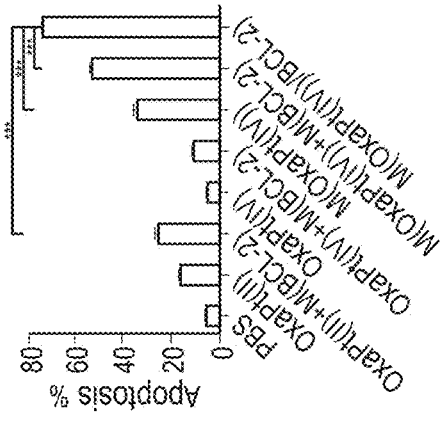
Figure 19B:
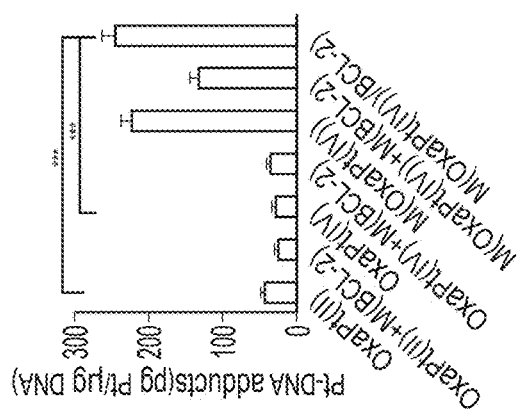
Figure 19E:
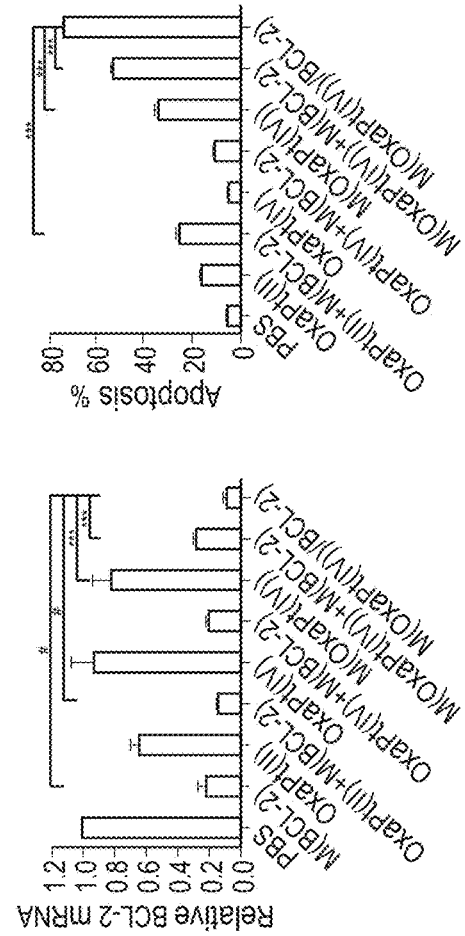
Figure 19A:
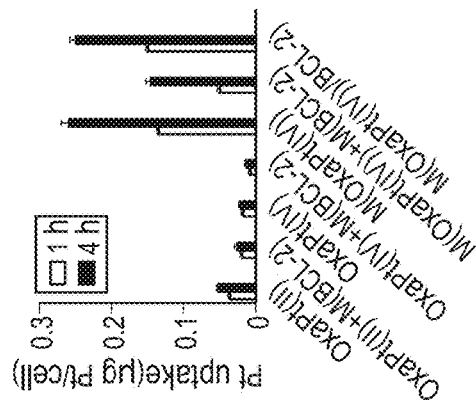

FIG. 19C is a plot of relative cell viability (as determined by the MTT cell viability assay, which was performed 48 h after incubation with each treatment group as defined in the description of FIG. 19A) as a function of platinum concentration (μM). Experiments were performed in triplicate. Data are displayed as the mean value±standard deviation of the mean. $IC_{50}$ values were derived from three independent experiments each with four technical replicates per condition. Only mean values are displayed. In all cases, significance is defined as * p<0.05, p<0.01, and * p<0.001.

Figure 19D:
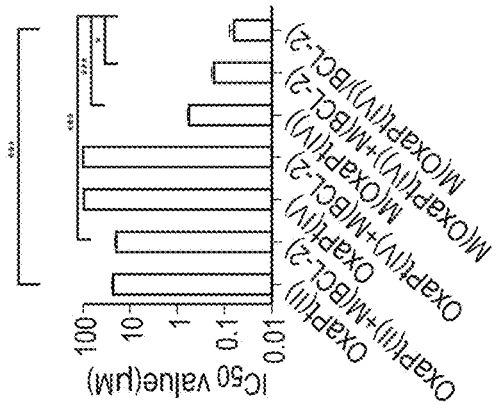

FIG. 19D is a bar graph showing $IC_{50}$ values (μM) for cellular toxicity as determined by the MTT cell viability assay, which was performed 48 h after incubation with each treatment group as defined in the description of FIG. 19A. Only mean values are displayed. In all cases, significance is defined as * p<0.05, p<0.01, and * p<0.001.

FIG. 19E is a bar graph showing relative BCL-2 mRNA levels, as determined by qRT-PCR conducted 48 h after treatment with each experimental combination as defined in the description of FIG. 19A. Experiments were performed in triplicate. Data are displayed as the mean value±standard deviation of the mean. $IC_{50}$ values were derived from three independent experiments each with four technical replicates per condition.

FIG. 19F is a bar graph showing total percentage of MCF-7 cells that underwent apoptosis as determine by flow cytometry after 36 h of treatment with various conditions. Equivalent platinum (10 uM) and siRNA concentration (100 nM) were used for each condition as defined in the description of FIG. 19A. 48 h after incubation, the fraction of MCF-7 cells undergoing apoptosis was detected by flow cytometry using the Annexin V-FITC Apoptosis Detection Kit I (BD Biosciences, San Jose, Calif.) and analyzed using WinMDI 2.9 software. Only mean values are displayed. In all cases, significance is defined as * p<0.05, p<0.01, and * p<0.001.

Figure 20:
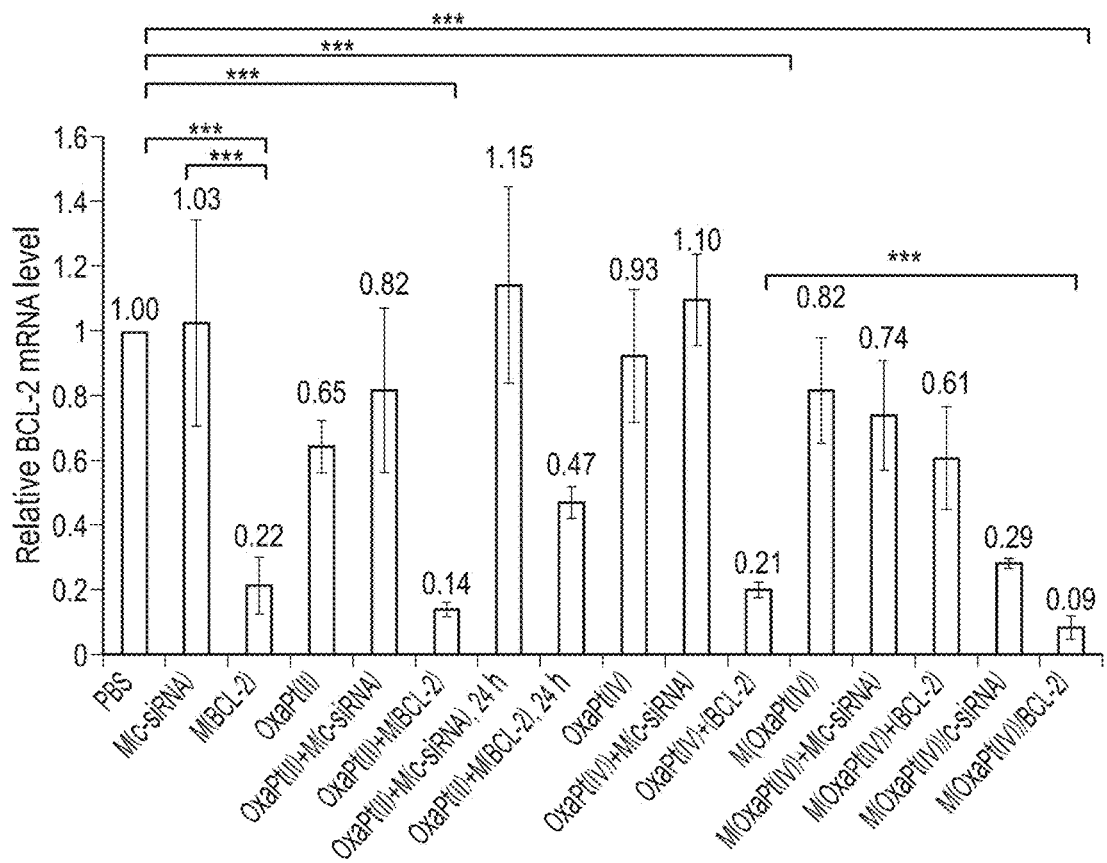

FIG. 20 is a bar graph showing relative BCL-2 mRNA levels after 48 h of treatment with various compositions. These data indicate the effectiveness of different strategies for combining Pt and BCL-2 siRNA to induce maximal BCL-2 RNAi. Various Pt species were administered to cells in 6-well plates at equal Pt concentrations (10 μM); 100 nM of either control (c-siRNA) or BCL-2 siRNA were added in each siRNA containing treatment. Two additional groups were compared in which OxaPt(II) was preincubated with either M(BCL-2) or M(c-siRNA) for 24 h at 37° C. prior to cellular addition. Cells were incubated with all treatment groups for 48 h and were then subject to RNA extraction followed by RT-qPCR to determine relative BCL-2 mRNA levels. Data are displayed as mean values±the standard deviation of the mean (n=3 replicates per condition). Significance is defined as ***p<0.001.

Figure 21A:
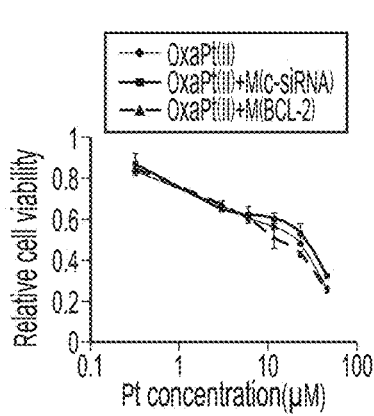

FIG. 21A is a plot of the relative in vitro viability of MCF-7 cells as a function of platinum concentration (μM). Cells were incubated with OxaPt(II) containing treatments, with and without micellar-complexed control (i.e. M(c-siRNA)) or BCL-2 siRNA (i.e. M(BCL-2)) for 72 h. Viability was measured using the MTT colorimetric assay.

Figure 21B:
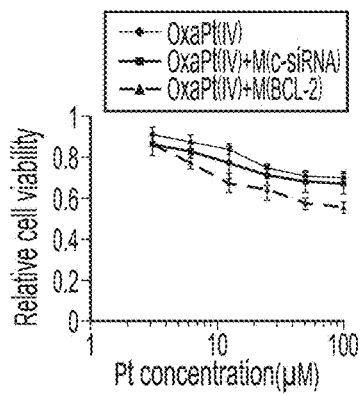

FIG. 21B is a plot of the relative in vitro viability of MCF-7 cells as a function of platinum concentration (μM). Cells were incubated with OxaPt(IV) containing treatments, with and without micellar-complexed control (i.e. M(c-siRNA)) or BCL-2 siRNA (i.e. M(BCL-2)) for 72 h. Viability was measured using the MTT colorimetric assay.

Figure 21C:
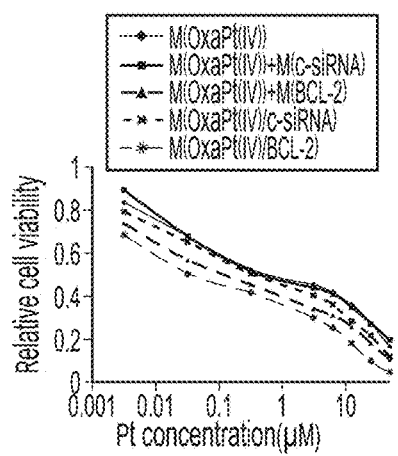

FIG. 21C is a plot of the relative in vitro viability of MCF-7 cells as a function of platinum concentration (μM). Cells were incubated with M(OxaPt(IV)) containing treatments, with and without micellar-complexed control (i.e. M(c-siRNA)) or BCL-2 siRNA (i.e. M(BCL-2)) for 72 h. Viability was measured using the MTT colorimetric assay.

Figure 22A:
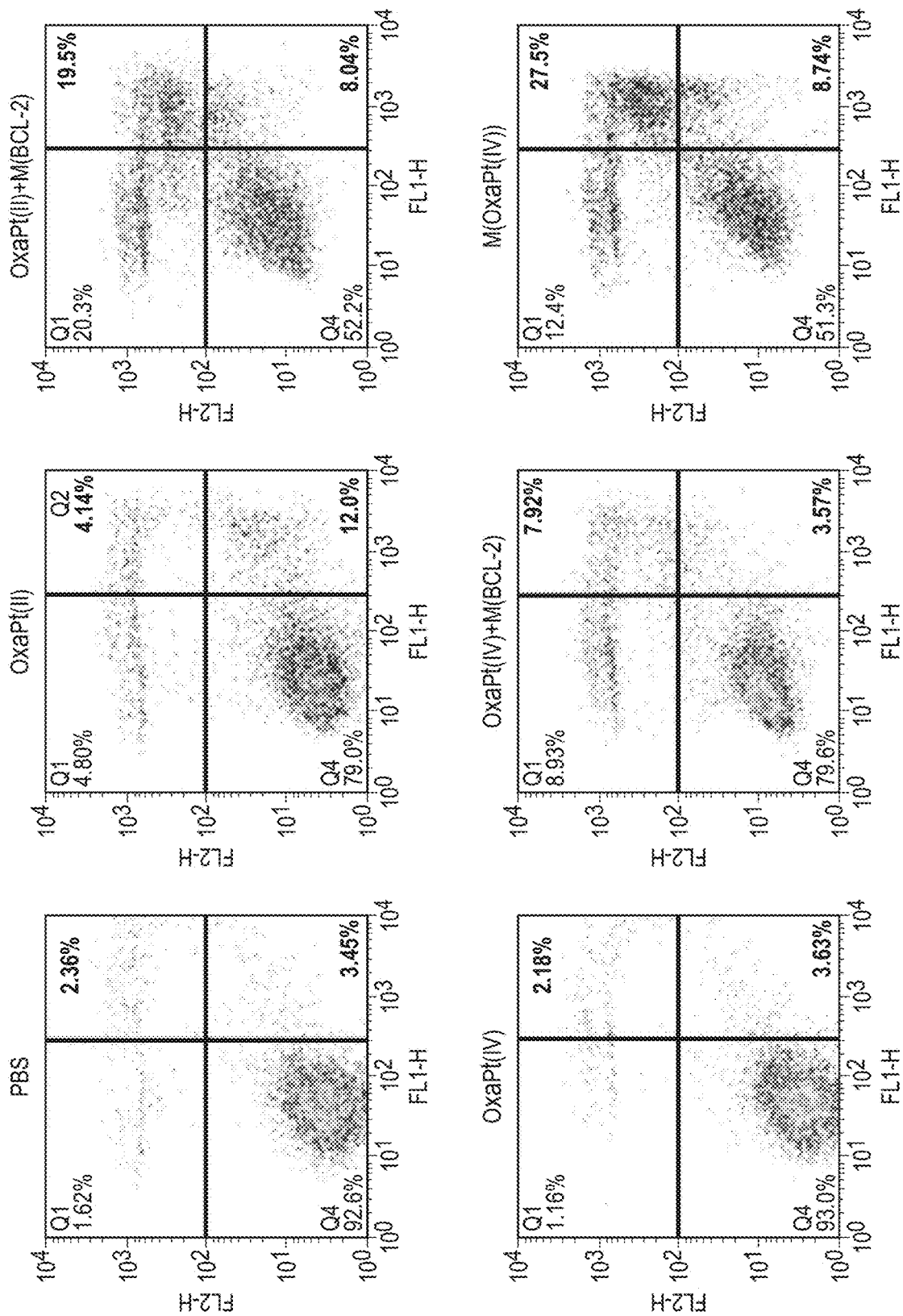

FIG. 22A is a series of plots showing the results of flow cytometry histograms (FL2-H vs. FL1-H). These data are a comparison of the effectiveness of different strategies for combining oxaliplatin species and BCL-2 siRNA to induce maximal cellular apoptosis. Oxaliplatin species were administered to MCF-7 cells in 6-well plates at equal Pt concentrations (10 μM); 100 nM of either micellar-complex c-siRNA or BCL-2 siRNA were added in each siRNA containing treatment. Apart from the various OxaPt(II) and OxaPt(IV) containing groups, as well as the single siRNA groups (i.e. M(c-siRNA) and M(BCL-2)), two additional groups were included in which OxaPt(II) was preincubated with either M(BCL-2) or M(c-siRNA) for 24 h at 37° C. prior to cellular addition. Cells were incubated with all treatment groups for 48 h and the cellular fractions undergoing apoptosis were detected by flow cytometry using the Annexin V-FITC Apoptosis Detection Kit I; the results were analyzed using WinMDI 2.9 software. Flow cytometry histograms of cells treated with different combinations of oxaliplatin species and/or BCL-2 siRNA; early apoptotic events are captured in the upper right panel of each graph while late events are found in the lower right panel.

Figure 22B:
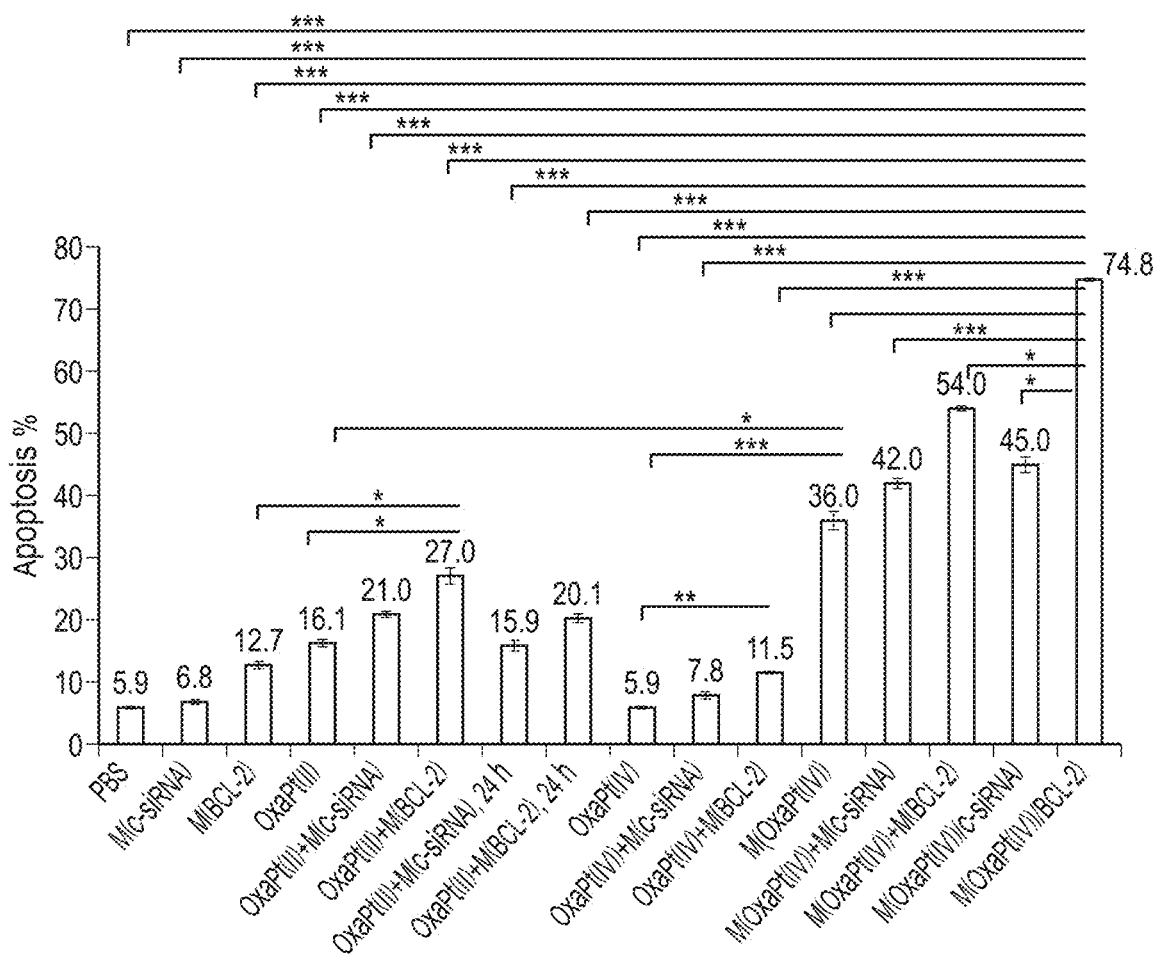

FIG. 22B is a bar graph of the total percentages of MCF-7 cells undergoing apoptosis after 48 h of treatment with each experimental group as defined in the description of FIG. 22A. Data are displayed as mean values±the standard deviation of the mean (n=3 technical replicates). Significance is defined as *p<0.05,  p<0.01, * p<0.001.

Figure 23A:
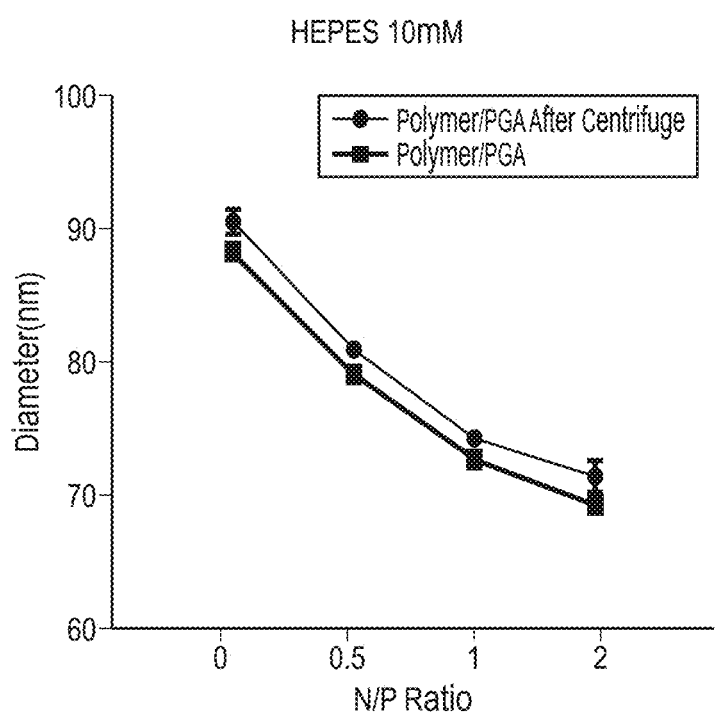

FIG. 23A is a plot of coated micelle diameter (nm) as a function of N/P ratio. Coating cationically charged PEO-b-PBzLL-PASP (i.e. "polymer") based micelles with anionically charged PEG-PGA in 10 mM HEPES (pH 7.4) with different ratios of negatively charged PEO-b-PGA ("N") to positively charged PEO-b-PBzLL-PASP ("P") affects the particle diameter.

Figure 23B:
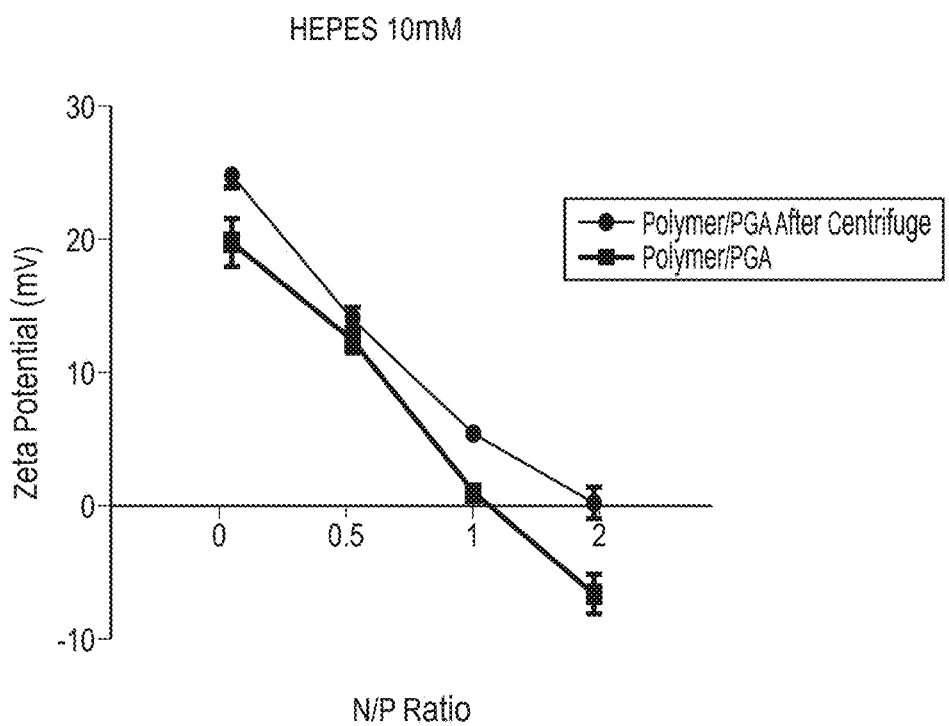

FIG. 23B is a plot of zeta potential (mV) as a function of N/P ratio. Coating cationically charged PEO-b-PBzLL-PASP (i.e. "polymer") based micelles with anionically charged PEG-PGA in 10 mM HEPES (pH 7.4) with different ratios of negatively charged PEO-b-PGA ("N") to positively charged PEO-b-PBzLL-PASP ("P") affects the overall charge (zeta potential) in solution.

Figure 24A:
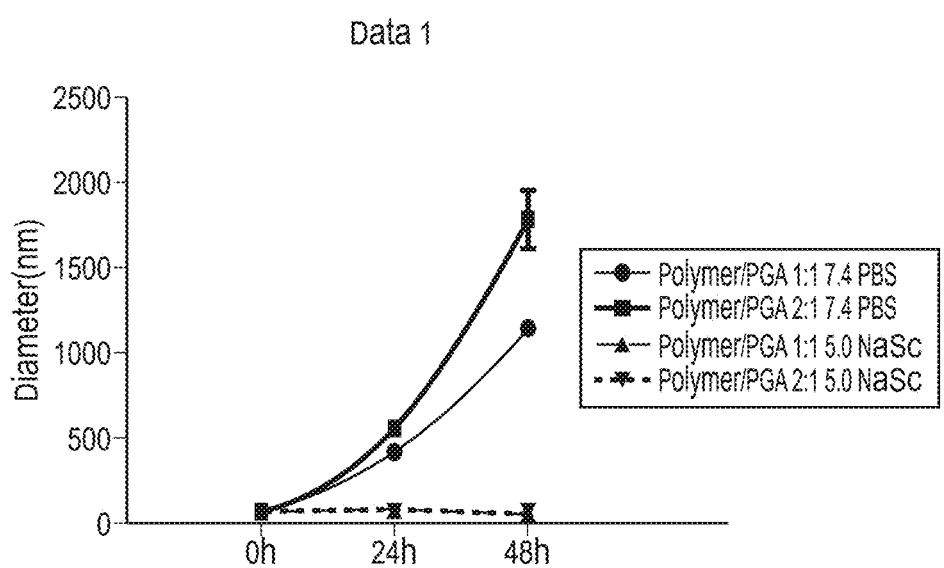

FIG. 24A is a plot of coated micelle diameter (nm) as a function of time in different buffer solutions.

Figure 24B:
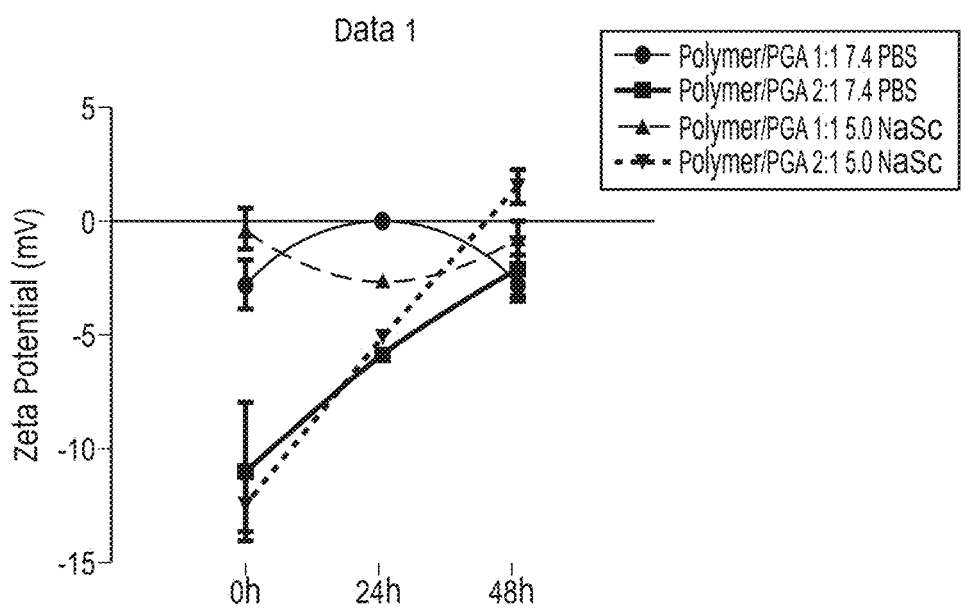

FIG. 24B is a plot of zeta potential (mV) as a function of time for coated micelles in different buffer solutions.

Figure 25A:
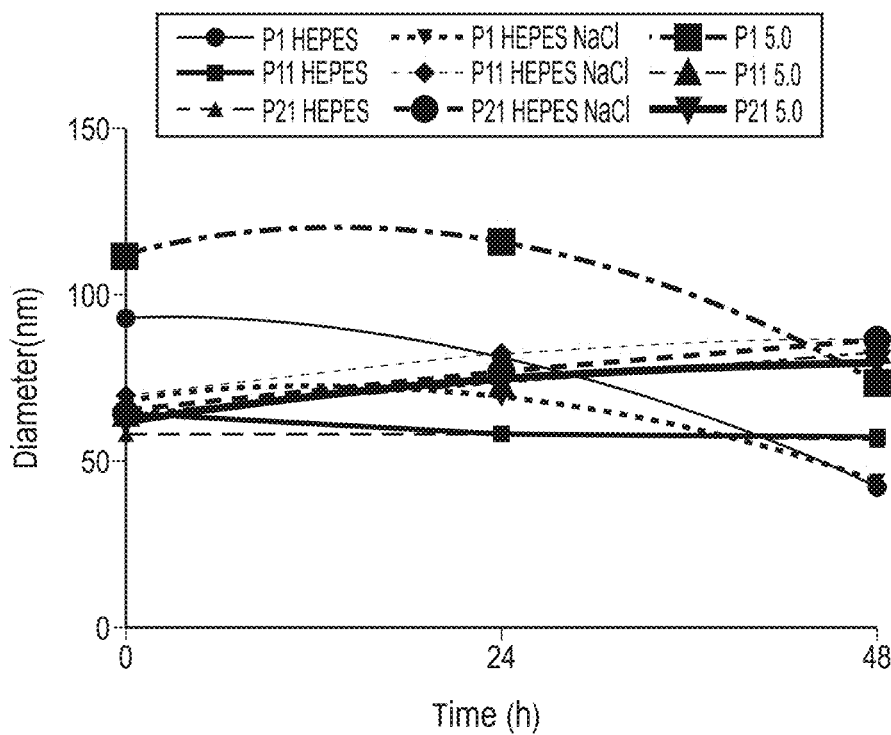

FIG. 25A is a plot of coated micelle diameter (nm) as a function of time in different buffer solutions after centrifugation to remove excess PEO-b-PGA.

Figure 25B:
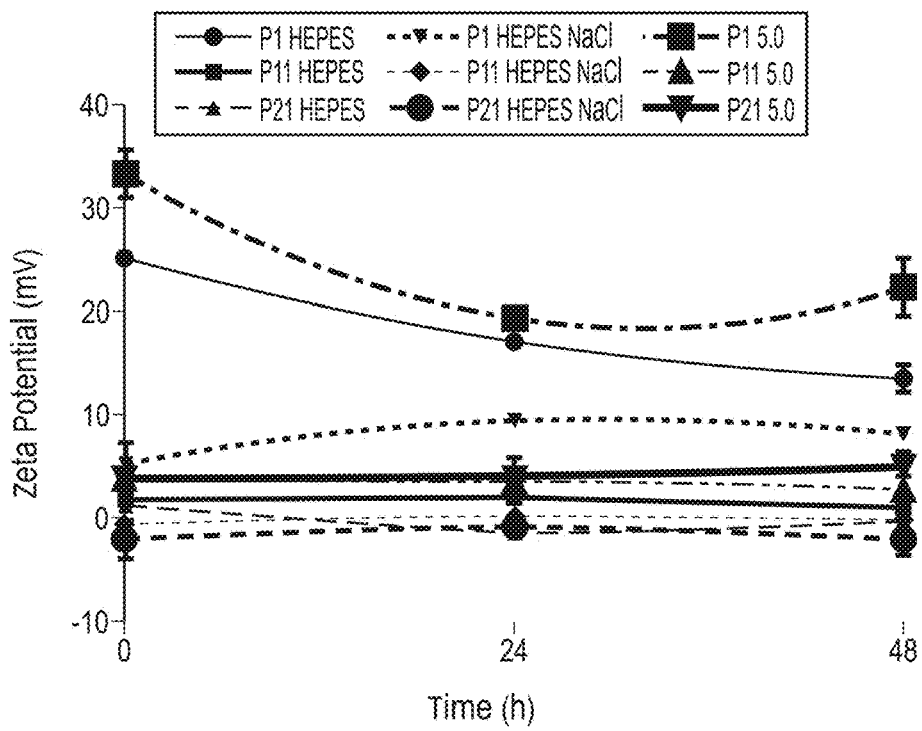

FIG. 25B is a plot of zeta potential (mV) as a function of time for coated micelles in different buffer solutions after centrifugation to remove excess PEO-b-PGA.

Figure 26A:
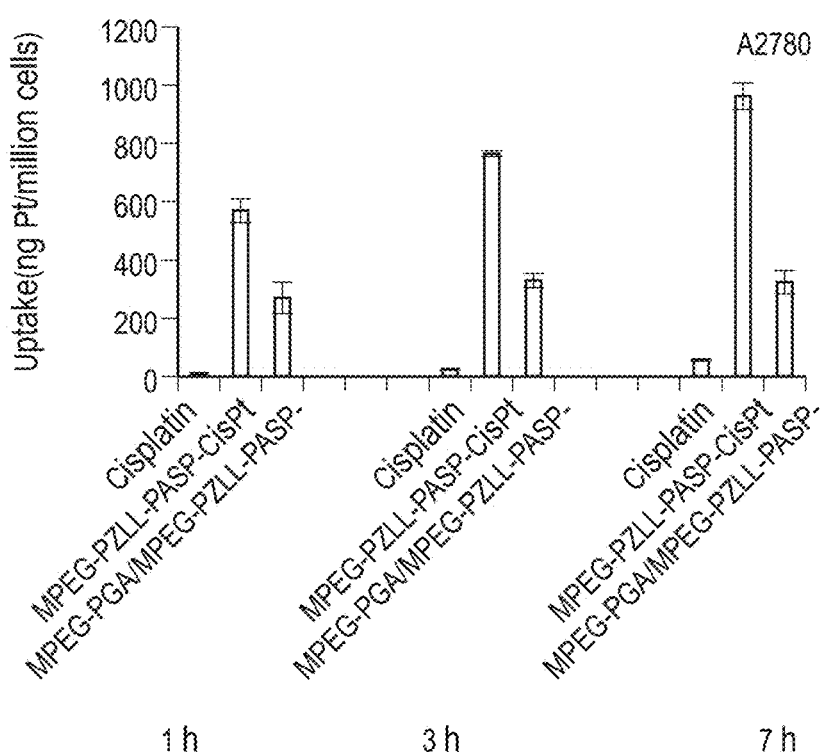

FIG. 26A is a bar graph indicating uptake (ng Pt/million cells) for coated and uncoated polymer micelles. A2780 cells were plated in 6-well plate at 1 million cells/well and uptake of coated and uncoated polymeric micelles conjugated to cisplatin (IV) were monitored as a function of time (1 h, 3 h, or 7 h) after cellular addition. All cells were treated at a final concentration Pt=40 μM.

Figure 26B:
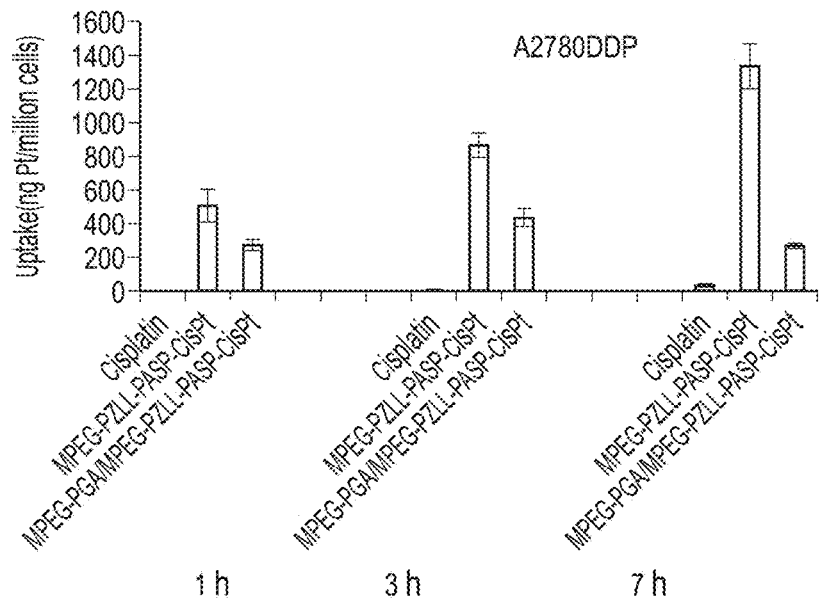

FIG. 26B is a bar graph indicating uptake (ng Pt/million cells) for coated and uncoated polymer micelles. A2780DDP cells were plated in 6-well plate at 1 million cells/well and uptake of coated and uncoated polymeric micelles conjugated to cisplatin (IV) were monitored as a function of time (1 h, 3 h, or 7 h) after cellular addition. All cells were treated at a final concentration Pt=40 µM.

Figure 27:
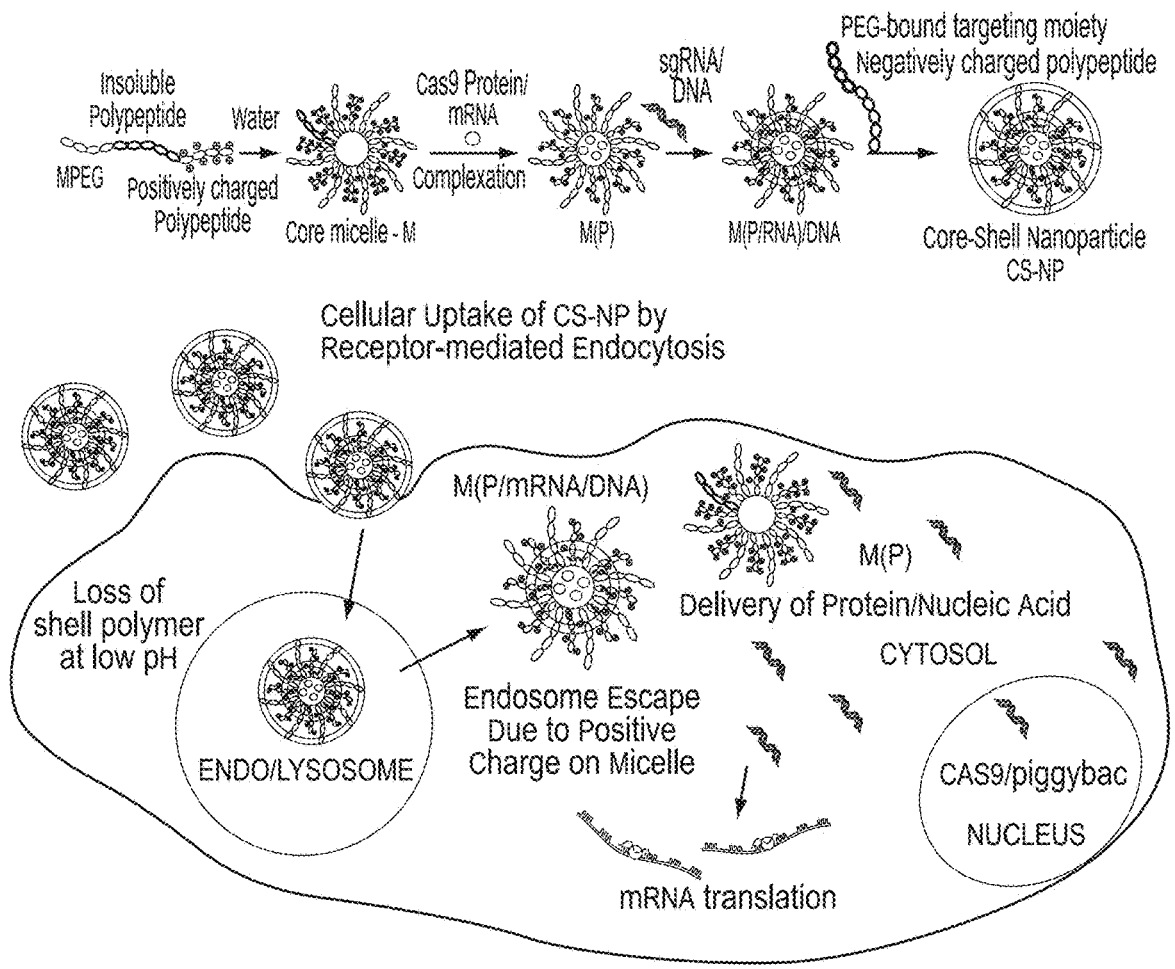

FIG. 27 is a schematic representation of delivery of CRISPR/Cas9 gene editing tools to a cell.

FIG. 28A is a schematic representation of the chemical structure of PEO-PZLL-PASP. The particle consists of three components: (i) an outer PEG surface, (ii) a PASP layer that plays two roles: (a) acting as a polymer matrix loaded with nonpolar drugs and (b) protecting and promoting siRNA molecule retention inside the NP core and controlling drug release, and (iii) an aqueous inner core containing Cas9 mRNA and gRNA.

FIG. 28B shows the chemical structure of the hydrophobic platinum(IV) and the chemistry by which the active drug cisplatin is released after reduction in the cell.

FIG. 28C is a bar graph showing the size distribution of the NPs containing Cas9 mRNA and gRNA determined by dynamic light scattering.

FIG. 28D is a bar graph showing the zeta potential distribution of the NPs containing Cas9 mRNA and gRNA determined by dynamic light scattering.

FIG. 28E is a series of representative transmission EM images of the NPs.

FIG. 28F is a bar graph showing heparin displacement assay of siRNA after complexation with copolymers at an N/P ratio of 0 to 16.

Figure 28H:
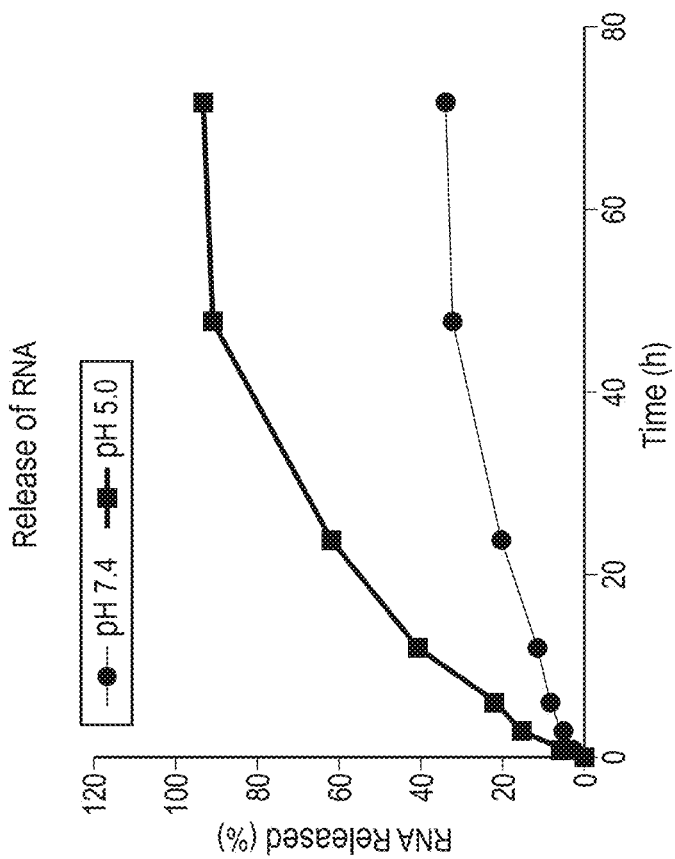
Figure 28G:
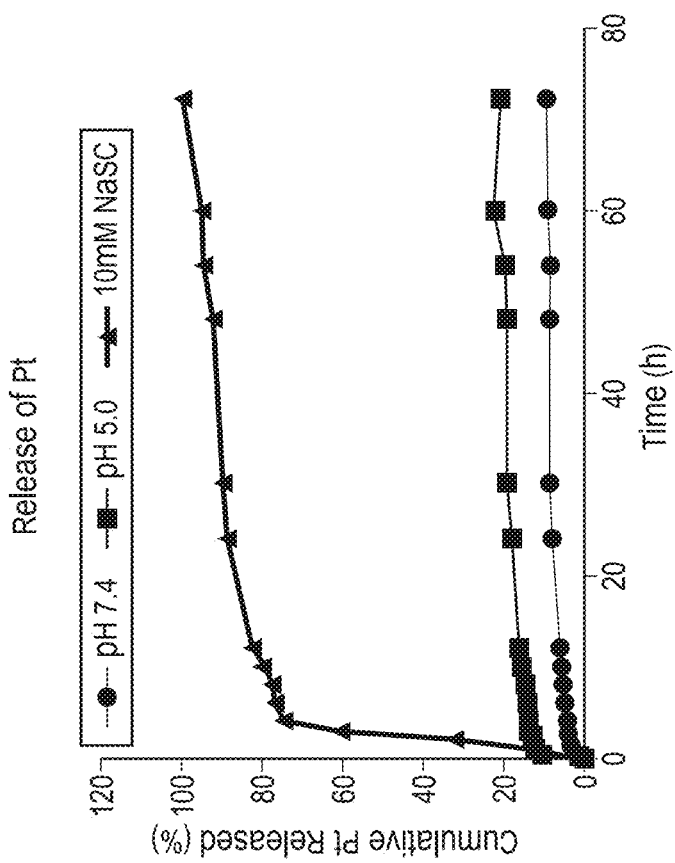

FIG. 28G is a plot of Pt release profiles (%) of NPs at pH 7.4 and 5.0.

FIG. 28H is a plot of RNA release profiles (%) of NPs at pH 7.4 and 5.0.

Figure 29A:
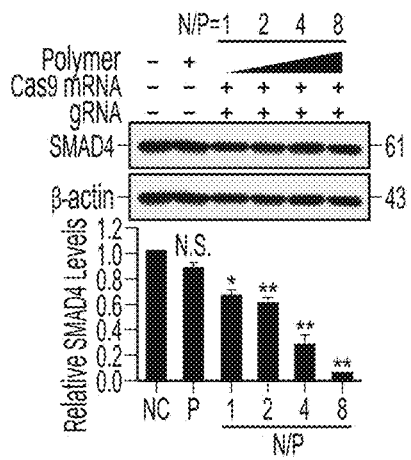

FIG. 29A summarizes data showing the silencing efficacy of NPs at N/P ratio from 1 to 8. SMAD4 expression were detected by western blotting 3 days post transfection.

Figure 29B:
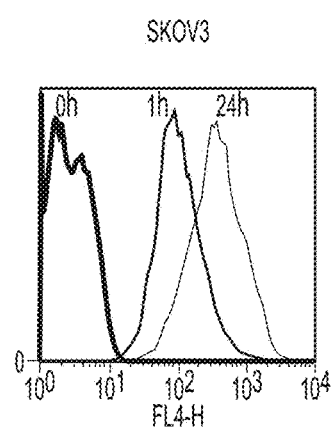

FIG. 29B is a plot of the uptake of RNA. Cy5-labeled RNA were incorporated in NPs and transfected to SKOV3 cells at N/P ration 8. Flow cytometry were used to analyze the uptake of RNAs.

Figure 29C:
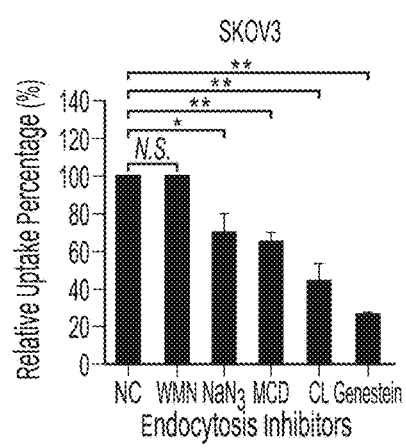

FIG. 29C is a bar graph showing uptake into SKOV3 cells. Cells were treated with various endocytosis inhibitors for 2 hours and then transfected with NPs containing cy5-labeled RNAs for 2 hours. WMN, wortmannin; $NaN_3$, sodium azide; MCD, methyl-beta-cyclodextrin; CL. Uptake percentages normalized as to positive control. Means±SEM of a representative experiment (n=3) performed in triplicates are shown.

Figure 29D:
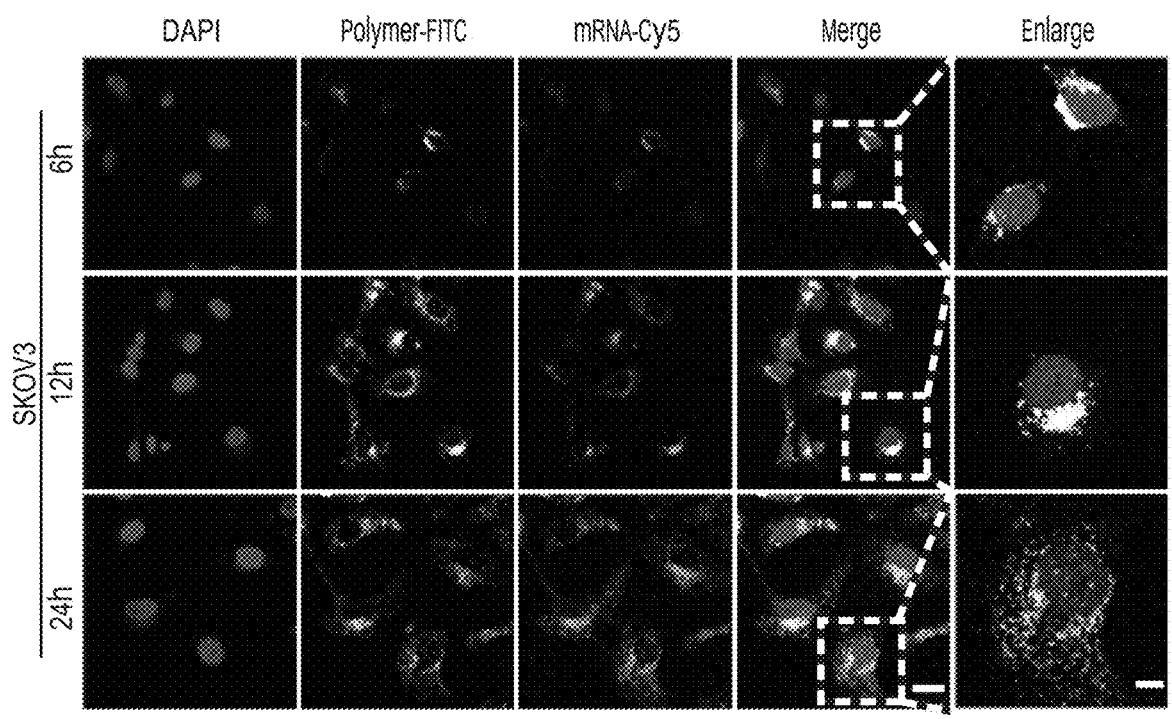

FIG. 29D is a series of confocal laser scanning micrographs of SKOV3 cells incubated with FITC-labeled NPs loading with cy5-labeled RNA for 6 hours, 12 hours and 24 hours. Blue: DAPI; Green: FITC; Red: Cy5. Left bar: 30 µm. Right bar: 10 µm.

Figure 30A:
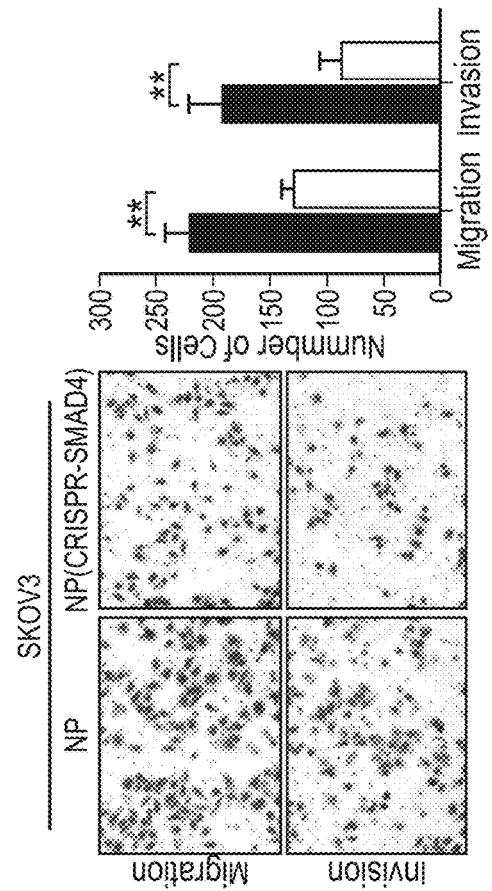

FIG. 30A summarizes data showing NPs containing Cas9 mRNA and gRNA targeting SMAD4 decrease SMAD4 expression 3 days after transfection in SKOV3 and A2780 cells. Western blotting were used to detect the expression of SMAD4.

Figure 30B:
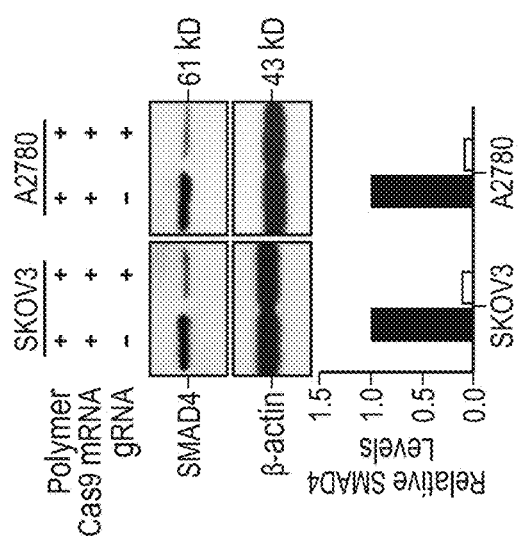

FIG. 30B summarizes data showing silencing SMAD4 using NPs containing CRISPR/Cas9 system decrease migration and invasion in SKOV3 cells.

Figure 30D:
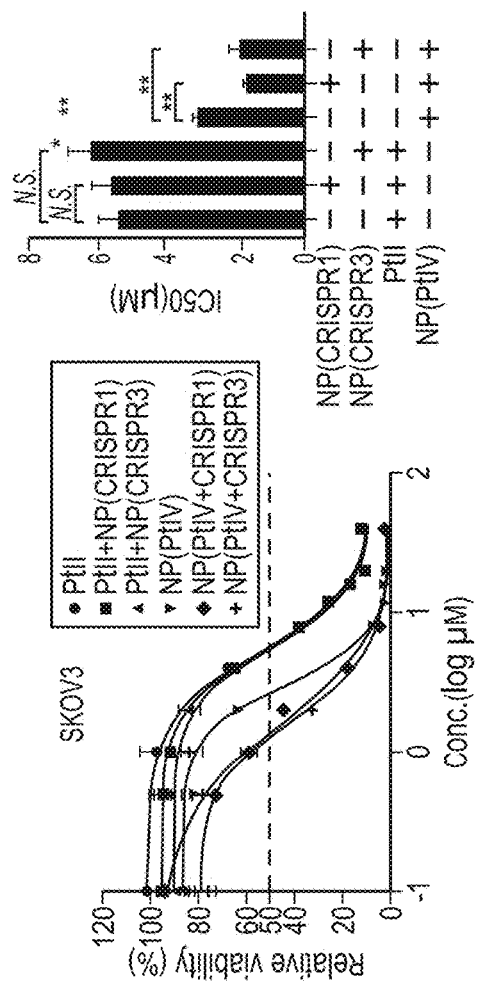
Figure 30C:
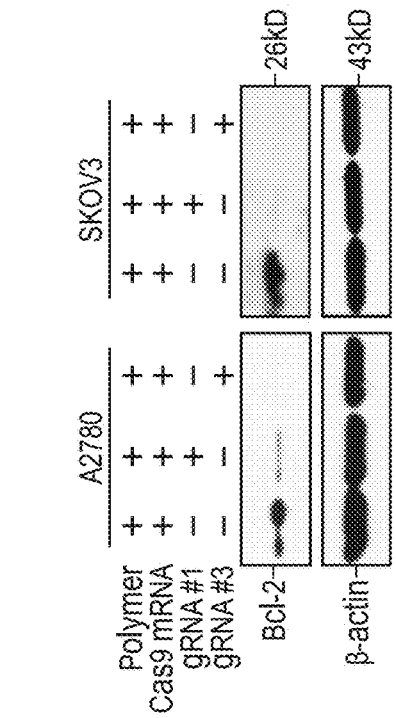

FIG. 30C summarizes data showing NPs containing Cas9 mRNA and gRNA targeting BCL-2 decrease its expression 3 days after transfection in SKOV3 and A2780 cells. Western blotting were used to detect the expression of BCL-2.

FIG. 30D summarizes data showing: Left—Cell viability after being treated with escalating dosage of cisplatin or NP (Cisplatin IV) with or without NP(CRISPR1) or NP(CRISPR3); Right—$IC_{50}$ of cisplatin.

Figure 30E:
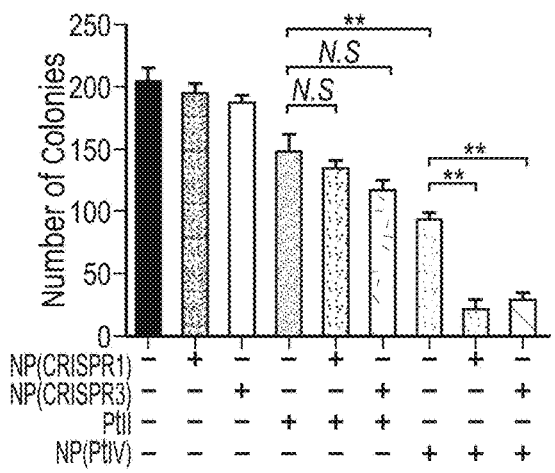

FIG. 30E is a bar graph showing colony formation assay of SKOV3 cells treated with cisplatin or NP (Cisplatin IV) with or without NP(CRISPR1) or NP(CRISPR3) for 10 days. Platinum concentration: 1 uM.

Figure 30F:
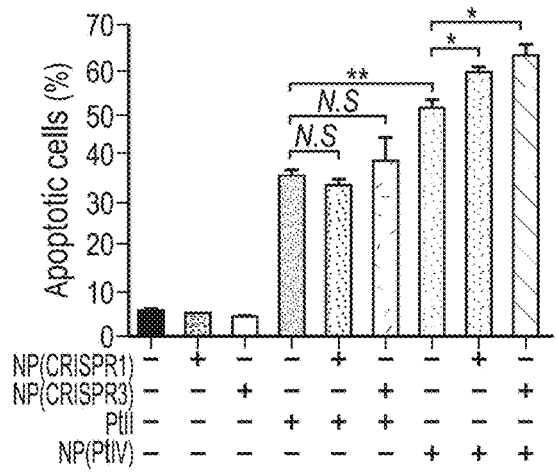

FIG. 30F is a bar graph showing apoptosis assay of SKOV3 cells treated with cisplatin or NP (Cisplatin IV) with or without NP(CRISPR1) or NP(CRISPR3) for 72 hours. Platinum concentration: 10 uM.

Figure 30G:
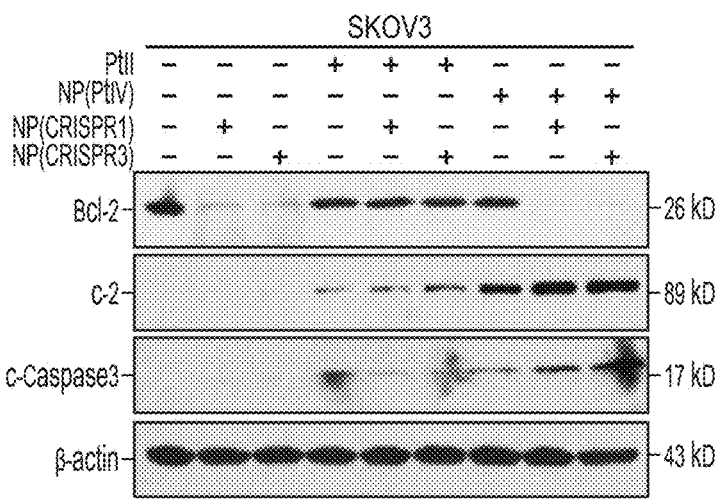

FIG. 30G is a western blotting assay of BCL-2, cleaved-PARP1, and cleaved-CASEPASE3 in SKOV3 cells treated with cisplatin or NP (Cisplatin IV) with or without NP(CRISPR1) or NP(CRISPR3) for 72 hours. Platinum concentration: 10 uM. Means±SEM of a representative experiment (n=3) performed in triplicates are shown.

FIG. 31A is an illustration depicting core-shell nanoparticles comprised of PEO-b-PCL polymer (yellow), the organic NIR-I fluorophore DiR (red), and LNPs (blue).

FIG. 31B is a cryo-TEM image of core-shell nanoparticles (DiR-Er/PEO-PCL) in aqueous suspension (scale bar=100 nm).

FIG. 31C are normalized fluorescence spectra of intrinsic reports (LUC and RFP) as well as emissive components of various core-shell nanoparticle formulations. 980-nm laser-excitation of DiR-Er/PEO-PCL resulted in UC (UC-Er; red) and DC emission (DC-Er; orange) from core NaYF4:Yb, Er-based LNPs; 700-nm irradiation of the same particles resulted in DC emission from DiR (DiR; navy blue) in their PCL shells. 980-nm irradiation of DiR-Er,Tm/PEO-PCL resulted in UC (UC-Er, Tm; cyan) from core NaYF4:Yb, Er,Tm-based LNPs; similar excitation of DiR-Ho/Folate-PEO-PCL resulted in both UC and DC emission (DC-Ho; magenta) from core NaYF4:Yb,Ho-based LNPs.

FIG. 31D is a plot showing measurements of the photostability of various emissive components of core-shell nanoparticles under continuous irradiation. Note, the same excitation energies were utilized as in FIG. 31C; and, emission was detected using various excitation and emission filters. The photostability of DiR in THF (DiR in THF; black) was included for comparative purposes.

Figure 32A:
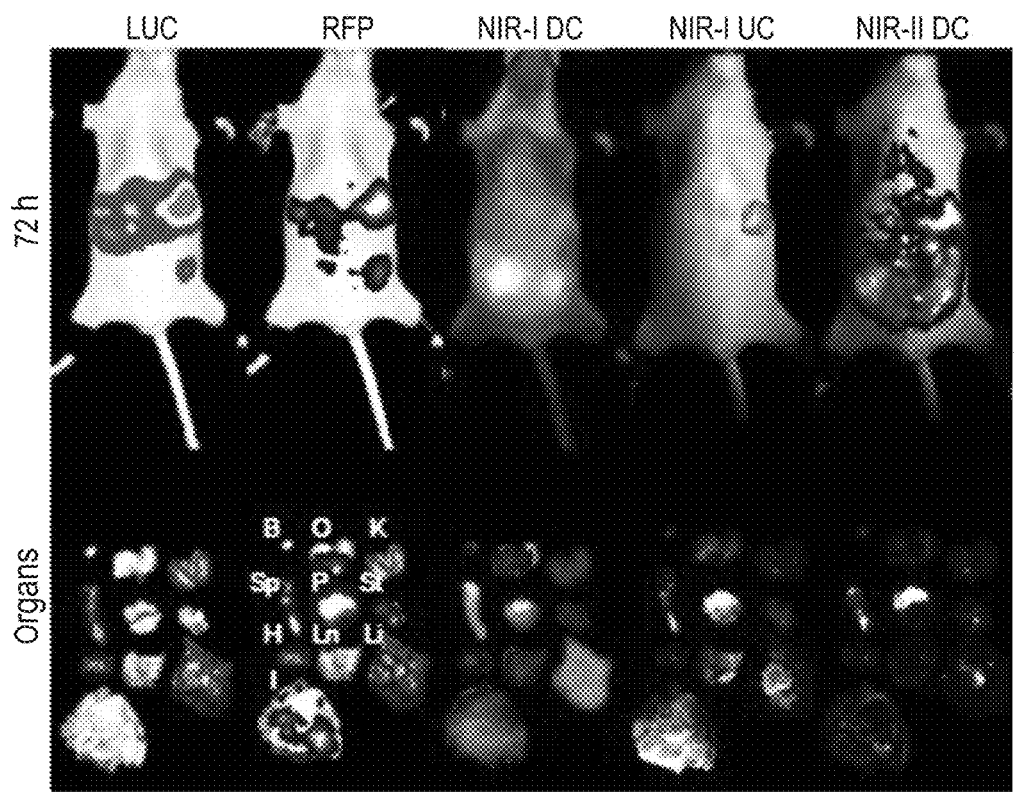

FIG. 32A are images taken of a representative mouse at two-weeks after implantation of $LUC^+/RFP^+$ OVCAR-8 ovarian cancer cells and 72 h after IP injection of untargeted core-shell nanoparticles (DiR-Er,Tm/PEO-PCL). Upper Row: in vivo images of intrinsic reporters (LUC and RFP) as well as various emissive components of core-shell nanoparticles (DiR and LNPs). LUC, RPF and NIR-I DC (DiR) signals were detected using an IVIS imaging system; NIR-I UC (UC-Tm, Er) and NIR-II DC (DC-Er) emission from core LNPs were visualized using a custom designed imaging instrument (Materials and Methods). Bottom Row: ex vivo images were obtained after animal sacrifice and corresponded to the detection of the same reporters in excised organs, including (from left to right and from top to bottom) the bladder (B), ovaries (O), kidneys (K), spleen (Sp), pancreas (P), stomach (St), heart (H), lung (Ln), liver (Li) and intestines (I) of the animal.

Figure 32B:
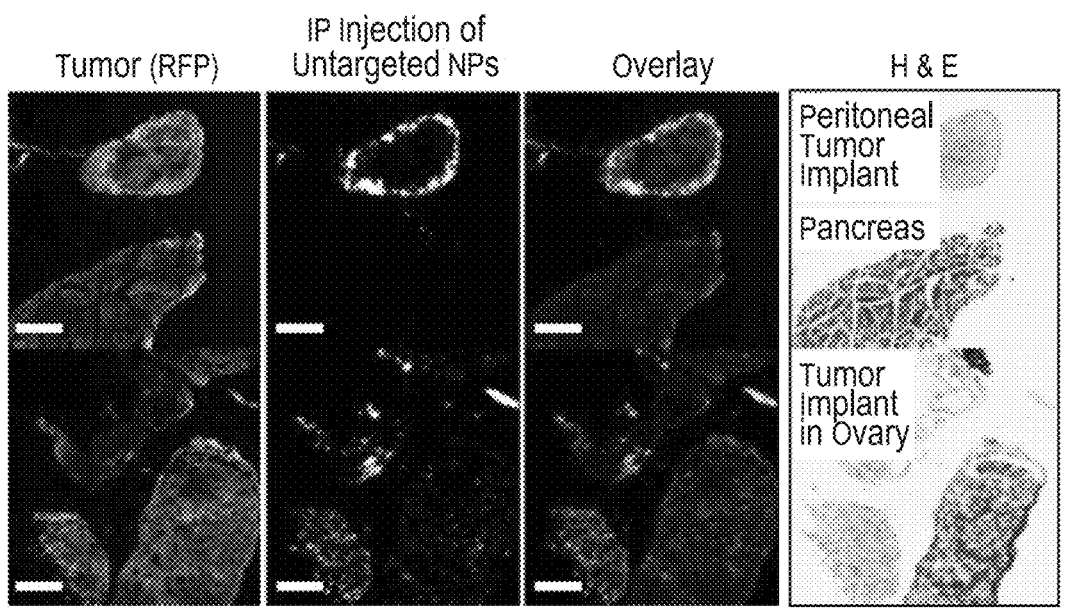

FIG. 32B shows confocal microscope images of tissue sections obtained from excised organs of the same animal. Tumors were identified by RFP fluorescence while all tissues exhibited green auto-fluorescence. Untargeted nanoparticles (NPs) were imaged by 980-nm multi-photon excitation and by detection of their visible UC emission. H&E staining was also performed to identify tumor implants vs. normal tissue in each organ. Scale bar=300 µm.

FIG. 33A is a plot showing the comparison of the sensitivity of various intrinsic and extrinsic reporters to detect peritoneal tumor implants. The numbers of tumors detected using different reporters were enumerated from in vivo vs. ex vivo images taken at two-weeks post-implantation of LUC$^+$/RFP$^+$ OVCAR-8 cells in nude mice (n=4 mice per group).

FIG. 33B is a plot showing the comparison of the sensitivity of various intrinsic and extrinsic reporters to detect peritoneal tumor implants. The numbers of tumors detected using different reporters were enumerated from in vivo vs. ex vivo images taken at 1 week post-implantation of LUC$^+$/RFP$^+$ OVCAR-8 cells in nude mice (n=4 mice per group).

FIG. 33C shows a determination of the maximum depth of tissue penetration for various reporters. A tumor deposit excised from the pancreas of the mouse in FIG. 32A was immersed at different depths under polymer phantoms that mimicked the optical properties of the human breast. Emissive signals emanating from the phantoms were imaged utilizing analogous techniques to those employed for in vivo imaging; the maximum depth of emission for a reporter was determined as the thickness of the overlying phantom at which its signal was no longer detectable. Note, NIR-I DC emission from DIR as well as NIR-I UC (UC-Er, Tm) and NIR-II DC emission (DC-Er) from the core-shell nanoparticles (DiR-Er,Tm/PEOPCL) were independently monitored.

FIG. 34A is a flow cytometry histogram demonstrating FR expression on the surface of LUC$^+$/RFP$^+$ OVCAR-8 cells, using FITC-labeled mouse anti-human FR antibody (green) and several controls: no antibody (Ab) (red), no primary Ab (blue) and anti-rabbit IgG (orange).

FIG. 34B is a plot of relative uptake of untargeted and FR-targeted nanoparticles (NPs) as determined by flow cytometric analyses of LUC$^+$/RFP$^{neg}$ OVCAR-8 cells over time. Untargeted (DiL/PEO-PCL) and FR-targeted NPs (DiL/Folate-PEO-PCL) were incubated with aliquots of OVCAR-8 cells for different time periods: 0, 0.5, 1, 2, 4, 6, 12, 16, and 24 h. Cells were then trypsinized, fixed, and flowed to quantify the relative levels of DiL ($\lambda_{em}$=488 nm/$\lambda_{ex}$=585 nm) emanating from populations of intracellular nanoparticles. Note, a statistically significant increase in cellular uptake was seen for FR-targeted as compared to untargeted NPs at time points longer than 1 h (p value <0.01).

FIG. 34C are representative flow cytometry histograms depicting differences in the uptake of untargeted (DiL/PEO-PCL) and FR-targeted NPs (DiL/Folate-PEO-PCL) after 6 h of incubation as compared to those of control (untreated) cells.

FIG. 34D are fluorescence images of LUC$^+$/RFP$^+$ OVCAR-8 cells taken after 6 h of incubation with untargeted (Er/PEO-PCL) and FR-targeted NPs (Er/Folate-PEO-PCL). Multiphoton confocal microscopy was used to image RFP (red) signals emanating from OVCAR-8 cells as well as UC-Er emission from core LNPs (green). Scale bar=50 µm.

Figure 35A:
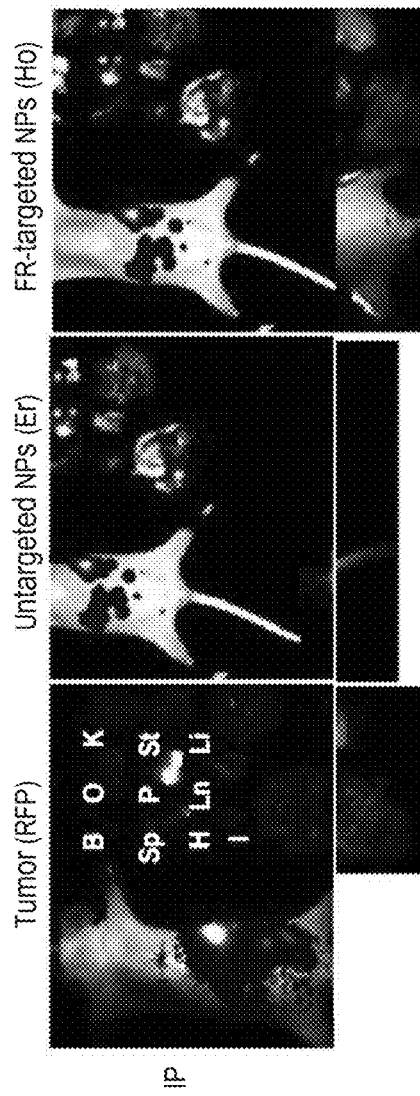

FIG. 35A shows representative images of two different mice taken at 72 h after simultaneous administration of both nanoparticles via either IP (upper row—mouse 1) or IV injection (lower row—mouse 2), detecting the intrinsic reporter RFP as well NIR-II DC emission from core LNPs in untargeted (Er) and FR-targeted (Ho) nanoparticles (NPs). Fluorescence intensities for each reporter were also measured in all excised organs immediately after in vivo imaging, including (from left to right and top to bottom) the bladder (B), heart (H), intensities (I), kidneys (K), liver (Li), lungs (Lu), ovaries (O), pancreas (P), spleen (Sp) and stomach (St) of 4 separate mice for each route of administration.

Figure 35D:
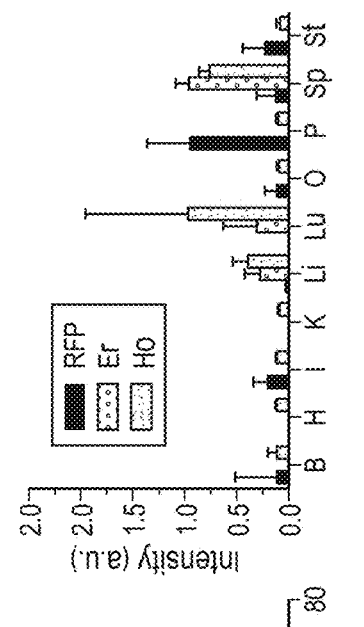
Figure 35C:
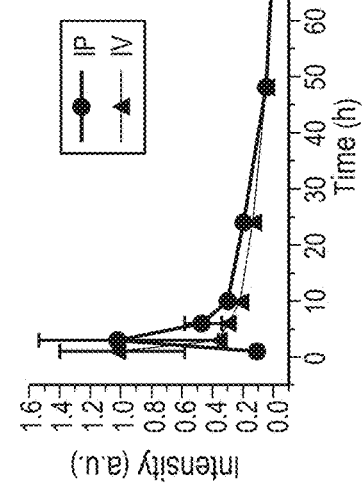
Figure 35B:
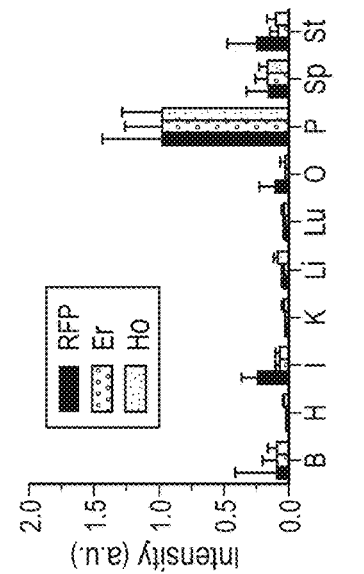

FIG. 35B is a bar graph showing the relative distribution of emissive signals obtained via ex vivo imaging of intrinsic (RFP) and extrinsic reporters (Er and Ho) in major organs at 72 h post IP-administration of core-shell nanoparticles. For each reporter, the fluorescence intensities from all organs were normalized to the value obtained from the organ with the highest fluorescence intensity (pancreas) and are reported as the mean+SD (n=4 mice).

FIG. 35C is a plot showing the pharmacokinetic analyses of core-shell nanoparticles in blood after IP vs. IV administration to tumor-bearing mice.

FIG. 35D is a bar graph showing the relative distribution of emissive signals obtained via ex vivo imaging of intrinsic and extrinsic reporters in major organs at 72 h after IV administration of core-shell nanoparticles to tumor-bearing mice (n=4 animals). In vivo imaging commenced and organs were processed for ex vivo analysis in a fashion analogous to that described in FIG. 5B (vide supra).

Figure 35F:
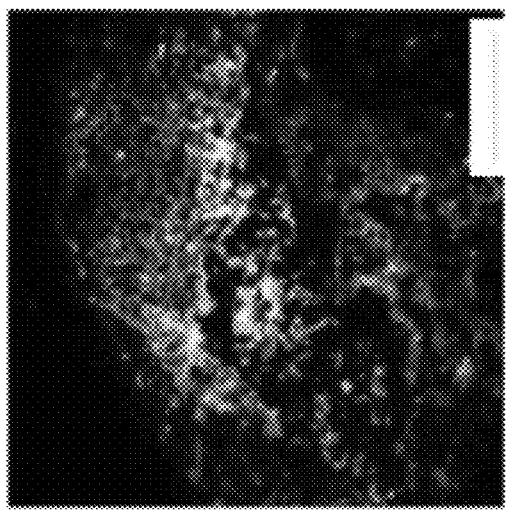
Figure 35G:
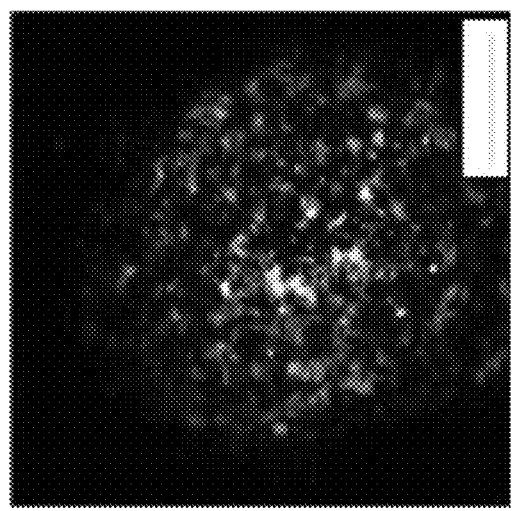
Figure 35E:
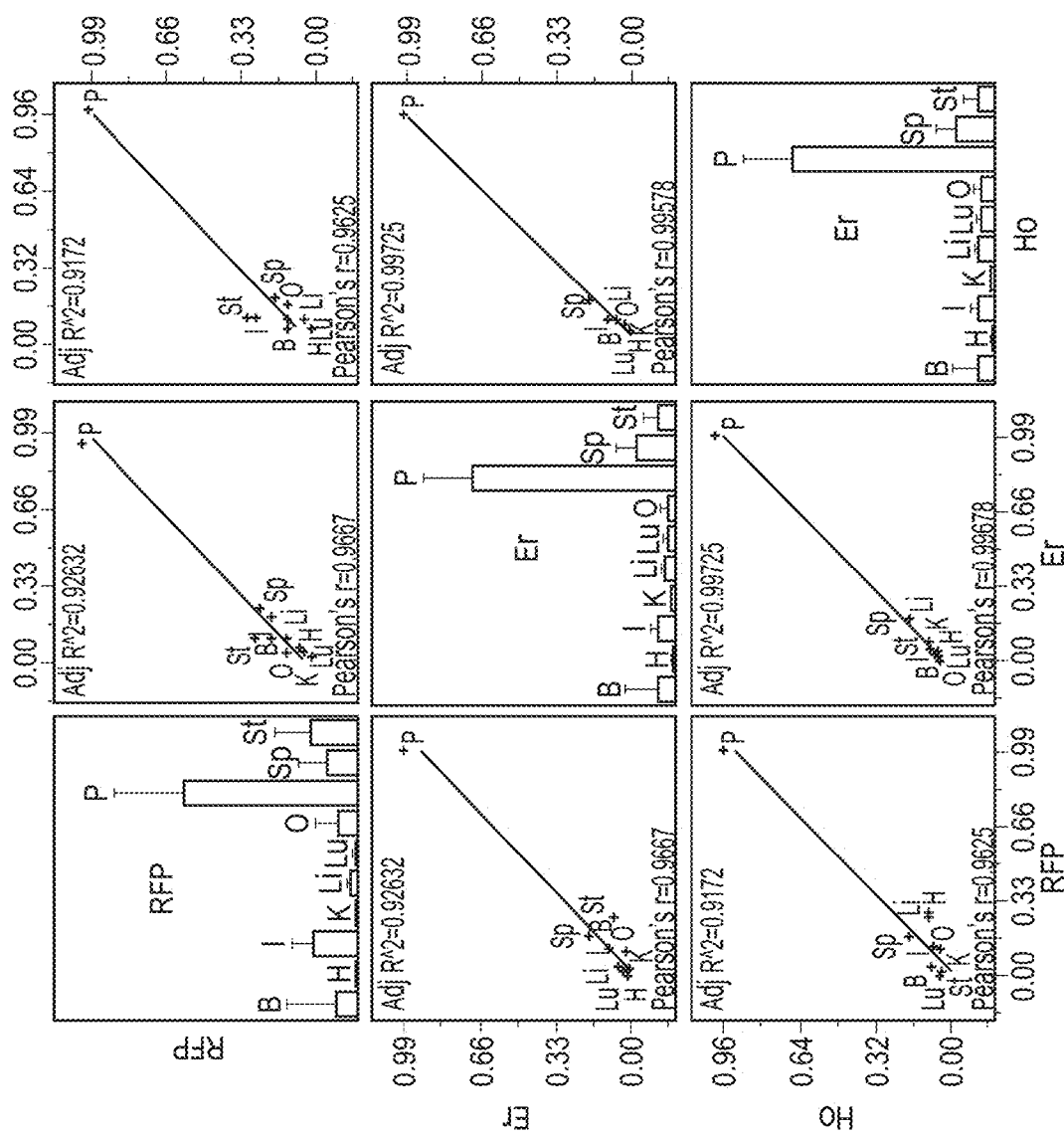

FIG. 35E is a correlation matrix of the relative in vivo distribution of RFP, Er, and Ho emissive signals as determined via ex vivo imaging of excised organs at 72 h after simultaneous IP administration of untargeted (Er) and FR-targeted core-shell nanoparticles (Ho) to tumor-bearing mice (n=4 animals). Each diagonal graph shows the distribution of fluorescence signals for a given reporter and correlates to the values shown in FIG. 35B. Each off-diagonal graph depicts the correlation for a pair of fluorescent reporters with a linear-fit red line, a value for the Pearson's correlation coefficient (r), and an adjusted $R^2$ value.

FIG. 35F is a confocal microscopic image of immunostained untargeted (Er/PEO-PCL) nanoparticles showing intratumoral distribution (blue) with respect to tumor cells (red) and macrophages (green). Scale bar=300 µm.

FIG. 35G is a confocal microscopic image of immunostained FR-targeted nanoparticles (Er/Folate-PEO-PCL) showing intratumoral distribution (blue) with respect to tumor cells (red) and macrophages (green). Scale bar=300 µm.

Figure 36B:
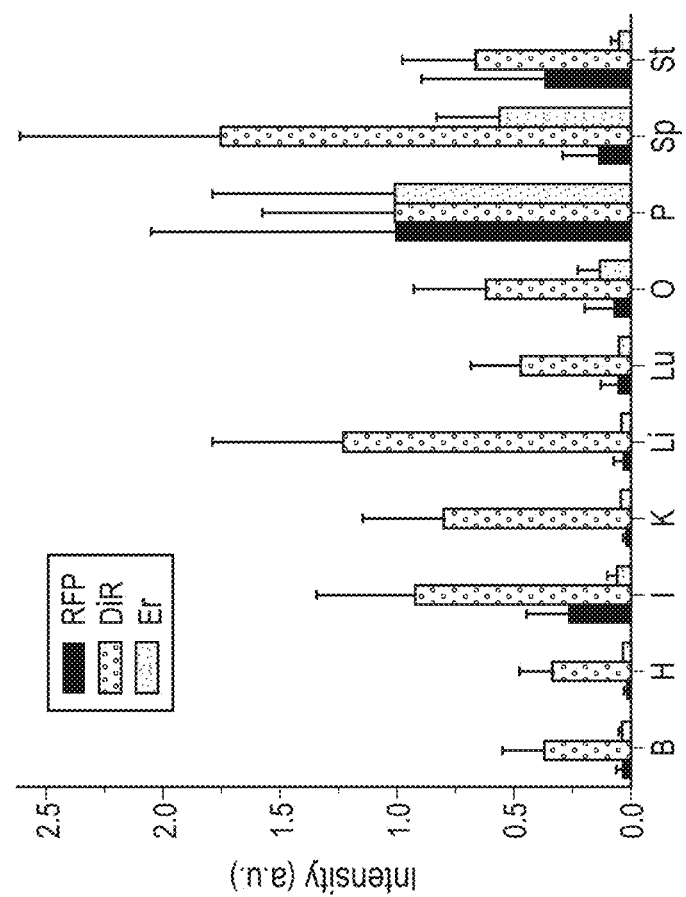
Figure 36A:
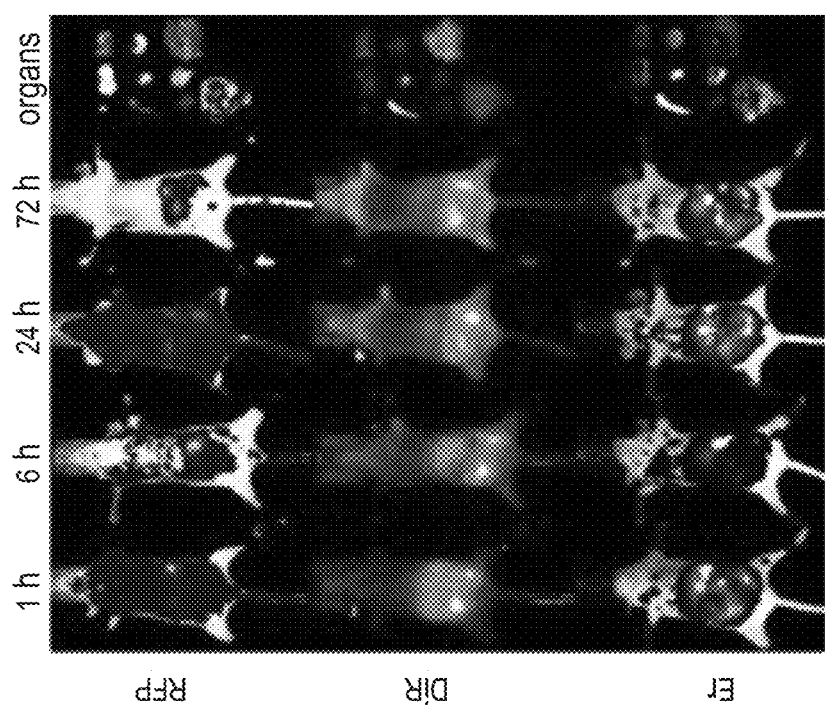

FIG. 36A shows representative images taken at various time points after nanoparticle administration, visualizing the distribution of NIR-I DC (DiR) and NIR-II DC emissive signals (Er) in relation to the cell intrinsic reporter RFP. Fluorescence intensities for each reporter were measured in all excised organs immediately after in vivo imaging, including (from left to right and top to bottom) the bladder (B), heart (H), intensities (I), kidneys (K), liver (Li), lungs (Lu), ovaries (O), pancreas (P), spleen (Sp) and stomach (St) of 4 separate mice that were similarly processed.

FIG. 36B is a bar graph showing the relative distribution of emissive signals obtained via ex vivo imaging of intrinsic (RFP) and extrinsic reporters (DiR and Er) in major organs at the time of animal sacrifice (72 h post administration of untargeted core-shell nanoparticles). For each reporter, the fluorescence intensities from all organs were normalized to the value obtained from the pancreas and are reported as the mean+SD (n=4 mice).

Figure 36C:
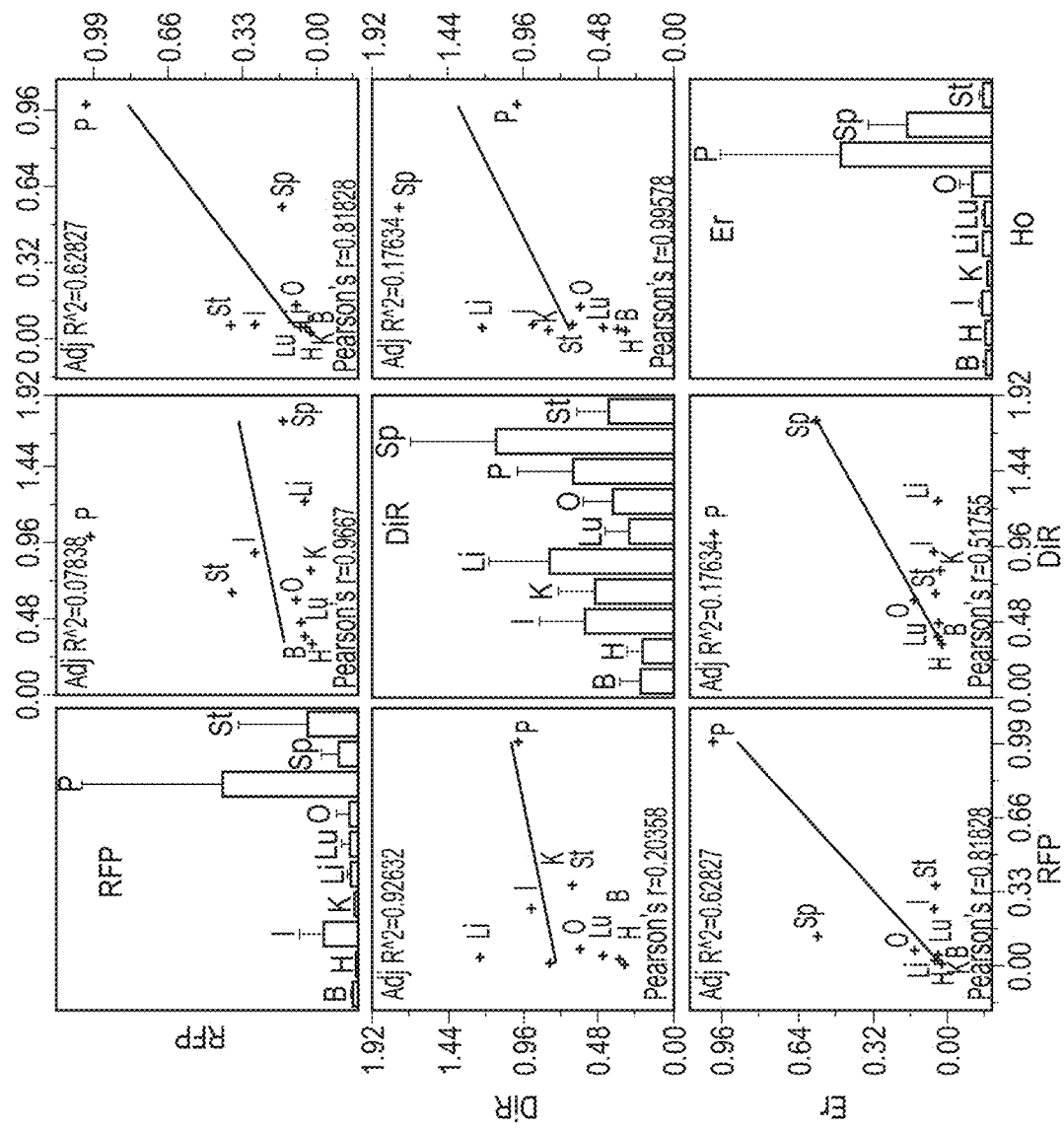

FIG. 36C is a correlation matrix of the relative in vivo distribution of RFP, DiR, and Er emissive signals as determined via ex vivo imaging of excised organs at 72 h after IP administration of untargeted core-shell nanoparticles to tumor-bearing mice (n=4 animals). Each diagonal graph shows the distribution of fluorescence signals for a given reporter and correlates to the values shown in FIG. 36B. Each off-diagonal graph depicts the correlation for a pair of fluorescent reporters with a linear-fit red line, a value for the Pearson's correlation coefficient (r), and an adjusted $R^2$ value.

Figure 37:
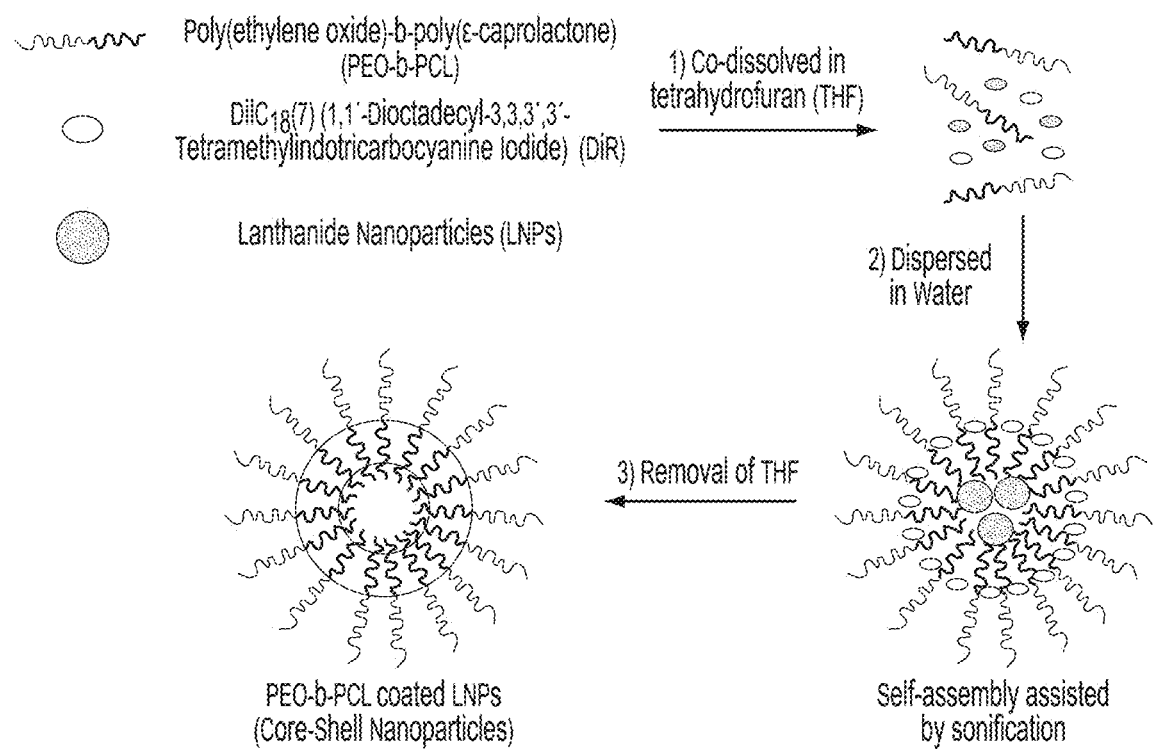

FIG. 37 is a schematic representation showing steps in an exemplary preparation protocol for generating core-shell nanoparticles.

Figure 38A:
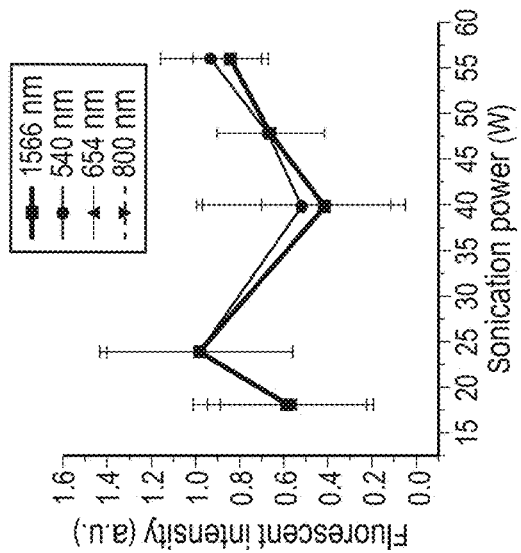

FIG. 38A is a plot showing the measurements of the relative concentrations of core-shell nanoparticles in aqueous suspensions as a function of sonication power used for aqueous dispersion (W). $PEO_{5k}$-$PCL_{16k}$ diblock copolymer was combined with NaYF4:Yb3+,Er3+,Tm3+-based LNPs in THF. The THF solution was then dispersed in a larger aqueous volume under continuous sonication, enabling encapsulation of LNPs within core-shell nanoparticles. The relative concentrations of LNPs in the aqueous suspensions were subsequently determined by measuring the peak intensities of UC (540, 644, and 800 nm) and DC emission (1566 nm).

Figure 38B:
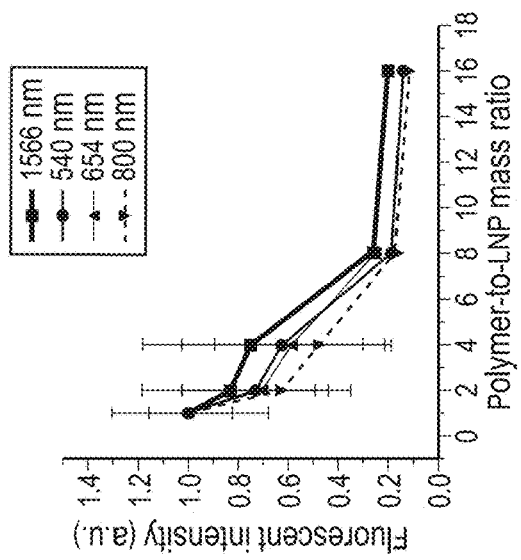

FIG. 38B is a plot showing the measurements of the relative concentrations of core-shell nanoparticles in aqueous suspensions as a function of initial polymer-to-LNP mass ratio in THF. $PEO_{5k}$-$PCL_{16k}$ diblock copolymer was combined with NaYF4:Yb3+,Er3+,Tm3+-based LNPs in THF. The THF solution was then dispersed in a larger aqueous volume under continuous sonication, enabling encapsulation of LNPs within core-shell nanoparticles. The relative concentrations of LNPs in the aqueous suspensions were subsequently determined by measuring the peak intensities of UC (540, 644, and 800 nm) and DC emission (1566 nm).

Figure 38C:
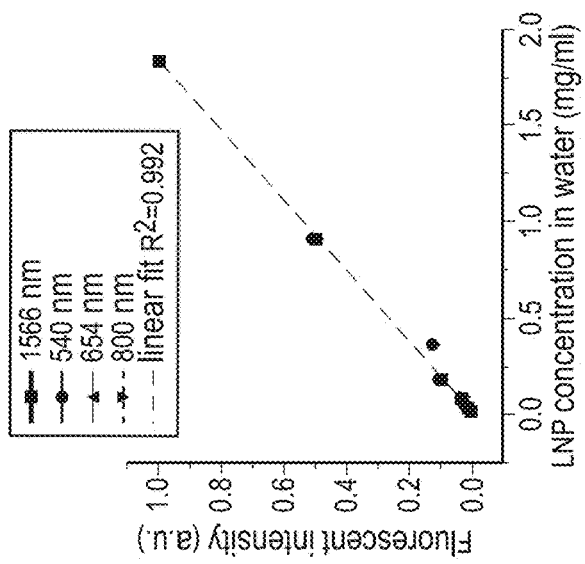

FIG. 38C is a plot showing the measurements of the relative concentrations of core-shell nanoparticles in aqueous suspensions as a function of the concentration of LNPs in the THF solution (mg/mL) that was added to water (4 mL). $PEO_{5k}$-$PCL_{16k}$ diblock copolymer was combined with NaYF4:Yb3+,Er3+,Tm3+-based LNPs in THF. The THF solution was then dispersed in a larger aqueous volume under continuous sonication, enabling encapsulation of LNPs within core-shell nanoparticles. The relative concentrations of LNPs in the aqueous suspensions were subsequently determined by measuring the peak intensities of UC (540, 644, and 800 nm) and DC emission (1566 nm).

Figure 39A:
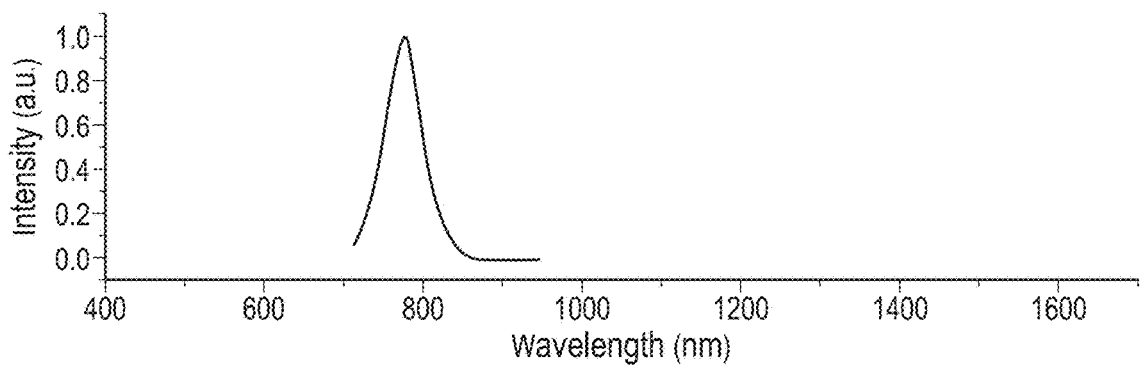

FIG. 39A is the normalized fluorescence spectra in THF for DiR ($\lambda_{ex}$=700 nm).

Figure 39B:
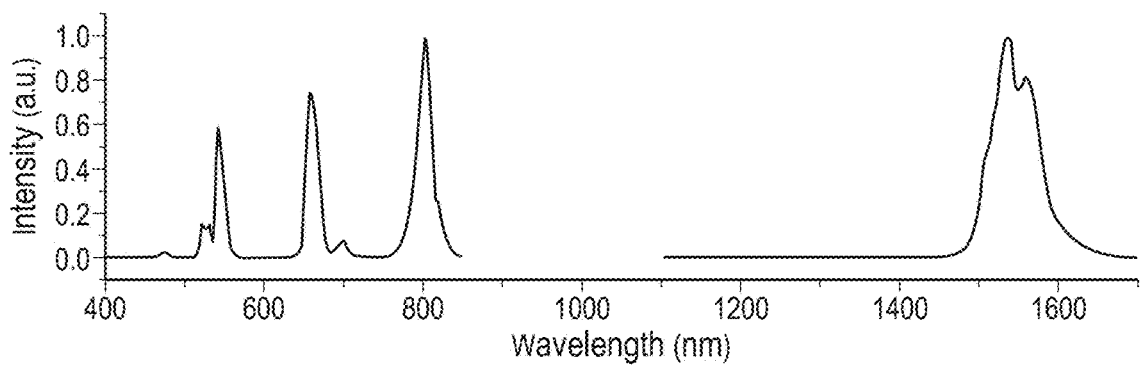

FIG. 39B is the normalized fluorescence spectra in THF for NaYF4:Yb3+,Er3+,Tm3+-based LNPs ($\lambda_{ex}$=980 nm).

Figure 39C:
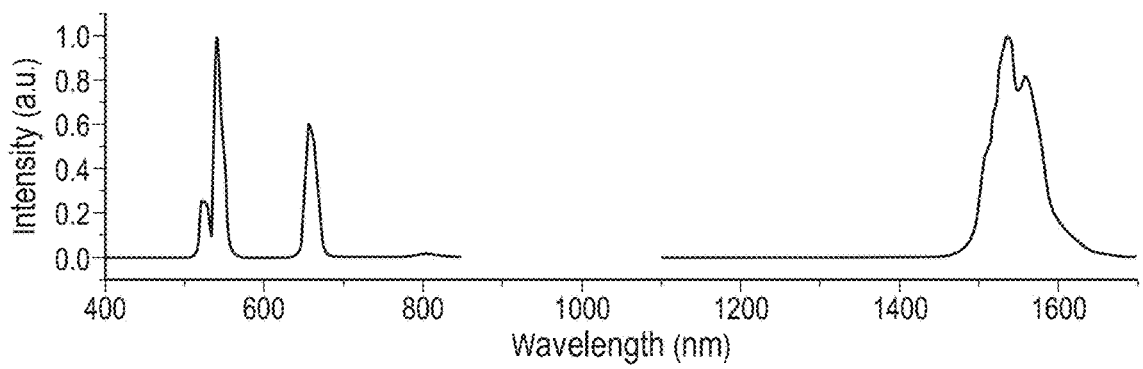

FIG. 39C is the normalized fluorescence spectra in THF for NaYF4:Yb3+,Er3+-based LNPs ($\lambda_{ex}$=980 nm).

Figure 39D:
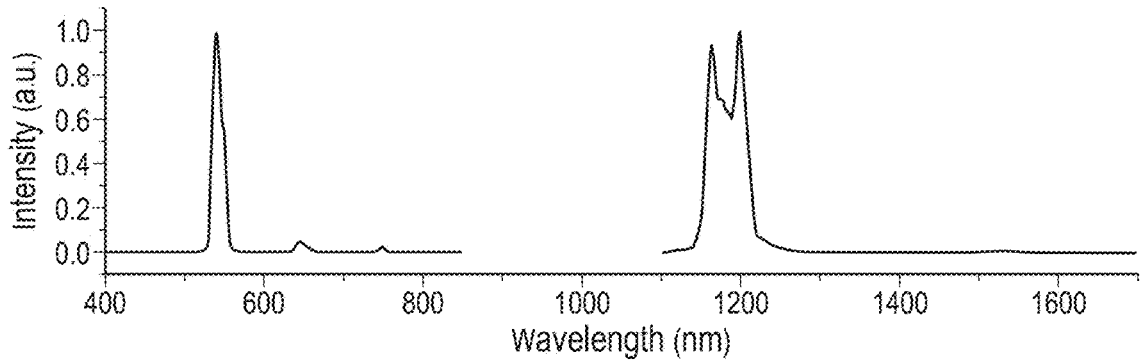

FIG. 39D is the normalized fluorescence spectra in THF for NaYF4:Yb3+,Ho3+-based LNPs ($\lambda_{ex}$=980 nm).

Figure 40A:
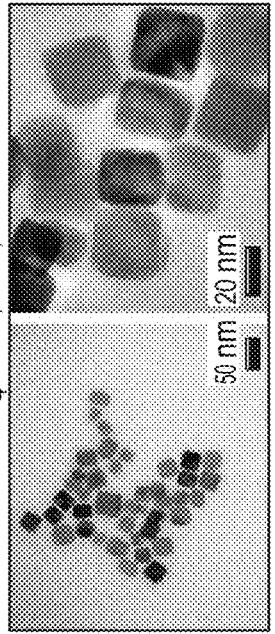

FIG. 40A are analytical TEM images of NaYF4:Yb3+, Er3+,Tm3+-based LNPs.

Figure 40B:
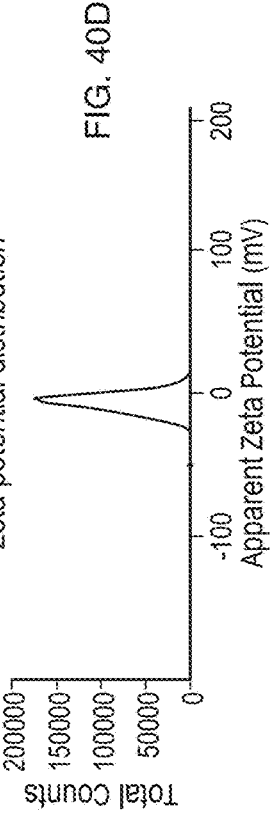

FIG. 40B are cryo-TEM images of an aqueous suspension of DiR-Er,Tm/PEO-PCL (i.e., PEO5k-PCL16k wrapped NaYF4:Yb3+,Er3+,Tm3+-based LNPs, containing DiR in the PCL shell).

Figure 40C:
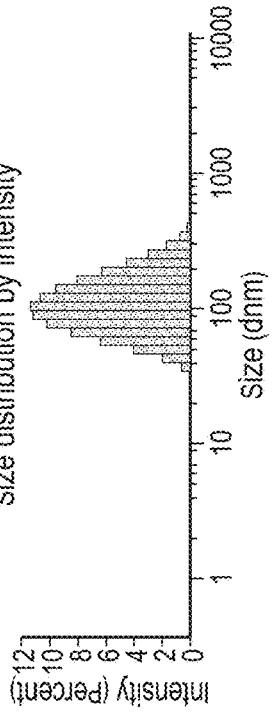
Figure 40D:
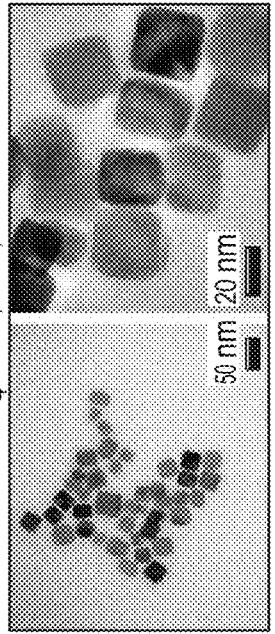

FIG. 40C is a DLS histogram depicting the size distribution (by intensity) of DiR-Er, Tm/PEO-PCL in water FIG. 40D is a plot showing the zeta potential distribution of DiR-Er, Tm/PEO-PCL in water.

Figure 40E:
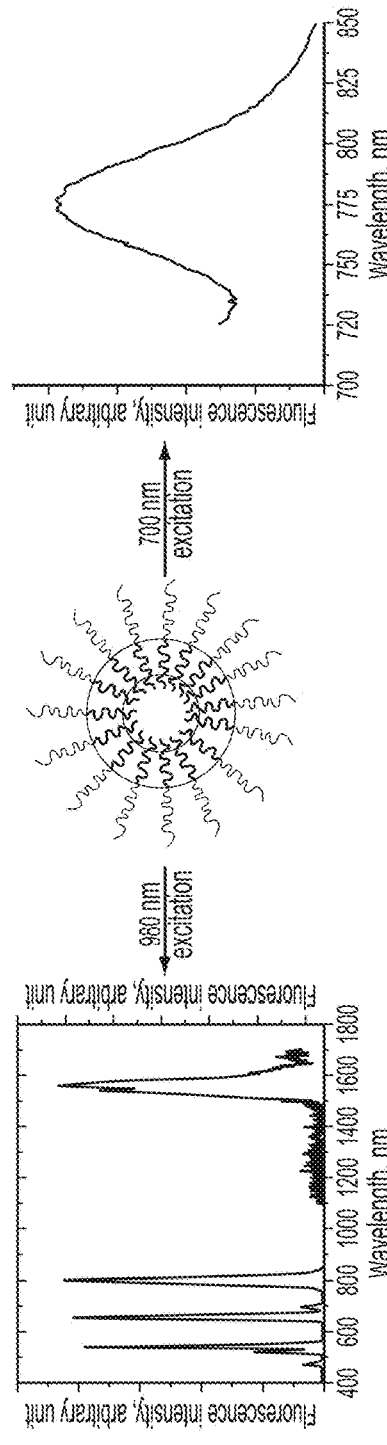

FIG. 40E are normalized fluorescence spectra of an aqueous suspension of core-shell nanoparticles, demonstrating simultaneous visible UC (blue), NIR-I UC (blue) and NIR-II DC emission (red) from core NaYF4:Yb3+,Er3+,Tm3+-based LNPs ($\lambda_{ex}$=980 nm) as well as NIR-I DC emission from DiR (green) ($\lambda_{ex}$=700 nm).

FIG. 41A are analytical TEM images of NaYF4:Yb3+, Er3+-based LNPs.

FIG. 41B are cryo-TEM images of an aqueous suspension of DiR-Er/PEO-PCL (i.e., PEO5k-PCL16k wrapped NaYF4:Yb3+,Er3+-based LNPs, containing DiR in the PCL shell).

FIG. 41C is a DLS histogram depicting the size distribution (by intensity) of DiR-Er/PEO-PCL in water FIG. 41D is a plot showing the zeta potential distribution of DiR-Er/PEO-PCL in water.

FIG. 41E are normalized fluorescence spectra of an aqueous suspension of core-shell nanoparticles, demonstrating simultaneous visible UC (blue) and NIR-II DC emission (red) from core NaYF4:Yb3+,Er3+-based LNPs ($\lambda_{ex}$=980 nm) as well as NIR-I DC emission from DiR (green) ($\lambda_{ex}$=700 nm).

Figure 42A:
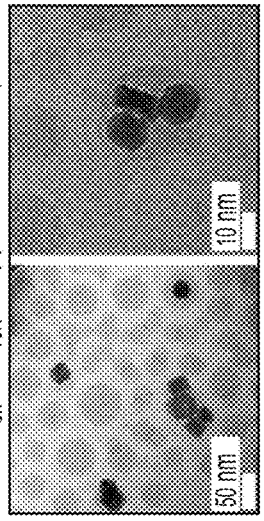

FIG. 42A are analytical TEM images of NaYF4:Yb3+, Ho3+-based LNPs.

Figure 42B:
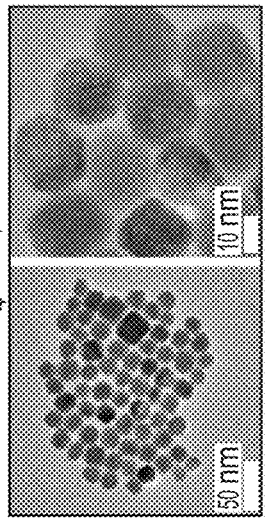

FIG. 42B are cryo-TEM images of an aqueous suspension of DiR-Ho/PEO-PCL (i.e., PEO5k-PCL16k wrapped NaYF4:Yb3+,Ho3+-based LNPs, containing DiR in the PCL shell).

Figure 42C:
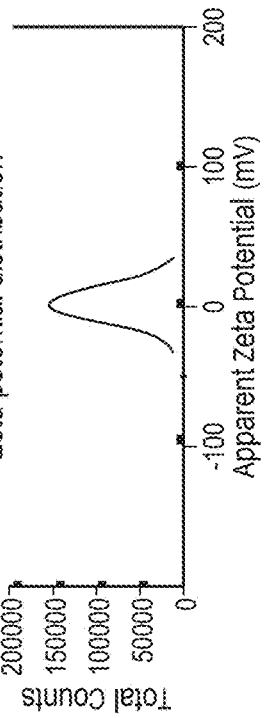

FIG. 42C is a DLS histogram depicting the size distribution (by intensity) of DiR-Ho/PEO-PCL in water.

Figure 42D:
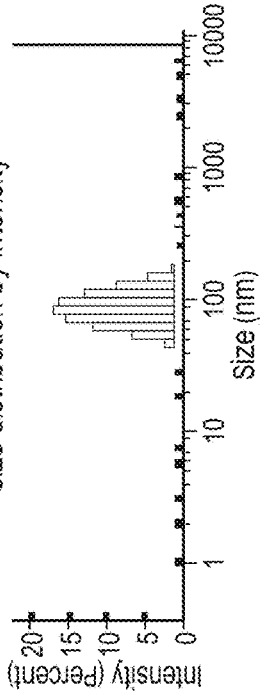

FIG. 42D is a plot showing the zeta potential distribution of DiR-Ho/PEO-PCL in water.

Figure 42E:
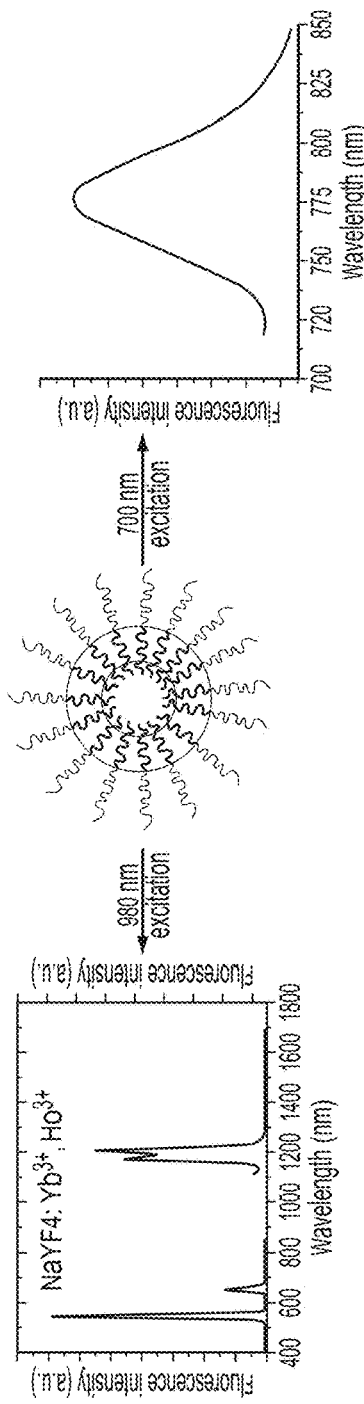

FIG. 42E are normalized fluorescence spectra of an aqueous suspension of core-shell nanoparticles, demonstrating simultaneous visible UC (blue) and NIR-II DC emission (red) from core NaYF4:Yb3+,Ho3+-based LNPs ($\lambda_{ex}$=980 nm) as well as NIR-I DC emission from DiR (green) ($\lambda_{ex}$=700 nm).

FIG. 43 is a table summarizing the physicochemical properties of various core-shell nanoparticles (n=4 experimental replicates per measurement).

Figure 44:
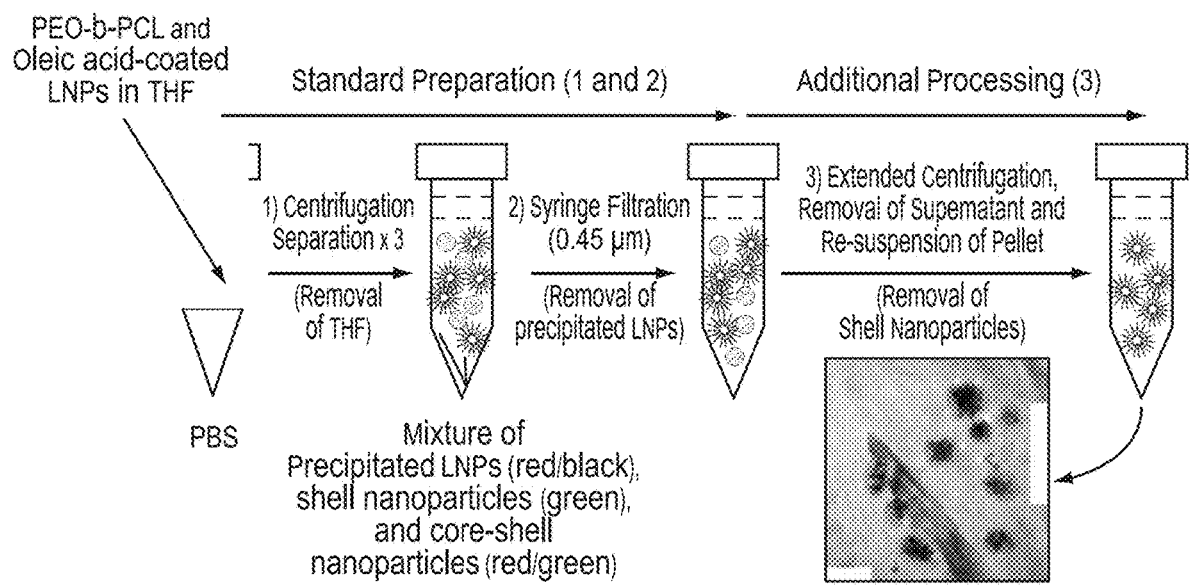

FIG. 44 is a schematic representation of an exemplary preparation protocol (steps 1 and 2) as well as additional processing steps (3) to generate homogenous populations of core-shell nanoparticles; the cryo-TEM image of the final suspension of DiR-Er,Tm/PEO-PCL demonstrates a population of core-shell nanoparticles that each contain multiple LNPs surrounded by a PEO-b-PCL shell. The final core-shell particles are approximately 100 nm in diameter (scale bar=100 nm).

Figure 45:
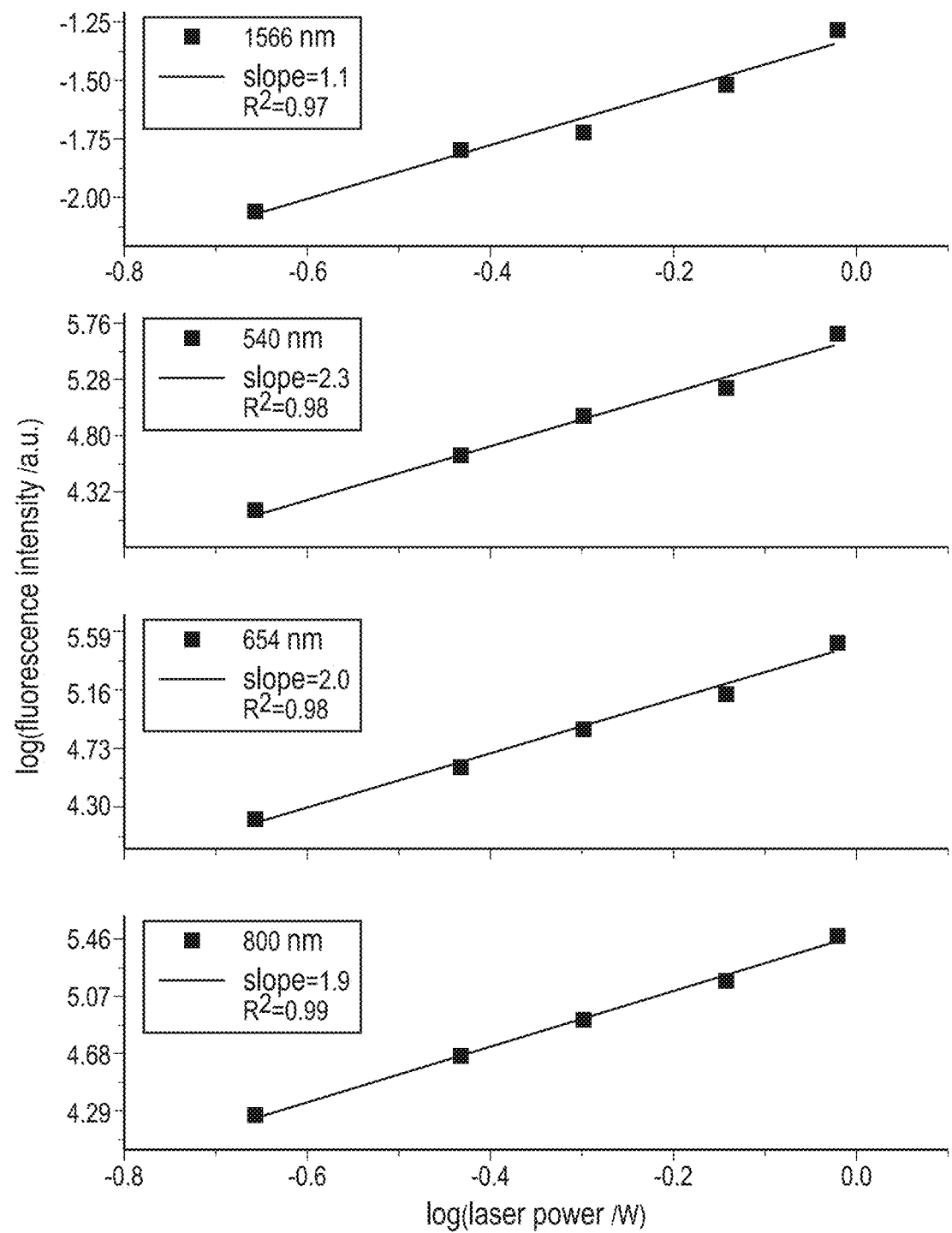

FIG. 45 is a series of graphs showing the emission of LNPs as a function of laser power. A suspension of NaYF4: Yb3+,Er3+,Tm3+-based LNPs in THF (1 mg/mL) was exposed to irradiation with a 980 nm laser and the peak intensities of its NIR-II DC (1566 nm) and UC emission bands (654, 540, and 800 nm) were independently monitored at different laser powers. Log(fluorescence intensity) is displayed a function of log(laser power); the slope and correlation of determination ($R^2$) for the linear fit regression are reported as monitored at each of the 4 different wavelengths.

Figure 46:
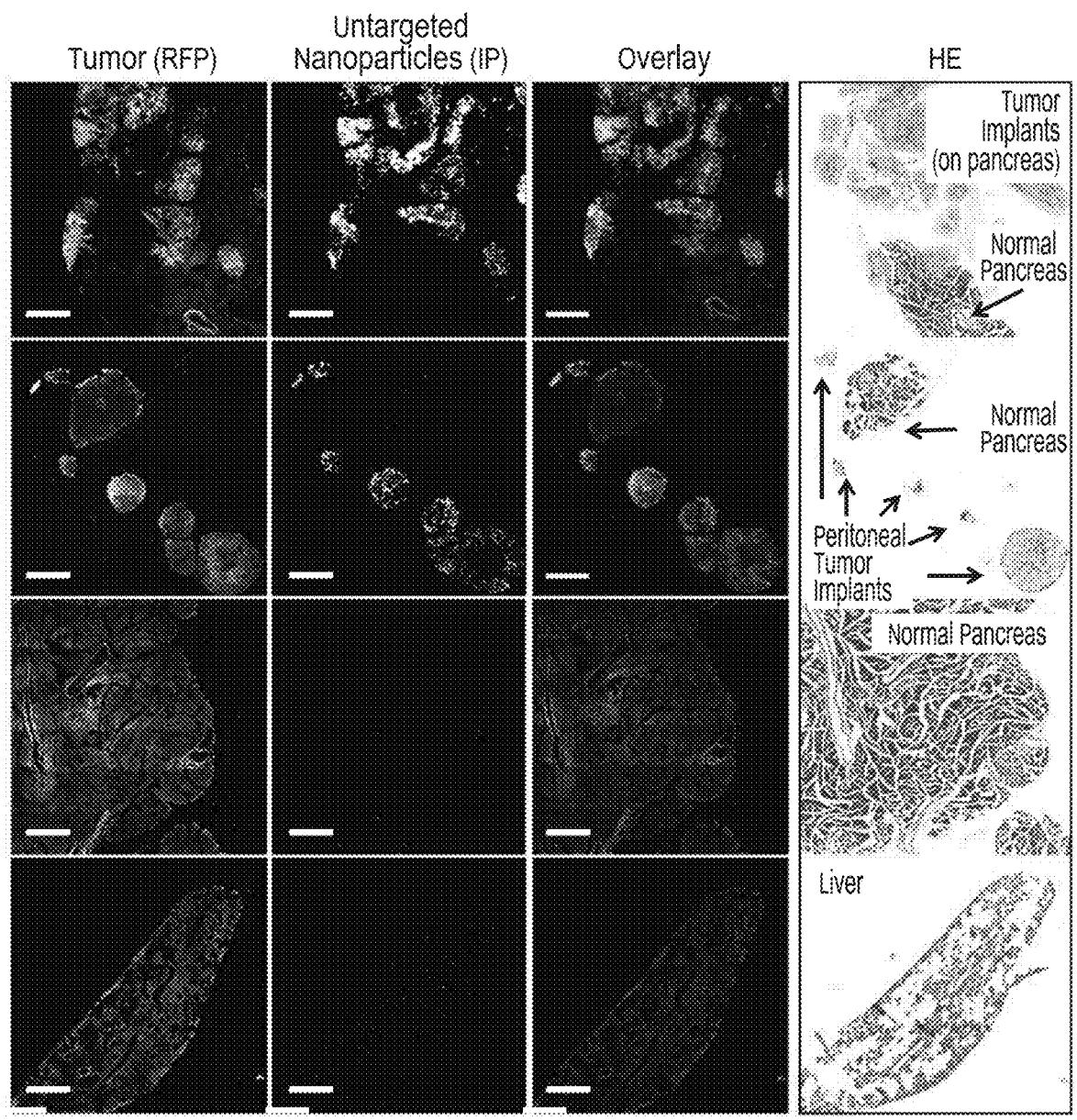

FIG. 46 shows confocal microscope images of tissue sections obtained from excised organs of a representative nude mouse that had been orthotopically xenotransplanted with LUC+/RFP+ OVCAR8 ovarian cancer cells and that had been administered untargeted core-shell nanoparticles (Er/PEO-PCL) by IP injection. Nanoparticles were introduced 2 weeks after tumor cell implantation and animals were sacrificed at 72 h post-nanoparticle injection. Tumors were identified by RFP fluorescence while all tissues exhibited green auto-fluorescence. Nanoparticles were imaged by 980-nm multi-photon excitation and by detection of their visible UC emission. H&E staining was also performed to identify tumor implants vs. normal tissue in each organ. Scale bar=300 µm.

Figure 47A:
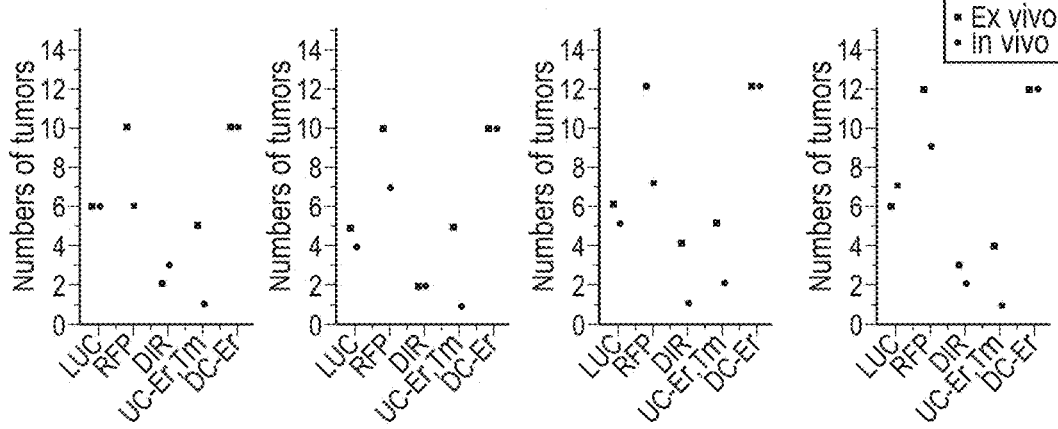

FIG. 47A is a series of graphs showing the numbers of tumor deposits detected either by in vivo vs. ex vivo (whole tissue) imaging at 2 weeks after tumor cell implantation; tumors were detected by in vivo (red) and ex vivo imaging (black) with each optical reporter and plotted individually for an n=4 total mice (each image corresponds to the numbers of tumors detected in a single mouse by each modality).

Figure 47B:
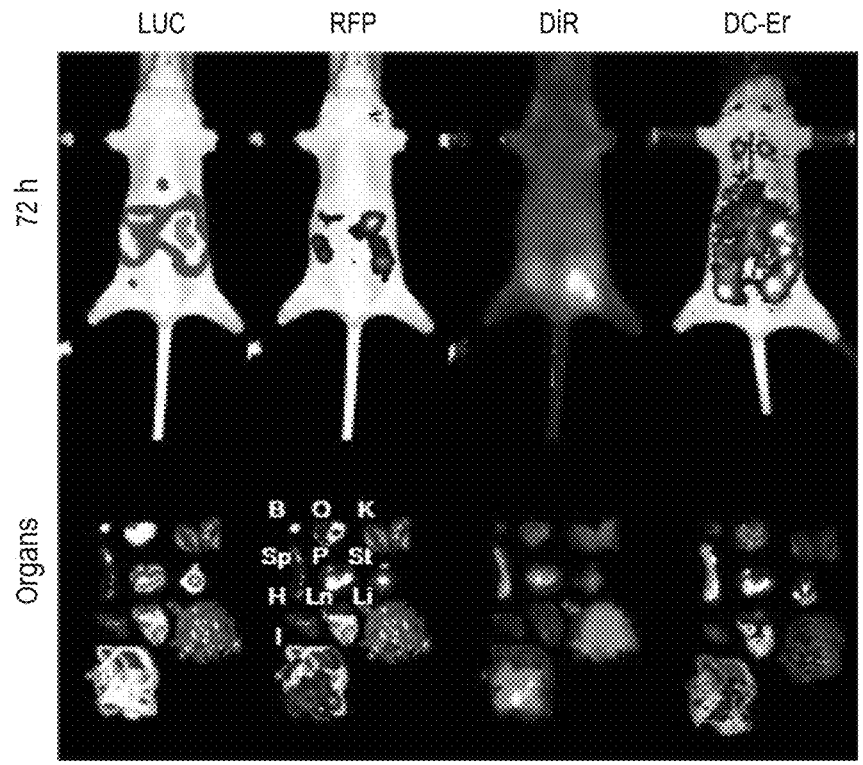

FIG. 47B shows in vivo and ex vivo (whole organ) images from a single nude mouse performed at 1 week after xenotransplantation of LUC$^+$/RFP$^+$ OVCAR-8 cells.

Figure 47C:
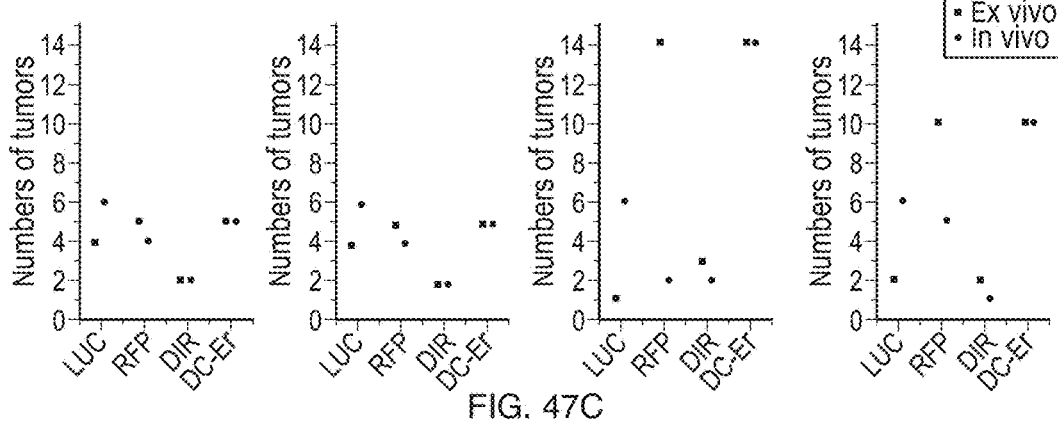

FIG. 47C is a series of graphs showing the numbers of tumor deposits as detected by in vivo vs. ex vivo imaging of each optical reporter, which were performed at 1 week after xenotransplantation of LUC$^+$/RFP$^+$ OVCAR-8 cells. Tumors were detected by in vivo (red) vs. ex vivo (black) imaging with the same fluorescence channel and plotted individually for an n=4 total mice. Note, each plot corresponds to a single mouse and each point represents the numbers of tumors detected by each modality.

Figure 48:
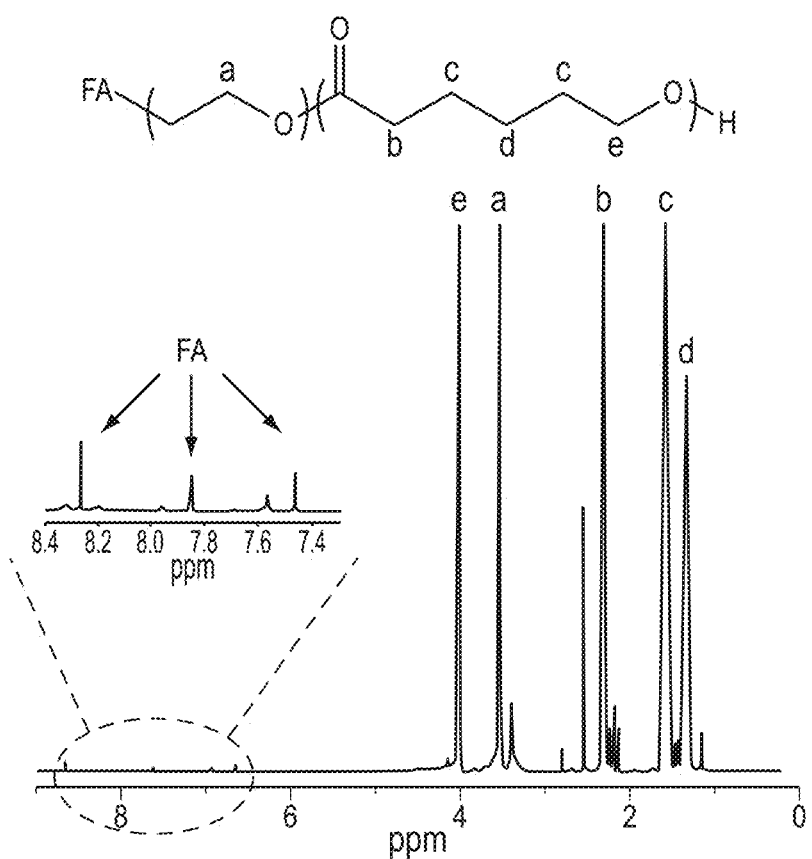

FIG. 48 is a H$^1$-NMR spectrum of FA-conjugated PEO$_{6k}$-PCL$_{16k}$ (Folate-PEG-PCL). The content of FA in the purified polymer product was calculated by comparing the ratio of the integrated peaks at 6.63, 7.6 and 8.653 ppm (assigned to FA) to the value for the peak at 3.52 ppm (assigned to PEO); the final molar ratio of FA to PEO-b-PCL was determined to be 1:1.

Figure 49:
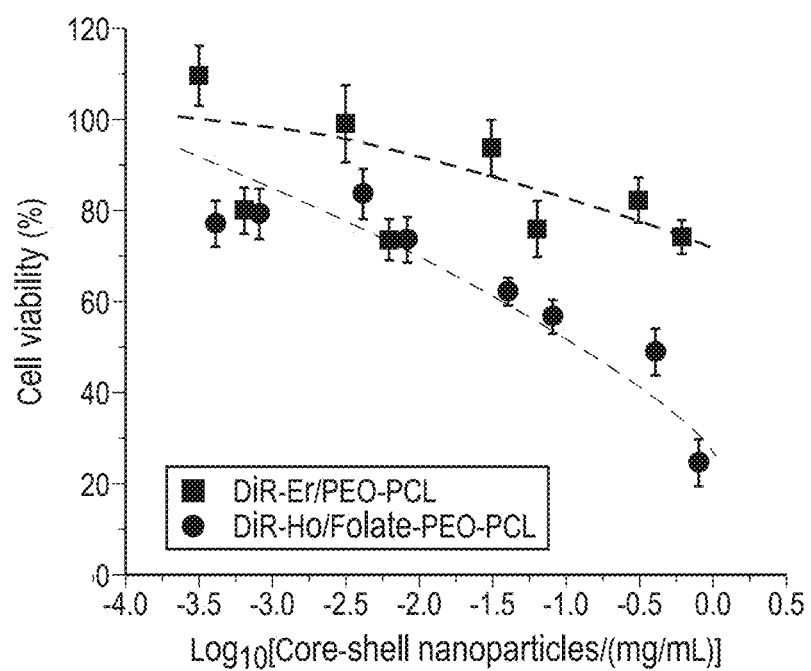

FIG. 49 is a graph of in vitro viability of OVCAR-8 cells after 72 h of incubation with untargeted (DiREr/PEO-PCL) and FR-targeted core-shell nanoparticles (DiR-Ho/Folate-PEO-PCL) as a function of the concentration of core-shell nanoparticles ($\log_{10}$(polymer/(mg/mL)) in suspension. Negative control: cells that were treated with media alone. Each data point represents the mean+/−SD for an n=6 technical replicates per condition.

FIG. 50A is a series of representative images taken at various time points after simultaneous IP injection of both formulations to a single mouse, detecting fluorescence from an intrinsic reporter (RFP), an extrinsic organic NIR-I fluorophore (DiR), as well NIR-II DC emission from core LNPs in untargeted (Er) and FR-targeted core-shell nanoparticles (Ho).

FIG. 50B representative images taken at various time points of emissive signals obtained via ex vivo imaging of cell intrinsic and extrinsic reporters in major organs at 72 h after simultaneous IV administration of untargeted (Er) and FR-targeted (Ho) core-shell nanoparticles to tumor-bearing mice (n=4 animals).

FIG. 50C is a bar graph showing the relative distribution of emissive signals obtained via ex vivo imaging of intrinsic (RFP) and extrinsic reporters (DiR, Er and Ho) in major organs at the time of animal sacrifice (72 h post simultaneous IP-administration of untargeted (Er) and FR-targeted (Ho) core-shell nanoparticles). Fluorescence intensities for each reporter were measured in all major organs, including the bladder (B), heart (H), intensities (I), kidneys (K), liver (Li), lungs (Lu), ovaries (O), pancreas (P), spleen (Sp) and stomach (St) of 4 separate mice that were similarly processed. For each reporter, the fluorescence intensities from all organs were normalized to the value obtained from the organ with the highest fluorescence intensity (pancreas) and are reported as the mean+SD (n=4 mice).

FIG. 50D is a graph showing pharmacokinetic analyses of core-shell nanoparticles in blood after IP administration to tumor-bearing mice. Small volume blood draws (<20 µL) were made at various time points and the intensities of NIR-I DC (DiR) and NIR-II DC emission (Er) of core-shell nanoparticles were measured and normalized to their highest values after administration (n=4 mice).

FIG. 50E is a bar graph showing the relative distribution of emissive signals obtained via ex vivo imaging of cell intrinsic and extrinsic reporters in major organs at 72 h after simultaneous IV administration of untargeted (Er) and FR-targeted (Ho) core-shell nanoparticles to tumor-bearing mice (n=4 animals).

FIG. 50F is a graph showing pharmacokinetic analyses of core-shell nanoparticles in blood after IV administration to tumor-bearing mice; small volume blood draws were made from mice at various time points and the intensities of NIR-I DC (DiR) and NIR-II DC emission (Er) of core-shell nanoparticles were measured and normalized to their highest values after administration (n=4 mice).

Figure 50G:
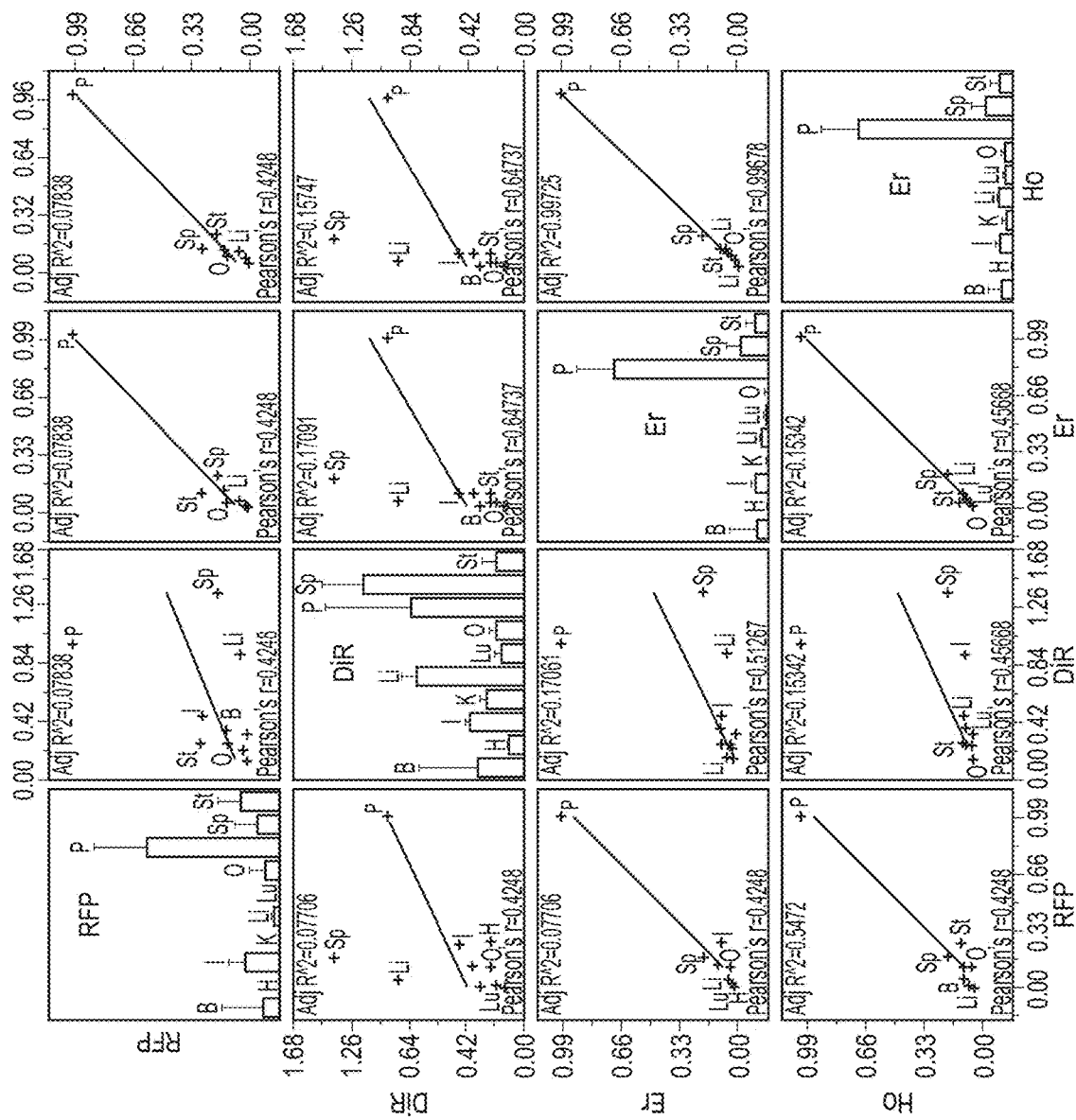

FIG. 50G is a correlation matrix for the relative distribution of RFP, DiR, Er, and Ho emissive signals as determined via ex vivo imaging of excised organs at 72 h after simultaneous IP administration of untargeted (Er) and FR-targeted (Ho) core-shell nanoparticles to tumor-bearing mice (n=4 animals). Each off-diagonal graph depicts the correlation for a pair of fluorescent reporters with a linear-fit red line, a value for the Pearson's correlation coefficient (r), and an adjusted R$^2$ value.

Figure 51:
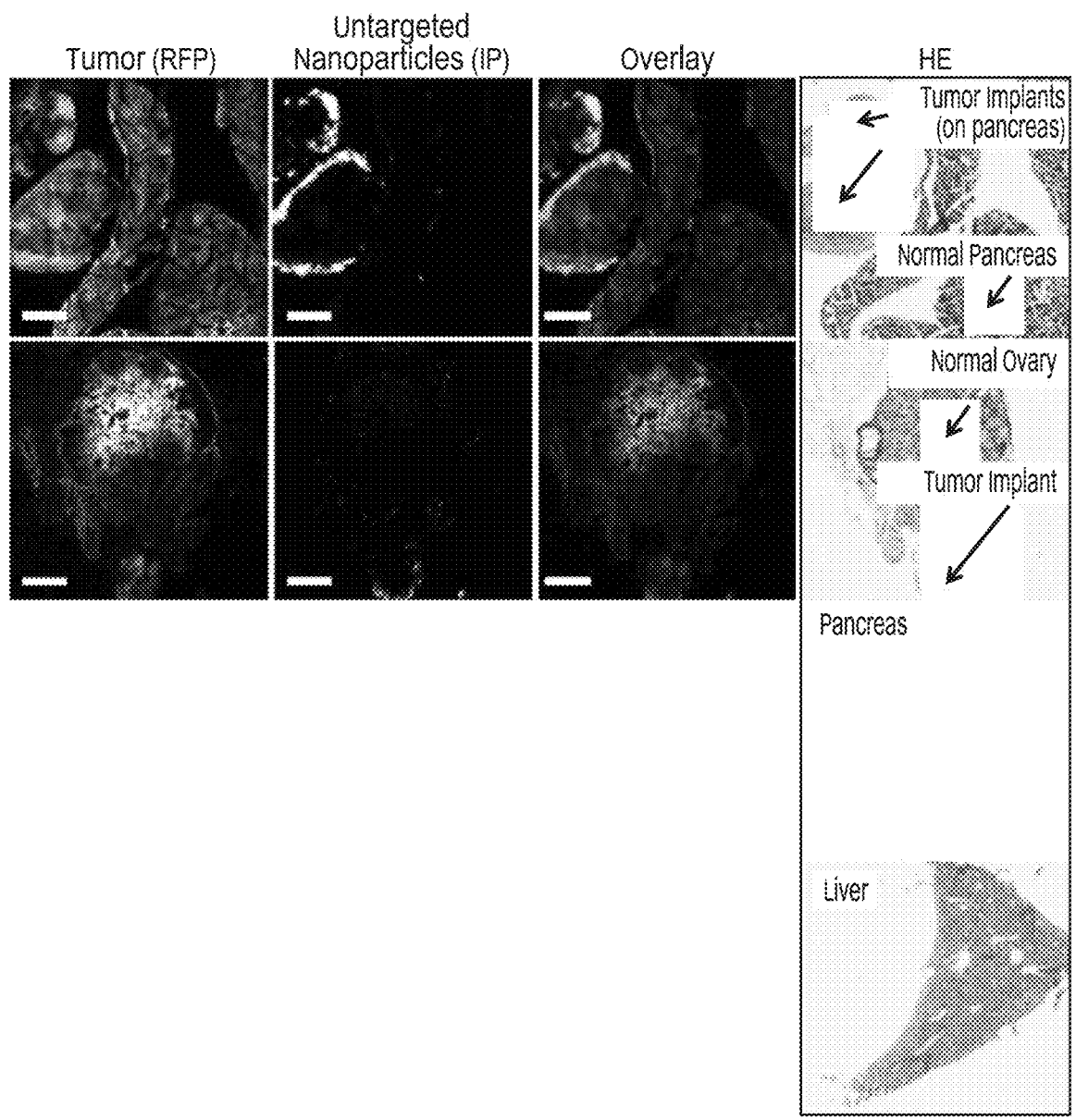

FIG. 51 is a series of confocal microscope images of tissue sections obtained from excised organs of a representative nude mouse that had been orthotopically xenotransplanted with LUC$^+$/RFP$^+$ OVCAR8 ovarian cancer cells and that had been administered FR-targeted core-shell nanoparticles (Er/Folate-PEO-PCL) by IP injection. Nanoparticles were introduced at 2 weeks after tumor-cell implantation and animals were sacrificed at 72 h post-nanoparticle injection. Tumors were identified by RFP fluorescence while all tissues exhibited green autofluorescence. Nanoparticles were imaged by 980-nm multi-photon excitation and by detection of their visible UC emission. H&E staining was also performed to identify tumor implants vs. normal tissue in each organ. Scale bar=300 µm.

Figure 52:
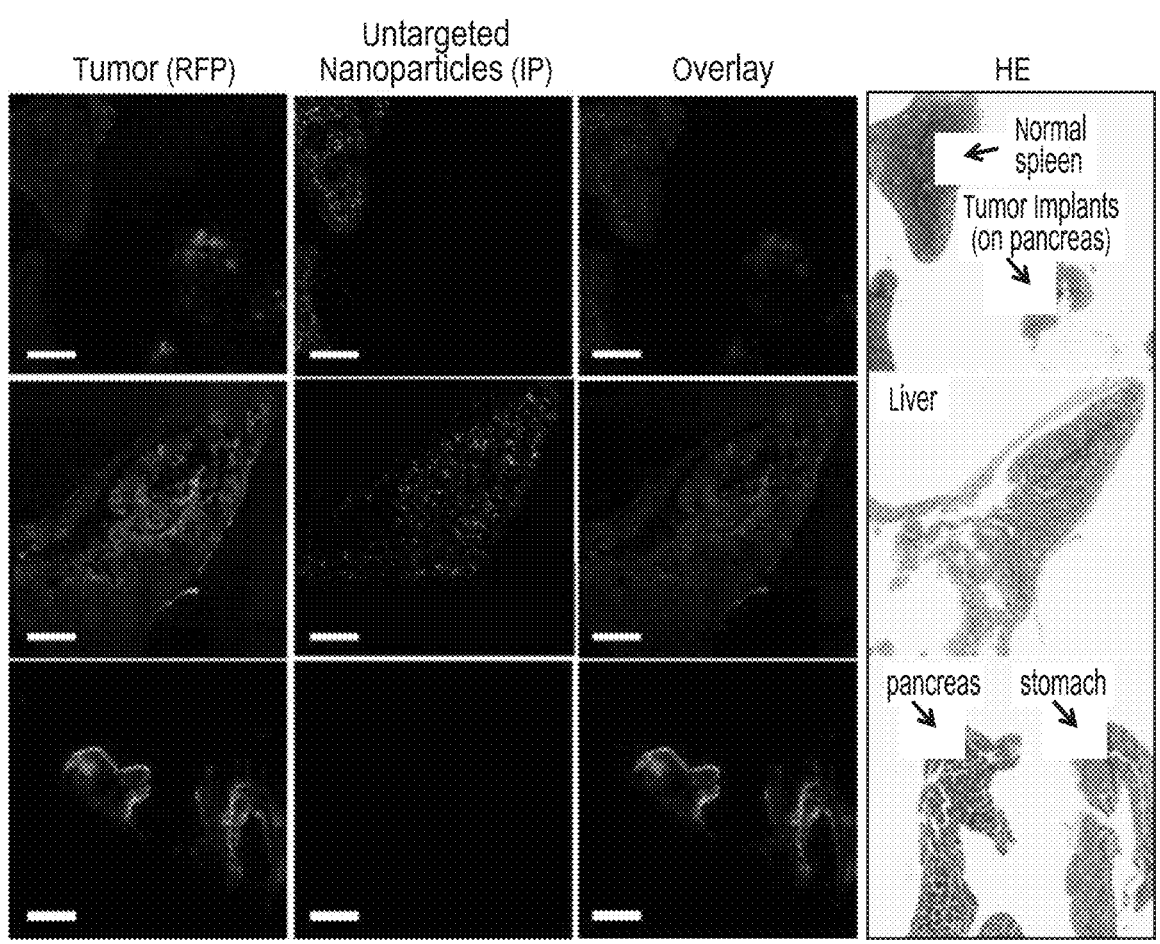

FIG. 52 is a series of confocal microscope images of tissue sections obtained from excised organs of a representative nude mouse that had been orthotopically xenotransplanted with LUC$^+$/RFP$^+$ OVCAR8 ovarian cancer cells and that had been administered untargeted core-shell nanoparticles (Er/PEO-PCL) by IV injection. Nanoparticles were introduced at 2 weeks after tumor-cell implantation and animals were sacrificed at 72 h post-nanoparticle injection. Tumors were identified by RFP fluorescence while all tissues exhibited green autofluorescence. Nanoparticles were imaged by 980-nm multi-photon excitation and by detection of their visible UC emission. H&E staining was also performed to identify tumor implants vs. normal tissue in each organ. Scale bar=300 µm.

Figure 53:
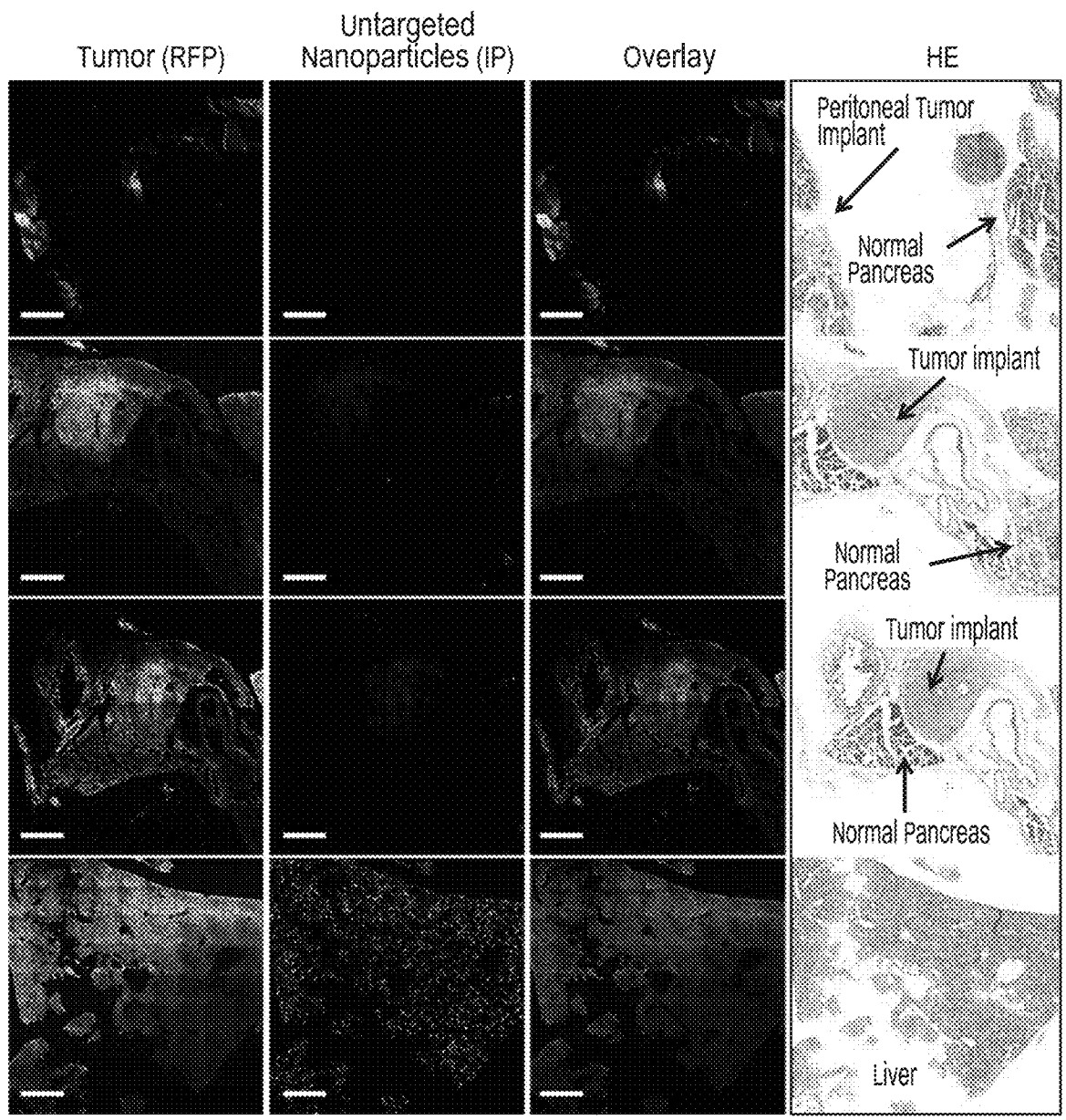

FIG. 53 is a series of confocal microscope images of tissue sections obtained from excised organs of a representative nude mouse that had been orthotopically xenotransplanted with LUC$^+$/RFP$^+$ OVCAR8 ovarian cancer cells and that had been administered FR-targeted core-shell nanoparticles (Er/Folate-PEO-PCL) by IV injection. Nanoparticles were introduced at 2 weeks after tumor-cell implantation and animals were sacrificed at 72 h post-nanoparticle injection. Tumors were identified by RFP fluorescence while all tissues exhibited green autofluorescence. Nanoparticles were imaged by 980-nm multi-photon excitation and by detection of their visible UC emission. H&E staining was also performed to identify tumor implants vs. normal tissue in each organ. Scale bar=300 µm.

FIG. 54A is a confocal micrograph of tumor deposits excised from representative mice at two-weeks post-implantation of LUC+/RFP+ OVCAR-8 cells and at 72 h after IV injection of untargeted (Er/PEO-PCL) core-shell nanoparticles (Er/Folate-PEO-PCL). Immunostaining was performed and confocal microscopy images were obtained in order to visualize the intratumoral distribution of nanoparticles (blue) with respect to tumor cells (red) and macrophages (green). Scale bar=300 µm.

FIG. 54B is a confocal micrograph of tumor deposits excised from representative mice at two-weeks post-implantation of LUC+/RFP+ OVCAR-8 cells and at 72 h after IV injection of FR-targeted core-shell nanoparticles (Er/Folate-PEO-PCL). Immunostaining was performed and confocal microscopy images were obtained in order to visualize the intratumoral distribution of nanoparticles (blue) with respect to tumor cells (red) and macrophages (green). Scale bar=300 µm.

FIG. 55A are chemical structures of the biodegradable and amphiphilic polymer of methoxy-poly(ethylene glycol)-block-poly(benzyl L-lysine)-block-poly(aspartamide) (mPEG-b-PZLL-b-PASP(DET)), a novel reductive sensitive linker and the highly potent microtubule inhibitor monomethyl auristatin E (MMAE).

FIG. 55B is a schematic representation of a fabrication of nanoparticles formed from spontaneous self-assembly of the MMAE-coupled polymer (NP(MMAE)) and after further complexation of the polyanionic diblock copolymer of methoxypoly(ethylene glycol)-block-poly(glutamic acid) (mPEG-b-PGA), which aids to further stabilize these coated nanoparticles (CNP(MMAE)), preventing premature drug release and enabling tumor-specific updake.

FIG. 55C is a schematic representation showing intracellular uptake and release of MMAE from CNP(MMAE). While not wishing to be bound by any particular theory, the PEO-b-PGA polymer dissociates from NP(MMAE) in low pH environments such as those found in the tumor cells or within the tumor microenvironment; the anionic charge of PGA is known to be neutralized at a pH below its pKa of 5.5-6.0; and, uptake of cellular uptake and endosomal escape of cationically charged nanoparticles follows. Release of free MMAE occurs intracellularly and would proceed in a triggered fashion due to the high intracellular concentrations of reductants found within EOC cells.

FIG. 55D is a schematic representation of a possible mechanism of the release of free MMAE from the polymer conjugate. With respect to the mechanism of MMAE release, the self-immolative linker was designed to contain a disulfide bond whose reduction would be triggered by high intracellular concentrations of glutationine (GSH). This results in spontaneous nucleophilic attack by the free thiol on the carbonamide bond that coupled the MMAE in its prodrug form, which would then result in release of the active toxin.

FIG. 56A is a series of UV-Vis detection spectra of different elution bands corresponding to the products formed from the reaction of the MMAE-bound and reductive-sensitive linker with 5 mM GSH as determined by HPLC.

FIG. 56B is a graph of the rates of release of free MMAE vs. time.

FIG. 56C is a graph of retention times, charge to mass ratios (m/z), putative chemical structures, and the calculated masses of the isolated products from each of the different elution bands corresponding to the traces in FIG. 56A; reaction products with different m/z values were determined by LC/MS and could be assigned to the linker conjugate that incorporates MMAE in a prodrug form (MMAE Pro), the reaction products formed after its exposure to GSH (i.e. MMAE-SH and MMAE-GSH), and the free and unmodified toxin (MMAE).

Figure 57A:
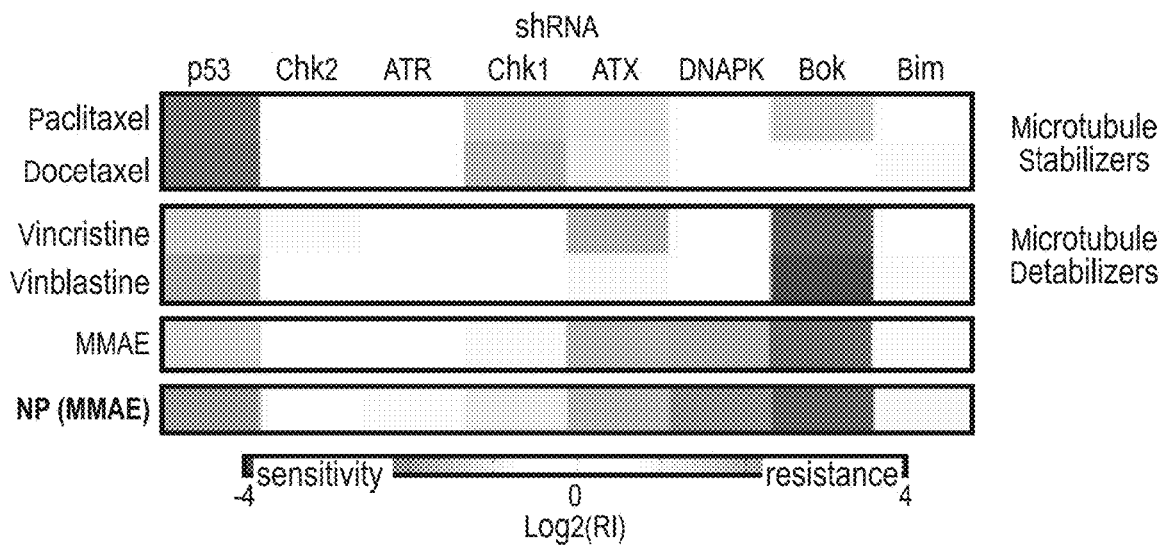

FIG. 57A are heat maps of conventional microtubule stabilizers (paclitaxel, docetaxel) and destabilizers (vincristine, vinblastine), the highly potent toxin MMAE and its nanoparticle conjugate (NP(MMAE)).

Figure 57B:
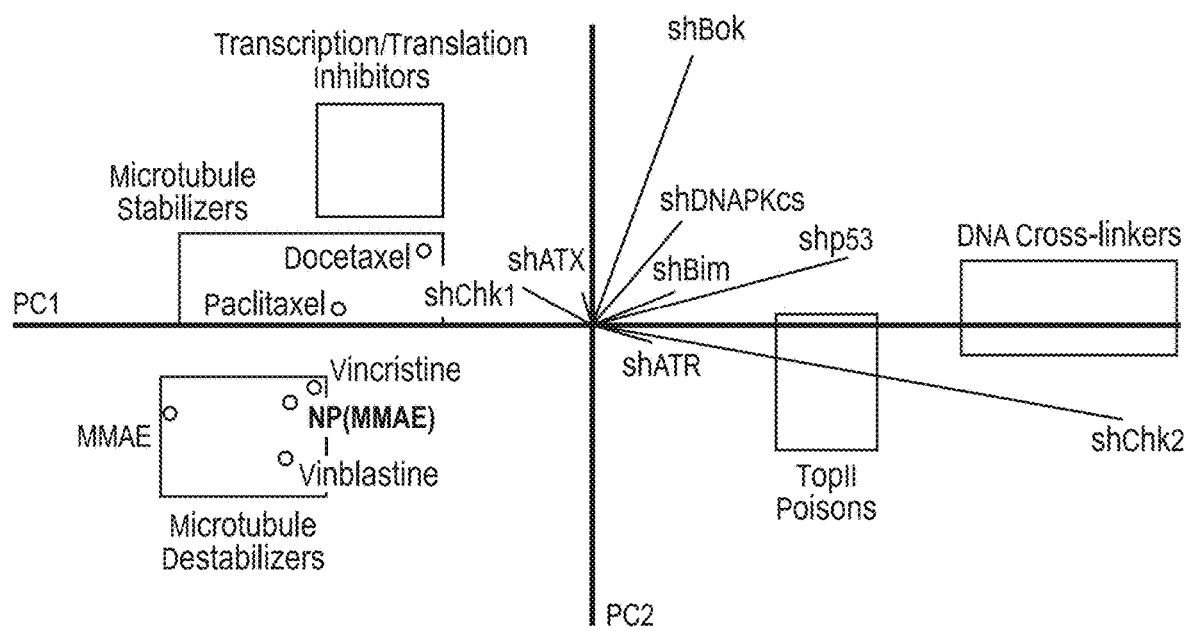

FIG. 57B is a principal component analysis of RNAi signatures from each of these agents in FIG. 57A as well as in relation to transcription/translation (Txn/Tln) inhibitors, Topoisomerase II (Top2) poisons, and DNA cross-linker reference set categories.

Figure 58A:
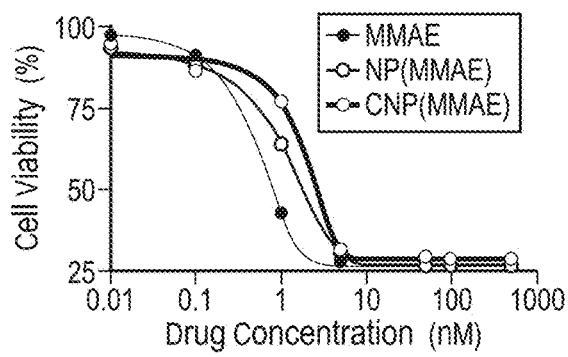

FIG. 58A is a graph showing the relative cellular viability of OVCAR8 cells treated with free MMAE, NP(MMAE), and CNP(MMAE) at 72 h, as compared to untreated cells, and as determined by the colorimetric MTT cellular viability assay.

Figure 58B:
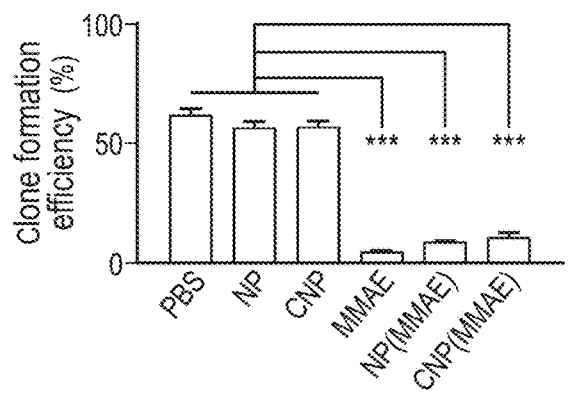

FIG. 58B is a bar graph showing relative efficiency of clone formation for OVCAR8 cells plated in petri dishes as determined at 7 days after cellular exposure to MMAE, NP(MMAE), and CNP(MMAE) and in comparison to various controls (PBS, empty nanoparticles (NP), and empty coated nanoparticles (CNP)).

Figure 58C:
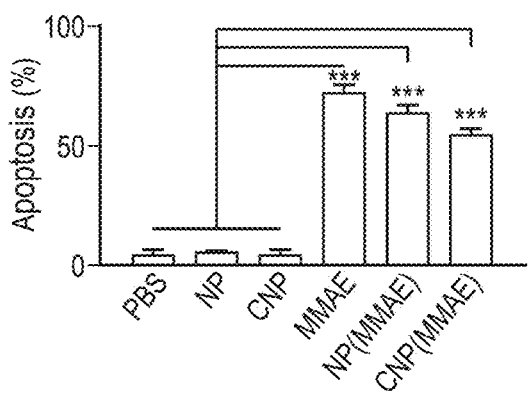

FIG. 58C is a bar graph comparing experiments performed by flow cytometry to determine the percentages of cells undergoing apoptosis at 48 h after continuous exposure to different MMAE-conjugated nanoparticles or various control treatments.

Figure 58D:
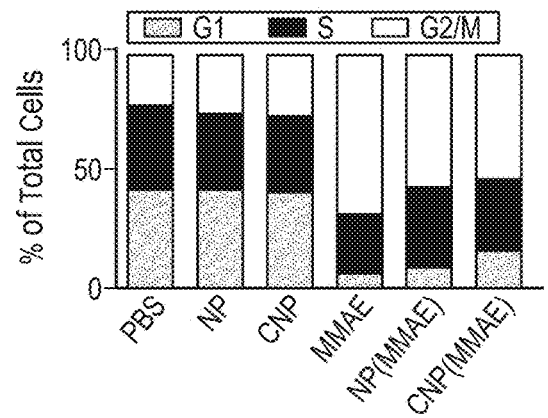

FIG. 58D is a bar graph comparing experiments performed by flow cytometry to analyze the cell cycle of OVCAR8 cells at 48 h after continuous exposure to different MMAE-conjugated nanoparticles or various control treatments.

Figure 58E:
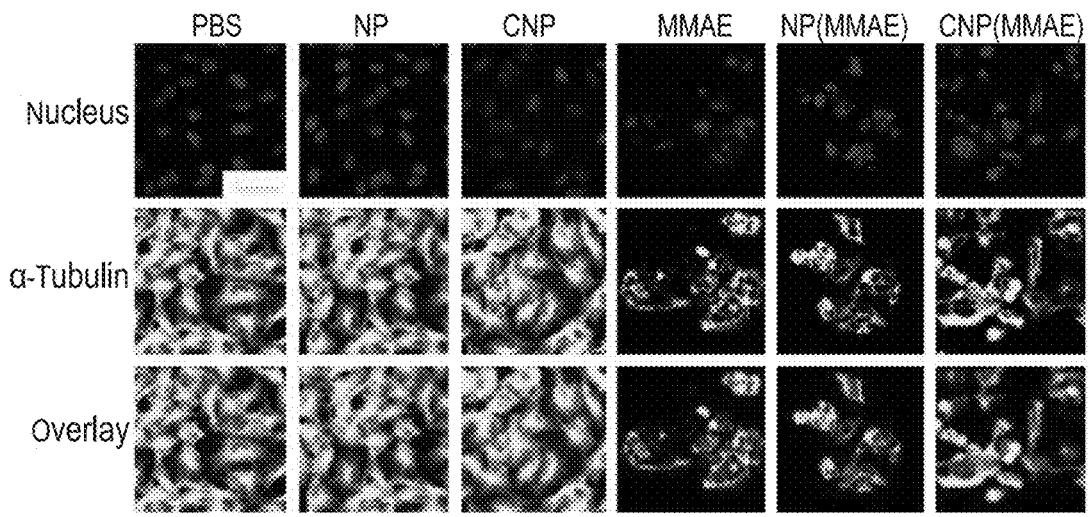

FIG. 58E is a series of confocal microscope images using α-tubulin immunodetection confirming the preserved ability of MMAE-conjugated nanoparticles to enable destabilization of tubulin within the cytoskeleton of OVCAR8 cells and as compared to the cells response to free MMAE. Scale bar=40 µm. ***p-value <0.001.

Figure 59A:
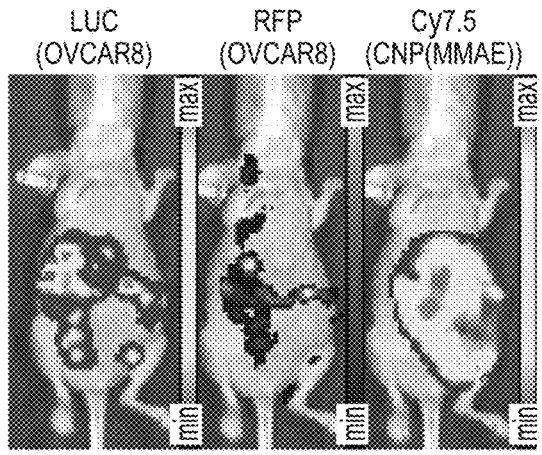

FIG. 59A are representative in vivo images of a single LUC$^+$/RFP$^+$ OVCAR8 tumor-bearing nude mouse at 72 h after IP administration of Cy7.5-conjugated CNP(MMAE).

Figure 59B:
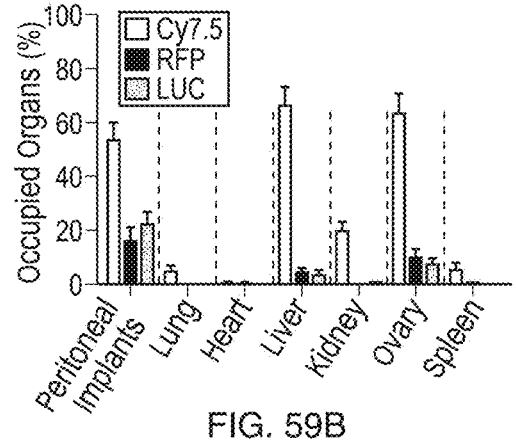

FIG. 59B is a bar graph quantifying the relative ex vivo signal intensities in each organ at the time of animal sacrifice (n=3 identically processed mice). The signal intensity from each report channel was normalized to the value measured from the intestines of each animal, which had high burdens of micrometastatic tumor foci.

Figure 59C:
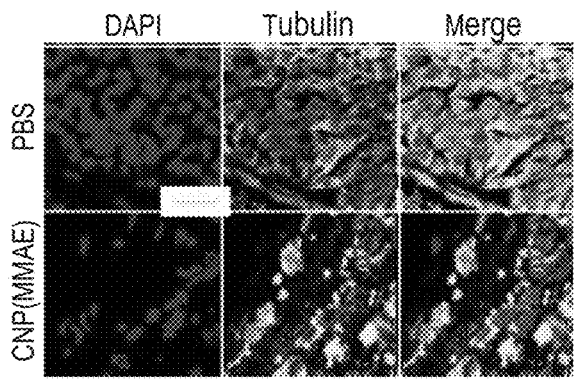

FIG. 59C are images showing immunofluorescence staining for α-tubulin in OVCAR8 tumors excised from nude mice at 72 h after IP administration of CNP(MMAE) or PBS (control).

Figure 59D:
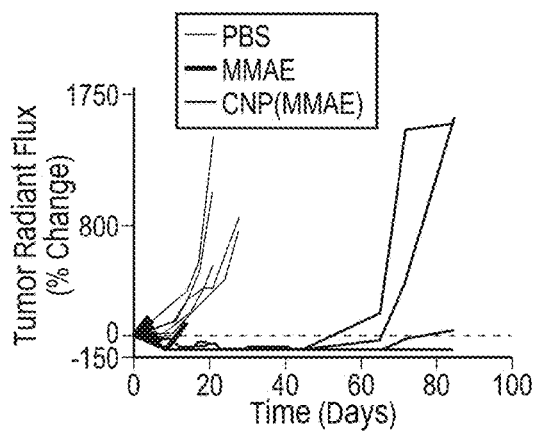

FIG. 59D is a plot of tumor burden over time as determined by changes in the radiant flux associated with the BLI signal intensity in OVCAR8 tumor-bearing nude mice that received ×4 weekly IP injections of CNP(MMAE) (at an equivalent dose of 3 mg/kg MMAE), free MMAE (at 0.25 mg/kg), or PBS (control treatment).

Figure 59E:
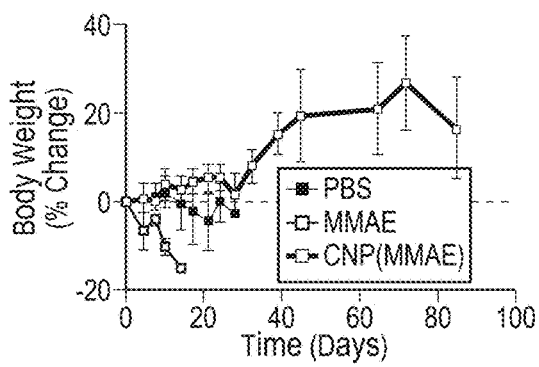

FIG. 59E is a plot of changes in the body weights as compared to baseline in OVCAR8 tumor-bearing nude mice that received ×4 weekly IP injections of CNP(MMAE) (at an equivalent dose of 3 mg/kg MMAE), free MMAE (at 0.25 mg/kg), or PBS (control treatment). p-value <0.01, *p-value <0.001.

Figure 59F:
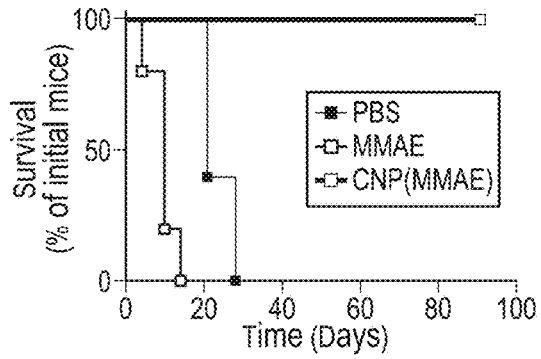

FIG. 59F is a plot of survival of OVCAR8 tumor-bearing nude mice that received ×4 weekly IP injections of CNP (MMAE) (at an equivalent dose of 3 mg/kg MMAE), free MMAE (at 0.25 mg/kg), or PBS (control treatment). p-value <0.01, *p-value <0.001.

Figure 60A:
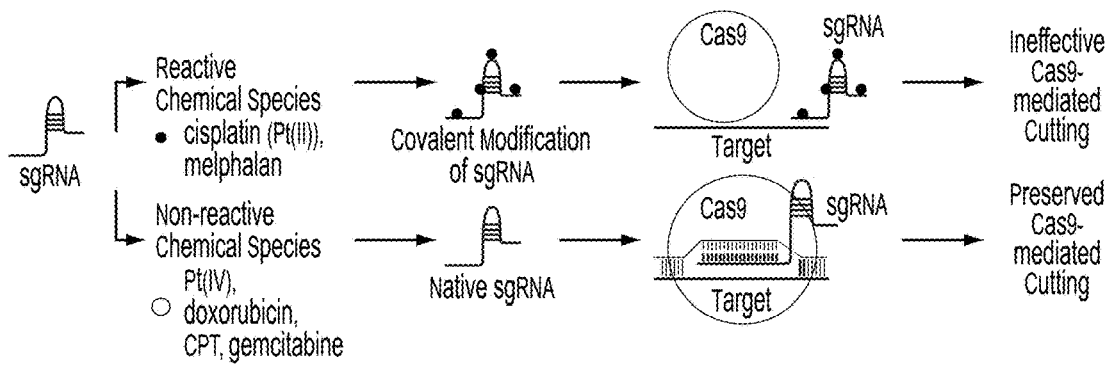

FIG. 60A is a schematic representation of reactive small molecule chemotherapeutics, such as platinum(II)-based anticancer agents (e.g. cisplatin; Pt(II)) or DNA-alkylators (e.g. melphalan), rapidly forming covalent adducts with sgRNA that prevent its binding to genomic DNA, resulting in ineffective cutting of target genes by the Cas9 nuclease. Non-reactive chemical species such as a lipophilic platinum (IV) prodrug (Pt(IV)), the topoisomerase inhibitors doxorubicin and campothecin (CPT), as well as the antimetabolite gemcitabine do not form covalent adducts with sgRNA, do not interfere with its ability to bind and recognize genomic DNA, and, hence, do not affect Cas9-mediated gene silencing.

Figure 60B:
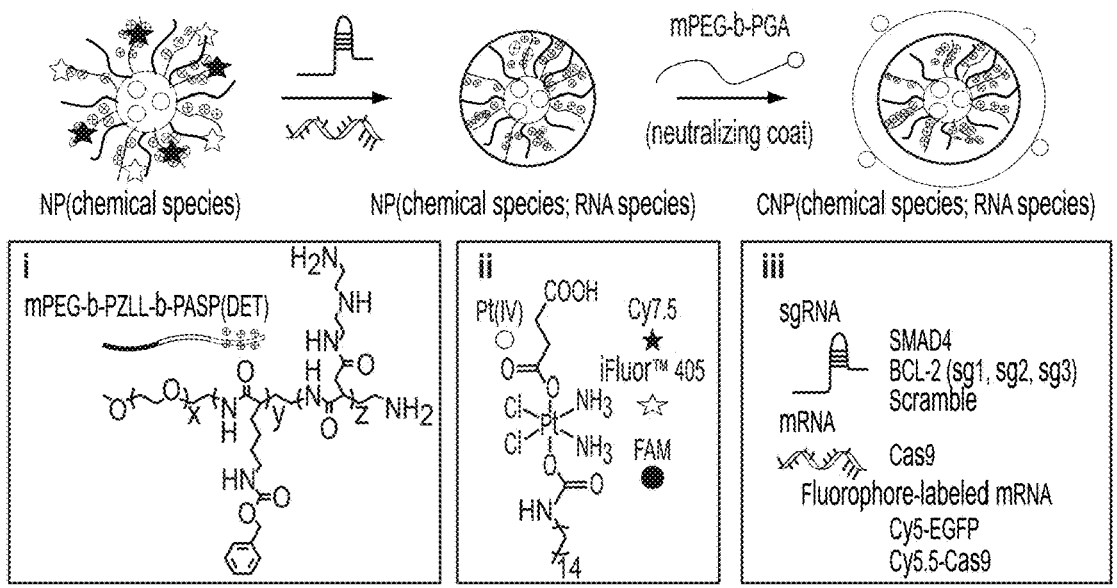

FIG. 60B is a schematic depiction of a nanoparticle composition (NP) that may be used to incorporate small molecule chemotherapeutic agents (purple circles) and/or fluorescent dyes (grey and blue stars) as well as to electrostatically complex RNA species (red). The remaining cationic charge of the core NPs is neutralized via electrostatic binding of a shell polymer (e.g. poly(ethylene glycol)-block-poly(glutamic acid); mPEG-b-PGA), forming core-shell nanoparticles (CNPs) that protect their nucleic acid payload from degradation.

Figure 60C:
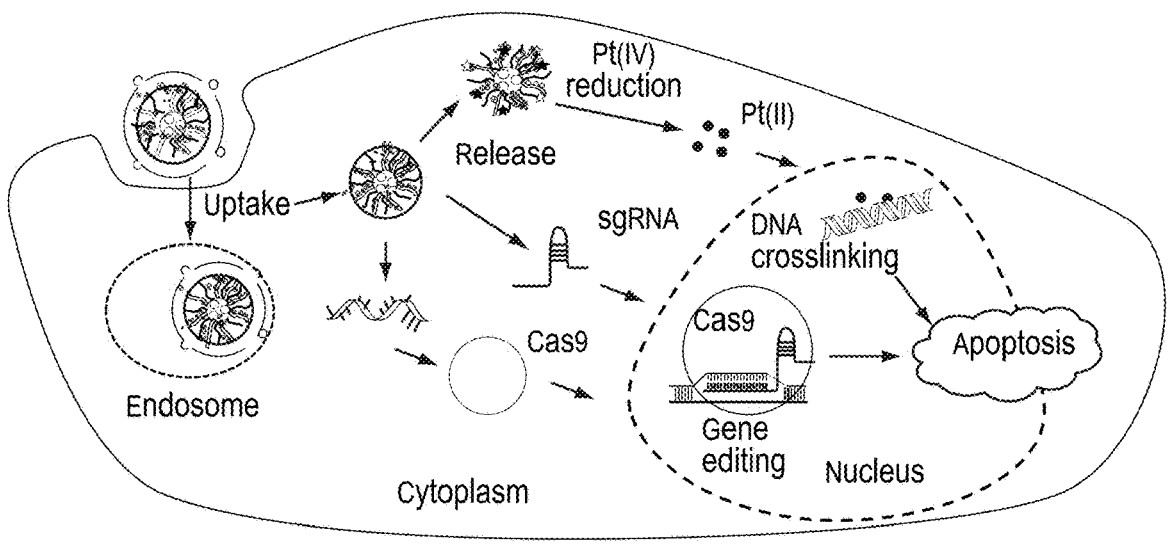

FIG. 60C is a schematic representation of uptake of into tumor cells and within their endosomes, the drop in pH (from 7.4, extracellularly, to approximately 5.5-6.0, intracellularly) results in release of the electrostatically complexed shell polymer (pKa of mPEG-b-PGA is 5.5-6.0) from the core nanoparticle followed by delivery of the RNA payload (i.e. the Cas9 mRNA and sgRNA species). Intracellular reduction of the Pt(IV) prodrug to active Pt(II) further results in its release from the nanoparticles. The CRISPR/Cas9 complex assembles in the cytoplasm and mediates cutting of target genomic DNA; released Pt(II) forms covalent Pt-DNA complexes; and, these two disparate species work in concert to augment cellular apoptosis.

Figure 61:
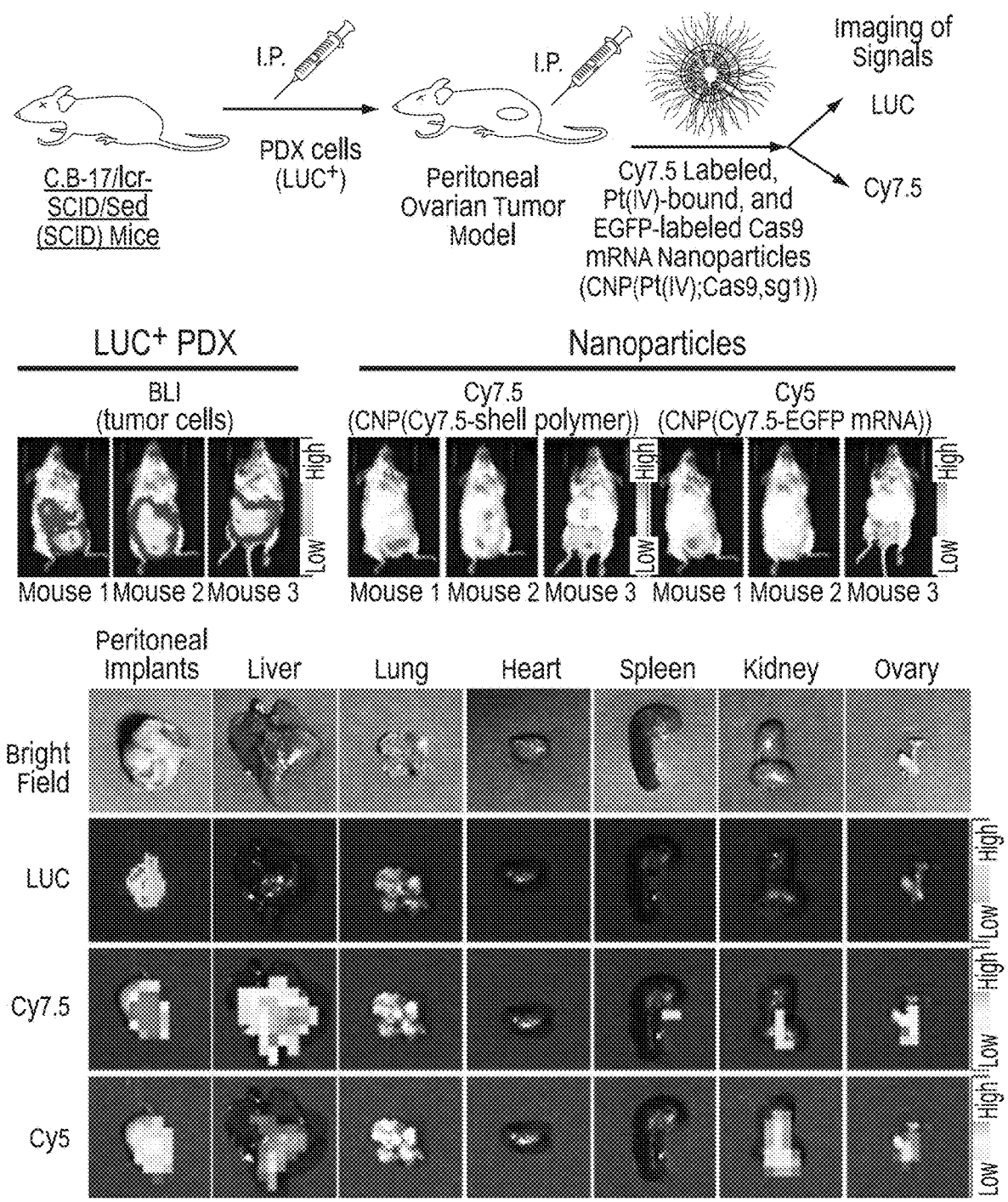

FIG. 61 shows a schematic representation and confocal images of in vivo and ex vivo biodistribution data showing co-localization of nanoparticles from FIG. 60 with peritoneal tumors in ovarian cancer PDX mice after IP injection.

FIG. 62A shows the results of silencing of BCL-2 in primary cells derived from a patient with "platinum-resistant" and high-grade serous ovarian cancer (HGSOC) as assessed by WB; Cas9 mRNA and either negative control (neg cont) or BCL-2 sgRNA (sg1) were delivered with nanoparticles that were conjugated to Pt(IV) (NP(Pt(IV)). The relative expression levels of BCL-2 (right) were determined by normalizing values to B-actin (house-keeping gene) and are displayed in comparison to control (untreated cells).

FIG. 62B is a graph showing in vitro dose response curves and corresponding $IC_{50}$ values for the same primary HGSOC cells as determined by the CCK8 cellular viability assay.

FIG. 62C are in vivo images showing biodistribution of fluorescently-tagged core-shell nanoparticles (CNPs) in PDX mice derived by IP dissemination of LUC+ primary cells from a patient with "platinum-resistant" HGSOC. BLI image (left) demonstrates peritoneal dissemination of the tumors cells; fluorescent images of Cy7.5 (middle) and Cy5 emission from the same mouse (right) depict the location of the CNPs and mRNA, respectively.

FIG. 62D is a CT image of the same mouse depicting the approximate location of the CNPs as determined by contrast enhancement afforded by their high concentrations of Pt(IV).

FIG. 62E is a plot of relative biodistribution of the BLI signals (tumor cells; blue), Cy7.5 emission (CNPs; green), Cy5 (mRNA; red) and platinum (Pt; purple) in tissues excised from 3 mice that were similarly treated and processed, demonstrating the high intratumoral delivery of Cy5.5-conjugated CNPs along with a separate CNP formulation containing Cy5-labeled mRNA.

FIG. 62F are images showing the high intratumoral delivery of Cy5.5-conjugated CNPs along with a separate CNP formulation containing Cy5-labeled mRNA.

FIG. 62G are IF images for cleaved caspase 3 (cCaspase 3) in the BCL-2 locus of PDX tumors from mice that were treated with ×2 weekly doses of various experimental groups.

FIG. 62H is a bar graph showing WB of BCL-2 expression levels in the BCL-2 locus of PDX tumors from mice that were treated with ×2 weekly doses of various experimental groups.

FIG. 62I shows next-generation sequencing for the frequency of indels in the BCL-2 locus of PDX tumors from mice that were treated with ×2 weekly doses of various experimental groups.

Figure 62L:
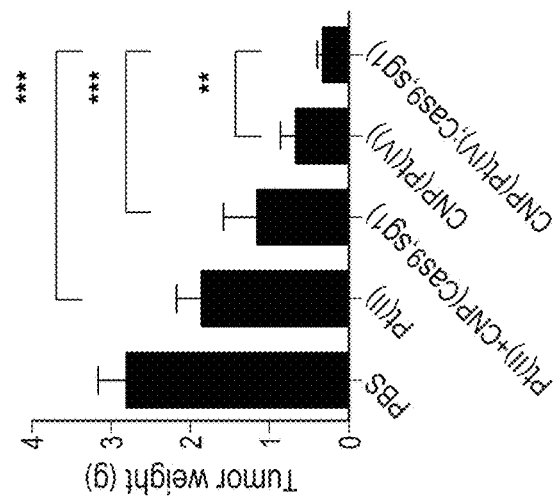
Figure 62K:
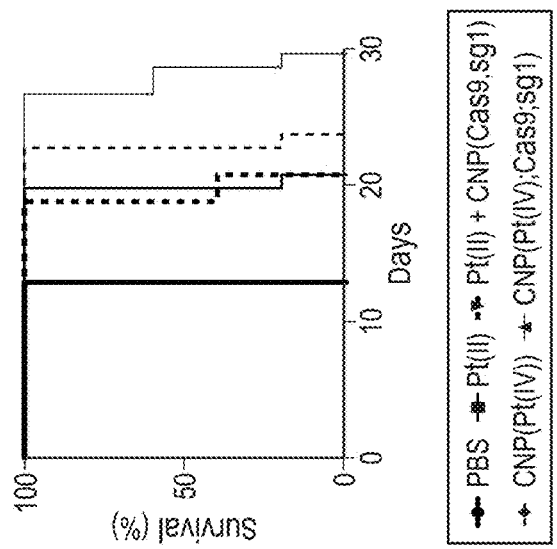
Figure 62J:
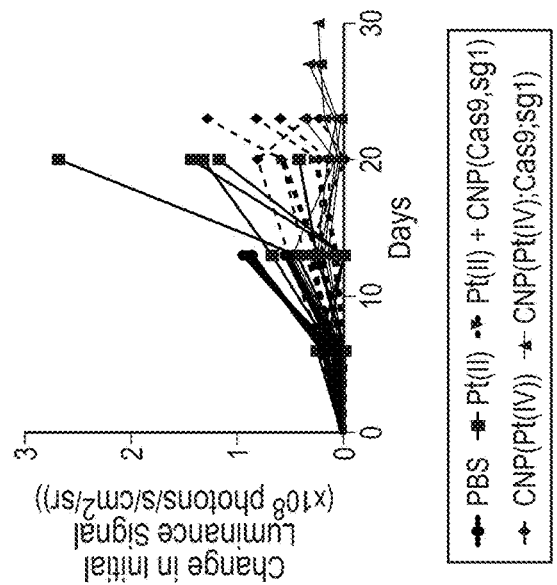

FIG. 62J is a graph showing relative inhibition of BLI signals generated from LUC+ PDX tumors excised upon sacrifice from PDX mice that were treated with ×4 weekly IP injections of each of the various experimental groups. *p<0.05, p<0.01, *p<0.001.

FIG. 62K shows the Kaplan-Meir survival curve from PDX mice that were treated with ×4 weekly IP injections of each of the various experimental groups. *p<0.05, p<0.01, *p<0.001.

FIG. 62L is a bar graph showing the weights of tumors excised upon sacrifice from PDX mice that were treated with ×4 weekly IP injections of each of the various experimental groups. *p<0.05, p<0.01, *p<0.001.

Figure 63A:
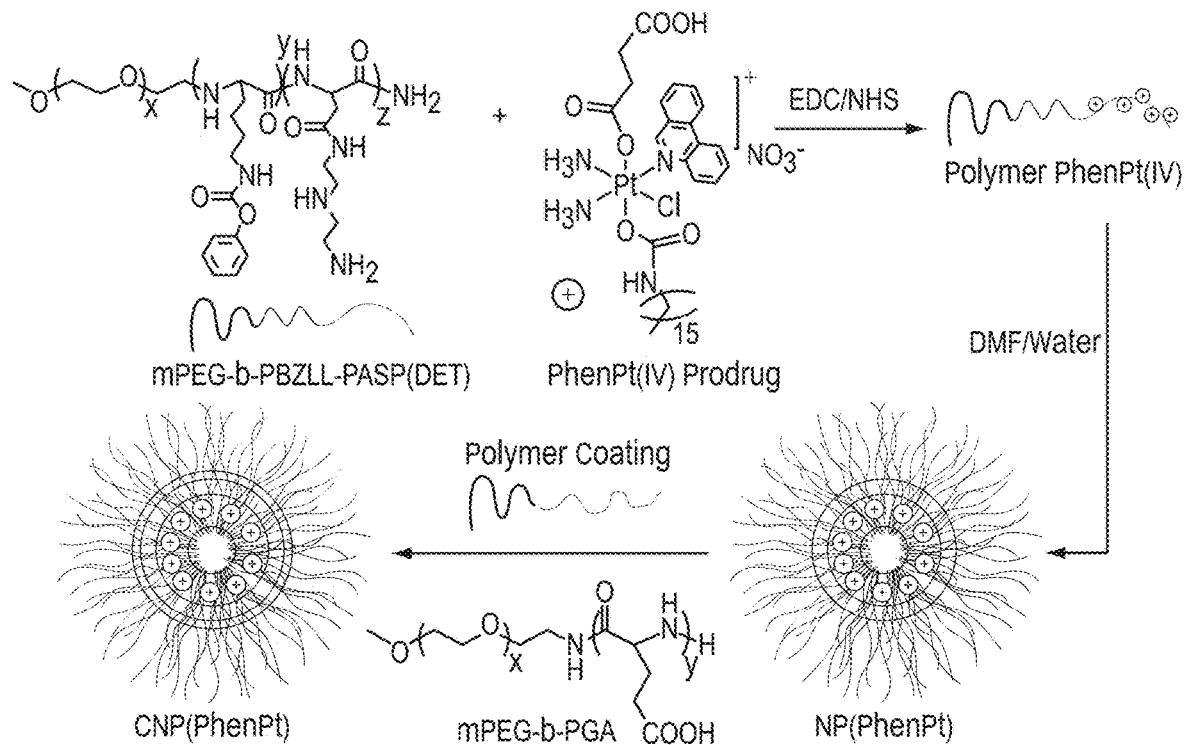

FIG. 63A is a schematic representation of a diblock copolymer of PEO-b-PGA coating nanoparticles formed from a triblock copolymer of PEO-b-PZLL-b-PASP conjugated to a phenathriplatin(IV) (PhenPt(IV)) prodrug.

Figure 63B:
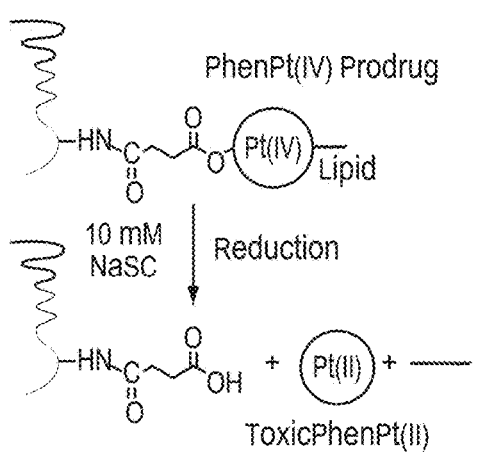

FIG. 63B is a schematic representation showing the chemical cleavage of the Pt(IV) prodrug.

Figure 63C:
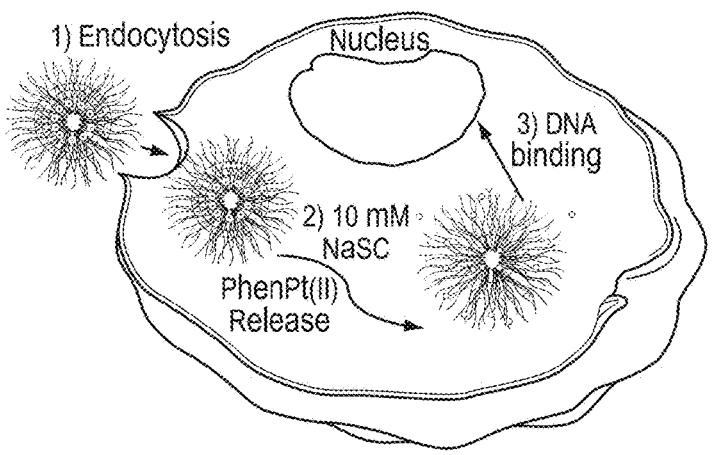

FIG. 63C is a schematic representation showing the intracellular cleavage of the Pt(IV) prodrug.

Figure 64:
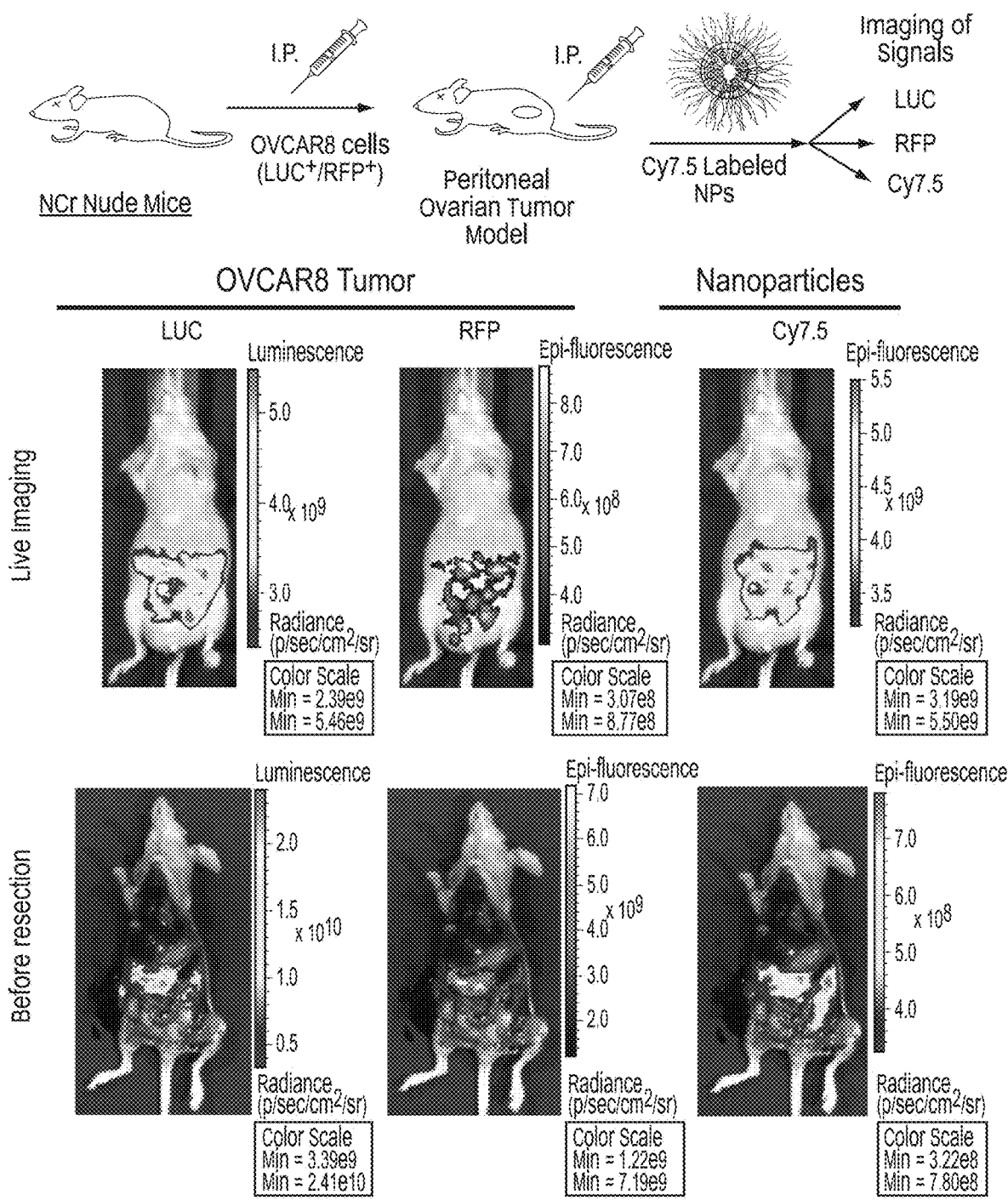

FIG. 64 shows a schematic representation and confocal images of in vivo biodistribution data showing co-localization of nanoparticles with peritoneal tumors in OVCAR8-bearing nude mice after IP injection.

FIG. 65 shows images and data relating to ex vivo biodistribution data showing co-localization of nanoparticles with peritoneal tumors in OVCAR8-bearing nude mice after IP injection.

Figure 66:
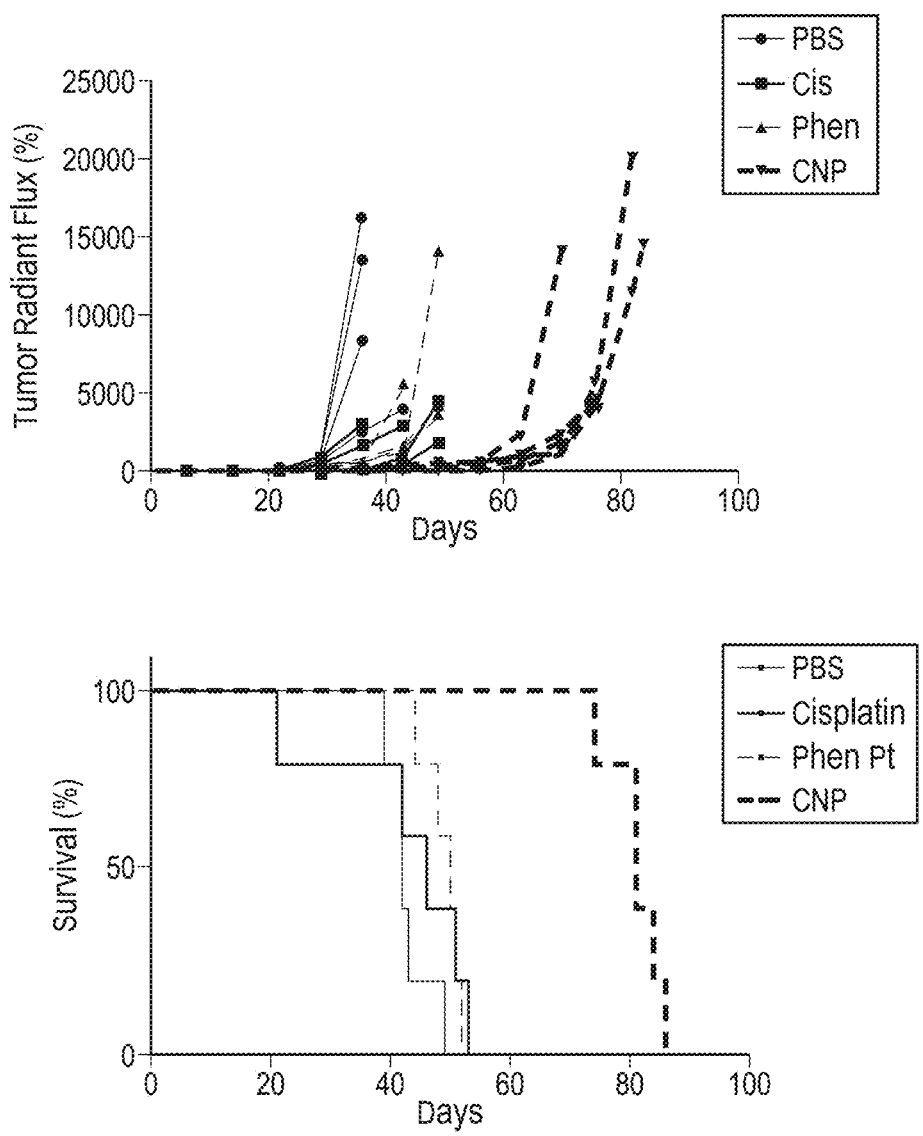

FIG. 66 are plots showing the efficacy of nanoparticle-bound phenathriplatin(CNP) to treat peritoneal tumors in OVCAR8-bearing nude mice after IP injection and as compared to controls.

Figure 67:
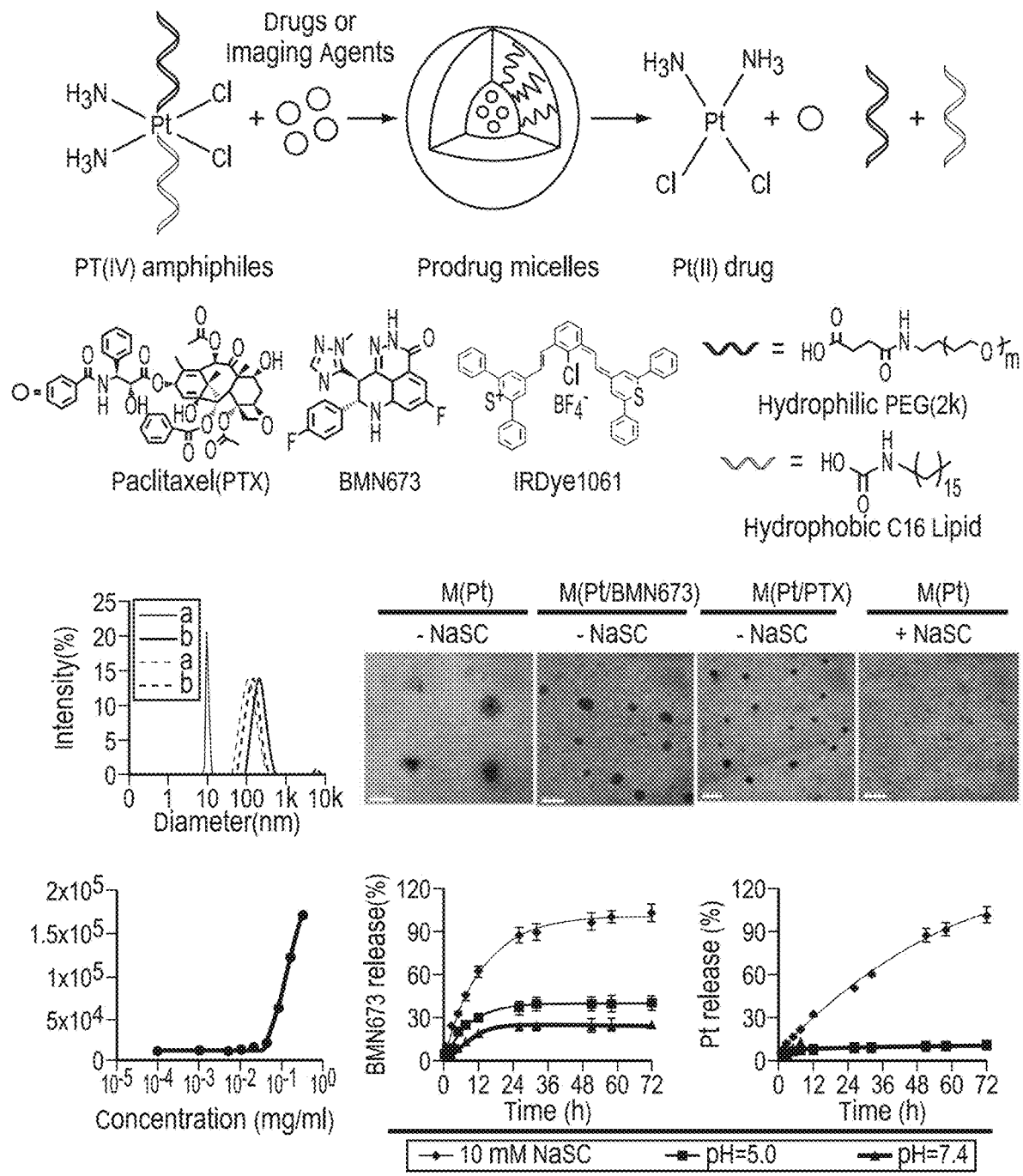

FIG. 67 is a schematic representation of, and data relating to, a platinum(IV) amphiphile that spontaneously assembles into nanoparticles with a PEG surface and that can trap drugs and/or imaging agents (e.g. IRDye1061) in its lipid cavity.

Figure 68:
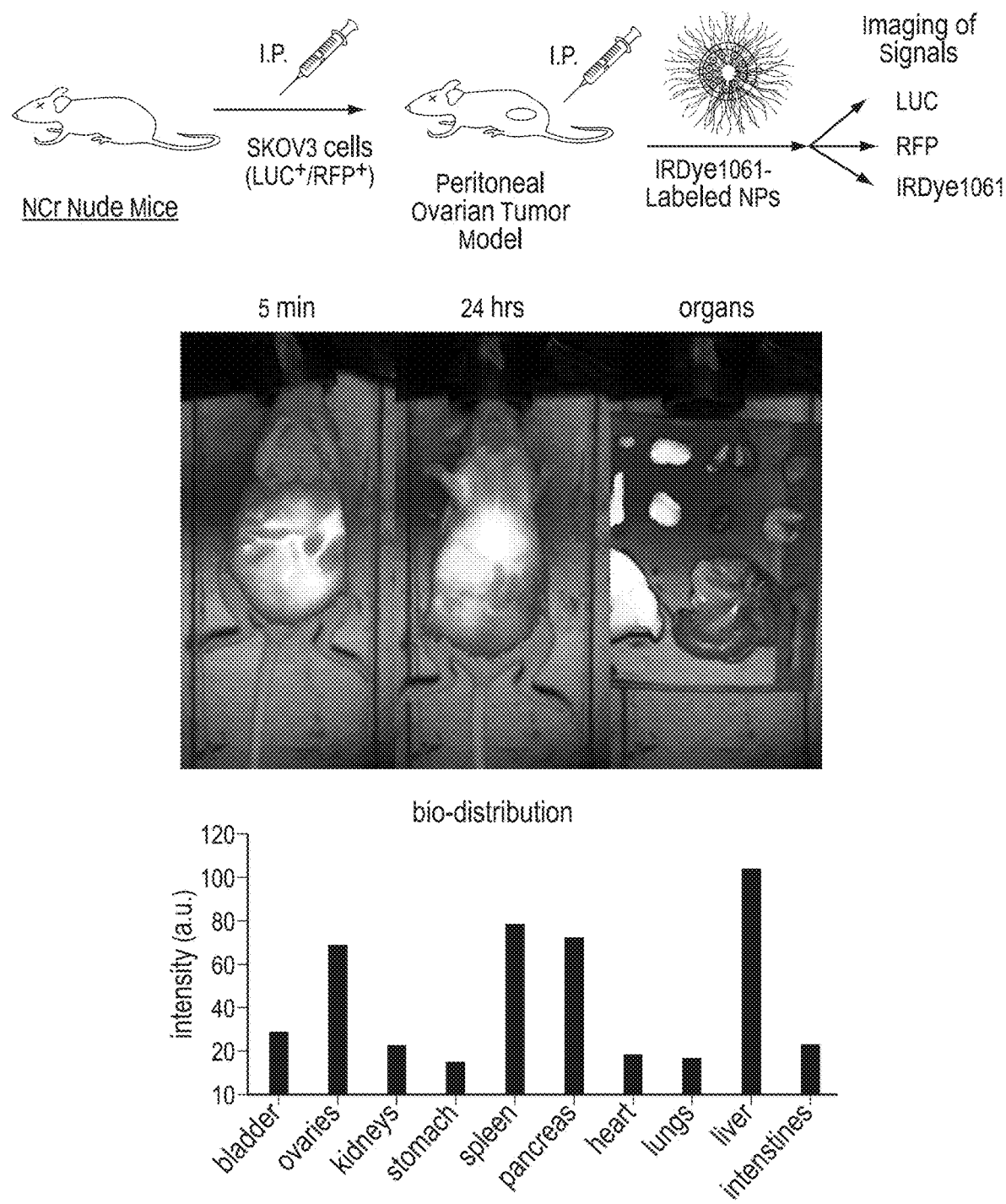

FIG. 68 shows a schematic representation, images, and data relating to in vivo biodistribution data showing co-localization of nanoparticles with peritoneal tumors in OVCAR8-bearing nude mice after IP injection.

DETAILED DESCRIPTION

Overview

In certain embodiments, the invention relates to nanoparticles that comprise highly potent toxins or anticancer agents, wherein the toxins display unprecedented activity against "platinum-resistant" EOC cells (i.e. ones with single- or sub-nanomolar $IC_{50}$s). Small molecule toxins may be chemically conjugated (as opposed to encapsulated) in NPs to enable incorporation in their prodrug form. In certain embodiments the anticancer agents are conjugated to the NPs by a linker that is cleaved in vivo under certain conditions, such as high concentrations of reductants, acidity, and/or enzymatic activity within tumor cells or in their surrounding microenvironment to release the active toxins. In certain embodiments, thousands of prodrug molecules are bound to a single NP, which increases potency as compared to ADCs on a per macromolecule basis. In certain embodiments, the NPs adopt the best features of ADCs while overcoming their limitations, as described above.

In certain embodiments, the invention relates to intraperitoneal (IP) as opposed to intravenous (IV) injection. In certain embodiments, NP conjugation followed by IP delivery improves in vivo stability, prevents premature loss, and augments tumor uptake of highly potent toxins, which helps to avoid the systemic side effects seen with ADCs. In certain embodiments, NP conjugates of prodrugs display shorter circulatory half-lives and more rapid uptake into the tumor environment as compared to their delivery via ADCs, which enables more effective utilization of tunable linker chemistries to optimize drug release properties.

In certain embodiments, the invention relates to the use of a transfection reagent comprised of biodegradable poly(ethylene glycol)-block-poly-(ε-caprolactone)-block-poly(L-lysine) triblock copolymer (i.e. PEO-b-PCL-b-PLL) that self-assembles into polymeric micelles that are capable of OxaPt(IV) conjugation or siRNA electrostatic complexation. Notably, co-incorporation of OxaPt(IV) and BCL-2 siRNA within a single micellar construct prevents siRNA transcript inactivation, promotes the highest intracellular levels of both oxaliplatin and siRNA, maximizes in vitro potency, and affords the greatest degree of synergistic biological activity.

Figure 1A:
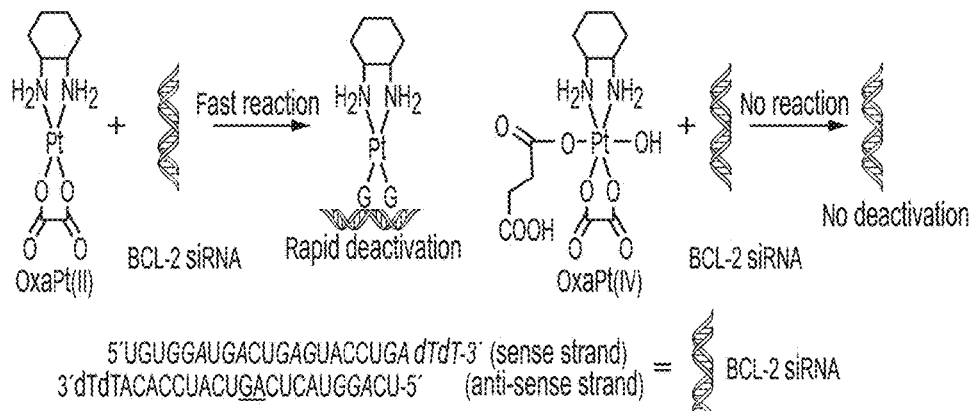
FIG. 1A is a series of two reaction schemes. On the left is shown a schematic representation of planar OxaPt(II) rapidly forming Pt-RNA adducts with BCL-2 siRNA, resulting in transcript inactivation. On the right is shown a schematic representation of kinetically inert octahedral OxaPt(IV) species, which does not form Pt-RNA adducts with BCL-2 siRNA. Notably, as seen from the sequence of the BCL-2 siRNA (bottom), platination of a single GG region in the non-seed portion of the anti-sense strand (red/underlined) would be expected to affect silencing efficacy; the sense (SEQ ID NO: 4) and anti-sense (SEQ ID NO: 3) strands also contain other potential sites for further platination (red/italics).
Figure 1B:
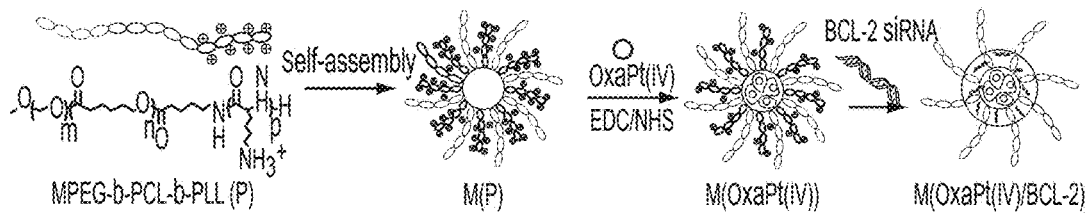
FIG. 1B is a reaction scheme for forming MPEG-b-PCL-b-PLL micelles (i.e. M(P)) incorporating OxaPt(IV) (i.e. M(OxaPt(IV)) or both OxaPt(IV) and Bcl-2 siRNA (i.e. M(OxaPt(IV)/BCL-2) in a single nanoparticle construct; note, OxaPt(IV) is linked through an amide bond while BCL-2 siRNA is bound through electrostatic complexation to amine groups on the PLL chains of the micelles.
Figure 1C:
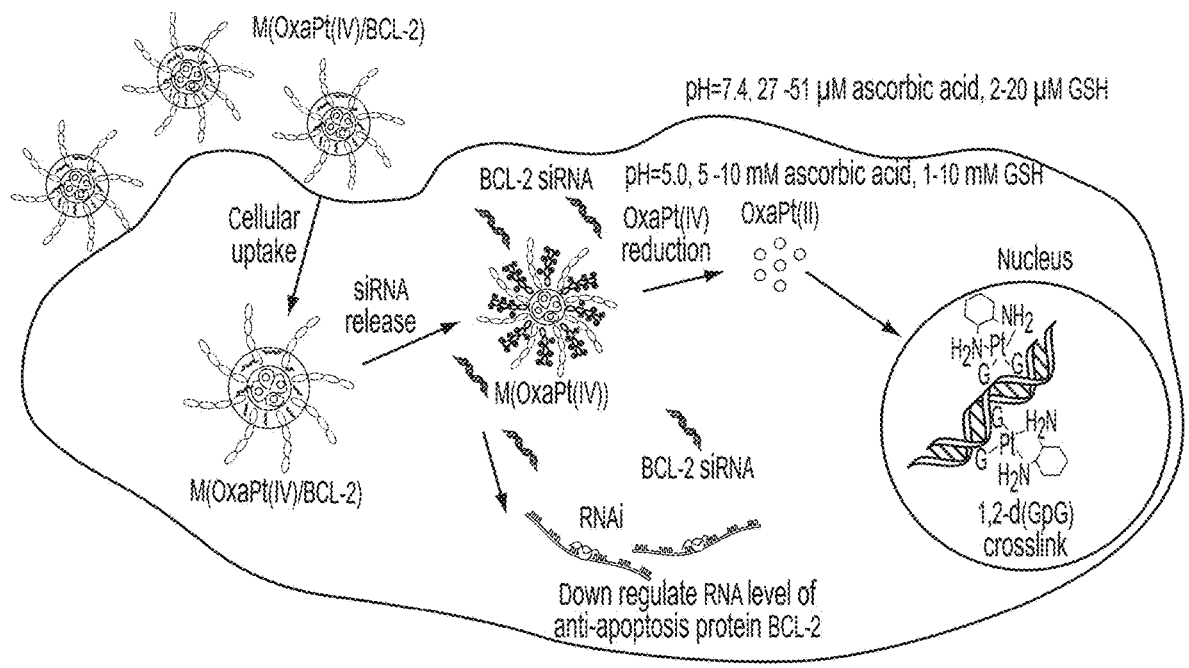
FIG. 1C is a schematic representation of the intracellular uptake and ultimate fate of M(OxaPt(IV)/Bcl-2) micelles. The micelles are taken up by endocytosis, where Bcl-2 siRNA is liberated at low pH; siRNA then enters the cytoplasm and results in suppression of BCL-2 mRNA expression. High intracellular concentrations of glutathione and ascorbic acid subsequently convert the OxaPt(IV) species to OxaPt(II), which is released due to liberation of the axial ligand on the platinum. Free OxaPt(II) subsequently binds DNA, resulting in Pt-DNA adduct formation and eventual cell death via apoptosis.
Figure 2:
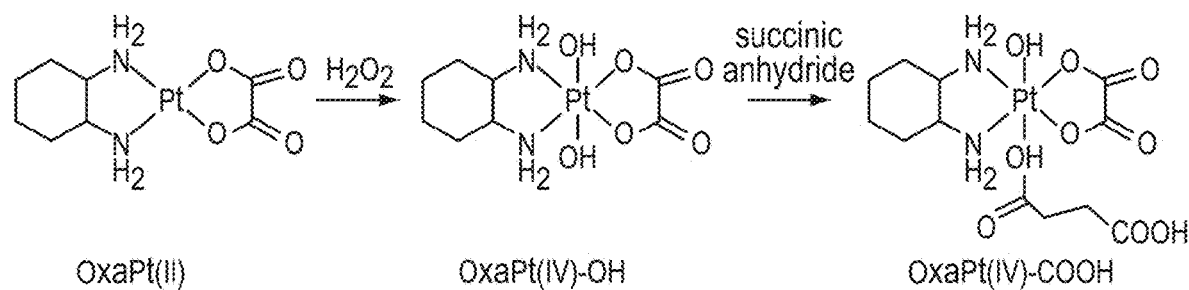
FIG. 2 is a schematic representation of the synthesis and chemical structures of OxaPt(IV)-OH and OxaPt(IV)—two platinum(IV) analogs of oxaliplatin (OxaPt(II)).
Figure 3:
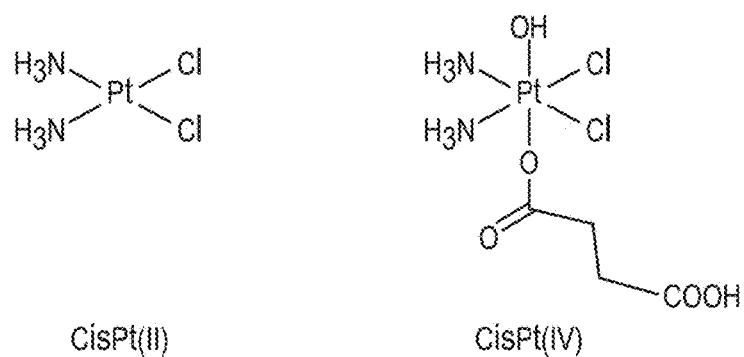
FIG. 3 is the chemical structures of cisplatin (CisPt(II)) (left) and a platinum(IV) analog (CisPt(IV)) (right).

In certain embodiments, the invention relates to the use of octahedral platinum(IV) derivatives of OxaPt(II) and CisPt(II), which derivatives would expectedly have less chemical reactivity to guanine and adenine nucleotides (FIG. 1A, FIG. 2, FIG. 3). These platinum(IV) derivatives are converted to the active platinum(II) species only after cellular uptake, due to increased quantities of reductants found within cancer cells (e.g. 5-10 mM concentrations of glutathione and ascorbic acid exist intracellular as compared to 20-50 uM in either normal cells or within the extracellular milieu). The MCF-7 breast cancer and the OVCAR4 ovarian cancer cell lines were employed as in vitro model systems and the anti-apoptosis protein BCL-2 was selected as the target for RNAi; BCL-2 up-regulation has previously been shown to promote acquired platinum resistance in various malignancies. As an exemplary polynucleotide, a double-stranded siRNA transcript that contains multiple GG and GA regions but only a single GG sequence outside of the seed portion in the antisense strand was used; platination at this site would expectedly result in maximal thermal destabilization with decreased mRNA silencing (FIG. 1A). A nanoparticle transfection reagent comprised of the triblock copolymer of poly(ethylene glycol)-block-poly-(ε-caprolactone)-block-poly(L-lysine) (i.e. PEO-b-PCL-b-PLL) was further utilized to bind OxaPt(IV) and/or siRNA (FIG. 1B); it was employed to develop an optimal intracellular delivery strategy for combining RNAi and platinum-based small molecules (FIG. 1C).

In certain embodiments, the invention relates to water-soluble contrast agents for in vivo imaging comprising LNPs coated with a diblock copolymer of poly(ethylene oxide)-block-poly(ε-caprolactone) (PEO-b-PCL). The core of these core-shell nanoparticles comprise sodium yttrium fluoride (NaYF4) doped with ytterbium (Yb) and either erbium (Er) or holmium (Ho) with or without thulium (Tm). Yb served as an acceptor ion that absorbed excitation light at 980 nm while Er, Tm, and Ho then generated various visible and NIR-I emission bands (through UC energy transfer) as well as signals in the NIR-II spectrum (through a normal DC emission process). In certain embodiments, the nanoparticles are biodegradable, exhibit prolonged circulatory half-lives, and evade in vivo immune recognition and uptake. PCL is known to slowly degrade through hydrolysis of ester linkages, leading to safe byproducts that have not affected local pH nor induced otherwise deleterious environmental reactions. In certain embodiments, the particles further comprise a lipophilic carbocyanine dye, such as 1,1'-dioctadecyl-3,3,3',3'-tetramethylindotricarbocyanine iodide (DiR), which enable direct comparisons between imaging of NIR-I DC emission from this conventional organic fluorophore (in the nanoparticle shell) to detection of NIR-I UC and NIR-II DC emissive bands generated from the inorganic LNPs (in the nanoparticle core).

Glossary

As used herein, the term "monomer," unless otherwise indicated, includes both isolated monomers and residues of monomers in an oligomer or a polymer (i.e. repeat units or residues).

The term "alkyl," as used herein, refers to a saturated aliphatic branched or straight-chain monovalent hydrocarbon radical having the specified number of carbon atoms. Thus, "$C_1$-$C_6$ alkyl" means a radical having from 1-6 carbon atoms in a linear or branched arrangement. Examples of "$C_1$-$C_6$ alkyl" include, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl. An alkyl can be optionally substituted with halogen, —OH, $C_1$-$C_6$ alkyl, $C_1$-$C_6$ alkoxy, $C_6$-$C_{18}$ aryl, —$NO_2$, —CN, and —$N(R^1)(R^2)$ wherein $R^1$ and $R^2$ are each independently selected from —H and $C_1$-$C_3$ alkyl.

The term "alkenyl," as used herein, refers to a straight-chain or branched alkyl group having one or more carbon-carbon double bonds. Thus, "$C_2$-$C_6$ alkenyl" means a radical having 2-6 carbon atoms in a linear or branched arrangement having one or more double bonds. Examples of "$C_2$-$C_6$ alkenyl" include ethenyl, propenyl, butenyl, pentenyl, hexenyl, butadienyl, pentadienyl, and hexadienyl. An alkenyl can be optionally substituted with the substituents listed above with respect to alkyl.

The term "carbocyclyl," as used herein, refers to refers to a ring system (monocyclic or polycyclic, including fused) wherein each of the atoms forming the ring is a carbon atom. Carbocyclyes include aryl and cycloalkyl rings. A carbocyclyl can be optionally substituted with the substituents listed above with respect to alkyl.

The term "cycloalkyl," as used herein, refers to a saturated monocyclic or fused polycyclic ring system containing from 3-12 carbon ring atoms. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. A cycloalkyl can be optionally substituted with the substituents listed above with respect to alkyl.

The term "amino," as used herein, means an "—NH$_2$," an "NHR$_p$," or an "NR$_p$R$_q$," group, wherein R$_p$ and R$_q$ can be alkyl, alkenyl, alkynyl, alkoxy, cycloalkyl, aryl, and heteroaryl. Amino may be primary (NH$_2$), secondary (NHR$_p$) or tertiary (NR$_p$R$_q$).

The term "alkylamino," which includes "cycloalkylamino," as used herein, refers to an "NHR$_p$," or an "NR$_p$R$_q$" group, wherein R$_p$ and R$_q$ can be alkyl, or cycloalkyl. The term "dialkylamino," as used herein, refers to an "NR$_p$R$_q$" group, wherein R$_p$ and R$_q$ can be alkyl, or cycloalkyl.

The term "alkoxy", as used herein, refers to an "alkyl-O—" group, wherein alkyl is defined above. Examples of alkoxy group include methoxy or ethoxy groups. The "alkyl" portion of alkoxy can be optionally substituted as described above with respect to alkyl.

The term "aryl," as used herein, refers to an aromatic monocyclic or polycyclic ring system consisting of carbon atoms. Thus, "C$_6$-C$_{18}$ aryl" is a monocylic or polycyclic ring system containing from 6 to 18 carbon atoms. Examples of aryl groups include phenyl, indenyl, naphthyl, azulenyl, heptalenyl, biphenyl, indacenyl, acenaphthylenyl, fluorenyl, phenalenyl, phenanthrenyl, anthracenyl, cyclopentacyclooctenyl or benzocyclooctenyl. An aryl can be optionally substituted with halogen, —OH, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_6$-C$_{18}$ aryl, C$_6$-C$_{18}$ haloaryl, (5-20 atom) heteroaryl, —C(O)C$_1$-C$_3$ haloalkyl, —S(O)$_2$—, —NO$_2$, —CN, and oxo.

The terms "halogen," or "halo," as used herein, refer to fluorine, chlorine, bromine, or iodine.

The term "heterocyclyl," as used herein, refers to a non-aromatic ring having at least one heteroatom or a heteroaryl ring. containing one to four heteroatoms each selected from O, S, and N, wherein each heterocyclic group has from 4 to 10 atoms in its ring system. Herein, whenever the number of carbon atoms in a heterocycle is indicated (e.g., C$_1$-C$_6$ heterocycle), at least one other atom (the heteroatom) must be present in the ring. Designations such as "C$_1$-C$_6$ heterocycle" refer only to the number of carbon atoms in the ring and do not refer to the 25 total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. A heterocyclyl can be optionally substituted with the substituents listed above with respect to alkyl. Binding to a heterocycle can be at a heteroatom or via a carbon atom.

The term "heteroaryl," as used herein, refers a monocyclic or fused polycyclic aromatic ring containing one or more heteroatoms, such as oxygen, nitrogen, or sulfur. For example, a heteroaryl can be a "5-20 atom heteroaryl," which means a 5 to 20 membered monocyclic or fused polycyclic aromatic ring containing at least one heteroatom. Examples of heteroaryl groups include pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. A heteroaryl can be optionally substituted with the same substituents listed above with respect to aryl.

The term "haloalkyl," as used herein, includes an alkyl substituted with one or more of F, Cl, Br, or I, wherein alkyl is defined above. The "alkyl" portion of haloalkyl can be optionally substituted as described above with respect to alkyl.

The term "haloaryl," as used herein, includes an aryl substituted with one or more of F, Cl, Br, or I, wherein aryl is defined above. The "aryl" portion of haloaryl can be optionally substituted as described above with respect to aryl.

The term "oxo," as used herein, refers to =O.

The term "nitro," as used herein, refers to —NO$_2$.

"$\sim\!\sim\!\sim$" as used herein, refers to a point of attachment between two atoms.

In certain embodiments, linkers (also known as "linker molecules" or "cross-linkers" or "spacers") may be used to conjugate one atom to another in a composition. The majority of known linkers react with amine, carboxyl, and sulfhydryl groups. Linker molecules may be responsible for different properties of the composition. The length of the linker should be considered in light of molecular flexibility during the conjugation step, and the availability of the conjugated molecule for its target. Longer linkers may thus improve the biological activity of the compositions of the invention, as well as the ease of preparation of them. The geometry of the linker may be used to orient a molecule for optimal reaction with a target. A linker with flexible geometry may allow the entire composition to conformationally adapt as it binds a target sequence. The nature of the linker may be altered for other various purposes. For example, the hydrophobicity of a polymeric linker may be controlled by the order of monomeric units along the polymer, e.g. a block polymer in which there is a block of hydrophobic monomers interspersed with a block of hydrophilic monomers.

The chemistry of preparing and utilizing a wide variety of molecular linkers is well-known in the art and many premade linkers for use in conjugating molecules are commercially available from vendors such as Pierce Chemical Co., Roche Molecular Biochemicals, United States Biological. Exemplary linker molecules for use in the compositions of the invention include, but are not limited to: aminocaproic acid (ACA); polyglycine, and any other amino acid polymer, polymers such as polyethylene glycol (PEG), polymethyl methacrylate (PMMA), polypropylene glycol (PPG); homobifunctional reagents such as APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS; heterobifunctional reagents such as ABH, AEDP, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, MBuS, M2C2H, MPBH, MSA, NHS-ASA, PDPH, PMPI, SADP, SAED. SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MB S. Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS; and trifunctional linkers such as Sulfo-SBED.

Branched linkers may be prepared or used so that multiple moieties per linker are able to react. Such multiply reactive linkers allow the creation of multimeric binding sites.

The term "pKa," as used herein, includes the negative decadic logarithm of the ionization constant ($K_a$) of an acid; equal to the pH value at which equal concentrations of the acid and conjugate base forms of a substance (often a buffer) are present.

The term "hydrophobic," as used herein, refers to a compound that has an octanol/water partition coefficient ($K_{ow}$) greater than about 10 at about 23° C.

The term "hydrophilic," as used herein, refers to a compound that has an octanol/water partition coefficient ($K_{ow}$) less than about 10 at about 23° C.

A therapeutically effective amount can be achieved in the methods or compositions of the invention by co-administering a first amount of a first agent, for example a nucleic acid or an enzyme, and a second amount of at least one second agent, for example an anticancer agent or a second nucleic acid. In one embodiment, the two agents are each administered in a therapeutically effective amount (i.e., each in an amount which would be therapeutically effective if administered alone). In another embodiment, the first agent and the second agent are each administered in an amount which alone does not provide a therapeutic effect (a sub-therapeutic dose). In yet another embodiment, the first agent can be administered in a therapeutically effective amount, while the second agent is administered in a sub-therapeutic dose. In still another embodiment, the first agent can be administered in a sub-therapeutic dose, while the second agent is administered in a therapeutically effective amount. In example embodiment, the compositions exhibit enhanced therapeutic effect (synergy) compared to either the first agent or the second agent alone, or their expected additive effect.

As used herein, the term "pharmaceutically acceptable carrier" refers to a pharmaceutically-acceptable material, composition or vehicle for administration of an active agent described herein. Pharmaceutically acceptable carriers include any and all solvents, dispersion media, coatings, antibacterial and antifungal agents, isotonic and absorption delaying agents, and the like which are compatible with the activity of the active agent and are physiologically acceptable to the subject. Some examples of materials which can serve as pharmaceutically-acceptable carriers include: (i) sugars, such as lactose, glucose and sucrose; (ii) starches, such as corn starch and potato starch; (iii) cellulose, and its derivatives, such as sodium carboxymethyl cellulose, methylcellulose, ethyl cellulose, microcrystalline cellulose and cellulose acetate; (iv) powdered tragacanth; (v) malt; (vi) gelatin; (vii) lubricating agents, such as magnesium stearate, sodium lauryl sulfate and talc; (viii) excipients, such as cocoa butter and suppository waxes; (ix) oils, such as peanut oil, cottonseed oil, safflower oil, sesame oil, olive oil, corn oil and soybean oil; (x) glycols, such as propylene glycol; (xi) polyols, such as glycerin, sorbitol, mannitol and polyethylene glycol (PEG); (xii) esters, such as ethyl oleate and ethyl laurate; (xiii) agar; (xiv) buffering agents, such as magnesium hydroxide and aluminum hydroxide; (xv) alginic acid; (xvi) pyrogen-free water; (xvii) isotonic saline; (xviii) Ringer's solution; (xix) ethyl alcohol; (xx) pH buffered solutions; (xxi) polyesters, polycarbonates and/or polyanhydrides; (xxii) bulking agents, such as polypeptides and amino acids (xxiii) serum component, such as serum albumin, HDL and LDL; (xxiv) $C_2$-$C_{12}$ alcohols, such as ethanol; and (xxv) other non-toxic compatible substances employed in pharmaceutical formulations. Wetting agents, coloring agents, release agents, coating agents, sweetening agents, flavoring agents, perfuming agents, preservative and anti-oxidants can also be present in the formulation. For formulations described herein to be administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutically acceptable carriers can vary in a formulation described herein, depending on the administration route. The formulations described herein can be delivered via any administration mode known to a skilled practitioner. For example, the formulations described herein can be delivered in a systemic manner, via administration routes such as, but not limited to, oral, and parenteral including intravenous, intramuscular, intraperitoneal, intradermal, and subcutaneous. In some embodiments, the formulations described herein are in a form that is suitable for injection. In other embodiments, the formulations described herein are formulated for oral administration.

When administering parenterally, a formulation described herein can be generally formulated in a unit dosage injectable form (solution, suspension, emulsion). The formulations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g., PBS).

The formulations can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to formulations described herein, however, any vehicle, diluent, or additive used should have to be biocompatible with the active agents described herein. Those skilled in the art will recognize that the components of the formulations should be selected to be biocompatible with respect to the active agent. This will present no problem to those skilled in chemical and pharmaceutical principles, or problems can be readily avoided by reference to standard texts or by simple experiments (not involving undue experimentation).

For in vivo administration, the formulations described herein can be administered with a delivery device, e.g., a syringe. Accordingly, an additional aspect described herein provides for delivery devices comprising at least one chamber with an outlet, wherein the at least one chamber comprises a pre-determined amount of any formulation described herein and the outlet provides an exit for the formulation enclosed inside the chamber. In some embodiments, a delivery device described herein can further comprise an actuator to control release of the formulation through the outlet. Such delivery device can be any device to facilitate the administration of any formulation described herein to a subject, e.g., a syringe, a dry powder injector, a nasal spray, a nebulizer, or an implant such as a microchip, e.g., for sustained-release or controlled release of any formulation described herein.

The nomenclature used to define the peptides is that typically used in the art wherein the amino group at the N-terminus appears to the left and the carboxyl group at the C-terminus appears to the right.

As used herein, the term "amino acid" includes both a naturally occurring amino acid and a non-natural amino acid. The term "amino acid," unless otherwise indicated, includes both isolated amino acid molecules (i.e. molecules that include both, an amino-attached hydrogen and a carbonyl carbon-attached hydroxyl) and residues of amino acids (i.e. molecules in which either one or both an amino-attached hydrogen or a carbonyl carbon-attached hydroxyl are removed). The amino group can be alpha-amino group, beta-amino group, etc. For example, the term "amino acid alanine" can refer either to an isolated alanine H-Ala-OH or to any one of the alanine residues H-Ala-, -Ala-OH, or -Ala-. Unless otherwise indicated, all amino acids found in the compounds described herein can be either in D or L configuration. The term "amino acid" includes salts thereof, including pharmaceutically acceptable salts. Any amino acid can be protected or unprotected. Protecting groups can be attached to an amino group (for example alpha-amino group), the backbone carboxyl group, or any functionality of the side chain. As an example, phenylalanine protected by a benzyloxycarbonyl group (Z) on the alpha-amino group would be represented as Z-Phe-OH.

A protected amino acid is an amino acid in which one or more functional groups are protected with a protecting group. A protected peptide fragment is a dipeptide, tripeptide, or tetrapeptide, in which one or more functional groups of the amino acid of the peptide fragment are protected with a protecting group. Preferably, the protected amino acid and/or protected peptide fragment of the present invention have a protected amino group. The term "amino protecting group" refers to protecting groups which can be used to replace an acidic proton of an amino group in order to reduce its nucleophilicity.

Examples of amino protecting groups (e.g. $X^1$, $X^2$, $X^3$, $X^4$, etc.) include but are not limited to substituted or unsubstituted groups of acyl type, such as the formyl, acrylyl (Acr), benzoyl (Bz), acetyl (Ac), trifluoroacetyl, substituted or unsubstituted groups of aralkyloxycarbonyl type, such as the benzyloxycarbonyl (Z), p-chlorobenzyloxycarbonyl, p-bromobenzyloxycarbonyl, p-nitrobenzyloxycarbonyl, p-methoxybenzyloxycarbonyl, benzhydryloxycarbonyl, 2(p-biphenylyl)isopropyloxycarbonyl, 2-(3,5-dimethoxyphenyl)isopropyloxycarbonyl, p-phenylazobenzyloxycarbonyl, triphenylphosphonoethyloxycarbonyl or 9-fluorenylmethyloxycarbonyl group (Fmoc), substituted or unsubstituted groups of alkyloxycarbonyl type, such as the tert-butyloxycarbonyl (BOC), tert-amyloxycarbonyl, diisopropylmethyloxycarbonyl, isopropyloxycarbonyl, ethyloxycarbonyl, allyloxycarbonyl, 2 methyl sulphonylethyloxycarbonyl or 2,2,2-trichloroethyloxycarbonyl group, groups of cycloalkyloxycarbonyl type, such as the cyclopentyloxycarbonyl, cyclohexyloxycarbonyl, adamantyloxycarbonyl or isobornyloxycarbonyl group, and groups containing a hetero atom, such as the benzenesulphonyl, p-toluenesulphonyl, mesitylenesulphonyl, methoxytrimethylphenylsulphonyl, 2-nitrobenzenesulfonyl, 2-nitrobenzenesulfenyl, 4-nitrobenzenesulfonyl or 4-nitrobenzenesulfenyl group. Among these groups X, those comprising a carbonyl, a sulfenyl or a sulphonyl group are preferred. An amino protecting groups $X^1$, $X^2$, $X^3$, $X^4$, etc. is preferably selected from allyloxycarbonyl groups, tert-butyloxycarbonyl (BOC), benzyloxycarbonyl (Z), 9 fluorenylmethyloxycarbonyl (Fmoc), 4-nitrobenzenesulfonyl (Nosyl), 2-nitrobenzenesulfenyl (Nps) and substituted derivatives.

Preferred amino protecting groups $X^1$, $X^2$, $X^3$, $X^4$, etc. for the process of the present invention are tert-butyloxycarbonyl (Boc), a 9-fluorenylmethyloxycarbonyl (Fmoc), and a benzyloxy-carbonyl (Z). Even more preferred amino protecting groups for the process of the present invention are tert-butyloxycarbonyl (Boc) and a benzyloxy-carbonyl (Z).

Amino protecting groups $X^1$, $X^2$, $X^3$, $X^4$, etc. can be introduced by various methods as known in the art. For example, by reaction with suitable acid halides or acid anhydrides. On the other hand, amino protecting groups $X^1$, $X^2$, $X^3$, $X^4$, etc. can be removed (i.e., the step of deprotecting), for example, by acidolysis, hydrogenolysis (e.g., in the presence of hydrogen (e.g. bubbled through the liquid reaction medium) and catalyst such as palladium catalyst), treatment with dilute ammonium hydroxide, treatment with hydrazine, treatment with sodium and treatment with sodium amide.

As used herein, the term "peptide fragment" refers to two or more amino acids covalently linked by at least one amide bond (i.e. a bond between an amino group of one amino acid and a carboxyl group of another amino acid selected from the amino acids of the peptide fragment). The terms "polypeptide" and "peptide fragments" are used interchangeably. The term "peptide fragment" includes salts thereof, including pharmaceutically acceptable salts.

The term "DNA editing template," as used herein refers to an exogenous strand of DNA that bears homology arms to a section of genomic DNA that has been cut by a nuclease (CAS9, TALEN or zinc finger) along with an intervening sequence between these homology arms that differs with the natural segment of genomic DNA that has been cut. This intervening segment serves as the template for repair of the cut genomic DNA; and, in so doing, the cell corrects it own DNA to match that of the DNA template. The DNA template may be included in a single DNA expression vector that also encodes the nuclease.

The term "guide RNA," as used herein, includes an engineered, non-naturally occurring Clustered Regularly Interspaced Short Palindromic Repeats (CRISPR) guide RNA that hybridizes with a target nucleic acid sequence of interest.

The term "Cas9 mRNA," as used herein, includes a nucleotide sequence encoding a Type-II Cas9 protein.

The CRISPR-Cas system is useful for precise editing of genomic nucleic acids (e.g., for creating null mutations). In such embodiments, the CRISPR guide RNA and/or the Cas enzyme may be expressed. For example, a composition containing only the guide RNA can be administered to an animal or cells transgenic for the Cas9 enzyme. Similar strategies may be used (e.g., designer zinc finger, transcription activator-like effectors (TALEs) or homing meganucleases). Such systems are well known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011)

Nat. Biotech. 29:135-136; Boch et al. (2009) Science 326: 1509-1512; Moscou and Bogdanove (2009) Science 326: 1501; Weber et al. (2011) PLoS One 6:e19722; Li et al. (2011) Nucl. Acids Res. 39:6315-6325; Zhang et al. (2011) Nat. Biotech. 29:149-153; Miller et al. (2011) Nat. Biotech. 29:143-148; Lin et al. (2014) Nucl. Acids Res. 42:e47).

The CRISPR-Cas system is known in the art for incorporating transgenes. By "transgene" is meant any nucleotide sequence, particularly a DNA sequence, that is integrated into one or more chromosomes of a host cell by human intervention, such as by the methods of the present invention. In one embodiment, a transgene is an "RNA coding region." In another embodiment the transgene comprises a "gene of interest." In other embodiments the transgene may be a nucleotide sequence, preferably a DNA sequence, that is used to mark the chromosome where it has integrated or may indicate a position where nucleic acid editing, such as by the CRISPR-CAS system, may occur. In this situation, the transgene does not have to comprise a gene that encodes a protein that may be expressed.

A "gene of interest" is a nucleic acid sequence that encodes a protein or other molecule, such as an RNA or targeting nucleic acid sequence, that is desirable for integration in a host cell. The gene of interest may be a 1, 2, 3, 4, 5, 6, 7, 8, 9, 10, or more genes of interest.
Genes of interest are useful for modulating the expression and/or activity of target biomolecules either within the transduced cell or expressed for secretion outside of the transduced cell. Generally, genes of interest may be nucleic acids themselves or encode a polypeptide, a naturally-occurring binding partner of a target of interest, an antibody against a target of interest, a combination of antibodies against a target of interest and antibodies against other immune-related targets, an agonist or antagonist of a target of interest, a peptidomimetic of a target of interest, a peptidomimetic of a target of interest, a small RNA directed against or a mimic of a target of interest, and the like. Such modulators are well known in the art and include, for example, an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule such as a Piwi RNA, triplex oligonucleotide, ribozyme, coding sequence for a target of interest. Such agents modulate the expression and/or activity of target biomolecules, which includes any decrease in expression or activity of the target biomolecule of at least about 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more as compared to the expression or activity of the target biomolecule which has not been targeted by a modulating agent.

In one embodiment, the gene of interest is useful for overexpressing and/or enhancing the activity of a nucleic acid or protein of interest. For example, the gene of interest may encode a protein or other molecule the expression of which is desired in the host cell. Such protein-encoding nucleic acid sequences are not particularly limited and are selected based on the desired exogenous perturbation desired. Thus, the gene of interest includes any gene that the skilled practitioner desires to have integrated and/or expressed. For example, exogenous expression of proteins related to autoimmune, allergic, vaccination, immunotolerance, cancer immunotherapy, immune exhaustion, immunological memory, or immunological epitope responses may be used. The gene of interest encode a protein or be a nucleic acid that serves as a marker to identify cells of interest or transduced cells. The gene of interest may encode a protein that modifies a physical characteristic of the transduced cell, such as a protein that modifies size, growth, or eventual tissue composition. In another example, the gene of interest may encode a protein of commercial value that may be harvested. Generally, the gene of interest is operatively linked to other sequences that are useful for obtaining the desired expression of the gene of interest, such as transcriptional regulatory sequences like inducible promoters, as described further below.

In another embodiment, the gene of interest is useful for inhibiting the expression and/or activity of a nucleic acid or protein of interest. For example, target biomolecule expression and/or activity, such as an RNA coding region, may be reduced or inhibited using inhibitory RNAs. An "RNA coding region" is a nucleic acid that may serve as a template for the synthesis of an RNA molecule, such as an siRNA. "RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see, for example, Coburn and Cullen (2002) J. Virol. 76:9225), thereby inhibiting expression of the target biomarker nucleic acid. In one embodiment, the RNA coding region is a DNA sequence. The ability to down-regulate a target gene has many therapeutic and research applications, including identifying the biological functions of particular genes. Moreover, such inhibition may be achieved in screening assays that take advantage of pooling techniques, whereby groups of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more, or any number or range in between, of RNA inhibitory agents are transduced into cells of interest. Suitable inhibitory RNAs include, but are not limited to siRNAs, shRNAs, miRNAs, Piwis, dicer-substrate 27-mer duplexes, single-stranded interfering RNA, and the like. In particular, the combination of RNA inhibitory technology and lentiviruses as a tool for a gene specific knock-down in animal models is well known in the art (see, for example, U.S. Pat. Publ. 2005/0251872; EP Pat. Publ. 2166107; PCT Publs. WO 2004/022722 and 2007/109131; Tiscornia et al. (2003) Proc. Natl. Acad. Sci. U.S.A. 100: 1844-1848; Rubinson et al. (2003) Nat. Genet. 33:401-406; and Dann et al. (2006) Proc. Natl. Acad. Sci. U.S.A. 103: 11246-11251).

siRNAs typically refer to a double-stranded interfering RNA unless otherwise noted. In various embodiments, suitable siRNA molecules include double-stranded ribonucleic acid molecules comprising two nucleotide strands, each strand having about 19 to about 28 nucleotides (i.e. about 19, 20, 21, 22, 23, 24, 25, 26, 27, or 28 nucleotides). Thus, the phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules may be used. Examples of other interfering RNA molecules that may to inhibit target biomolecules include, but are not limited to, short hairpin RNAs (shRNAs), single-stranded siRNAs, microRNAs (miRNAs), piwiRNA, dicer-substrate 27-mer duplexes, and variants thereof containing one or more chemically modified nucleotides, one or more non-nucleotides, one or more deoxyribonucleotides, and/or one or more non-phosphodiester linkages. Typically, all RNA or RNA-like molecules that may interact with transcripts RISC complexes and participate in RISC-related changes in gene expression may be referred to as "interfering RNAs" or "interfering RNA molecules."

Suitable interfering RNAs may readily be produced based on the well-known nucleotide sequences of target biomolecules. In various embodiments interfering RNAs that inhibit target biomolecules may comprise partially purified RNA, substantially pure RNA, synthetic RNA, recombinantly produced RNA, as well as altered RNA that differs from naturally-occurring RNA by the addition, deletion, substitution, and/or alteration of one or more nucleotides. Such alterations may include, for example, addition of non-nucleotide material, such as to the end(s) of the interfering RNAs or to one or more internal nucleotides of the interfering RNAs, including modifications that make the interfering RNAs resistant to nuclease digestion. Such alterations result in sequences that are generally at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or more, or 100% identical to the sequence of the target biomolecule. When the gene to be down regulated is in a family of highly conserved genes, the sequence of the duplex region may be chosen with the aid of sequence comparison to target only the desired gene. On the other hand, if there is sufficient identity among a family of homologous genes within an organism, a duplex region may be designed that would down regulate a plurality of genes simultaneously.

In various embodiments one or both strands of the interfering RNAs may comprise a 3' overhang. As used herein, a "3' overhang" refers to at least one unpaired nucleotide extending from the 3'-end of an RNA strand. Thus in one embodiment, the interfering RNAs comprises at least one 3' overhang of from 1 to about 6 nucleotides (which includes ribonucleotides or deoxynucleotides) in length, from 1 to about 5 nucleotides in length, from 1 to about 4 nucleotides in length, or about 2 to about 4 nucleotides in length. In an illustrative embodiment in which both strands of the interfering RNAs molecule comprise a 3' overhang, wherein the length of the overhangs may be the same or different for each strand. In certain embodiments the 3' overhang is present on both strands of the interfering RNAs and is one, two, or three nucleotides in length. For example, each strand of the interfering RNAs may comprise 3' overhangs of dithymidylic acid ("TT") or diuridylic acid ("uu").

In order to enhance the stability of the interfering RNAs, the 3' overhangs may be also stabilized against degradation. In one embodiment, the overhangs are stabilized by including purine nucleotides, such as adenosine or guanosine nucleotides. In certain embodiments, substitution of pyrimidine nucleotides by modified analogues, e.g., substitution of uridine nucleotides in the 3' overhangs with 2'-deoxythymidine, is tolerated and does not affect the efficiency of RNA interference degradation. In particular, it is believed the absence of a 2' hydroxyl in the 2'-deoxythymidine may significantly enhance the nuclease resistance of the 3' overhang.

Interfering RNAs may be expressed from a composition described herein either as two separate, complementary RNA molecules, or as a single RNA molecule with two complementary regions.

In certain embodiments, the interfering RNAs may be delivered as a small hairpin RNA or short hairpin RNA (shRNA) (see, for example, U.S. Pat. Nos. 8,697,359 and 8,642,569). shRNA is a sequence of RNA that makes a tight hairpin turn that may be used to silence gene expression via RNA interference. The shRNA hairpin structure is cleaved by the cellular machinery into siRNA, which is then bound to the RNA-induced silencing complex (RISC). This complex binds to and cleaves mRNAs that match the siRNA that is bound to it.

In certain embodiments, the sense sequence of the shRNA will be from about 19 to about 30, more nucleotides (e.g. about 19, 20, 21, 22, 23, 24, 25, 26, 27, 28, 29, or 30 nucleotides) in length, more typically from about 19 to about 22 nucleotides in length, the antisense sequence will be from about 19 to about 30, more typically from 19 to about 22 nucleotides (e.g. about 19, 20, 21 or 22 nucleotides), in length, and the loop region will be from about 3 to about 19 nucleotides (e.g., about 3, 4, 5, 6, 7, 8, 9, 10, 11, 12, 13, 14, 15, 16, 17, 18, and 19 nucleotides) in length. In some embodiments, the sense and antisense sequences are the same length, i.e. the shRNA will form a symmetrical hairpin, but this is not necessarily the case. In some cases, the sense or antisense strand may be shorter than its complementary strand, and an asymmetric hairpin is formed. Further, while in some instances the base pairing between the sense and antisense sequences is exact, this also need not be the case. Thus, some mismatch between the sequences may be tolerated, or even desired, e.g. to decrease the strength of the hydrogen bonding between the two strands. However, in one illustrative embodiment, the sense and antisense sequences are the same length, and the base pairing between the two is exact and does not contain any mismatches. The shRNA molecule may also comprise a 5'-terminal phosphate group that may be chemically modified. In addition, the loop portion of the shRNA molecule may comprise, for example, nucleotides, non-nucleotides, linker molecules, conjugate molecules, etc.

In certain embodiments, the PIWI RNA pathway is used to provide inhibition of target biomolecules. Piwi-interacting RNAs (piRNAs) were identified through association with Piwi proteins in mammalian testes (Aravin et al. (2006); Girard et al. (2006); Grivna et al. (2006); Lau et al. (2006). piRNAs and methods of making and using same to target and degrade nucleic acids are well known in the art (see, for example, U.S. Pat. Publ. 2011-0207625). These RNAs range from 26-30 nucleotides in length and are produced from discrete loci. Generally, genomic regions spanning 50-100 kB in length give rise to abundant piRNAs with profound strand asymmetry. Although the piRNAs themselves are not conserved, even between closely related species, the positions of piRNA loci in related genomes are conserved, with virtually all major piRNA-producing loci having synthetic counterparts in mice, rats and humans (Girard et al. (2006)). The loci and consequently the piRNAs themselves are relatively depleted of repeat and transposon sequences, with only 17% of human piRNAs corresponding to known repetitive elements as compared to a nearly 50% repeat content for the genome as a whole. In certain embodiments, methods are provided for inhibiting such targets in a cell, comprising administering an effective amount of a siRNA/shRNA/piwiRNA to the cell, such that target mRNA is degraded.

As described below, internal promoters may also be included in order to allow for the independent expression of more than one gene of interest. If a second or additional gene of interest is included, an internal ribosomal entry site (IRES) sequence may be included (see, for example, U.S. Pat. No. 4,937,190). The IRES sequence may facilitate the expression of the reporter gene and may be used to create multigene, or polycistronic, messages. IRES elements are able to bypass the ribosome scanning model of 5'-methylated cap-dependent translation and begin translation at internal sites (Pelletier and Sonenberg, 1988). IRES elements are well known in the art and be isolated from, for example, at least two members of the picornavirus family (polio and encephalomyocarditis) have been described (Pelletier and Sonenberg, 1988), as well as from a mammalian message (Macejak and Sarnow, 1991). IRES elements may be linked to heterologous open reading frames. Multiple open reading frames may be transcribed together, each separated by an IRES, creating polycistronic messages. By virtue of the IRES element, each open reading frame is accessible to ribosomes for efficient translation. Multiple genes may be efficiently expressed using a single promoter/enhancer to transcribe a single message.

In certain embodiments of the invention, cells transduced with the delivery systems of the present invention may be identified in vitro or in vivo by including a marker in the sequence. Such markers would confer an identifiable change to the transduced cell permitting easy identification of cells containing the marker. For example, a gene of interest encoding a marker protein may be placed after the primary gene of interest that is, for example, an RNA interfering nucleic acid, to allow for identification of cells that are expressing the desired protein.

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Usually the inclusion of a drug selection marker aids in the cloning and identification of transformants, for example, genetic constructs that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Many useful reporter markers are known and include, for example, a fluorescence marker, preferably selected from green fluorescent protein (GFP), enhanced GFP (eGFP), DsRed, AsRed, HcRed, Tomatoe, Cherry, Katushka, and variants thereof (see, for example, U.S. Pat. Nos. 5,487,932 and 5,464,763). Examples of other useful reporters include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

The term "alkylating agent," as used herein, means a compound that is able to transfer alkyl groups to DNA. Alkylation can result in miscoding of DNA strands, incomplete repair of alkylated segments (which leads to strand breakage or depurination), excessive cross-linking of DNA, and inhibition of strand separation at mitosis. Monofunctional alkylating agents transfer a single alkyl group and usually result in miscoding of DNA, strand breakage, or depurination. These reactions can result in cell death, mutagenesis, or carcinogenesis. Polyfunctional alkylating agents typically cause strand cross-linking and inhibition of mitosis with consequent cell death. Resistance to one alkylating agent often implies resistance to other drugs in the same class and can be caused by increased production of nucleophilic substances that compete with the target DNA for alkylation. Decreased permeation of alkylating agents and increased activity of DNA repair systems are also common mechanisms of resistance.

Individual alkylating agents are generally cell-cycle non-specific and can be subgrouped according to chemical structure into nitrogen mustards, ethyleneamines, alkyl sulfonates, nitrosoureas, and triazene derivatives.

The most common subgroup of alkylating agents used is the nitrogen mustard group. Mechlorethamine hydrochloride is the prototype of the nitrogen mustards and is commonly used in veterinary medicine to treat lymphoma in conjunction with other chemotherapeutics. Because of the highly unstable nature and extremely short duration of action of mechlorethamine, its use is somewhat limited in veterinary medicine. Derivatives of mechlorethamine commonly used for various neoplasias include cyclophosphamide, chlorambucil, and melphalan.

Cyclophosphamide is a cyclic phosphamide derivative of mechlorethamine that requires metabolic activation by the cytochrome P450 oxidation system in the liver. Cyclophosphamide is given PO or IV, and dose-limiting leukopenia associated with bone marrow suppression is the primary toxicity. However, among the alkylating chemotherapy agents, the myelosuppressive effect of cyclophosphamide is considered relatively sparing of platelets and progenitor cells. Sterile hemorrhagic cystitis may result from aseptic chemical inflammation of the bladder urothelium caused by acrolein, a metabolite of cyclophosphamide. Prevention of this toxicity is key to its management. Specifically, concurrent administration of a diuretic, such as furosemide, may be used when cyclophosphamide is given as a single dose to provide a dilutional effect. In addition, cyclophosphamide may be given in the morning so that patients can be provided several opportunities to urinate throughout the day to minimize contact time of acrolein with the bladder lining. In patients with evidence of sterile hemorrhagic cystitis, cyclophosphamide use should be discontinued. Although the signs may be self-limiting, treatment with fluids, NSAIDs, methylsulfonylmethane (MSM), and intravesicular DMSO may be considered. Mesna is a drug that binds and inactivates the urotoxic metabolites of cyclophosphamide within the bladder. Mesna coadministered with fluid diuresis is recommended when ifosfamide (an analogue of cyclophosphamide) or high-dose cyclophosphamide is used.

Chlorambucil, the slowest-acting nitrogen mustard, achieves effects gradually and often can be used in animals with compromised bone marrow. It can cause bone marrow suppression, which is usually mild; however, periodic monitoring is recommended with longterm administration. This drug is given PO and is most commonly used in treatment of chronic, well-differentiated cancers; it is considered ineffective in rapidly proliferating tumors.

Melphalan, an L-phenylalanine derivative of mechlorethamine, is given PO or IV and is primarily used in veterinary medicine to treat multiple myeloma.

Of the other subgroups of alkylating agents, several have limited but specific uses. Triethylenethiophosphoramide (thiotepa), an ethylenimine, has been reported as an intravesicular treatment for transitional cell carcinoma of the bladder or as an intracavitary treatment for pleural and peritoneal effusions. Busulfan, an alkyl sulfonate, is used specifically in treatment of chronic myelocytic leukemia and polycythemia vera. Streptozotocin, a naturally occurring nitrosourea, is used for palliation of malignant pancreatic islet-cell tumors or insulinomas. Other nitrosoureas, such as carmustine and lomustine, readily cross the blood-brain barrier and have been useful in management of lymphoma (including epitheliotropic cutaneous lymphoma), mast cell tumors, histiocytic sarcomas, and CNS neoplasias. Dacarbazine (DTIC), a triazene derivative, has been used either in combination with doxorubicin or as a single-agent treatment for relapsed canine lymphoma and soft-tissue sarcomas.

Temozolomide is an oral imidazotetrazine derivative of dacarbazine and belongs to a class of chemotherapeutic agents that enter the CSF and do not require hepatic metabolism for activation. In people, it is used for refractory malignant gliomas and malignant melanomas. There have been reports in the veterinary literature of its use as a substitute for dacarbazine (DTIC).

As used herein, the term "characteristic size" as determined by DLS means characteristic diameter, or, for a plurality of particles, mean, median, or mode diameter. In some embodiments, "characteristic size" for a plurality of particles means that at least about 50%, at least about 60%, at least about 70%, at least about 80%, or at least about 90% of the particles have the recited characteristic size.

As used herein, the term "cleavable linker" means a linker that is sufficiently stable outside the cell, but which upon entry into a target cell is cleaved to release the two parts the linker is holding together. In a preferred embodiment, the cleavable linker is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linkers are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linker by reduction; esterases; endosomes or agents that can create an acidic environment, e.g., those that result in a pH of five or lower; enzymes that can hydrolyze or degrade an acid cleavable linker by acting as a general acid, peptidases (which can be substrate specific), and phosphatases.

A cleavable linker, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some spacers will have a linker that is cleaved at a preferred pH, thereby releasing the agent from the particle inside the cell, or into the desired compartment of the cell.

A spacer can include a linker that is cleavable by a particular enzyme. Spacers that contain peptide bonds can be used when the particles are targeting cell types rich in peptidases.

In general, the suitability of a candidate cleavable linker can be evaluated by testing the ability of a degradative agent (or condition) to cleave the candidate linker. It will also be desirable to also test the candidate cleavable linker for the ability to resist cleavage in the blood or when in contact with other non-target tissue.

One class of cleavable linkers are redox cleavable linkers that are cleaved upon reduction or oxidation. An example of reductively cleavable linker is a disulphide linker (—S—S—).

Phosphate-based linkers are cleaved by agents that degrade or hydrolyze the phosphate group. An example of an agent that cleaves phosphate groups in cells are enzymes such as phosphatases in cells. Examples of phosphate-based linkers are —O—P(O)(ORk)-O—, —O—P(S)(ORk)-O—, —O—P(S)(SRk)-O—, —O—P(O)(ORk)-S—, —S—P(O)(ORk)-S—, —O—P(S)(ORk)-S—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid cleavable linkers are linkers that are cleaved under acidic conditions. In preferred embodiments acid cleavable linkers are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linkers. Examples of acid cleavable linkers include but are not limited to hydrazones, esters, and esters of amino acids.

Ester-based linkers are cleaved by enzymes such as esterases and amidases in cells. Examples of ester-based cleavable linkers include but are not limited to esters of alkylene, alkenylene and alkynylene groups. Ester cleavable linkers have the general formula —C(O)O—, or —OC(O)—.

Peptide-based linkers are cleaved by enzymes such as peptidases and proteases in cells. Peptide-based cleavable linkers are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group.

As used herein, the phrase "targeting agent" means any moiety a moiety that localizes to or away from a specific locale. The attachment of a targeting moiety to a compound increases the concentration of the compound at a site of treatment, for example, a tumor site. A targeting agent includes, but is not limited to, a lectin, glycoprotein, lipid or protein, e.g., an antibody, that binds to a specified cell type such as a tumor cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Effective amounts, toxicity, and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ as determined in an in vitro enzyme assay or cell culture (i.e., the concentration of the anticancer agent that achieves half-maximal inhibition of an enzyme or half-maximal inhibition of symptoms). Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Exemplary Embodiments

In certain embodiments, the invention relates to a method of treating cancer in a human subject in need thereof comprising
administering by intraperitoneal injection or infusion to the intraperitoneal cavity a composition comprising a plurality of particles in an aqueous pharmaceutically acceptable carrier,
wherein
the cancer is a cancer that forms a peritoneal implant on the serosal surface of an organ of the peritoneal cavity;
each particle comprises a biodegradable core having an outer surface and a polymer non-covalently associated with the outer surface of the core;
the polymer comprises a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;
the biodegradable core comprises an anticancer agent; and
the characteristic size of the particles, as determined by dynamic light scattering (DLS), is about 20 nm to about 300 nm.

In certain embodiments, the invention relates to any one of the methods described herein, wherein the composition does not comprise a targeting agent.

In certain embodiments, the invention relates to any one of the methods described herein, wherein the particle does not comprise a targeting agent.

In certain embodiments, the invention relates to any one of the methods described herein, wherein the cancer is a cancer that spreads by peritoneal carcinomatosis.

In certain embodiments, the invention relates to any one of the methods described herein, wherein the cancer is ovarian, gastric, appendiceal, liver, pancreatic, colorectal, uterine, lobular breast, cervical, or primary peritoneal cancer.

In certain embodiments, the invention relates to any one of the methods described herein, wherein the cancer is endometrial cancer, abdominal methothelioma, or a soft tissue sarcoma.

In certain embodiments, the invention relates to any one of the methods described herein, wherein the biodegradable core comprises a second polymer.

In certain embodiments, the invention relates to any one of the methods described herein, wherein the anticancer agent has an $IC_{50}$ of less than 10 nM. In certain embodiments, the invention relates to any one of the methods described herein, wherein the anticancer agent has an $IC_{50}$ of less than 1 nM. In certain embodiments, the invention relates to any one of the methods described herein, wherein the anticancer agent has an $IC_{50}$ of from about 1 pM to about 10 nM. In certain embodiments, the invention relates to any one of the methods described herein, wherein the anticancer agent has an $IC_{50}$ of from about 1 pM to about 5 nM. In certain embodiments, the invention relates to any one of the methods described herein, wherein the anticancer agent has an $IC_{50}$ of from about 1 pM to about 1 nM.

In certain embodiments, the invention relates to any one of the methods described herein, wherein the anticancer agent is a molecule having a molecular weight from about 300 Da to about 1,000 Da.

In certain embodiments, the invention relates to any one of the methods described herein, wherein the polymer is a diblock copolymer comprising a first block and a second block; and the first block comprises the plurality of first monomers. In certain embodiments, the invention relates to any one of the methods described herein, wherein each first monomer is selected from the group consisting of ethylene glycol and propylene glycol. In certain embodiments, the invention relates to any one of the methods described herein, wherein each first monomer is ethylene glycol.

In certain embodiments, the invention relates to any one of the methods described herein, further comprising debulking the cancer prior to administering the composition. In certain embodiments, the invention relates to any one of the methods described herein, wherein the cancer is debulked to a volume less than about 1 cm$^3$. In certain embodiments, the invention relates to any one of the methods described herein, wherein the cancer is debulked to a volume less than about 0.5 cm$^3$.

In certain embodiments, the invention relates to any one of the methods described herein, further comprising removing the composition from the intraperitoneal cavity after about 1 hour (h), about 2 h, about 3 h, about 4 h, or about 5 h.

In certain embodiments, the invention relates to any one of the methods described herein, wherein the composition is at a temperature of about 38° C., about 39° C., about 40° C., about 41° C., about 42° C., or about 43° C.

In certain embodiments, the invention relates to any one of the methods described herein, wherein the characteristic size of the particles, as determined by DLS, is about 20 nm to about 160 nm.

In certain embodiments, the invention relates to any one of the methods described herein, wherein the biodegradable core further comprises
a block copolymer comprising:
(i) a first block comprising a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;
(ii) a second block comprising a plurality of second monomers, wherein each second monomer is selected from the group consisting of 6-hydroxycaproic acid, side-chain N-protected lysine, lactic acid, glycolic acid, hydroxybutyrate, valine, isoleucine, leucine, methionine, phenylalanine, tryptophan, cysteine, alanine, proline, glycine, tyrosine, side-chain carbonyl-protected aspartic acid, side-chain carbonyl-protected glutamic acid, propylene carbonate, butyl acrylate, butyl methacrylate, and benzyl methacrylate; and
(iii) a third block comprising a plurality of third monomers, wherein each third monomer is selected from the group consisting of lysine, side-chain aminoalkyl-functionalized lysine, asparagine, side-chain aminoalkyl-functionalized asparagine, arginine, aspartamide, side-chain aminoalkyl-functionalized aspartamide, and ethyleneimine,
wherein the anticancer agent is covalently bound to the block copolymer.

In certain embodiments, the invention relates to any one of the methods described herein, wherein the anticancer agent is an alkylating agent, a nucleic acid cross-linking agent, or a microtubule inhibitor.

In certain embodiments, the invention relates to any one of the methods described herein, wherein the anticancer agent is an alkylating agent.

In certain embodiments, the invention relates to any one of the methods described herein, wherein the anticancer agent is a nucleic acid cross-linking agent.

In certain embodiments, the invention relates to any one of the methods described herein, wherein the anticancer agent is a microtubule inhibitor.

In certain embodiments, the invention relates to any one of the methods described herein, wherein the anticancer agent is selected from the group consisting of an auristatin (e.g., MMAE, MMAF), vincristine, vinblastine, a calicheamicin, a maytansinoid or maytansine (e.g., DM1, DM4), a tubulysin, a pyrrolobenzodiazepine (PBD) or a PBD dimer, an indolinobenzodiazepine, an irinotecan, a duocarmycin, a camptothecin, doxorubicin, α-amanitin, a cryptophycin, an anthracycline, rhizoxin, a splicostatin, a thailanstatin, and an amanitin. In certain embodiments, the invention relates to any one of the methods described herein, wherein the anticancer agent is an auristatin. In certain embodiments, the invention relates to any one of the methods described herein, wherein the anticancer agent is MMAE.

In certain embodiments, the invention relates to any one of the methods described herein, wherein the anticancer agent is covalently bound to at least one third monomer.

In certain embodiments, the invention relates to any one of the methods described herein, wherein the anticancer agent is covalently bound to at least one third monomer via a self-immolative or cleavable linker.

In certain embodiments, the invention relates to any one of the methods described herein, wherein the self-immolative or cleavable linker comprises a disulfide functionality.

In certain embodiments, the invention relates to any one of the methods described herein, wherein the self-immolative or cleavable linker comprises a dipeptide.

In certain embodiments, the invention relates to any one of the methods described herein, wherein the self-immolative or cleavable linker comprises valine-citrulline (Val-Cit).

In certain embodiments, the invention relates to any one of the methods described herein, wherein at least one third monomer has the structure of Formula I:

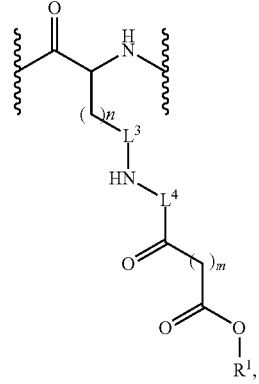

Formula I wherein
$R^1$ comprises the anticancer agent and, optionally, a self-immolative or cleavable linker;
$L^3$ is a bond or —C(=O)—;
$L^4$ is a bond or $[-(C_1-C_6)alkylene-NR-]_p$;
p is 1, 2, or 3;
R is H or $C_1-C_6$alkyl;
n is 1, 2, 3, 4, 5, or 6; and
m is 1, 2, 3, 4, 5, or 6.

In certain embodiments, the invention relates to any one of the methods described herein, wherein the block copolymer is MPEG-b-PCL-b-PLL, wherein at least one PLL monomer has a structure of Formula I:

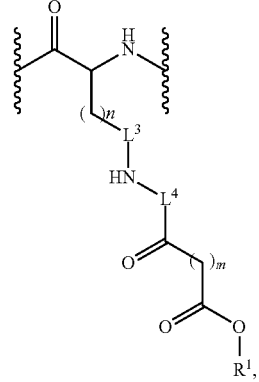

Formula I wherein

R[1] comprises the anticancer agent and, optionally, a self-immolative or cleavable linker;

L[3] is a bond or —C(=O)—;

L[4] is a bond or [—(C$_1$-C$_6$)alkylene-NR—]$_p$;

p is 1, 2, or 3;

R is H or C$_1$-C$_6$alkyl;

n is 4; and m is 1, 2, 3, 4, 5, or 6.

In certain embodiments, the invention relates to any one of the methods described herein, wherein n is 3, 4, or 5. In certain embodiments, the invention relates to any one of the methods described herein, wherein n is 4.

In certain embodiments, the invention relates to any one of the methods described herein, wherein m is 1, 2, or 3. In certain embodiments, the invention relates to any one of the methods described herein, wherein m is 2.

In certain embodiments, the invention relates to any one of the methods described herein, wherein L[3] is a bond. In certain embodiments, the invention relates to any one of the methods described herein, wherein L[3] is —C(=O)—.

In certain embodiments, the invention relates to any one of the methods described herein, wherein L[4] is a bond. In certain embodiments, the invention relates to any one of the methods described herein, wherein L[4] is [—(C$_1$-C$_6$)alkylene-NR—]$_p$. In certain embodiments, the invention relates to any one of the methods described herein, wherein L[4] is [—(CH$_2$CH$_2$)—NR—]$_2$.

In certain embodiments, the invention relates to any one of the methods described herein, wherein R is H.

In certain embodiments, the invention relates to any one of the methods described herein, wherein R[1] is a moiety represented by the structural formula:

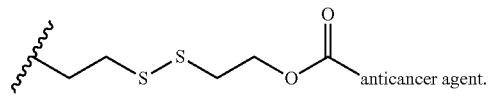

In certain embodiments, the invention relates to any one of the methods described herein, wherein R[1] is a moiety represented by the structural formula:

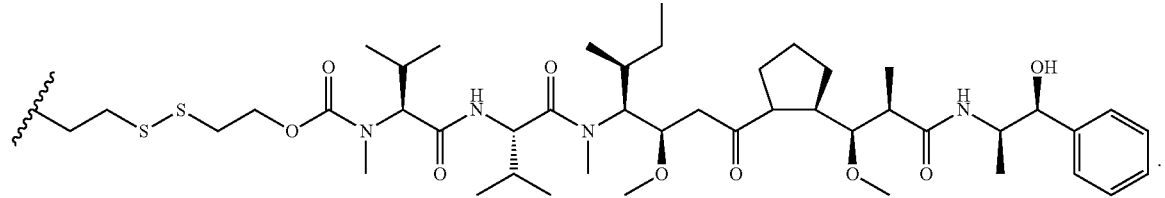

In certain embodiments, the invention relates to any one of the methods described herein, wherein the anticancer agent comprises Pt(II) or Pt(IV).

In certain embodiments, the invention relates to any one of the methods described herein, wherein the anticancer agent is covalently bound to at least one third monomer.

In certain embodiments, the invention relates to any one of the methods described herein, wherein the anticancer agent is covalently bound to at least one third monomer via a self-immolative or cleavable linker.

In certain embodiments, the invention relates to any one of the methods described herein, wherein the self-immolative or cleavable linker comprises a disulfide functionality.

In certain embodiments, the invention relates to any one of the methods described herein, wherein the self-immolative or cleavable linker comprises a dipeptide.

In certain embodiments, the invention relates to any one of the methods described herein, wherein the self-immolative linker or cleavable comprises Val-Cit.

In certain embodiments, the invention relates to any one of the methods described herein, wherein at least one third monomer has the structure of Formula I:

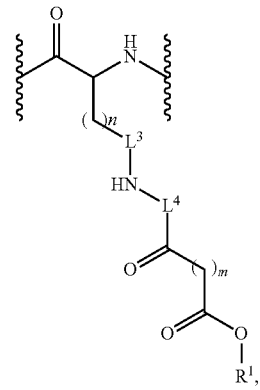

Formula I wherein

R[1] comprises the anticancer agent and, optionally, a self-immolative or cleavable linker;

L[3] is a bond or —C(=O)—;

L[4] is a bond or [—(C$_1$-C$_6$)alkylene-NR—]$_p$;

p is 1, 2, or 3;

R is H or C$_1$-C$_6$alkyl;

n is 1, 2, 3, 4, 5, or 6; and m is 1, 2, 3, 4, 5, or 6.

In certain embodiments, the invention relates to any one of the methods described herein, wherein the block copolymer is MPEG-b-PCL-b-PLL, wherein at least one PLL monomer has a structure of Formula I:

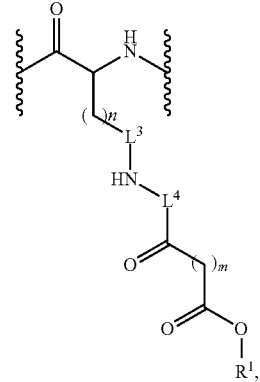

Formula I wherein

R¹ comprises the anticancer agent and, optionally, a self-immolative or cleavable linker;

L³ is a bond or —C(=O)—;

L⁴ is a bond or [—(C₁-C₆)alkylene-NR—]$_p$;

p is 1, 2, or 3;

R is H or C₁-C₆alkyl;

n is 4; and m is 1, 2, 3, 4, 5, or 6.

In certain embodiments, the invention relates to any one of the methods described herein, wherein n is 3, 4, or 5. In certain embodiments, the invention relates to any one of the methods described herein, wherein n is 4.

In certain embodiments, the invention relates to any one of the methods described herein, wherein m is 1, 2, or 3. In certain embodiments, the invention relates to any one of the methods described herein, wherein m is 2.

In certain embodiments, the invention relates to any one of the methods described herein, wherein L³ is a bond. f In certain embodiments, the invention relates to any one of the methods described herein, wherein L³ is —C(=O)—.

In certain embodiments, the invention relates to any one of the methods described herein, wherein L⁴ is a bond. In certain embodiments, the invention relates to any one of the methods described herein, wherein L⁴ is [—(C₁-C₆)alkylene-NR—]$_p$ In certain embodiments, the invention relates to any one of the methods described herein, wherein L⁴ is [—(CH₂CH₂)—NR—]₂.

In certain embodiments, the invention relates to any one of the methods described herein, wherein R is H.

In certain embodiments, the invention relates to any one of the methods described herein, wherein R¹ is a moiety represented by the structural formula:

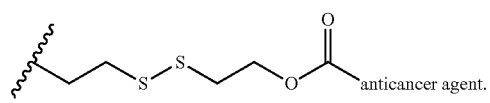

In certain embodiments, the invention relates to any one of the methods described herein, wherein the anticancer agent comprises Pt(IV).

In certain embodiments, the invention relates to any one of the methods described herein, wherein the anticancer agent is a moiety represented by the structural formula:

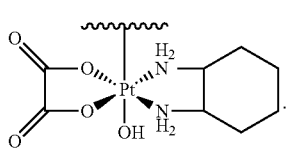

In certain embodiments, the invention relates to any one of the methods described herein, wherein the anticancer agent is a moiety represented by the structural formula:

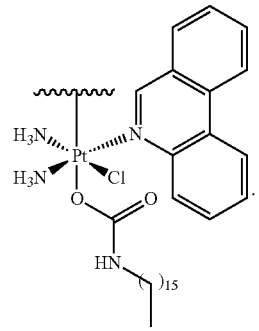

In certain embodiments, the invention relates to any one of the methods described herein, wherein the block copolymer comprises from about 3 to about 60 contiguous second monomers.

In certain embodiments, the invention relates to any one of the methods described herein, wherein the block copolymer comprises from about 10 to about 60 contiguous third monomers.

In certain embodiments, the invention relates to any one of the methods described herein, wherein the block copolymer comprises from about 40 to about 300 contiguous first monomers.

In certain embodiments, the invention relates to any one of the methods described herein, wherein the biodegradable core further comprises Pt(IV).

In certain embodiments, the invention relates to any one of the methods described herein, wherein the polymer comprises a first anionic end-group; and the biodegradable core further comprises Pt(IV) coordinated to the first anionic end-group of the polymer.

In certain embodiments, the invention relates to any one of the methods described herein, wherein the biodegradable core further comprises a hydrophobic polymer; the hydrophobic polymer comprises a second anionic end-group; and the second anionic end-group is coordinated to Pt(IV).

In certain embodiments, the invention relates to any one of the methods described herein, wherein the particle comprises the anticancer agent and a compound represented by the structural formula:

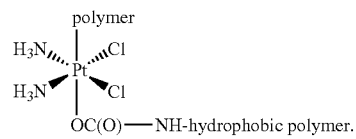

In certain embodiments, the invention relates to any one of the methods described herein, wherein the particle comprises the anticancer agent and a compound represented by the structural formula:

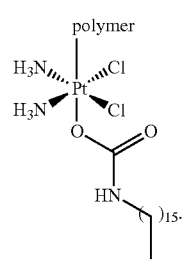

In certain embodiments, the invention relates to any one of the methods described herein, wherein the anticancer agent is non-covalently associated with the biodegradable core.

In certain embodiments, the invention relates to any one of the methods described herein, wherein the anticancer agent is paclitaxel or BMN 673.

In certain embodiments, the invention relates to any one of the methods described herein, wherein the polymer is a compound represented by the structural formula:

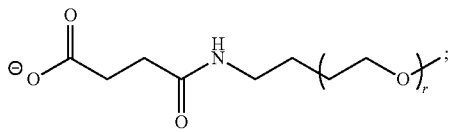

and r is from about 40 to about 80.

In certain embodiments, the invention relates to any one of the methods described herein, wherein r is from about 40 to about 50.

In certain embodiments, the invention relates to any one of the methods described herein, wherein r is about 45.

In certain embodiments, the invention relates to any one of the methods described herein, wherein the biodegradable core further comprises an siRNA; and a block copolymer comprising:
(i) a first block comprising a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;
(ii) a second block comprising a plurality of second monomers, wherein each second monomer is selected from the group consisting of 6-hydroxycaproic acid, side-chain N-protected lysine, lactic acid, glycolic acid, hydroxybutyrate, valine, isoleucine, leucine, methionine, phenylalanine, tryptophan, cysteine, alanine, proline, glycine, tyrosine, side-chain carbonyl-protected aspartic acid, side-chain carbonyl-protected glutamic acid, propylene carbonate, butyl acrylate, butyl methacrylate, and benzyl methacrylate; and
(iii) a third block comprising a plurality of third monomers, wherein each third monomer is selected from the group consisting of lysine, side-chain aminoalkyl-functionalized lysine, asparagine, side-chain aminoalkyl-functionalized asparagine, arginine, aspartamide, side-chain aminoalkyl-functionalized aspartamide, and ethyleneimine,
wherein
the siRNA is non-covalently associated with the block copolymer; and
the anticancer agent is associated with the block copolymer.

In certain embodiments, the invention relates to any one of the methods described herein, wherein the anticancer agent is covalently bound to the block copolymer.

In certain embodiments, the invention relates to any one of the methods described herein, wherein the anticancer agent is an alkylating agent or a nucleic acid cross-linking agent.

In certain embodiments, the invention relates to any one of the methods described herein, wherein the anticancer agent is an alkylating agent.

In certain embodiments, the invention relates to any one of the methods described herein, wherein the anticancer agent is a nucleic acid cross-linking agent.

In certain embodiments, the invention relates to any one of the methods described herein, wherein the anticancer agent comprises Pt(II) or Pt(IV).

In certain embodiments, the invention relates to any one of the methods described herein, wherein the anticancer agent is covalently bound to at least one third monomer.

In certain embodiments, the invention relates to any one of the methods described herein, wherein at least one third monomer has the structure of Formula I:

Formula I

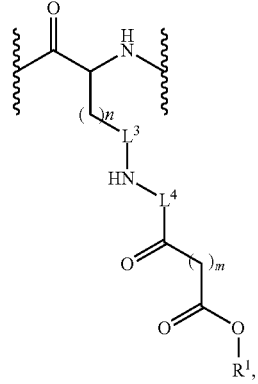

wherein $R^1$ comprises the anticancer agent;

$L^3$ is a bond or —C(=O)—;

$L^4$ is a bond or $[-(C_1-C_6)\text{alkylene-NR}-]_p$;

p is 1, 2, or 3;

R is H or $C_1$-$C_6$alkyl;

n is 1, 2, 3, 4, 5, or 6; and m is 1, 2, 3, 4, 5, or 6.

In certain embodiments, the invention relates to any one of the methods described herein, wherein the anticancer agent is a nucleic acid cross-linking agent.

In certain embodiments, the invention relates to any one of the methods described herein, wherein the anticancer agent comprises Pt(II) or Pt(IV).

In certain embodiments, the invention relates to any one of the methods described herein, wherein the anticancer agent comprises Pt(IV).

In certain embodiments, the invention relates to any one of the methods described herein, wherein $R^1$ is a moiety represented by the structural formula

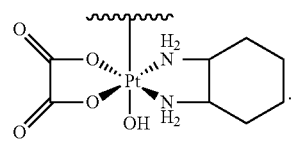

In certain embodiments, the invention relates to any one of the methods described herein, wherein the anticancer agent is a moiety represented by the structural formula:

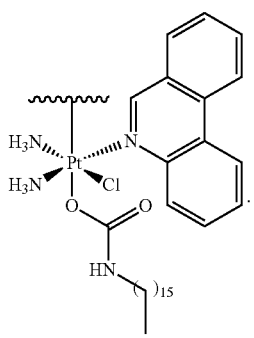

In certain embodiments, the invention relates to any one of the methods described herein, wherein n is 3, 4, or 5. In certain embodiments, the invention relates to any one of the methods described herein, wherein n is 4.

In certain embodiments, the invention relates to any one of the methods described herein, wherein m is 1, 2, or 3. In certain embodiments, the invention relates to any one of the methods described herein, wherein m is 2.

In certain embodiments, the invention relates to any one of the methods described herein, wherein $L^3$ is a bond. In certain embodiments, the invention relates to any one of the methods described herein, wherein $L^3$ is —C(=O)—.

In certain embodiments, the invention relates to any one of the methods described herein, wherein $L^4$ is a bond. In certain embodiments, the invention relates to any one of the methods described herein, wherein $L^4$ is [—($C_1$-$C_6$)alkylene-NR—]$_p$. In certain embodiments, the invention relates to any one of the methods described herein, wherein $L^4$ is [—($CH_2CH_2$)—NR—]$_2$.

In certain embodiments, the invention relates to any one of the methods described herein, wherein R is H.

In certain embodiments, the invention relates to any one of the methods described herein, wherein the anticancer agent is non-covalently associated with the block copolymer.

In certain embodiments, the invention relates to any one of the methods described herein, wherein the anticancer agent is an alkylating agent or a nucleic acid cross-linking agent.

In certain embodiments, the invention relates to any one of the methods described herein, wherein the anticancer agent is an alkylating agent.

In certain embodiments, the invention relates to any one of the methods described herein, wherein the anticancer agent is a nucleic acid cross-linking agent.

In certain embodiments, the invention relates to any one of the methods described herein, wherein the anticancer agent comprises Pt(II) or Pt(IV).

In certain embodiments, the invention relates to any one of the methods described herein, wherein the anticancer agent comprises Pt(II).

In certain embodiments, the invention relates to any one of the methods described herein, wherein the block copolymer has the following structure:

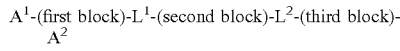

$A^1$ is OH or —O—($C_1$-$C_6$)alkyl;
$A^2$ is H, an amine protecting group, or an amino acid;
$L^1$ is a covalent bond or a first linker; and
$L^2$ is a covalent bond or a second linker.

In certain embodiments, the invention relates to any one of the methods described herein, wherein $L^1$ is a first linker. In certain embodiments, the invention relates to any one of the methods described herein, wherein $L^1$ is —C(=O)—($C_1$-$C_{10}$-alkylene)-O—. In certain embodiments, the invention relates to any one of the methods described herein, wherein $L^1$ is a bond.

In certain embodiments, the invention relates to any one of the methods described herein, wherein $L^2$ is a second linker. In certain embodiments, the invention relates to any one of the methods described herein, wherein $L^2$ is —C(=O)—($C_1$-$C_{10}$-alkylene)-NH—. In certain embodiments, the invention relates to any one of the methods described herein, wherein $L^2$ is a bond.

In certain embodiments, the invention relates to any one of the methods described herein, wherein the block copolymer comprises from about 3 to about 60 contiguous second monomers.

In certain embodiments, the invention relates to any one of the methods described herein, wherein the block copolymer comprises from about 10 to about 60 contiguous third monomers.

In certain embodiments, the invention relates to any one of the methods described herein, wherein the block copolymer comprises from about 40 to about 300 contiguous first monomers.

In certain embodiments, the invention relates to any one of the methods described herein, wherein the block copolymer is MPEG-b-PCL-b-PLL, wherein at least one PLL monomer has a structure of Formula I:

Formula I

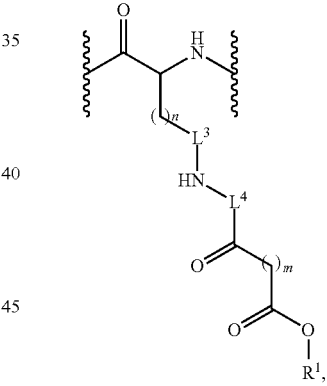

wherein
$R^1$ comprises the anticancer agent;
$L^3$ is a bond or —C(=O)—;
$L^4$ is a bond or [—($C_1$-$C_6$)alkylene-NR—]$_p$;
p is 1, 2, or 3;
R is H or $C_1$-$C_6$alkyl;
n is 4; and
m is 1, 2, 3, 4, 5, or 6.

In certain embodiments, the invention relates to any one of the methods described herein, wherein the block copolymer is MPEG-b-PCL-b-PLL.

In certain embodiments, the invention relates to a method of treating cancer in a human subject in need thereof comprising administering by intraperitoneal injection or infusion to the intraperitoneal cavity a composition comprising a plurality of particles in an aqueous pharmaceutically acceptable carrier, wherein
the cancer is a cancer that forms a peritoneal implant on the serosal surface of an organ of the peritoneal cavity;
each particle comprises a biodegradable core having an outer surface and a polymer non-covalently associated with the outer surface of the core;
the biodegradable core comprises
an agent, wherein the agent is (a) a nuclease selected from the group consisting of Cas9, TALEN, and zinc finger, or (b) a nucleic acid encoding a nuclease selected from the group consisting of Cas9, TALEN, and zinc finger;
an optional DNA editing template; and
a block copolymer comprising:
(i) a first block comprising a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;
(ii) a second block comprising a plurality of second monomers, wherein each second monomer is hydrophobic; and
(iii) a third block comprising a plurality of third monomers, wherein each third monomer is positively charged at a pH from about 6.8 to about 7.4,
wherein
the agent is non-covalently associated with the block copolymer; and
the DNA editing template, when present, is non-covalently associated with the block copolymer;
the polymer comprises a plurality of first monomers; and
the characteristic size of the particles, as determined by dynamic light scattering (DLS), is about 20 nm to about 300 nm.

In certain embodiments, the invention relates to any one of the methods described herein, wherein the composition does not comprise a targeting agent.

In certain embodiments, the invention relates to any one of the methods described herein, wherein the particle does not comprise a targeting agent.

In certain embodiments, the invention relates to any one of the methods described herein, wherein the cancer is a cancer that spreads by peritoneal carcinomatosis.

In certain embodiments, the invention relates to any one of the methods described herein, wherein the cancer is ovarian, gastric, appendiceal, liver, pancreatic, colorectal, uterine, lobular breast, cervical, or primary peritoneal cancer.

In certain embodiments, the invention relates to any one of the methods described herein, wherein the cancer is endometrial cancer, abdominal methothelioma, or a soft tissue sarcoma.

In certain embodiments, the invention relates to any one of the methods described herein, wherein the agent is Cas9 or a nucleic acid encoding Cas9; and a guide nucleic acid non-covalently associated with the block copolymer.

In certain embodiments, the invention relates to any one of the methods described herein, wherein the second block is a polyester, a polyanhydride, a polypeptide, or a polycarbonate. In certain embodiments, the invention relates to any one of the methods described herein, wherein the second block is a polypeptide.

In certain embodiments, the invention relates to any one of the methods described herein, wherein each second monomer is selected from the group consisting of 6-hydroxycaproic acid, side-chain N-protected lysine, lactic acid, glycolic acid, hydroxybutyrate, valine, isoleucine, leucine, methionine, phenylalanine, tryptophan, cysteine, alanine, proline, glycine, tyrosine, side-chain carbonyl-protected aspartic acid, side-chain carbonyl-protected glutamic acid, propylene carbonate, butyl acrylate, butyl methacrylate, and benzyl methacrylate.

In certain embodiments, the invention relates to any one of the methods described herein, wherein each second monomer has the structure of Formula II:

Formula II

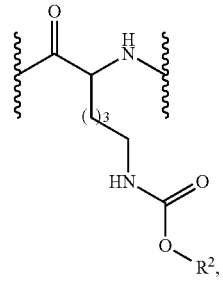

wherein
$R^2$ is $C_1$-$C_6$alkyl, $C_3$-$C_6$alkenyl, $C_5$-$C_{22}$carbocyclyl-substituted $C_1$-$C_6$alkyl, or 5-22-membered heterocyclyl-substituted $C_1$-$C_6$alkyl.

In certain embodiments, the invention relates to any one of the methods described herein, wherein $R^2$ is benzyl.

In certain embodiments, the invention relates to any one of the methods described herein, wherein each third monomer comprises a —$NHR_2^+$ functionality at pH about 7, wherein R is H or $C_1$-$C_6$ alkyl.

In certain embodiments, the invention relates to any one of the methods described herein, wherein each third monomer is selected from the group consisting of lysine, arginine, asparagine, side-chain aminoalkyl-functionalized asparagine, aspartamide, side-chain aminoalkyl-functionalized aspartamide, and ethyleneimine.

In certain embodiments, the invention relates to any one of the methods described herein, wherein each third monomer has the structure of Formula III or Formula IV:

Formula III

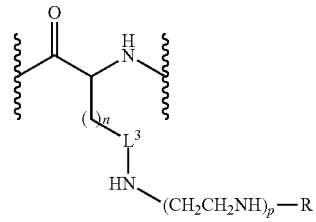

Formula IV

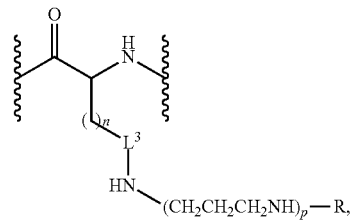

wherein
$L^3$ is a bond or —C(=O)—;
p is 1, 2, or 3;
R is H or $C_1$-$C_6$alkyl; and
n is 1, 2, 3, 4, 5, or 6.

In certain embodiments, the invention relates to any one of the methods described herein, wherein n is 1 or 2. In certain embodiments, the invention relates to any one of the methods described herein, wherein n is 1.

In certain embodiments, the invention relates to any one of the methods described herein, wherein $L^3$ is —C(=O)—.

In certain embodiments, the invention relates to any one of the methods described herein, wherein R is H.

In certain embodiments, the invention relates to any one of the methods described herein, wherein p is 2.

In certain embodiments, the invention relates to any one of the methods described herein, wherein the block copolymer has the following structure:

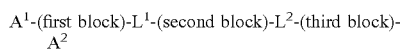

wherein $A^1$ is OH or —O—($C_1$-$C_6$)alkyl;

$A^2$ is H, an amine protecting group, or an amino acid;

$L^1$ is a covalent bond or a first linker; and $L^2$ is a covalent bond or a second linker.

In certain embodiments, the invention relates to any one of the methods described herein, wherein $A^1$ is —O—($C_1$-$C_6$)alkyl. In certain embodiments, the invention relates to any one of the methods described herein, wherein $A^1$ is —OCH$_3$.

In certain embodiments, the invention relates to any one of the methods described herein, wherein $A^2$ is H.

In certain embodiments, the invention relates to any one of the methods described herein, wherein $L^1$ is a first linker. In certain embodiments, the invention relates to any one of the methods described herein, wherein $L^1$ is —$C_1$-$C_6$alkylene-NR—; and R is H or $C_1$-$C_6$alkyl. In certain embodiments, the invention relates to any one of the methods described herein, wherein $L^1$ is —CH$_2$CH$_2$—NH—.

In certain embodiments, the invention relates to any one of the methods described herein, wherein $L^2$ is a covalent bond.

In certain embodiments, the invention relates to any one of the methods described herein, wherein the block copolymer comprises from about 3 to about 60 contiguous second monomers.

In certain embodiments, the invention relates to any one of the methods described herein, wherein the block copolymer comprises from about 10 to about 60 contiguous third monomers.

In certain embodiments, the invention relates to any one of the methods described herein, wherein the block copolymer comprises from about 40 to about 300 contiguous first monomers.

In certain embodiments, the invention relates to any one of the methods described herein, wherein the block copolymer is MPEG-b-PCL-b-PLL.

In certain embodiments, the invention relates to any one of the methods described herein, wherein the block copolymer is

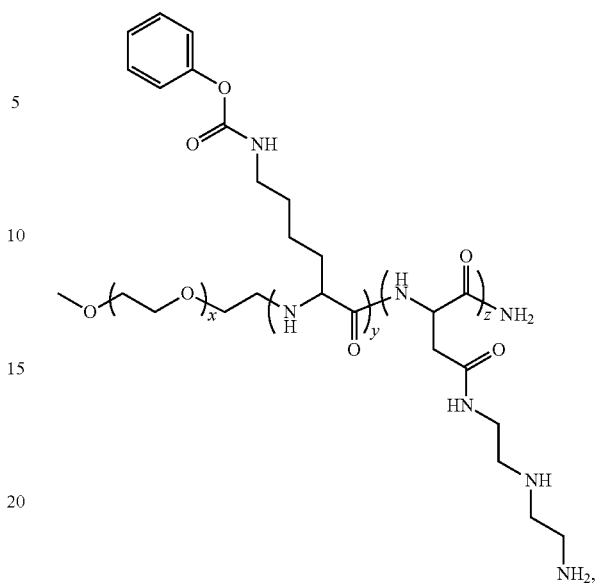

wherein x is from about 40 to about 300;

y is from about 3 to about 60; and z is from about 10 to about 60.

In certain embodiments, the invention relates to any one of the methods described herein, wherein the guide RNA is sgRNA.

In certain embodiments, the invention relates to any one of the methods described herein, wherein the Cas9 mRNA and guide RNA are in the form of a CRISPR Cas9 plasmid.

In certain embodiments, the invention relates to any one of the methods described herein, wherein the composition further comprises a DNA repair template non-covalently associated with the block copolymer. In certain embodiments, the invention relates to any one of the methods described herein, wherein the DNA repair template is a ssDNA repair template.

In certain embodiments, the invention relates to any one of the methods described herein, wherein the composition further comprises an anticancer agent.

In certain embodiments, the invention relates to any one of the methods described herein, wherein the anticancer agent is covalently bound to the block copolymer.

In certain embodiments, the invention relates to any one of the methods described herein, wherein the anticancer agent is an alkylating agent or a nucleic acid cross-linking agent.

In certain embodiments, the invention relates to any one of the methods described herein, wherein the anticancer agent is an alkylating agent.

In certain embodiments, the invention relates to any one of the methods described herein, wherein the anticancer agent is a nucleic acid cross-linking agent.

In certain embodiments, the invention relates to any one of the methods described herein, wherein the anticancer agent comprises Pt(II) or Pt(IV).

In certain embodiments, the invention relates to any one of the methods described herein, wherein the anticancer agent is covalently bound to at least one third monomer.

In certain embodiments, the invention relates to any one of the methods described herein, wherein at least one third monomer has the structure of Formula I:

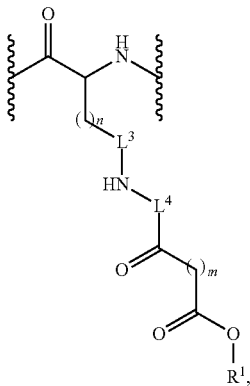

Formula I wherein
R¹ comprises the anticancer agent;
L³ is a bond or —C(=O)—;
L⁴ is a bond or [—(C₁-C₆)alkylene-NR—]$_p$;
p is 1, 2, or 3;
R is H or C₁-C₆alkyl;
n is 1, 2, 3, 4, 5, or 6; and
m is 1, 2, 3, 4, 5, or 6.

In certain embodiments, the invention relates to any one of the methods described herein, wherein the anticancer agent is a nucleic acid cross-linking agent.

In certain embodiments, the invention relates to any one of the methods described herein, wherein the anticancer agent comprises Pt(II) or Pt(IV). In certain embodiments, the invention relates to any one of the methods described herein, wherein the anticancer agent comprises Pt(IV).

In certain embodiments, the invention relates to any one of the methods described herein, wherein R¹ is a moiety represented by the structural formula

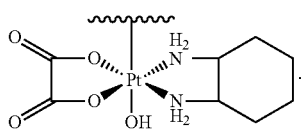

In certain embodiments, the invention relates to any one of the methods described herein, wherein the anticancer agent is a moiety represented by the structural formula:

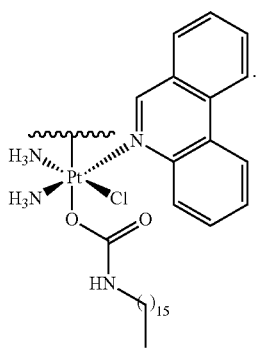

In certain embodiments, the invention relates to any one of the methods described herein, wherein n is 3, 4, or 5. In certain embodiments, the invention relates to any one of the methods described herein, wherein n is 4.

In certain embodiments, the invention relates to any one of the methods described herein, wherein m is 1, 2, or 3. In certain embodiments, the invention relates to any one of the methods described herein, wherein m is 2.

In certain embodiments, the invention relates to any one of the methods described herein, wherein L³ is a bond. In certain embodiments, the invention relates to any one of the methods described herein, wherein L³ is —C(=O)—.

In certain embodiments, the invention relates to any one of the methods described herein, wherein L⁴ is a bond. In certain embodiments, the invention relates to any one of the methods described herein, wherein L⁴ is [—(C₁-C₆)alkylene-NR—]$_p$. In certain embodiments, the invention relates to any one of the methods described herein, wherein L⁴ is [—(CH₂CH₂)—NR—]₂.

In certain embodiments, the invention relates to any one of the methods described herein, wherein R is H.

In certain embodiments, the invention relates to any one of the methods described herein, wherein the anticancer agent is non-covalently associated with the block copolymer.

In certain embodiments, the invention relates to any one of the methods described herein, wherein the anticancer agent is an alkylating agent or a nucleic acid cross-linking agent.

In certain embodiments, the invention relates to any one of the methods described herein, wherein the anticancer agent is an alkylating agent.

In certain embodiments, the invention relates to any one of the methods described herein, wherein the anticancer agent is a nucleic acid cross-linking agent.

In certain embodiments, the invention relates to any one of the methods described herein, wherein the anticancer agent comprises Pt(II) or Pt(IV). In certain embodiments, the invention relates to any one of the methods described herein, wherein the anticancer agent comprises Pt(II).

In certain embodiments, the invention relates to any one of the methods described herein, wherein the polymer is a diblock copolymer comprising a first block and a second block, and the second block comprises a plurality of fourth monomers, wherein each fourth monomer has a pKa less than or equal to about 6 in water.

In certain embodiments, the invention relates to any one of the methods described herein, wherein at least one fourth monomer comprises a —CO₂⁻ functionality at pH about 7.

In certain embodiments, the invention relates to any one of the methods described herein, wherein each fourth monomer is selected from the group consisting of aspartic acid, glutamic acid, glycolic acid, acrylic acid, and methacrylic acid.

In certain embodiments, the invention relates to any one of the methods described herein, wherein the second block comprises from about 5 to about 240 contiguous fourth monomers.

In certain embodiments, the invention relates to any one of the methods described herein, wherein the aqueous pharmaceutically acceptable carrier comprises a buffer.

In certain embodiments, the invention relates to any one of the methods described herein, wherein the pH of the aqueous pharmaceutically acceptable carrier is about 6.8 to about 7.4.

In certain embodiments, the invention relates to a particle comprising a biodegradable core having an outer surface and a polymer non-covalently associated with the outer surface of the core, wherein
the biodegradable core comprises
an anticancer agent; and
a block copolymer comprising:
(i) a first block comprising a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;
(ii) a second block comprising a plurality of second monomers, wherein each second monomer is selected from the group consisting of 6-hydroxycaproic acid, side-chain N-protected lysine, lactic acid, glycolic acid, hydroxybutyrate, valine, isoleucine, leucine, methionine, phenylalanine, tryptophan, cysteine, alanine, proline, glycine, tyrosine, side-chain carbonyl-protected aspartic acid, side-chain carbonyl-protected glutamic acid, propylene carbonate, butyl acrylate, butyl methacrylate, and benzyl methacrylate; and
(iii) a third block comprising a plurality of third monomers, wherein each third monomer is selected from the group consisting of lysine, side-chain aminoalkyl-functionalized lysine, asparagine, side-chain aminoalkyl-functionalized asparagine, arginine, aspartamide, side-chain aminoalkyl-functionalized aspartamide, and ethyleneimine,
wherein the anticancer agent is covalently bound to the block copolymer;
the polymer comprises a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin; and
the characteristic size of the particle, as determined by dynamic light scattering (DLS), is about 20 nm to about 300 nm.

In certain embodiments, the invention relates to any one of the particles described herein, wherein the particle does not comprise a targeting agent.

In certain embodiments, the invention relates to any one of the particles described herein, wherein the anticancer agent has an $IC_{50}$ of less than 10 nM. In certain embodiments, the invention relates to any one of the particles described herein, wherein the anticancer agent has an $IC_{50}$ of less than 1 nM. In certain embodiments, the invention relates to any one of the particles described herein, wherein the anticancer agent has an $IC_{50}$ of from about 1 pM to about 10 nM. In certain embodiments, the invention relates to any one of the particles described herein, wherein the anticancer agent has an $IC_{50}$ of from about 1 pM to about 5 nM. In certain embodiments, the invention relates to any one of the particles described herein, wherein the anticancer agent has an $IC_{50}$ of from about 1 pM to about 1 nM.

In certain embodiments, the invention relates to any one of the particles described herein, wherein the anticancer agent is a molecule having a molecular weight from about 300 Da to about 1,000 Da.

In certain embodiments, the invention relates to any one of the particles described herein, wherein the anticancer agent is an alkylating agent, a nucleic acid cross-linking agent, or a microtubule inhibitor.

In certain embodiments, the invention relates to any one of the particles described herein, wherein the anticancer agent is an alkylating agent.

In certain embodiments, the invention relates to any one of the particles described herein, wherein the anticancer agent is a nucleic acid cross-linking agent.

In certain embodiments, the invention relates to any one of the particles described herein, wherein the anticancer agent is a microtubule inhibitor.

In certain embodiments, the invention relates to any one of the particles described herein, wherein the anticancer agent is selected from the group consisting of an auristatin (e.g., MMAE, MMAF), vincristine, vinblastine, a calicheamicin, a maytansinoid or maytansine (e.g., DM1, DM4), a tubulysin, a pyrrolobenzodiazepine (PBD) or a PBD dimer, an indolinobenzodiazepine, an irinotecan, a duocarmycin, a camptothecin, doxorubicin, α-amanitin, a cryptophycin, an anthracycline, rhizoxin, a splicostatin, a thailanstatin, and an amanitin. In certain embodiments, the invention relates to any one of the particles described herein, wherein the anticancer agent is an auristatin. In certain embodiments, the invention relates to any one of the particles described herein, wherein the anticancer agent is MMAE.

In certain embodiments, the invention relates to any one of the particles described herein, wherein the anticancer agent is covalently bound to at least one third monomer.

In certain embodiments, the invention relates to any one of the particles described herein, wherein the anticancer agent is covalently bound to at least one third monomer via a self-immolative or cleavable linker. In certain embodiments, the invention relates to any one of the particles described herein, wherein the self-immolative or cleavable linker comprises a disulfide functionality. In certain embodiments, the invention relates to any one of the particles described herein, wherein the self-immolative or cleavable linker comprises a dipeptide. In certain embodiments, the invention relates to any one of the particles described herein, wherein the self-immolative linker comprises Val-Cit.

In certain embodiments, the invention relates to any one of the particles described herein, wherein at least one third monomer has the structure of Formula I:

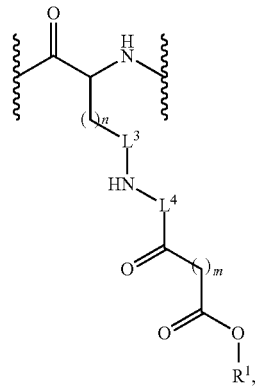

Formula I wherein
$R^1$ comprises the anticancer agent and, optionally, a self-immolative or cleavable linker;
$L^3$ is a bond or —C(=O)—;
$L^4$ is a bond or $[-(C_1-C_6)\text{alkylene-NR}-]_p$;
p is 1, 2, or 3;
R is H or $C_1$-$C_6$alkyl;
n is 1, 2, 3, 4, 5, or 6; and
m is 1, 2, 3, 4, 5, or 6.

In certain embodiments, the invention relates to any one of the particles described herein, wherein the block copolymer is MPEG-b-PCL-b-PLL, wherein at least one PLL monomer has a structure of Formula I:

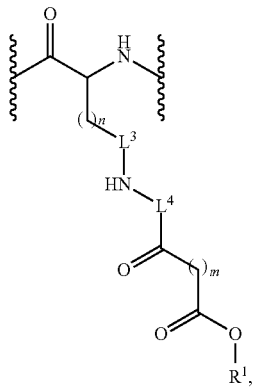

Formula I wherein $R^1$ comprises the anticancer agent and, optionally, a self-immolative or cleavable linker;

$L^3$ is a bond or —C(=O)—;

$L^4$ is a bond or [—(C$_1$-C$_6$)alkylene-NR—]$_p$;

p is 1, 2, or 3;

R is H or C$_1$-C$_6$alkyl;

n is 4; and m is 1, 2, 3, 4, 5, or 6.

In certain embodiments, the invention relates to any one of the particles described herein, wherein n is 3, 4, or 5. In certain embodiments, the invention relates to any one of the particles described herein, wherein n is 4.

In certain embodiments, the invention relates to any one of the particles described herein, wherein m is 1, 2, or 3. In certain embodiments, the invention relates to any one of the particles described herein, wherein m is 2.

In certain embodiments, the invention relates to any one of the particles described herein, wherein $L^3$ is a bond. In certain embodiments, the invention relates to any one of the particles described herein, wherein $L^3$ is —C(=O)—.

In certain embodiments, the invention relates to any one of the particles described herein, wherein $L^4$ is a bond. In certain embodiments, the invention relates to any one of the particles described herein, wherein $L^4$ is [—(C$_1$-C$_6$)alkylene-NR—]$_p$. In certain embodiments, the invention relates to any one of the particles described herein, wherein $L^4$ is [—(CH$_2$CH$_2$)—NR—]$_2$.

In certain embodiments, the invention relates to any one of the particles described herein, wherein R is H.

In certain embodiments, the invention relates to any one of the particles described herein, wherein $R^1$ is a moiety represented by the structural formula

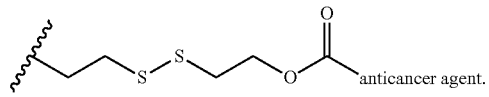
anticancer agent.

In certain embodiments, the invention relates to any one of the particles described herein, wherein $R^1$ is a moiety represented by the structural formula In certain embodiments, the invention relates to any one of the particles described herein, wherein the block copolymer comprises from about 3 to about 60 contiguous second monomers.

In certain embodiments, the invention relates to any one of the particles described herein, wherein the block copolymer comprises from about 10 to about 60 contiguous third monomers.

In certain embodiments, the invention relates to any one of the particles described herein, wherein the block copolymer comprises from about 40 to about 300 contiguous first monomers.

In certain embodiments, the invention relates to any one of the particles described herein, wherein the polymer is a diblock copolymer, and the second block comprises a plurality of fourth monomers, wherein each fourth monomer has a pKa less than or equal to about 6 in water.

In certain embodiments, the invention relates to any one of the particles described herein, wherein at least one fourth monomer comprises a —CO$_2^-$ functionality at pH about 7.

In certain embodiments, the invention relates to any one of the particles described herein, wherein each fourth monomer is selected from the group consisting of aspartic acid, glutamic acid, glycolic acid, acrylic acid, and methacrylic acid.

In certain embodiments, the invention relates to any one of the particles described herein, wherein the second block comprises from about 5 to about 240 contiguous fourth monomers.

In certain embodiments, the invention relates to a particle comprising a biodegradable core having an outer surface and a polymer non-covalently associated with the outer surface of the core, wherein the biodegradable core comprises an anticancer agent; and Pt(IV);

the polymer comprises a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin; and the characteristic size of the particle, as determined by dynamic light scattering (DLS), is about 20 nm to about 300 nm In certain embodiments, the invention relates to any one of the particles described herein, wherein the particle does not comprise a targeting agent.

In certain embodiments, the invention relates to any one of the particles described herein, wherein the polymer comprises a first anionic end-group; and the biodegradable core further comprises Pt(IV) coordinated to the first anionic end-group of the polymer.

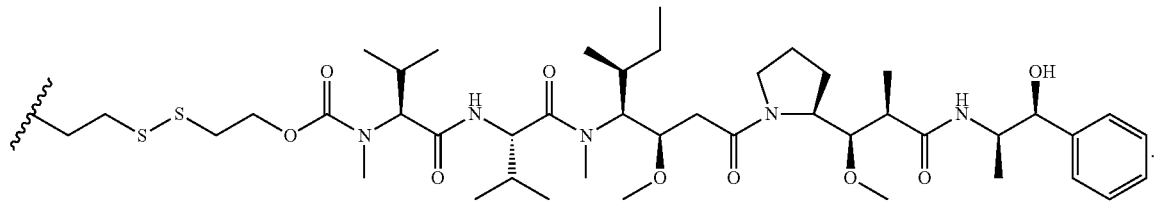 [SMILES: *CCSSCCOC(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

In certain embodiments, the invention relates to any one of the particles described herein, wherein the biodegradable core further comprises a hydrophobic polymer; the hydrophobic polymer comprises a second anionic end-group; and the second anionic end-group is coordinated to Pt(IV).

In certain embodiments, the invention relates to any one of the particles described herein, wherein the particle comprises the anticancer agent and a compound represented by the structural formula:

$$\begin{array}{c} \text{polymer} \\ H_3N_{\prime\prime\prime\prime}\underset{|}{\overset{|}{Pt}}^{\prime\prime\prime\prime\prime Cl} \\ H_3N^{\nearrow}\underset{OC(O)-NH\text{-hydrophobic polymer.}}{|}\searrow Cl \end{array}$$

In certain embodiments, the invention relates to any one of the particles described herein, wherein the particle comprises the anticancer agent and a compound represented by the structural formula:

$$\begin{array}{c} \text{polymer} \\ H_3N_{\prime\prime\prime\prime}\underset{|}{\overset{|}{Pt}}^{\prime\prime\prime\prime\prime Cl} \\ H_3N^{\nearrow}\underset{O}{|}\searrow Cl \\ O\diagdown\!\!\diagup\!\!O \\ HN\diagdown\!\!\diagdown_{15}. \end{array}$$

In certain embodiments, the invention relates to any one of the particles described herein, wherein the anticancer agent is non-covalently associated with the biodegradable core.

In certain embodiments, the invention relates to any one of the particles described herein, wherein the anticancer agent is paclitaxel or BMN 673.

In certain embodiments, the invention relates to any one of the particles described herein, wherein the polymer is represented by the structural formula:

<br> and r is from about 40 to about 80.

In certain embodiments, the invention relates to any one of the particles described herein, wherein r is from about 40 to about 50. In certain embodiments, the invention relates to any one of the particles described herein, wherein r is about 45.

In certain embodiments, the invention relates to a particle comprising a core and a polymer non-covalently associated with the core, wherein the polymer comprises a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;

the core comprises an imaging agent; and the characteristic size of the particle, as determined by DLS, is about 20 nm to about 300 nm.

In certain embodiments, the invention relates to any one of the particles described herein, wherein the particle does not comprise a targeting agent.

In certain embodiments, the invention relates to any one of the particles described herein, wherein the polymer is a diblock copolymer comprising a first block and a second block.

In certain embodiments, the invention relates to any one of the particles described herein, wherein the first block comprises the plurality of first monomers.

In certain embodiments, the invention relates to any one of the particles described herein, wherein each first monomer is selected from the group consisting of ethylene glycol and propylene glycol.

In certain embodiments, the invention relates to any one of the particles described herein, wherein each first monomer is ethylene glycol.

In certain embodiments, the invention relates to any one of the particles described herein, wherein the characteristic size of the particle, as determined by DLS, is about 20 nm to about 160 nm.

In certain embodiments, the invention relates to any one of the particles described herein, wherein the imaging agent is a chelator, an inorganic matrix, or a polymer that bind metals.

In certain embodiments, the invention relates to any one of the particles described herein, wherein the imaging agent is a lanthanide (e.g., gadolinium), a radioisotope that is detectable by SPECT or PET (e.g., $^{64}$Cu, $^{82}$Rb), or a metal that is detectable by Raman spectroscopy (e.g., Au).

In certain embodiments, the invention relates to any one of the particles described herein, wherein the imaging agent is a nitroxide compound, a fluorocarbon, or a PET emitting label (e.g., $^{18}$F, $^{15}$O, $^{11}$C).

In certain embodiments, the invention relates to any one of the particles described herein, wherein the imaging agent comprises a lanthanide.

In certain embodiments, the invention relates to any one of the particles described herein, wherein the imaging agent comprises $NaYF_4$ doped with Yb.

In certain embodiments, the invention relates to any one of the particles described herein, wherein the imaging agent comprises $NaYF_4$ doped with Yb and Er.

In certain embodiments, the invention relates to any one of the particles described herein, wherein the imaging agent comprises $NaYF_4$ doped with Yb and Ho.

In certain embodiments, the invention relates to any one of the particles described herein, wherein the imaging agent comprises $NaYF_4$ doped with Yb, Er, and Tm.

In certain embodiments, the invention relates to any one of the particles described herein, wherein the imaging agent comprises $NaYF4$ doped with Yb, Ho, and Tm.

In certain embodiments, the invention relates to a method of imaging cancer in a human subject in need thereof comprising administering by intraperitoneal injection or infusion to the intraperitoneal cavity a composition comprising a plurality of particles comprising an imagining agent, as described herein, in an aqueous pharmaceutically acceptable carrier; and obtaining an image of the cancer, wherein the cancer is a cancer that forms a peritoneal implant on the serosal surface of an organ of the peritoneal cavity.

In certain embodiments, the invention relates to any one of the methods described herein, wherein the composition does not comprise a targeting agent.

In certain embodiments, the invention relates to any one of the methods described herein, wherein the cancer is a cancer that spreads by peritoneal carcinomatosis.

In certain embodiments, the invention relates to any one of the methods described herein, wherein the cancer is ovarian, gastric, appendiceal, liver, pancreatic, colorectal, uterine, lobular breast, cervical, or primary peritoneal cancer.

In certain embodiments, the invention relates to any one of the methods described herein, wherein the cancer is endometrial cancer, abdominal methothelioma, or a soft tissue sarcoma.

In certain embodiments, the invention relates to any one of the methods described herein, further comprising removing the composition from the intraperitoneal cavity after about 1 h, about 2 h, about 3 h, about 4 h, or about 5 h.

In certain embodiments, the invention relates to any one of the methods described herein, wherein the composition is at a temperature of about 38° C., about 39° C., about 40° C., about 41° C., about 42° C., or about 43° C.

EXEMPLIFICATION

The invention now being generally described, it will be more readily understood by reference to the following, which is included merely for purposes of illustration of certain aspects and embodiments of the present invention, and is not intended to limit the invention.

Example 1—General Materials and Methods

Materials.

Methoxyl-poly(ethylene glycol)-block-poly-(c-caprolactone)-block-poly(L-lysine) (MPEG-b-PCL-b-PLL) was synthesized as described in Qi, R. et al. *J Control Release* 152 Suppl 1, e167-168 (2011). Its structure was verified by $^1$HNMR and found to be comprised of MPEG$_{114}$-b-PCL$_{20}$-b-PLL$_{25}$, where the subscript numbers denote the degrees of polymerization of each individual monomer in a given block. This polymer is abbreviated "P", hereafter. N-hydroxysuccinimide (NHS), 1-(3-dimethylaminopropyl)-3-ethylcarbodiimide hydrochloride (EDC.HCl), guanosine 5'-monophosphate disodium salt (5'-GMP) and sodium ascorbate were purchased from Sigma-Aldrich. Oxaliplatin and cisplatin were purchased from ChemiChem International Development Co., Ltd. They are abbreviated as Oxa (II) and Cis(II), respectively, to distinguish them from their platinum(IV) prodrugs in which the Pt atoms are in +4 valence. OxaPt(IV) prodrugs were synthesized and systematically characterized by NMR and MS following procedures described in Xiao, H. et al. *J Control Release* 163, 304-314 (2012). The CisPt(IV) derivatives were similarly synthesized. All other chemicals and solvents were used without further purification. Control (c-)siRNA that targets the sequence 5'-GGGUAAGUGUCCUACUGAAGU-3' (SEQ ID NO: 1), and BCL-2 siRNA that targets the sequence 5'-UGUGGAUGACUGA-GUACCUGA-3' (SEQ ID NO: 2) were purchased from Integrated DNA Technology. (IW, USA). The c-siRNA sequence did not match any known sequence in the human genome. Luciferase GL3 siRNA was purchased for GenePharma Co. Ltd. (Shanghai, China).

General Measurements.

$^1$HNMR spectra were measured using a Unity-300 MHz NMR spectrometer (Bruker) at room temperature. Fourier Transform Infrared (FT-IR) spectra were recorded on a Bruker Vertex 70 spectrometer. Mass Spectroscopy measurements were performed on a Quattro Premier XE system (Waters) equipped with an electrospray interface (ESI-MS). These methods along with matrix-assisted laser-desorption ionization and time-of-flight mass spectroscopy (MALDI-TOF-MS, Waters, USA) were used to study the reaction 5'-GMP and siRNA with various platinum species.

Atomic absorption spectroscopy (generation 8.0, Perkin Elmer) was used to study the kinetics of siRNA platination and to determine the platinum content in all micellar formulations. Inductively coupled plasma mass spectrometry (ICP-MS, Xseries II, Thermo scientific, USA) was used for quantitative determination of trace levels of platinum in cancer cells and to quantify Pt-DNA adduct formation. Sizes and distributions of micelles were determined by dynamic light scattering (DLS) with a vertically polarized He—Ne laser (DAWN EOS, Wyatt Technology, USA). The size and morphologies of the micelles very visualized using a JEOL JEM-1011 electron microscope. Particle size and zeta potential measurements were conducted on a Malvern Zetasizer Nano Z590. Micelles were prepared by directly dissolving various modified triblock copolymers in water at 0.5 mg/mL. The critical micelle concentration (CMC) values of M(P) and M(OxaPt(IV)) were measured using pyrene as a fluorescence probe.

Monitoring of 5'-GMP Binding with Various Platinum Species by $^1$HNMR.

(10 mM) 5'-GMP and (5 mM) OxaPt(II) were mixed in 700 µL of D$_2$O/H$_2$O (v/v=1:9), transferred to an NMR tube and placed in a 37° C. water bath for various time periods prior to $^1$HNMR measurement. Analogous methods were employed to obtain spectra for the reaction of 5'-GMP with OxaPt(IV), CisPt(II) and CisPt(IV). The binding kinetics of 5'-GMP to each platinum species were determined by measuring the relative amounts of free and Pt-bound 5'-GMP at each time point, integrating the ratio of the $^1$HNMR peaks at 8.5 ppm to 8.09 ppm.

Monitoring of Single-Stranded siRNA Binding with Various Platinum Species by MALDI-TOF-MS.

A single-stranded siRNA (UCA GGU ACU CAG UCA UCC ACA TT) (SEQ ID NO: 3) was mixed with OxaPt(II) at a molar ratio of 1:10 in RNAase free water (RNA final concentration: 50 µM; Pt final concentration: 500 µM; total volume: 100 µL). The reaction mixture was placed in a 37° C. incubator and 10 µL of sample were removed at various time points to obtain MALDI-TOF-MS spectra (positive model). Analogous methods were employed to obtain spectra of the reaction products of siRNA with OxaPt(IV), CisPt(II) and CisPt(IV).

Monitoring of Double-Stranded siRNA Binding with Various Platinum Species by AAS.

A double-stranded RNA (sense: UGUGGAUGACUGA-GUACCUG-ATT (SEQ ID NO: 4); antisense: UCAGGUA-CUCA-GUCAUCCACATT (SEQ ID NO: 3)) was mixed with OxaPt(II) at a molar ratio of 1:10 in RNAase free water (RNA final concentration: 5 µM; Pt final concentration at 50 µM; total volume of 100 µL). The reaction mixture was placed in a 37° C. incubator and samples were isolated after 30 m, 1 h, 6 h, and 12 h of incubation. The RNA was then isolated using a centrifugation separation device (molecular cut-off 3000 Da, spun at 10,000 rpm; Nanosep®3k, Pall Corporation, USA). Five wash cycles with RNAase free water (5×100 µL) then ensued. An aliquot of 2 µL from each sample was obtained for optical density (OD) measurements in order to quantify the concentration of RNA in the original sample, using a NanoDrop reader. The remainder of each sample was diluted in 3% HNO3 for Pt content measurement via AAS. The experiments were performed in triplicate and data are presented such that the concentration of Pt-RNA adducts at each time point are expressed as "µmol Pt/µmol RNA". Analogous methods were employed to obtain similar values for the numbers of Pt-RNA adducts formed by the reaction of siRNA with OxaPt(IV), CisPt(II) or CisPt(IV) at similar time points.

Cell Culture.

MCF-7 and OVCAR4 cell lines were obtained from ATCC and cultured in Dulbecco's Modified Eagle Medium (DMEM, Gibco, Carlsbad, Calif.)), containing RPMI 1640 supplemented with 10% fetal bovine serum (FBS, Gibco at 37° C. with 5% $CO_2$).

Real Time PCR.

BCL-2 siRNA was first pre-incubated with different platinum(II) (i.e. OxaPt(II) or CisPt(II)) or platinum(IV) containing species (i.e. OxaPt(IV) or CisPt(IV)) for various time periods and subsequently transfected into MCF-7 and OVCAR-4 cells in a 6-well plate format, using an RNAi-MAX Kit and by following the manufacturers instructions (Invitrogen, Thermo-Fisher, USA). 48 hours after transfection, total RNA was isolated using an RNeasy mini-kit (Qiagen, Germantown, Md.) and quantified by NanoDrop. 300 ng of mRNA were subsequently subjected to qRT-PCR analysis, targeting BCL-2 and glyceraldehyde 3-phosphate dehydrogenase (GAPDH) by using the SYBR Premix Ex (Takara, USA) and by using an Applied Biosystems StepOne Real-Time PCR System. Relative gene expression values were determined by the $\Delta\Delta CT$ method using StepOne Software v2.1 (Applied Biosystems). Data are presented as fold differences in siRNA expression normalized to GAPDH (house-keeping gene used as endogenous reference), employing a standard curve, and are reported relative to untreated (control) cells. The sequence of the primers used for BCL-2 and GAPDH are as follows: BCL-2 forward—5-CTGCACCTGACGCCCTTCACC-3 (SEQ ID NO: 5); Bcl-2 reverse—5-CACATGACCCCACCGAACTCAAAGA-3 (SEQ ID NO: 6); GAPDH forward—5-TTCACCACCATGGAGAAGGC-3 (SEQ ID NO: 7); and GAPDH reverse primer—5-GGCATGGACTGTGGT-CATGA-3 (SEQ ID NO: 8) (Integrated DNA Technology. IW, USA). The specificity of each set of primers was verified by melting curve analysis.

Formation of Polymeric Micelles.

PEO-b-PCL-b-PLL-based micelles (i.e. M(P)) were prepared as follows: 50 mg of P were dissolved in 10 mL DMF; 50 mL of water were then added drop-wise into the flask under continuous agitation, forming M(P) in suspension. The solution was then dialyzed against water to remove the organic solvent and freeze-dried for storage.

Conjugation of OxaPt(IV) to Polymeric Micelles.

OxaPt(IV) was conjugated to M(P) in aqueous solution, using EDC/NHS chemistry to prepare micellar constructs that were bound to the platinum(IV) species via amide bonds (i.e. M(OxaPt(IV)). Briefly, (0.191 g, 1 mmol) EDC.HCl and (0.115 g, 1 mmol) NHS were dissolved in deionized water under stirring. (0.42 g, 0.8 mmol) OxaPt(IV) was then added to the aqueous solution. After the suspension mixture became clear, (0.5 g) P (containing 1.25 mmol $NH_2$ groups) was added to the (100 mL) reaction mixture and stirred at RT for 24 h; the suspension was then dialyzed against water for an additional 12 h and lyophilized to obtain M(OxaPt(IV)).

The Pt content in M(OxaPt(IV)) was measured by ICP-OES and found to ~10 wt %.

Complexation of siRNA with Polymeric Micelles.

Suspensions of M(P) or M(OxaPt(IV)) were diluted with Opti-MEM medium (Invitrogen) to different final concentrations, varying the numbers of amine groups in solution. Equal volume solutions containing different Bcl-2 or control (c-)siRNA where then added to the micelles, varying the ratios of free animes to phosphates (N/P) in suspension. The suspensions were then mixed by gentle pipetting and the siRNA-complexed micelles were allowed to equilibrate at RT for 30 m. For electrophoresis-retardation analyses, complexes formed from either M(P) or M(OxaPt(IV)) and siRNA at different N/P ratios, ranging from 0.5 to 16, were prepared for a fixed (1 mM) concentration of siRNA; they were then ran on a 1% agarose gel in 0.5 mM tris-borate-EDTA buffer (TBE buffer; 89 mM Tris, 90 mM boric acid, 2 mM EDTA, pH 8.3) at 80 V for 30 m. Bands containing free and micellar bound siRNA were visualized using a UV illuminator (Tanon GIS System) after ethidium bromide staining.

In Vitro Cytotoxicity Measurements.

MCF-7 cells were seeded in 96-well plates at a density of $1 \times 10^4$ cells/well. 100 µL of DMEM supplemented with 10% FBS were added to each well and the cells were incubated at 37° C. for 24 h. The cells were then treated with OxaPt(II), OxaPt(IV), or M(OxaPt(IV) with and without micellar-complexed BCL-2 or c-siRNA. An equivalent (100 nM) concentration of siRNA was added to each well and media was replaced by fresh DMEM after 4 h; the cells were subsequently allowed to incubate at 37° C. for an additional 48 h prior to evaluation of any treatment cytotoxicity, using the MTT assay. In brief, (20 µL) MTT solution (5 mg/mL) in PBS buffer was added to each well and allowed to incubate for 4 h. (150 µL) DMSO was then added to the cells to replace the MTT-containing media. After gentle agitation for 5 min, the absorbance of each well at 570 nm was recorded on a Bio-Rad Plate Reader. All experiments were conducted in triplicate.

Intracellular Uptake of Fluorescently-Labeled Micelles.

For confocal microscopy experiments, MCF-7 cells were plated on coverslips in 6-well plates ($1 \times 10^5$ cells/well) and cultured with RPMI 1640 supplemented with 10% FBS for 24 h. The cells were then incubated with 50 nM Alexa488-labeled siRNA that was electrostatically complexed to micelles, which were also covalently conjugated to Cy5.5 (i.e. M(Cy5.5/Alexa488 siRNA)) or to Cy5.5 and OxaPt(IV) (i.e. M(Cy5.5/OxaPt(IV)/Alexa488 siRNA), for 1 or 4 h. After removal of media, the cells were then washed twice with cold phosphate buffered saline (PBS, pH 7.4, 0.01 M) and fixed with 4% formaldehyde (Sigma-Aldrich, St. Louis, USA). To label the cell nucleus, samples were incubated with 1 mg/mL DAPI (Sigma-Aldrich, St. Louis, USA) for 15 min in PBS, followed by extensive rinsing with PBS. Slides were mounted on a coverslip and observed by using an Olympus FV1000 laser confocal scanning microscope imaging system (Japan).

For flow cytometry measurements, LUC+ MCF-7 were similarly cultured in 12-well plates ($3 \times 10^4$ cells/well) prior to incubation with M(Cy5.5/Alexa488 siRNA) or M(Cy5.5/OxaPt(IV)/Alexa488 siRNA) for 1 or 4 h The cells were washed twice with cold PBS, lysed with trypsin—EDTA solution, collected by centrifugation (1500 rpm, 5 min), and finally analyzed for fluorescence content using a FACSCalibur flow cytometer (BD Biosciences, USA). Cells with fluorescence above the threshold intensity for untreated cells (i.e. blank) were quantified and compared. The percentage of such cells in the total population was considered as a measure of uptake efficiency. Data were analyzed using FlowJo software (Version 7.6.2)

Quantification of the Intracellular Uptake of Various Platinum Species.

MCF-7 cells were seeded in 12-well plates at a density of $10^5$ cells per well and incubated overnight in 1 mL of DMEM containing 10% FBS. 100 µL of each oxaliplatin containing treatment (e.g OxaPt(II), OxaPt(II)+M(c-siRNA), OxaPt(II)+M(Bcl-2), M(OxaPt(IV)/c-siRNA) or M(OxaPt(IV)/Bcl-2)) were then added to each well to a final Pt concentration of 2 µg/mL; note, for siRNA containing treatments, the final siRNA concentration in each well was 100 nM. After 4 h of treatment incubation, media was exchanged with an equal volume of DMEM, containing 10% FBS; and, cells were incubated for an additional 24 h followed by lysis and quantification of Pt content by ICP-MS.

Cellular Apoptosis Assays.

MCF-7 cells were cultured in 12-well plates and treated with various oxaliplatin formulations at a fixed platinum dose of 2 µg/mL. After 48 h, apoptotic cells were detected on flow cytometry using the Annexin V-FITC Apoptosis Detection Kit I (BD Biosciences, San Jose, Calif.); and, the results were analyzed using WinMDI 2.9 software.

Example 2—Monitoring the Reaction of siRNA with Various Platinum Species

OxaPt(II) and CisPt(II) are known to bind to guanine (G) and adenine (A) bases in both DNA and RNA. To compare the relative reactivity of these platinum(II) species as compared to their platinum(IV) counterparts (namely OxaPt(IV) and CisPt(IV)), we first incubated each of these four compounds with guanosine monophosphate (5'-GMP) for different time intervals and in conditions that would mimic a typical in vitro RNAi experiment (i.e. 30 min, 1 h, 3 h, 6 h and 12 h at 37° C.). Formation of Pt-(5'-GMP)$_2$ adducts were subsequently monitored by ESI-MS (FIG. 4A and FIG. 4B) and by MALDI/TOF MS (data not shown). Differences in the kinetics of adduct formation by various platinum(II) and platinum(IV) species were subsequently studied by $^1$H NMR spectroscopy under similar conditions. The chemical shifts of the H8 proton on the guanosine base (e.g. 8.5 ppm in the DACHPt(5'-GMP)$_2$ adduct vs. 8.09 ppm in unreacted 5'-GMP) were monitored at various time points after co-incubation of (10 mM) 5'-GMP with either (5 mM) OxaPt (II) or OxaPt(IV) species (data not shown). By integrating the ratio of the two peaks at each time point, the relative amount of DACHPt(5'-GMP)$_2$ adduct to total 5'-GMP could be calculated in solutions containing either OxaPt(II) (green) or OxaPt(IV) (red) and plotted as a function of time (FIG. 4C). The results showed that approximately 10% of the 5'-GMP pool already consisted of DACHPt(5'-GMP)$_2$ adducts by 30 m after incubation with OxaPt(II); the number of adducts that were formed increased exponential over the first 6 h, reaching >40% of the total pool, and thereby, continued to increase linearly over time. Similarly rapid formation and time dependent increases in the amounts of Pt(NH$_3$)$_2$(5'-GMP)$_2$ adducts were seen when 5'-GMP was reacted with CisPt(II) but not when it was incubated in solutions that contained CisPt(IV) (data not shown).

Figure 4H:
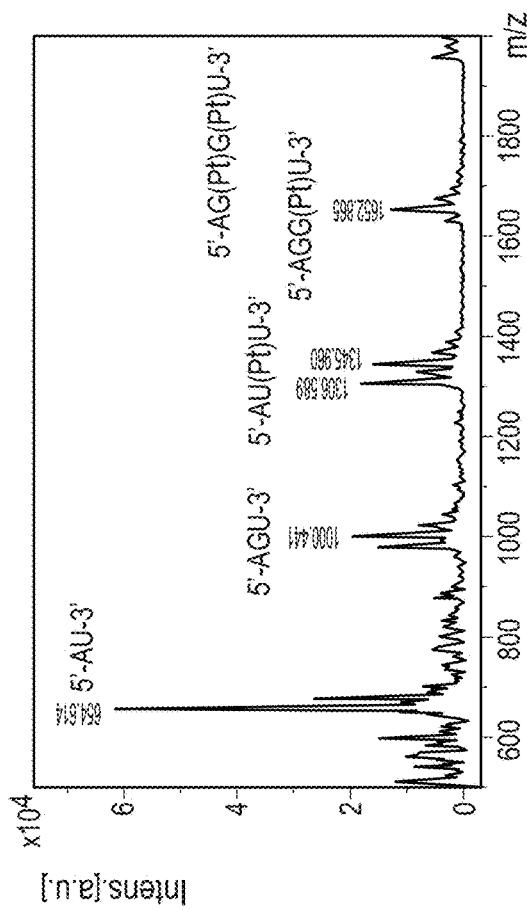
FIG. 4H is a MALDI-TOF-MS spectrum (intensity (a.u.) vs. m/z) of the species produced by enzymatic cleavage of the antisense chain of BCL-2 siRNA by RNase A after incubation with OxaPt(II) to demonstrate sites of platination.
Figure 4G:
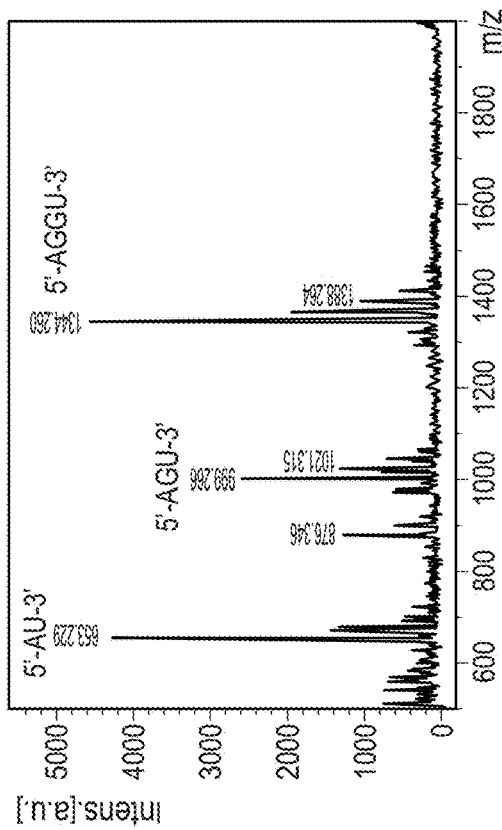
FIG. 4G is a MALDI-TOF-MS spectrum (intensity (a.u.) vs. m/z) of the species produced by enzymatic cleavage of the antisense chain of BCL-2 siRNA by RNase A before incubation with OxaPt(II) to demonstrate sites of platination.
Figure 5A:
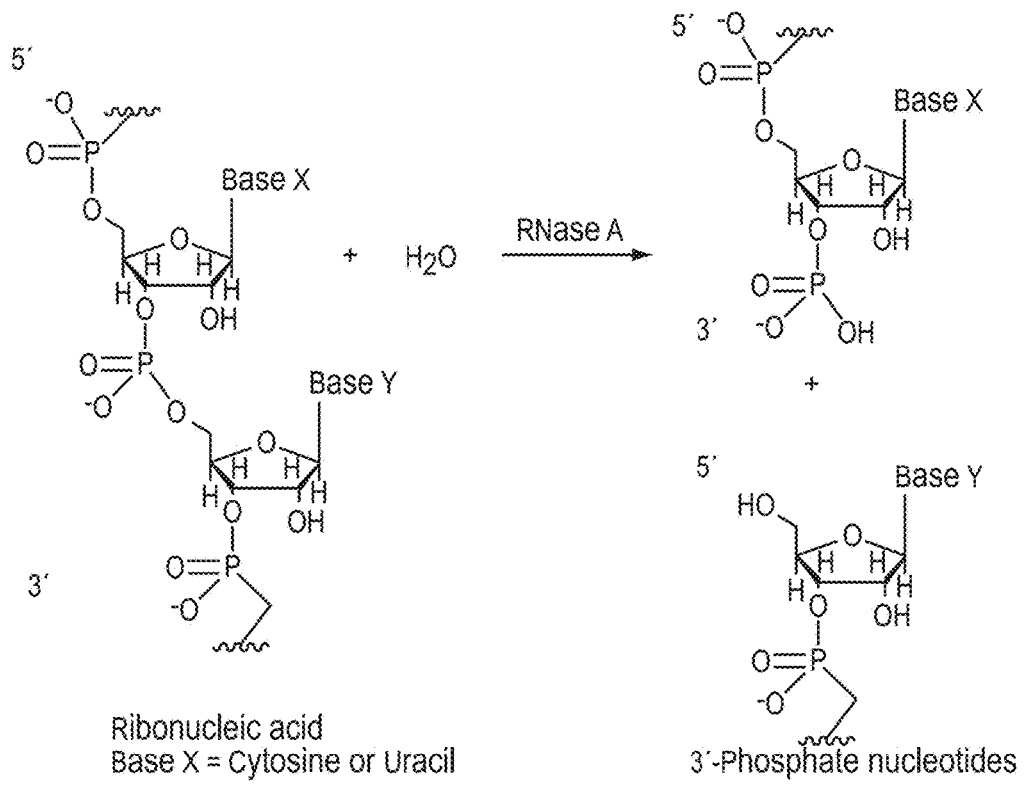
FIG. 5A is a schematic illustration of the reaction of RNase A with RNA.
Figure 5B:
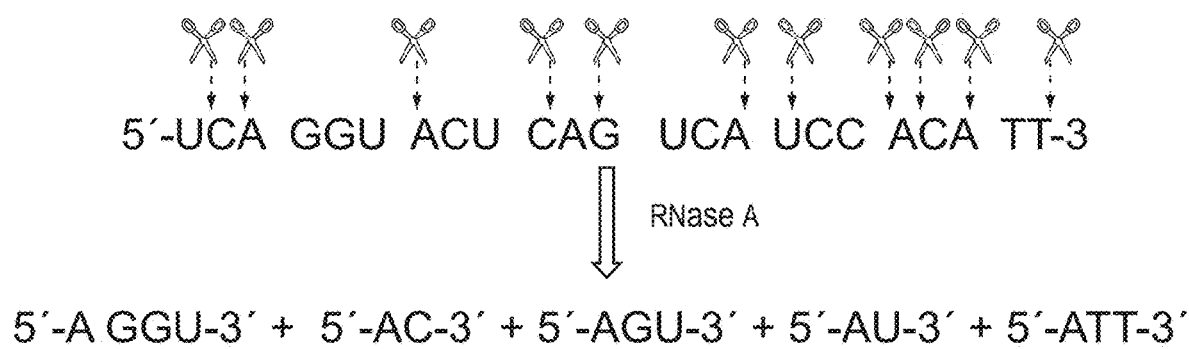
FIG. 5B is a schematic illustration of possible reaction products obtained after site specific cleavage of ss-BCL-2 siRNA (anti-sense) (SEQ ID NO: 3) by RNase A. Mass peaks of 5'-AU-3', 5'-AGU-3' and 5'-AGGU-3' can be found in the MALDI/TOF-MS spectra in FIG. 4E.

MALDI/TOF MS was used to ascertain the kinetics of platinum-RNA adduct formation using BCL-2 siRNA that was incubated with a 10-fold excess of various platinum(II) or platinum(IV) species. These experiments demonstrated that Pt-siRNA adducts could be detected as early as 1 h in the presence of oxaPt(II) and by 30 m when incubated with CisPt(II) (FIG. 4D). Notably, no Pt-siRNA adducts were detected in solutions of BCL-2 siRNA containing OxaPt(IV) or CisPt(IV) even after 24 h of co-incubation under physiological conditions (pH 7.4; FIG. 4E). AAS measurements of siRNA that had been isolated after co-incubation with various platinum species was conducted to determine the concentration of Pt-siRNA adducts formed over time. These results indicate that >50% of the siRNA transcripts were platinated by 3 h of incubation with OxaPt(II) (FIG. 4F). To determine the platination sites on the transcripts, MALDI/TOF MS experiments using a model SS oligonucleotide of DNA that contained a single GG site were used to verify the formation of mono- and bis-Pt-DNA adducts in the presence of OxaPt(II) but not OxaPt(IV) (data not shown). MALDI/TOF MS was then conducted after enzymatic cleavage of the antisense chain of BCL-2 siRNA by RNase A before (FIG. 4G) and after incubation (FIG. 4H) incubation with OxaPt (II), demonstrating two distinct reaction sites (FIG. 5).

Figure 6:
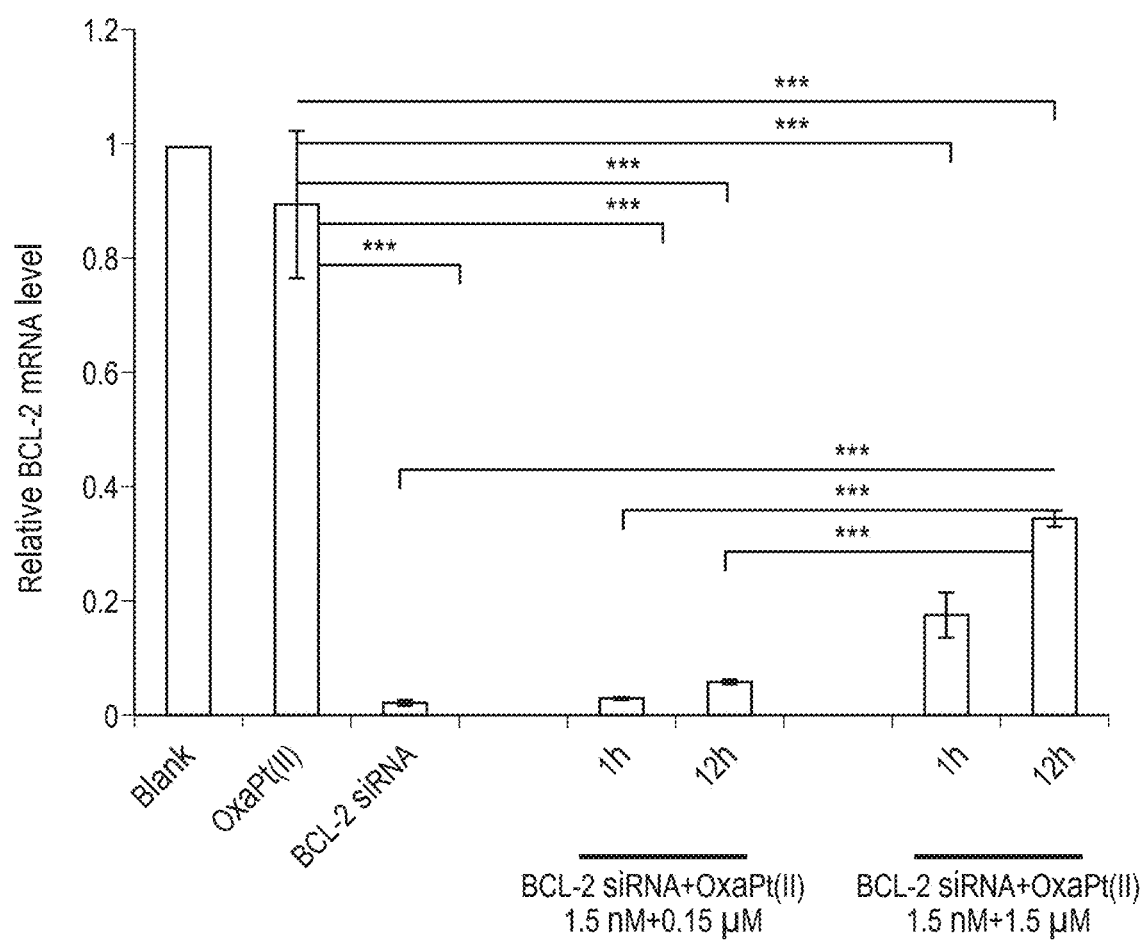
FIG. 6 is a bar graph of relative BCL-2 mRNA levels. These data show that incubation of OxaPt(II) with siRNA results in a concentration and time-dependent decrease in silencing efficiency. Relative BCL-2 mRNA levels in MCF-7 breast cancer cells were determined by RT-qPCR at 48 h after lipofectamine-based transfection with BCL-2 siRNA. The siRNA was either used directly or after pre-incubation with different concentrations of OxaPt(II) for various durations of time (1 vs. 12 h). Significance is denoted by ***p<0.001.
Figure 7A:
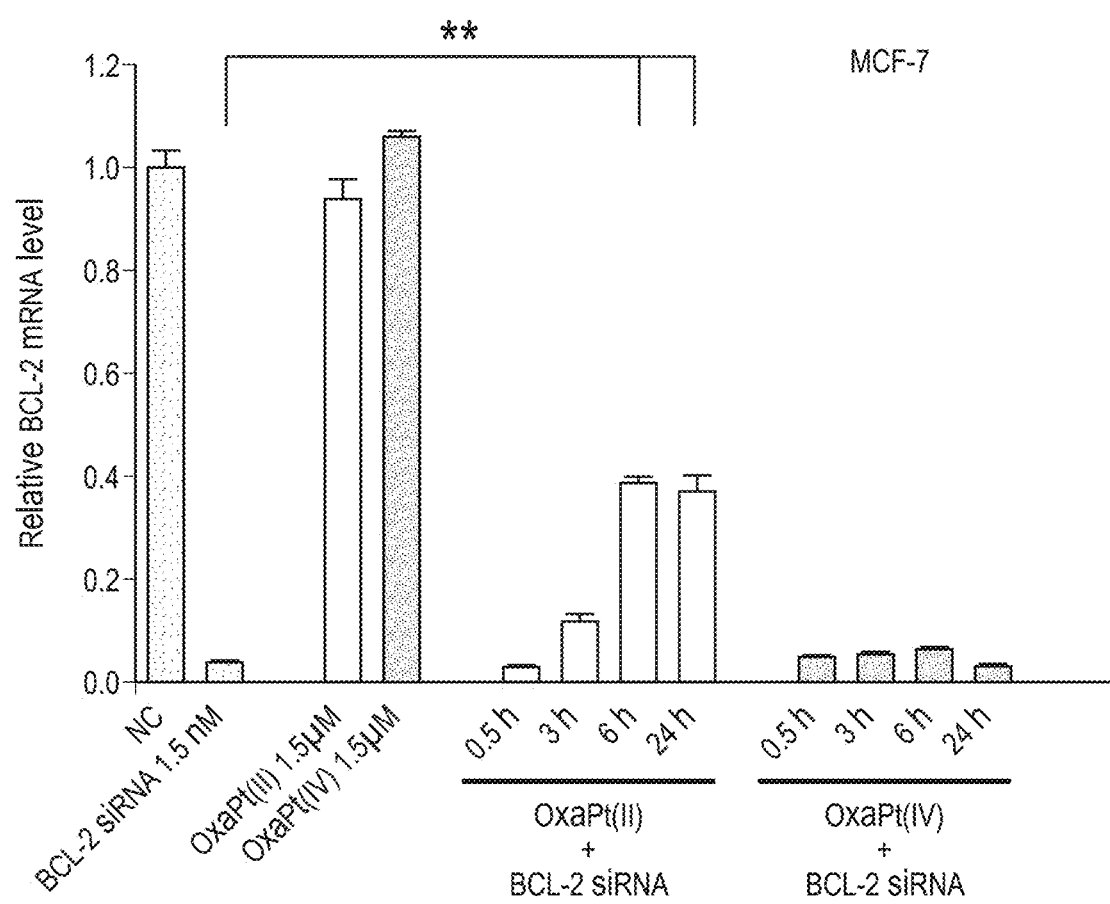
FIG. 7A is a bar graph of relative BCL-2 mRNA levels in MCF-7 breast cancer cells at 37° C. and at 24 h after lipofectamine-based transfection of BCL-2 siRNA. (1.5 nM) siRNA was utilized as is or similarly preincubated with either (1.5 uM) platinum(II) or platinum(IV) species for various time periods (as indicated) prior to transfection. Data are depicted as mean values±standard deviations of the mean (n=3 technical replicates per condition; note, 3 experimental replicates were similar conducted for each cell line and treatment, yielding analogous results. Significance is defined as  p<0.01; * p<0.001.
Figure 7B:
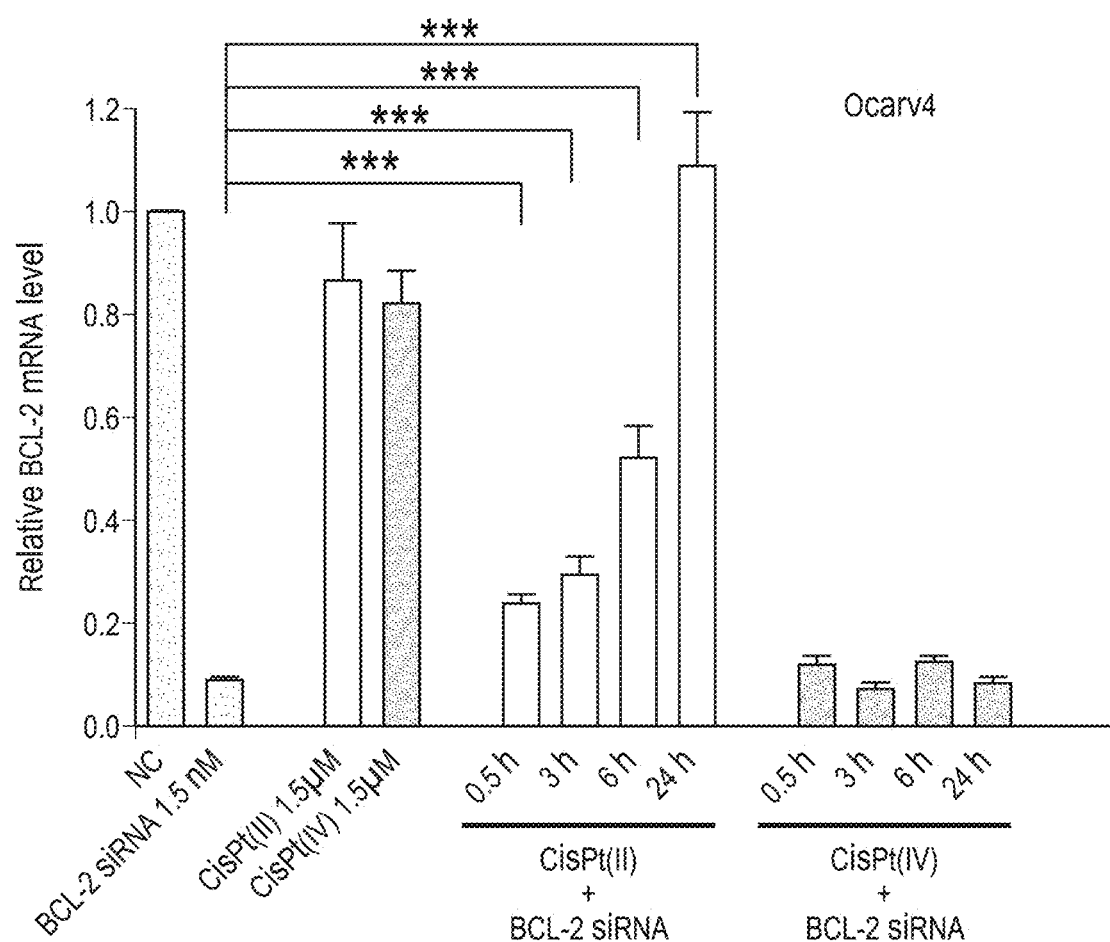
FIG. 7B is a bar graph of relative BCL-2 mRNA levels in OVCAR-4 ovarian cancer cells at 37° C. and at 24 h after lipofectamine-based transfection of BCL-2 siRNA. (1.5 nM) siRNA was utilized as is or similarly preincubated with either (1.5 uM) platinum(II) or platinum(IV) species for various time periods (as indicated) prior to transfection. Data are depicted as mean values±standard deviations of the mean (n=3 technical replicates per condition; note, 3 experimental replicates were similar conducted for each cell line and treatment, yielding analogous results. Significance is defined as  p<0.01; * p<0.001.

Changes in the relative silencing activity of BCL-2 siRNA that was preincubated with platinum(II) vs. platinum (IV) species prior to cellular exposure were determined. Various incubation times were examined in order to control the number of Pt-RNA adducts that would be present on the RNAi transcript. The commercially available cationic liposome-based transfection reagent lipofectamine (RNAi-MAX) was utilized for siRNA delivery and various concentrations of platinum to siRNA were first explored (FIG. 6). qRT-PCR of BCL-2 mRNA isolated from MCF-7 or OVCAR4 cells at 24 h after treatment showed ineffective BCL-2 silencing (i.e. >30% of baseline mRNA expression) by siRNA that had be pre-incubated for >3 h with a 1000 fold excess of either OxaPt(II) or CisPt(II) (FIG. 7); the activity of the siRNA was unperturbed by 24 h of exposure to similar concentrations of either OxaPt(IV) or CisPt(IV).

Example 3—Characterization of Nanoparticles

Figure 8:
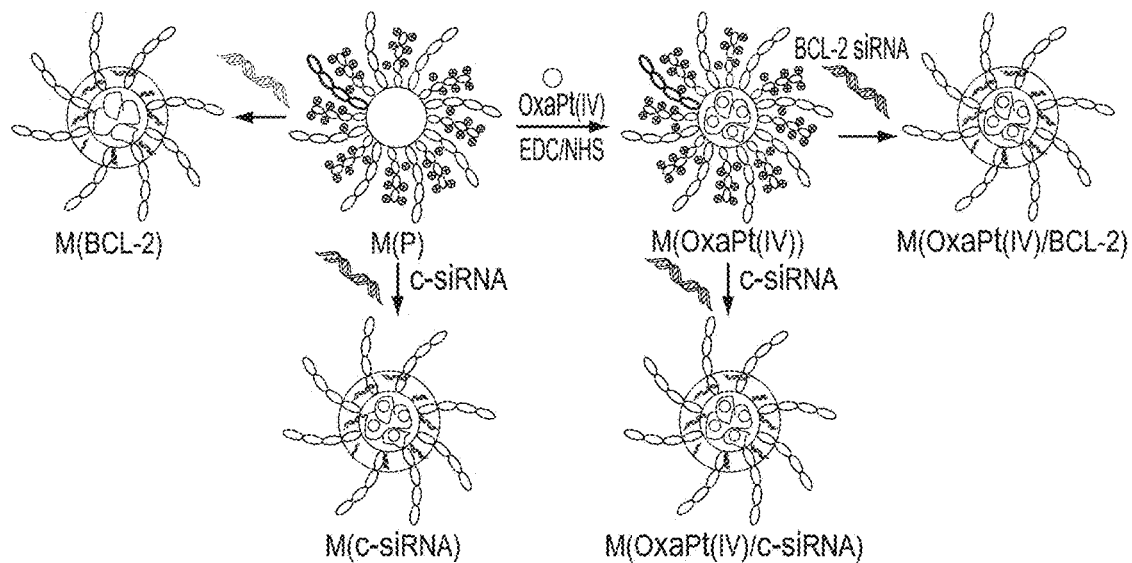
FIG. 8 is a schematic representation of the preparation of various siRNA-loaded micelles. Starting with empty polymer micelles (M(P)), M(c-siRNA) and M(BCL-2) represent micelles that are formed by electrostatic complexation of the mPEG-b-PCL-PLL polymer with either c-siRNA or BCL-2 siRNA, respectively. M(OxaPt(IV)) represent polymeric micelles that are formed after chemical conjugation of the free carboxylic acid moieties of OxaPt(IV) with amines on the surfaces of M(P) in the presence of EDC/NHS reagent. Further electrostatic complexation of these resultant micelles with either c-siRNA or BCL-2 siRNA yields M(Ox-aPt(IV)/c-siRNA) and M(OxaPt(IV)/BCL-2), respectively.

In order to deliver the largest intracellular concentrations of both siRNA and platinum-based small molecules while preserving their individual and synergistic activities, a transfection reagent comprised of the biodegradable triblock copolymer of methoxyl-terminated poly(ethylene glycol)-block-poly-(ε-caprolactone)-block-poly(L-lysine) (i.e. mPEG$_{114}$-b-PCL$_{25}$-b-PLL$_{25}$; "P") was synthesized. This polymer was designed to self-assemble into micelles with a hydrophobic PCL core and a corona that consisted of hydrophilic mPEG and positively-charged PLL segments (i.e. M(P), where "M" stands for micelles; FIG. 1B). OxaPt (IV) was coupled to the PLL polymer through formation of an amide bond between the carboxyl group of its auxiliary ligand and the free amino group in lysine, forming micelles that contained oxaPt(IV) species (i.e. M(oxaPt(IV)). Similarly, siRNA could be complexed with unreacted PLL chains through electrostatic interactions, forming micelles that contained BCL-2 (i.e. M(BCL-2)) or control siRNA (i.e. M(c-siRNA)) (FIG. 8). Note, both OxaPt(IV) and siRNA species may also be combined in a single micelle construct (i.e. M(oxaPt(IV)/BCL-2) or M(oxaPt(IV)/c-siRNA), respectively), consisting of a hydrophilic mPEG corona, a middle layer comprised of PLL/siRNA, and a hydrophobic core of PCL and PLL-OxaPt(IV) conjugates. In this later construct, the siRNA is protected from platination both through physical separation in different layers of the nanocomplex as well as by utilization of an unreactive platinum(IV) species (i.e. OxaPt(IV)). Each of these constructs was generated to examine its relative utility for protecting the siRNA transcript from platination and subsequent deactivation. Notably, when taken up intracellularly, the platinum species in M(Oxa(IV)) is reduced by ascorbic acid and/or glutathione, liberating free OxaPt(II) only after intracellular siRNA delivery; free oxaPt(II) is then capable of reacting with nuclear DNA (FIG. 1E).

Figures 9A, 9B, 9C:
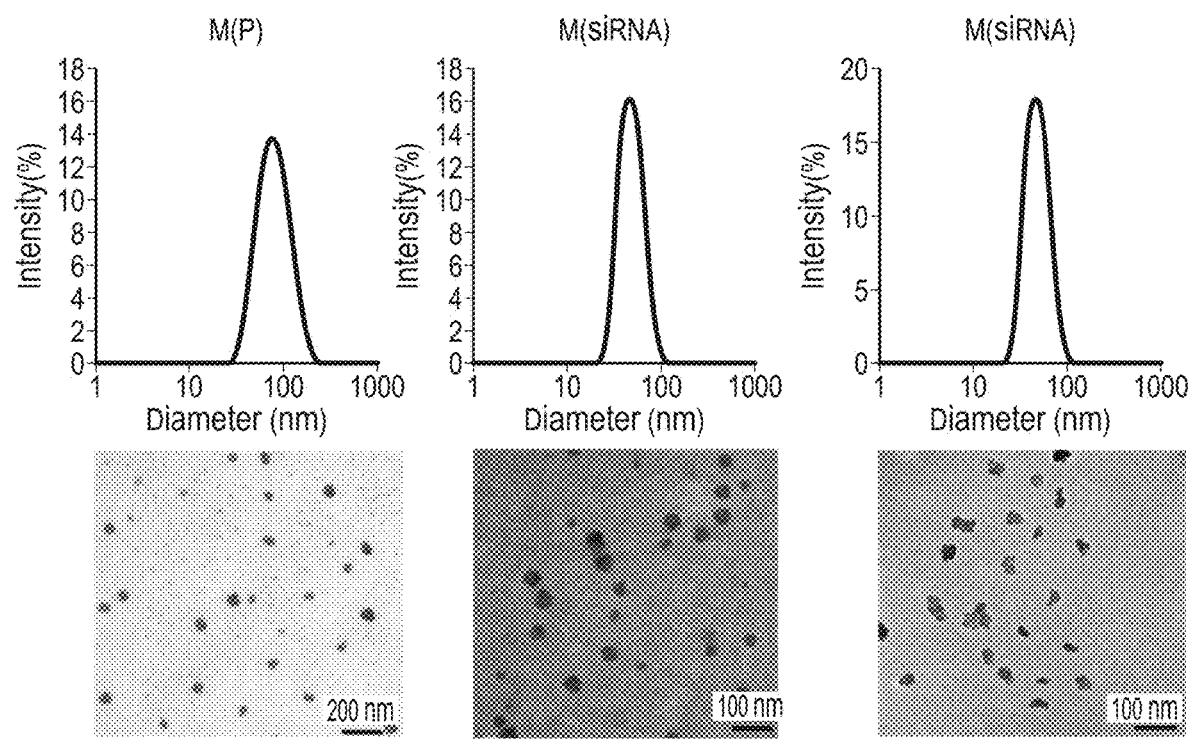
FIG. 9A is a DLS plot (% intensity vs. diameter (nm)) (upper) and a TEM image (lower) of empty polymeric micelles comprised of mPEG-b-PCL-b-PLL in water (i.e. M(P)).
FIG. 9B is a DLS plot (% intensity vs. diameter (nm)) (upper) and a TEM image (lower) of polymeric micelles complexed with BCL-2 siRNA (i.e. M(BCL-2)) in water.
FIG. 9C is a DLS plot (% intensity vs. diameter (nm)) (upper) and a TEM image (lower) of micelles that were chemically conjugated to OxaPt(IV) species (i.e. M(OxaPt (IV)) in water.

The mPEG$_{114}$-b-PCL$_{25}$-b-PLL$_{25}$ polymer was found to have a critical micelle concentration (CMC) of 31.9 μg/mL. It formed M(P) with a mean diameter of 70.8+/−0.5 nm (as assessed by DLS) and with a zeta potential of +46.1+/−4.2 mV (FIG. 9). Notably, once coupled to the PLL polymer, the OxaPt(IV) conjugate becomes less water soluble, driving its segregation within the PCL core and leaving unreacted PLL chains in the outer layer of M(OxaPt(IV)); this assertion is supported by experimental evidence that demonstrated a decrease in the CMC from 37 to 24 μg/mL (FIG. 10), an increase in the mean particle diameter to 92.6+/−2.6 nm by DLS, and a reduction in the zeta potential to +34.8+/−1.9 for M(OxaPt(IV)) as compared to M(P) (Table 1).

TABLE 1

Physical characterization of various polymeric micelle compositions

| Samples | Size | | PDI | Zeta Potential (mV) |
| --- | --- | --- | --- | --- |
| | TEM (nm) | DLS (nm) | | |
| M(P) | 58.6 ± 6.2 | 70.8 ± 0.5 | 0.196 ± 0.038 | 46.1 ± 4.2 |
| M(BCL-2) | 39.8 ± 7.8 | 55.4 ± 0.7 | 0.265 ± 0.029 | 35.5 ± 0.6 |
| M(OxaPt(IV)) | 41.1 ± 9.5 | 92.6 ± 2.6 | 0.203 ± 0.017 | 34.8 ± 1.9 |
| M(OxaPt(IV)/BCL-2) | 78.9 ± 10.4 | 104.9 ± 2.1 | 0.199 ± 0.018 | 26.6 ± 1.5 |

Figure 11A:
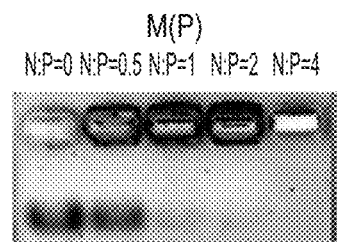
FIG. 11A is an image of a gel. These data show the electrophoretic mobility of siRNA on agarose gels before and after complexation with M(P) at different initial N/P ratios (0, 0.5, 1, 2, and 4 from left to right, respectively).
Figure 11B:
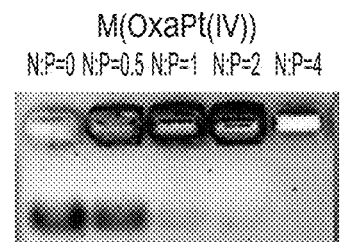
FIG. 11B is an image of a gel. These data show the electrophoretic mobility of siRNA on agarose gels before and after complexation with M(OxaPt(IV)) at different initial N/P ratios (0, 0.5, 1, 2, and 4 from left to right, respectively).
Figure 11C:
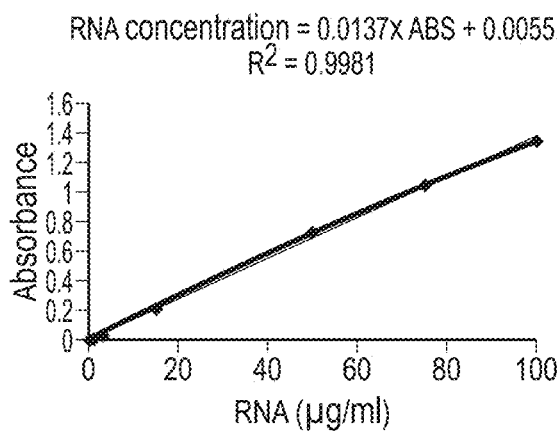
FIG. 11C is the standard curve (absorbance vs. RNA concentration (µg/mL)) for quantifying siRNA concentrations as a function of Alexa488-labeled siRNA absorbance in solution ($I_{ABS}$=488 nm).
Figure 11D:
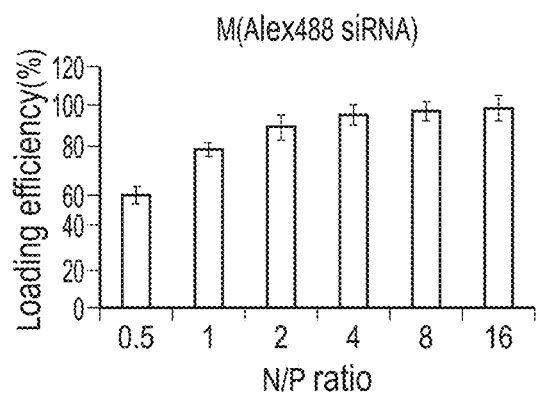
FIG. 11D is a bar graph of the loading efficiency of Alexa488-labeled siRNA to polymer in micelles formed from electrostatic complexation of Alexa448-labeled siRNA and M(P) (i.e. M(Alexa488 siRNA), as a function of the initial N/P ratio from 0.5 to 16.
Figure 11E:
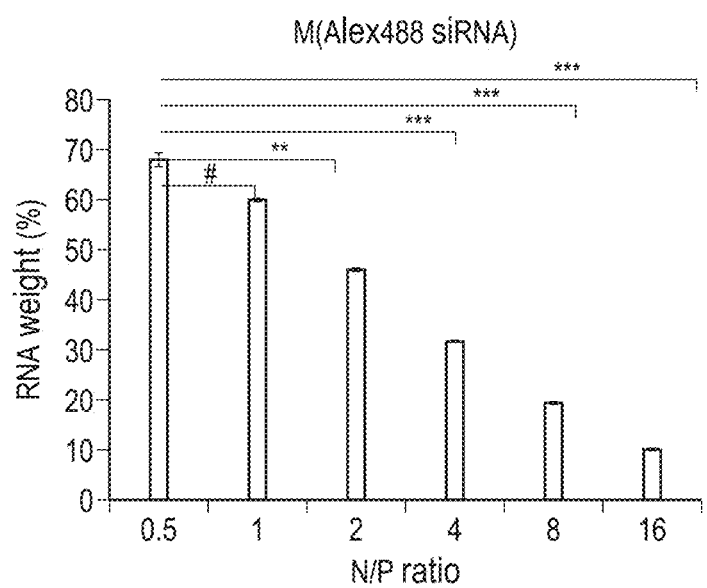
FIG. 11E is a bar graph of the final weight percentage of Alexa488-labeled siRNA to polymer in micelles formed from electrostatic complexation of Alexa448-labeled siRNA and M(P) (i.e. M(Alexa488 siRNA), as a function of the initial N/P ratio from 0.5 to 16. Significance is defined as p<0.01, *p<0.001. Note, # denotes p>0.05.

The reaction of OxaPt(IV) with mPEG$_{114}$-b-PCL$_{25}$-b-PLL$_{25}$ polymer was conducted at an initial molar ratio of 0.6:1 Pt to NH$_2$ groups (on the PLL block). Overall, M(OxaPt(IV)) was found to be comprised of 10 wt % Pt, corresponding to a final oxaliplatin content of 20.4 wt % (as determined by AAS). This degree OxaPt(IV) functionalization would be expected to yield 72% unreacted amine groups on the PLL corona of M(OxaPt(IV)), which would enable further complexation of siRNA through electrostatic interactions. To prove M(OxaPt(IV)) was able to complex with Bcl-2 siRNA, agarose gel electrophoresis experiments were conducted for siRNA after coincubation with either M(P) or M(OxaPt(IV)) (FIG. 11A and FIG. 11B). The results showed that the mobility of siRNA was completely inhibited when electrostatically complexed with M(P) above a N/P ratio (defined as the ratio of nitrogen atoms on the polymer to phosphate units on the siRNA) equal to 2; the mobility of siRNA was similarly reduced when it was complexed with M(OxaPt(IV)) above a N/P=4. Using Alexa488-labeled BCL-2 siRNA, the loading efficiency was found to be approximately 100% and the final micellar composition consisted of 30% RNA by weight (FIG. 11C, FIG. 11D, and FIG. 11E). Representative micelles containing both BCL-2 siRNA and OxaPt(IV) formed at a N/P=4 (i.e. M(OxaPt(IV)/Bcl-2)) exhibited spherical structure with mean particle diameter of 78.9+/−10.4 nm and 104.9+/−2.1 nm by TEM and DLS, respectively (FIG. 12A and FIG. 12B); M(OxaPt(IV)/Bcl-2) had a reduced zeta potential of +26.6+/−1.5 mV as compared to either M(P) or M(oxaPt(IV)) (Table 1), further supporting shielding of free amines on the PLL block by siRNA. M(OxaPt(IV)/BCL-2) demonstrated controlled release of both platinum and siRNA species (FIG. 12C and FIG. 12D). Notably, BCL-2 siRNA was also directly complexed to M(P) to generated M(Bcl-2) with a mean diameter of 55.4+/−0.7 nm (DLS) and a zeta potential of +35.5+/−0.6 mV.

Example 4—siRNA Activity

Figure 13B:
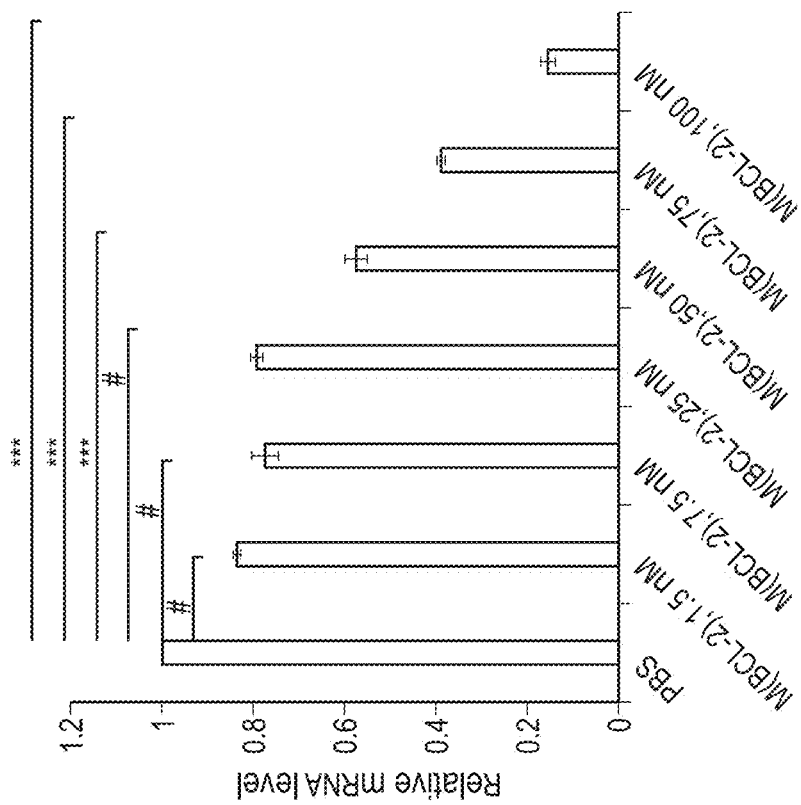
FIG. 13B is a bar graph showing the relative BCL-2 mRNA levels in MCF-7 breast cancer cells treated with different concentrations of BCL-2 siRNA. Note, the siRNA was transfected using polymeric micelles comprised of mPEG-b-PCL-b-PLL formed at a fixed N/P ratio=8:1 anionic siRNA to cationic polymer. Significance is defined as p<0.01 and *p<0.001. Note, # denotes p>0.05.
Figure 13A:
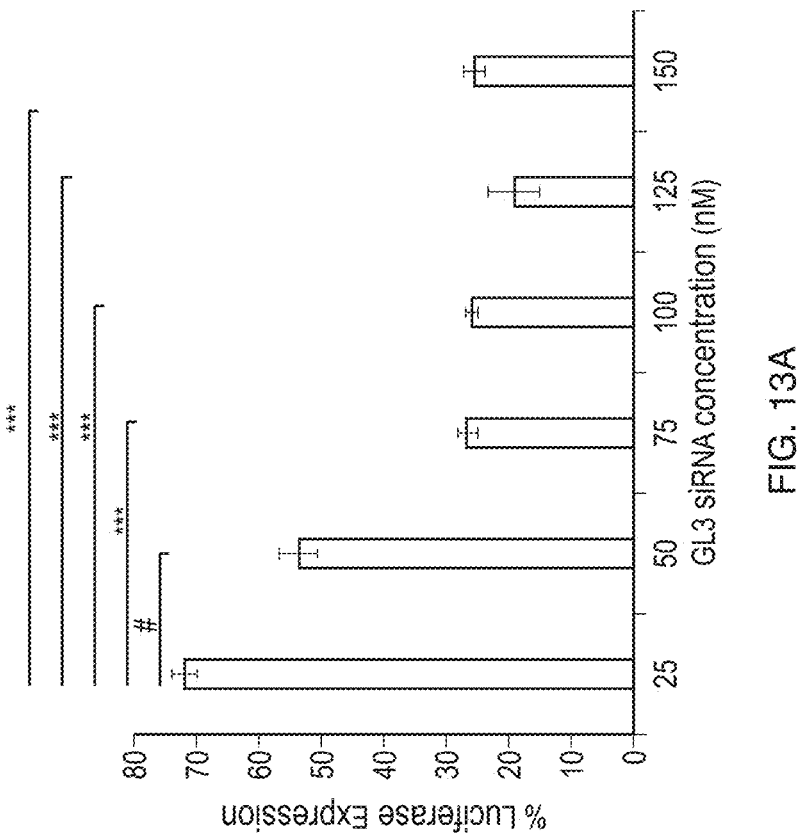
FIG. 13A is a bar graph showing the relative expression of luciferase in LUC$^+$ MCF-7 in MCF-7 breast cancer cells treated with different concentrations of anti-luciferase GL3 siRNA. Note, the siRNA was transfected using polymeric micelles comprised of mPEG-b-PCL-b-PLL formed at a fixed N/P ratio=8:1 anionic siRNA to cationic polymer. Significance is defined as p<0.01 and *p<0.001. Note, # denotes p>0.05.
Figure 14A:
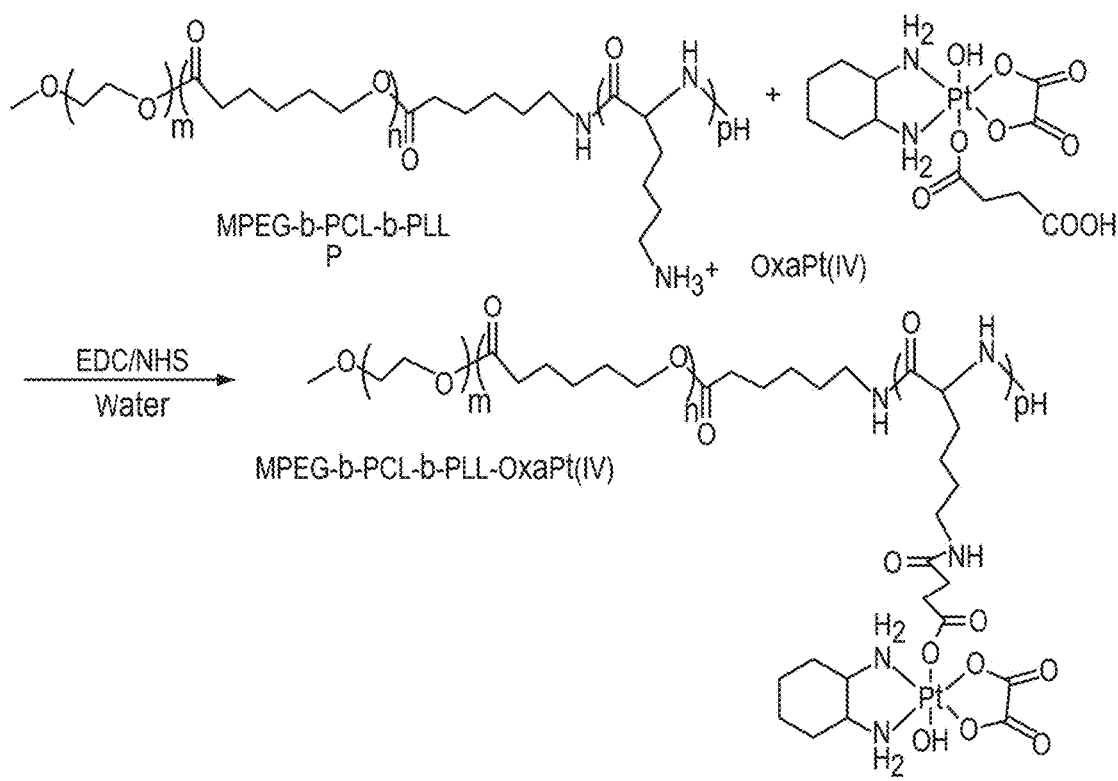
FIG. 14A is a schematic representation of a synthesis of mPEG-b-PCL-b-PLL-OxaPt(IV).
Figure 14B:
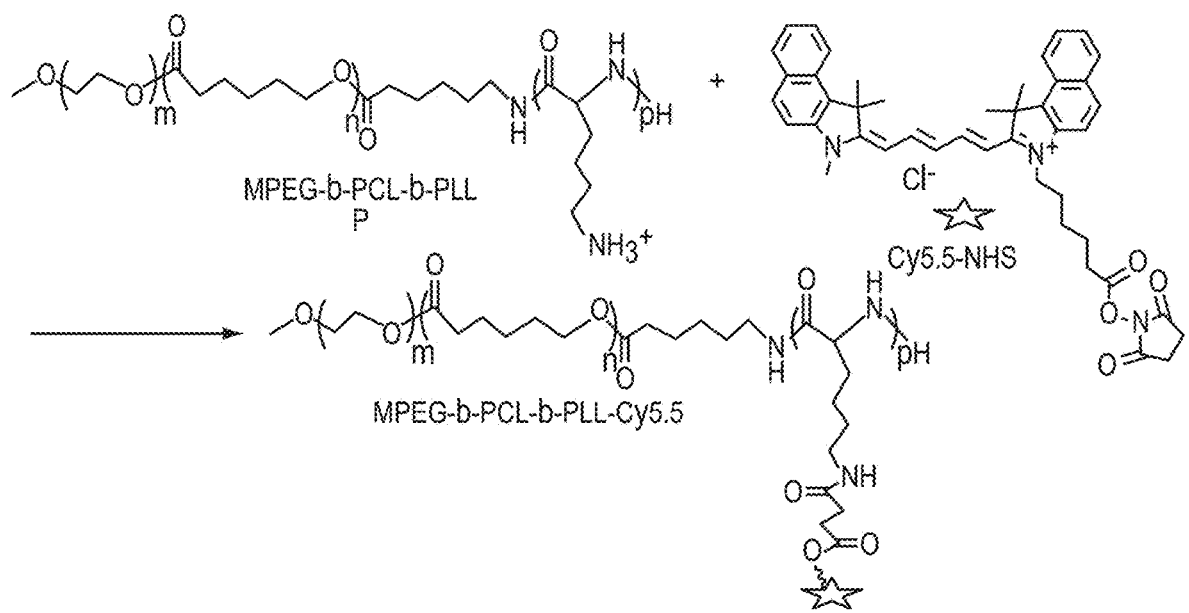
FIG. 14B is a schematic representation of conjugation of the polymer from FIG. 14A to Cy5.5.
Figure 15:
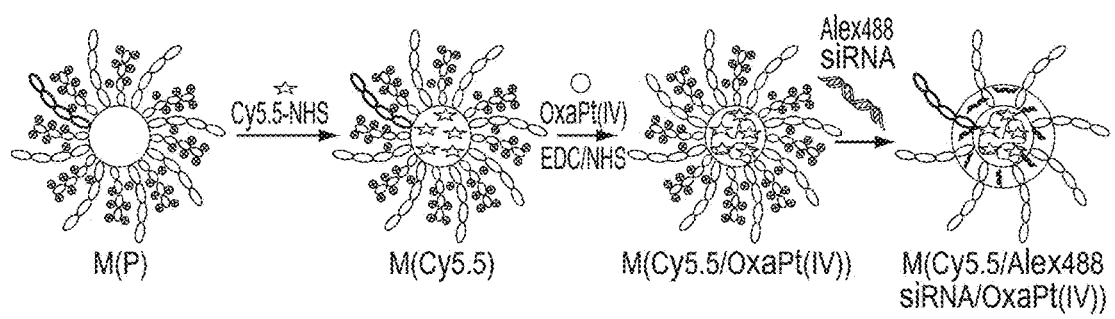
FIG. 15 is a schematic representation of a preparation of Cy5.5-conjugated polymeric micelles that contain OxaPt (IV) and Alex-488 labeled siRNA. Cy5.5-NHS (Lumiprobe, FL, USA) was conjugated to mPEG-b-PCL-b-PLL, yielding fluorescently labeled micelles in solution (i.e. M(Cy5.5)). Blending of the same polymer with mPEG-b-PCL-b-PLL-OxaPt(IV) generates dual-labeled micelles (i.e. M(Cy5.5/ OxaPt(IV)). Further complexation with Alexa-488 labeled siRNA yields M(Cy5.5/Alexa488 siRNA/OxaPt(IV)), which enables independent monitoring of each species within the micelle (e.g. polymer and siRNA by fluorescence and platinum by GFAAS/ICP-MS).
Figure 16A:
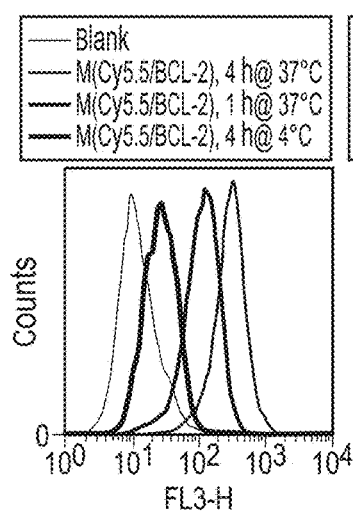
FIG. 16A is a plot of the intracellular uptake of BCL-2 siRNA-containing micelles by OVCAR4 ovarian cancer cells, as determined by flow cytometry for Cy5.5-labeled polymer. OVCAR4 cells were seeded in 6-well plates at a density of $4\times10^5$ cells/well. After attachment overnight, the cells were then treated with M(Cy5.5/BCL-2) at 1 µg or 4 µg Cy5.5/mL. The cells were incubated with each micellar formulation for 1 or 4 h and at either 37 or 4° C. prior to flow measurements of labeled populations.
Figure 16B:
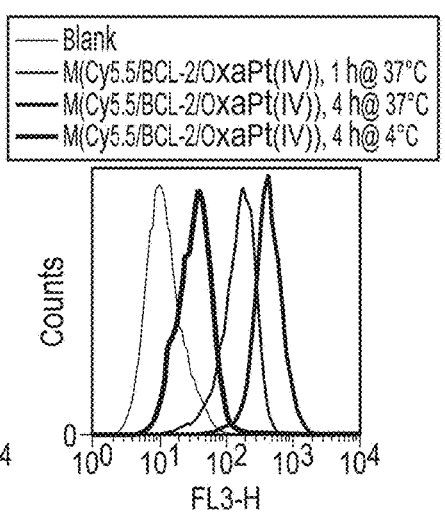
FIG. 16B is a plot of the intracellular uptake of BCL-2 siRNA-containing micelles by OVCAR4 ovarian cancer cells, as determined by flow cytometry for Cy5.5-labeled polymer. OVCAR4 cells were seeded in 6-well plates at a density of $4\times10^5$ cells/well. After attachment overnight, the cells were then treated with M(Cy5.5/BCL-2/OxaPt(IV)) at 1 µg or 4 Cy5.5/mL. The cells were incubated with each micellar formulation for 1 or 4 h and at either 37 or 4° C. prior to flow measurements of labeled populations.
Figure 16C:
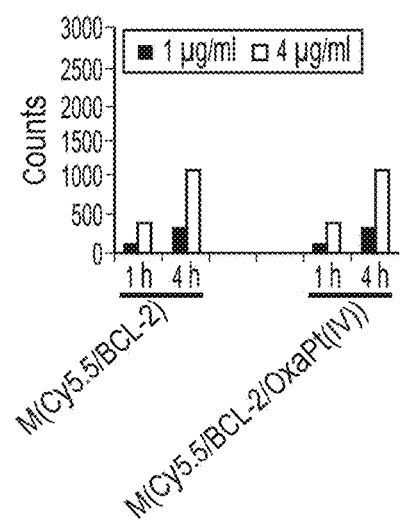
FIG. 16C is a bar graph showing the peak fluorescence intensities of Cy5.5 within OVCAR4 cells at various time points after incubation with the different micellar formulations from FIG. 16A and FIG. 16B.

Different concentrations of luciferase and BCL-2 siRNAs were used to achieve mRNA knockdown of their respective targets in a LUC+ MCF-7 cell line. For both M(P) and M(OxaPt(IV)), an N/P=4 was utilized for siRNA complexation. Maximal RNAi was obtained by utilizing 100 nM siRNA (FIG. 13). To better study the mechanisms of nanoparticle uptake, a Cy5.5-labeled PEO-b-PCL-b-PLL polymer was synthesized using EDC/NHS chemistry (FIG. 14). Alexa488-conjugated siRNA was then complexed to micelles comprised of this Cy5.5-labeled polymer (i.e. M(cy5.5/Alexa488 siRNA)) or Cy5.5-labeled polymer and OxaPt(IV) (i.e. M(Cy5.5/OxaPt(IV)/Alexa488 siRNA) to enable independent tracking of both siRNA and polymer species (FIG. 15); M(Cy5.5/OxaPt(IV)/Alexa488 siRNA) was subsequently incubated with MCF-7 cells for different time intervals and the cells were visualized by confocal laser scanning microscopy (CLSM) (FIG. 12E). Flow cytometry was also utilized to quantify intracellular levels of Cy5.5-labeled polymer and Alexa488-siRNA in MCF-7 (FIG. 12F and FIG. 12G) and in OVCAR-4 cells (FIG. 16). Notably, cells that were treated with either M(Cy5.5/Alexa488-siRNA) or M(Cy5.5/OxaPt(IV)/Alexa488 siRNA) showed that the siRNA was distributed throughout the cytoplasm, indicating effective intracellular distribution after endosomal uptake of each micellar construct (FIG. 17).

Example 5—Combining RNAi and Platinum Based Small Molecules

Intracellular platinum delivery and relative BCL-2 silencing efficiency were compared for various combinations of siRNA and oxaliplatin species. MCF-7 cells were treated with different concentrations of either free OxaPt(II), free OxaPt(IV), or M(OxaPt(IV)), either individually or in combination with M(BCL-2) or M(c-siRNA); cells were also treated with micelles that combined siRNA and platinum species in a single nanoparticle construct (i.e. M(OxaPt(IV)/BCL-2) or M(OxaPt(IV)/c-siRNA)). In all cases, BCL-2 mRNA levels were measured by qRT-PCR, intracellular platinum and Pt-DNA adducts were quantified via AAS, and cell viability was determined via MTT assays of cells treated with each combination. For all siRNA containing groups, the concentration of siRNA species was 100 nM, transfected using various mPEG-b-PCL-b-PLL-based micelles formed at an N/P ratio of 8:1, which showed no inherent effects on cellular viability in the absence of platinum species (FIG. 18).

When comparing the intracellular content of platinum after 1 and 4 h of treatment, decreased amounts of free OxaPt(IV) were retained as compared to free OxaPt(II) at each time point (FIG. 19A and Table 2).

TABLE 2

Quantification of platinum uptake (pg Pt/cell) over time (at 1 and 4 h) and the amount of Pt-DNA adducts formed in MCF-7 cells at 24 h after treatment with various combinations of oxaliplatin species and/or siRNA.

| Treatment groups | Platinum uptake (pg Pt/cell) | | Pt-DNA adducts (ng Pt/μg DNA) |
|---|---|---|---|
| | 1 h ($\times 10^{-4}$) | 4 h ($\times 10^{-4}$) | After 24 h |
| OxaPt(II) | 369 ± 24 | 535 ± 16 | 41.10 ± 9.84 |
| OxaPt(II) + M(c-siRNA) | 194 ± 51 | 395 ± 123 | 28.84 ± 6.70 |
| OxaPt(II) + M(BCL-2) | 194 ± 40 | 256 ± 62 | 25.98 ± 7.16 |
| OxaPt(IV) | 180 ± 20 | 205 ± 38 | 29.10 ± 9.80 |
| OxaPt(IV) + M(c-siRNA) | 57 ± 18 | 186 ± 45 | 32.42 ± 8.03 |
| OxaPt(IV) + M(BCL-2) | 77 ± 21 | 138 ± 11 | 35.9 ± 11.20 |
| M(OxaPt(IV)) | 1338 ± 20 | 2572 ± 169 | 225.40 ± 23.54 |
| M(OxaPt(IV)) + M(c-siRNA) | 686 ± 23 | 1720 ± 469 | 138.90 ± 17.42 |
| M(OxaPt(IV)) + M(BCL-2) | 488 ± 45 | 1440 ± 102 | 134.20 ± 17.97 |
| M(OxaPt(IV)/c-siRNA) | 1286 ± 34 | 2760 ± 156 | 214.48 ± 21.79 |
| M(OxaPt(IV)/BCL-2) | 1494 ± 28 | 2480 ± 122 | 245.30 ± 32.53 |

The intracellular levels were markedly enhanced by using M(OxaPt(IV)) as opposed to various free drug formulations of oxaliplatin. Co-administration of M(OxaPt(IV)) with a separate nanoparticle construct containing micellar-complexed siRNA (e.g. M(BCL2)), however, resulted in a relative decrease in the intracellular content of platinum as compared to M(OxaPt(IV)) or administration of M(OxaPt(IV)/BCL2); these results would support a saturated limit for nanoparticle uptake at each time point. This phenomena were further supported by measurements of the numbers of intracellular Pt-DNA adducts that could be detected after 24 h of treatment (FIG. 19B and Table 2). A markedly enhanced number of adducts were obtained after treatment with M(OxaPt(IV)) as opposed to either free OxaPt(II) or free OxaPt(IV). Co-administration of two separate nanoparticle constructs of M(BCL-2) and M(OxaPt(IV)) resulted in fewer Pt-DNA adducts as opposed to M(OxaPt(IV)) or M(OxaPt(IV)/BCL-2)), again supporting a saturated limit for nanoparticle uptake by MCF-7 cells. The relative BCL-2 mRNA levels within the cells after 24 h of treatment with each experimental group were also examined (FIG. 19C and FIG. 20). While all platinum-containing treatments were able to decrease BCL-2 levels, consistent with the known pro-apoptotic effects of oxaliplatin, maximal mRNA suppression was achieved with BCL-2 siRNA treatment. Co-administration of free OxaPt(II), free OxaPt(IV) or M(OxaPt(IV)) along with M(BCL-2) did not further inhibit mRNA levels beyond those that were obtained with M(BCL-2) treatment alone. Notably, co-incorporation of BCL-2 siRNA and OxaPt(IV) in the same nanoparticle construct (i.e. M(OxaPt(IV)/BCL-2)) did achieve a statistically significant improvement in BCL-2 mRNA knockdown. Given the results described above with Alexa488-labeled siRNA delivery, this would again indicate that incorporation of siRNA and OxaPt(IV) species in a single nanoparticle construct not only ensures transcript stability but further results in maximal RNAi activity.

Ultimately, the goals of combining RNAi with platinum-based therapies are to explore changes in treatment responses and biological activity mediated by suppression of specific gene products. As such, changes in MCF-7 cellular viability upon in vitro treatment with various experimental combinations of oxaliplatin species and BCL-2 siRNA were also investigated. Changes in cellular viability as a function of increasing quantities of free OxaPt(II), free OxaPt(IV), or M(OxaPt(IV)), either as single treatments or in combinations with either M(BCL-2) or M(c-siRNA) were measured (FIG. 19D and FIG. 21); cells were also treated with M(OxaPt(IV)/BCL-2) and M(OxaPt(IV)/c-siRNA) at equivalent platinum concentrations for comparison. Synergistic treatment responses from any of the combinations of siRNA and oxaliplatin species were defined as a decrease in the $IC_{50}$ as compared to cells that were exposed to the same platinum therapy alone. While combinations of free OxaPt(IV) with M(BCL-2) did show synergistic treatment effects, which were not obvious in similar combinations with free OxaPt(II) species, free OxaPt(IV) treatments were approximately 10-fold less potent at inducing cellular toxicity (FIG. 19E). Much of this activity was restored by combining M(BCL-2) with M(OxaPt(IV)) instead of employing free OxaPt(IV). Notably, the highest potency and synergistic activity were obtained from M(OxaPt(IV)/BCL-2), which was corroborated by testing the various treatment combinations on additional cell lines (i.e. OVCAR4, A2780 and A2780DDP; Table 3).

TABLE 3

Summary of $IC_{50}$ values (μM) for MCF-7, OVCAR4, A2780 and A2780DDP cells treated with various combinations of oxaliplatin species and/or siRNA.

| Treatment groups | MCF-7 | OVCAR4 | A2780 | A2780DDP |
|---|---|---|---|---|
| OxaPt(II) | 23.05 ± 0.25 | 15.45 ± 0.50 | 2.90 ± 0.28 | 18.80 ± 0.99 |
| OxaPt(II) + M(c-siRNA) | 28.51 ± 0.34 | 21.60 ± 0.71 | 3.75 ± 0.91 | 22.25 ± 1.63 |
| OxaPt(II) + M(BCL-2) | 19.20 ± 0.42 | 9.24 ± 1.50 | 1.60 ± 0.14 | 10.55 ± 1.34 |
| OxaPt(IV) | >100 | >100 | 15.85 ± 2.76 | >100 |
| OxaPt(IV) + M(c-siRNA) | >100 | >100 | 8.60 ± 1.13 | >100 |
| OxaPt(IV) + M(BCL-2) | >100 | >100 | 12.65 ± 1.20 | >100 |
| M(OxaPt(IV)) | 0.54 ± 0.03 | 1.79 ± 0.10 | 0.87 ± 0.13 | 1.45 ± 0.07 |
| M(OxaPt(IV)) + M(c-siRNA) | 0.43 ± 0.01 | 1.37 ± 0.12 | 0.72 ± 0.09 | 1.06 ± 0.20 |
| M(OxaPt(IV)) + M(BCL-2) | 0.17 ± 0.02 | 0.43 ± 0.01 | 0.51 ± 0.03 | 0.60 ± 0.08 |
| M(OxaPt(IV)/c-siRNA) | 0.43 ± 0.02 | 1.80 ± 0.25 | 0.59 ± 0.06 | 0.72 ± 0.05 |
| M(OxaPt(IV)/BCL-2) | 0.06 ± 0.01 | 0.12 ± 0.01 | 0.39 ± 0.02 | 0.42 ± 0.08 |

To investigate the biological mechanisms underlying this improved cytotoxicity, we next performed flow cytometry analyses for apoptosis on MCF-7 cells after 24 h of treatment with each combination therapy (FIG. 19F and FIG. 22). These experiments confirmed that M(OxaPt(IV)/BCL- 2) induced the highest fractions of both early and late apoptotic events as compared to all other strategies for combining siRNA and oxaliplatin (FIG. 22).

Example 6—Preparation of Polymer

Synthesis of PEG-Block Precursor

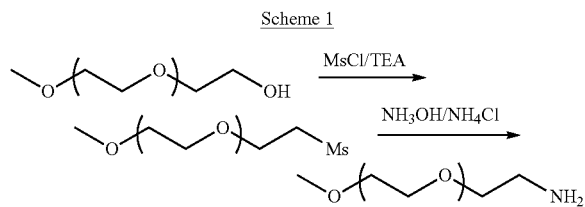

Scheme 1

To 30 mL DCM with mPEG5000 (10 g, 2 mmol) was added TEA (0.7 mL) and MSCl (0.3 mL 2 equiv.) at zero degree. The mixture was stirred overnight and precipitated by large amount of ether. The filtered product was dissolved in 100 mL ammonia/$NH_4Cl$ under stirring for 3 days. Then the solution was exacted by DCM, washed by water and brine, dried by $MgSO_4$, and precipitated by ether to get the amino-functionalized mPEG.

Synthesis of Lyz(Z)-NCA

Lys(Z) (5 g) was dried with P2O5 under vacuum by oil pump over 0.5 h, suspended in freshly anhydrous THF (100 mL) under nitrogen protection, and heated to 50° C. A solution of triphosgene (3 g) in dry THF (10 mL) was added in. After reaction at 50° C. for 2 h, the solution became completely clear. The mixture was cooled to room temperature, and purged with nitrogen for 0.5 h to remove extra HC. To the residue with a volume of 200 mL was slowly added hexane, the precipitation was resolve by ethyl acetate and washed by cold $NaHCO_3$aq. and water. And then, the ethyl acetate was removed by rotate evaporator, the NCA achieved was soluble in 10 ml THF in 40° C. and add 5 ml of hexane and resoluble in 60° C., and then cold to room temperature.

On the next morning, the supernatant was removed. The snow-shaped NCA crystals were filtered, rinsed with copious ether, and dried under vacuum by oil pump, repeat the circles for three times.

Synthesis of BLA-NCA

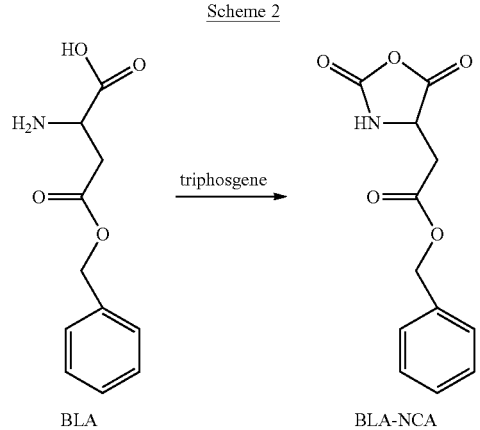 [SMILES: NC(CC(=O)OCc1ccccc1)C(=O)O ; O=C(CC1NC(=O)OC1=O)OCc1ccccc1]

Scheme 2

BLA (5 g) was dried with P2O5 under vacuum by oil pump over 0.5 h, suspended in freshly anhydrous THF (100 mL) under nitrogen protection, and heated to 50° C. A solution of triphosgene (3 g) in dry THF (10 mL) was added in. After reaction at 50° C. for 3 h, the solution became completely clear. The mixture was cooled to room temperature, and purged with nitrogen for 0.5 h to remove extra HC. To the residue with a volume of 200 mL was slowly added hexane, the precipitation was resolve by ethyl acetate and washed by cold $NaHCO_3$aq. and water. And then, the ethyl acetate was removed by rotate evaporator, the NCA achieved was soluble in 10 ml THF in 40° C. and add 5 ml of hexane and resoluble in 60° C., and then cold to room temperature.

On the next morning, the supernatant was removed. The snow-shaped NCA crystals were filtered, rinsed with copious ether, and dried under vacuum by oil pump, repeat the circles for three times.

Synthesis of mPEG-PZLL

The Lys(Z) NCA was dissolved in anhydrous DMF with PEG-NH2. The mixture was stirred in 30 degree for 4 days followed by precipitating in ether to get PEG-PZLL.

Synthesis of mPEG-PZLL-PBLA

The Asp(Bzl) NCA was dissolved in anhydrous DMF with PEG-PZLL-NH2. The mixture was stirred in 30 degree for 4 days followed by precipitating in ether to get PEG-PZLL-Pasp(Bzl).

Synthesis of mPEG-PZLL-PAspatamine

Briefly, PEG-PZLL-PBLA was dissolved in NMP containing 1 M thiourea at 35 degree and cooled to 4 C. Next, DET (0.6 mL, 50equiv. To Bzl groups) was diluted with NMP/thiourea (1.2 mL) and PEG-PZLL-PBLA solution was added dropwise into the DET solution. The mixture was stirred for 1 h at 15 C under argon atmosphere. Then, the reaction mixture was added drop wise into ice-cold 5 M HCl (5 mL) for neutralization. The polymer product was purified by dialysis against 0.01 M HCl overnight and then deionized water for 3 days at 4 C. The dialyzed solution was lyophilized to obtain the final product.

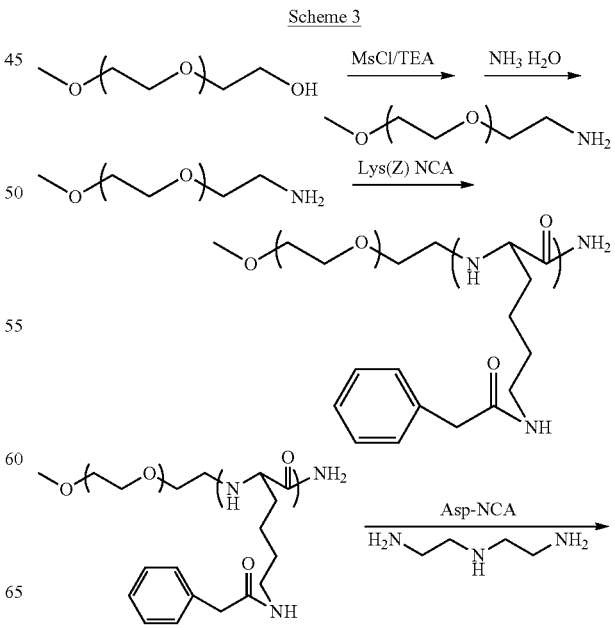

Scheme 3

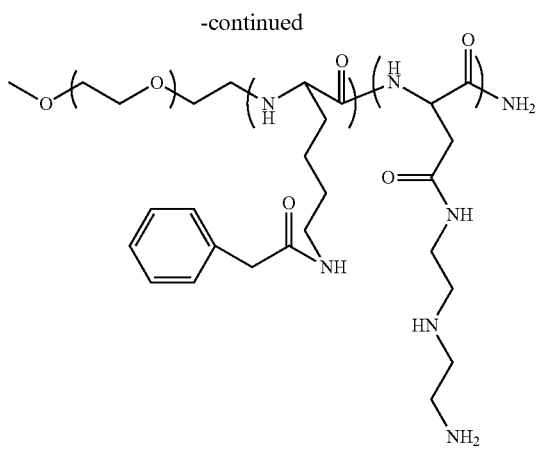

Synthesis of mPEG-PLL-OTC mPEG-PLL was dissolved in NaHCO3 Buffer (pH 9), Cis-aconitic anhydride (10 equiv. to amine group) was added dropwise and stirred for 24 h. The reaction system was dialysis against water for 3 days and lyophilized to get mPEG-PLL-OTC.

Example 7—Formation of Core/Shell Compositions

Positively charged nanoparticles (e.g., PEO-PCL-PLL or PEO-PBzLL-PASP) may be coated with negatively charged diblock copolymers (e.g. PEO-b-PGA). See FIGS. 23A, 23B, 24A, 24B, 25A, 25B, 26A, and 26B.

Example 8—Delivery of CRISPR/CAS9 with Small Molecule Chemotherapeutics

FIGS. 27-30 show data indicating that CRISPR/Cas9 components may be delivered to cells, with or without co-delivery of platinum. Details of the experiments for obtaining these data are summarized in the Brief Description of the Figures for FIGS. 27-30.

Example 9—Implantation of Cancer Cells into Mice (for Following Examples Unless Otherwise Indicated)

1) Implantation of luciferized (LUC+) and red fluorescent-protein (RFP+) expressing SKOV3 cells (an established human ovarian cancer cell line) into the peritoneal cavity of nude (NCr Nu/Nu) mice, establishing an orthotopic murine model of disseminated and advanced-stage human ovarian cancer: SKOV3 human ovarian cancer cells that expressed LUC and RFP were constructed as previously described (vide supra). LUC and RFP expression were assayed and confirmed using a plate reader (Infinite 200 PRO; Tecan group Ltd., Switzerland) and an IVIS Spectrum Bioluminescent and Fluorescent Imaging System (PerkinElmer; Akron, Ohio). To establish an orthotopic xenograft model of human ovarian cancer, LUC+/RFP+ SKOV3 cells (200 µl of a suspension of 10' cells/mL; i.e., 2 million cells) were implanted into female athymic nude mice (NCRNU-F, Taconic Biosciences; Hudson, N.Y.) by IP injection. Tumor growth was monitored weekly by imaging bioluminescence and RFP signals emanating from the animals, using the IVIS imaging instrument. For bioluminescence measurements, luciferin (200 µl of a 15 mg/mL solution in PBS) was administered to each animal by IP injection; after 10 min, mice were imaged both for bioluminescence and RFP signals ($\lambda_{ex}$=535 nm; $\lambda_{em}$=600 nm).

2) Implantation of luciferized (LUC+) and red fluorescent-protein (RFP+) expressing OVCAR8 cells (an established human ovarian cancer cell line) into the peritoneal cavity of nude (NCr Nu/Nu) mice, establishing an orthotopic murine model of disseminated and advanced-stage human ovarian cancer: Female NCR nu/nu mice were purchased from Taconic Co. (USA). All experimental procedures involving animals were carried out in accordance with the guidelines of the animal protocol of Massachusetts Institute of Technology. For tumor implant, $8\times10^5$ Luc+/red fluorescent protein-expressing OVCAR 8 cells were injected into the belly region of the 5-weeks old mice.

3) Implantation of luciferized (LUC+) expressing primary human cells from a patient with "platinum-resistant", advanced-stage, and high-grade serous ovarian cancer into the peritoneal cavity of SCID (C.B-17/Icr-SCID/Sed) mice, establishing an orthotopic patient-derived xenograft (PDX) model of disseminated, advanced-stage, and "platinum-resistant" human ovarian cancer: C.B-17/Icr-SCID/Sed mice were purchased from Charles River and bred at MGH. They were implanted with primary cells obtained from a patient with "platinum-resistant" and advanced-stage HGSOC after lentiviral transduction of firefly luciferase (2-10 million cells/animal; 0.5 mL PBS; IP injection). Tumor growth was monitored by BLI.

Example 10—Nanoparticle Conjugation of Highly Potent Toxins Enhances Efficacy and Overcome Therapeutic Resistance in Ovarian Cancer A triblock copolymer of methoxypoly(ethylene glycol)-block-poly(benzyl L-lysine)-block-poly(aspartamide) (mPEG-b-PZLL-b PASP(DET)) was synthesized that self-assembled into a biodegradable NP with a hydrophilic PEO surface, a hydrophobic PZLL core, and cationic polypeptide corona comprised of PASP(DET), which could be utilized for covalent conjugation of a multitude of highly potent toxins, each through a central reductive sensitive and self-immolative linker (FIG. 55A). Antimitotic agent monomethyl Auristatin E (MMAE), which is known to inhibit cellular division by blocking the depolymerization of tubulin, was chosen as the anticancer agent/toxin. MMAE has been shown to be 10-100× more potent than doxorubicin (in vitro $IC_{50}$=0.2-0.6 nM) and is widely used for the development of ADCs and small molecule drug conjugates (SM-DCs). Brentuximab vedotin (Adcetris®, Seattle Genetics) was the first clinically approved ADC and is an anti-CD30 antibody that is coupled to 1-4 MMAE molecules through a cathespsin (enzyme-sensitive) cleavable linker; despite its improved antitumor activity against CD30 positive lymphomas, a significant number of patients still suffer from peripheral neuropathy, myelosuppression, fatigue, and GI disturbances as a result of premature loss of free MMAE.

The cationic surface charge of NPs formed from the MMAE-coupled PEO-b-PBzLL-b-PASP(DET) polymer (NP(MMAE)) was neutralized through layer-by-layer deposition of an anionically charged diblock copolymer of methoxyl-poly(ethylene glycol)-block-poly(glutamic acid) (PEO-b-PGA), generating a coated and MMAE-bound NP (CNP(MMAE)).

Release of MMAE from the NP was investigated and detected by UV-Vis spectroscopy and HPLC; the results are shown in FIG. 56.

OVCAR8 cells were treated with free MMAE, NP(MMAE), and CNP(MMAE), and the cellular viability was investigated. The results are shown in FIG. 58. This figure also shows images indicating that MMAE-conjugated nanoparticles destabilize tubulin within the cytoskeleton of OVCAR8 cells.

LUC+/RFP+ OVCAR8 tumor cells were implanted into nude mice, and in vivo images were obtained after IP administration of Cy7.5-conjugated CNP(MMAE). The body weight and survival of the mice was also studies. Mice were sacrificed and their organs were imaged. The results are shown in FIG. 59.

Example 11—IP Delivery of CRISPR/Cas9 Gene Editing Tools

A diblock copolymer of PEO-b-PGA coating nanoparticles formed from a triblock copolymer of PEO-b-PZLL-b-PASP conjugated to a platinum(IV) (Pt(IV)) prodrug and electrostatically complexed to Cas9 mRNA and sgRNA (FIG. 60) were introduced via IP injection into SCID mice that had been orthotopically xenografted with platinum-resistant patient-derived ovarian cancer cells (PDX) (FIG. 61).

Confocal images of in vivo and ex vivo biodistribution data showed co-localization of nanoparticles with peritoneal tumors in ovarian cancer PDX mice after IP injection; the images are shown in FIG. 61.

The in vivo efficacy of the nanoparticles was also studied. FIG. 62 shows images and data showing improved treatment.

Example 12—IP Delivery of a Pt(IV) Prodrug

A diblock copolymer of PEO-b-PGA coating nanoparticles formed from a triblock copolymer of PEO-b-PZLL-b-PASP conjugated to a phenathriplatin(IV) (PhenPt(IV)) prodrug (FIG. 63A) were introduced via IP injection into nude mice that had been orthotopically xenografted with OVCAR8 cells (an established ovarian cancer cell line) (FIG. 64).

Confocal images of in vivo showed co-localization of nanoparticles with peritoneal tumors in OVCAR8-bearing nude mice after IP injection. FIG. 64.

Ex vivo biodistribution data also showed co-localization of nanoparticles with peritoneal tumors in OVCAR8-bearing nude mice after IP injection. FIG. 65

The efficacy of nanoparticle-bound phenathriplatin (CNP) to treat peritoneal tumors in OVCAR8-bearing nude mice after IP injection, as compared to controls, was studied; the results are summarized in FIG. 66.

Example 13—Combined IP Delivery of CRISPR/Cas9 and Small Molecule Anticancer Agents Methods Chemical and RNA Species: Cisplatin (Pt(II)) was purchased from ChemiChem International Development Co., Ltd (Shenzhen, China). Other small molecule anticancer agents, including doxorubicin, gemcitabine, camptothecin (CPT) and melphalan, as well as the various small molecule inhibitors of cellular uptake, including wortmannin (WNM), sodium azide (NaN$_3$), methyl-β-cyclodextrin (MCD), chlorpromazine (CL) and genistein (Gen) were purchased from Sigma-Aldrich; these reagent grade chemicals and all solvents were used without further purification. Pt(IV), Pt(IV)-OH and Pt(IV)-COOH prodrugs were synthesized from Pt(II); their structural properties were verified by $^1$H NMR, $^{13}$C NMR and by ESI-MS. The purity of Pt(IV) was verified by high-performance liquid chromatography (HPLC). Cas9 mRNA, Cy5-labeled EGFP mRNA and various sgRNA were purchased from TriLink Biotechnology, Inc. (FIG. 34); Cy5.5-labeled Cas9 mRNA was synthesized de novo using EDC/NHS chemistry. Reagents utilized for conjugation, including N-hydroxysuccinimide (NETS), 1-(3-dimethyl aminopropyl)-3-ethylcarbodiimide hydrochloride (ED-C.HCl), as well as the reducing agent sodium ascorbate (NaSC) were purchased from Sigma-Aldrich; fluorescent labels, including FITC, 5-FAM-NHS, and Cy5.5-NHS, were obtained from Luminiprobe INC. The Annexin V-FITC Apoptosis Detection Kit (ab14085, Abcam) was used for the cellular apoptosis assay.

General measurements: NMR, ESI-MS and MALDI/TOF MS were performed to characterize the various platinum(IV) prodrugs and to monitor the reactions of different small molecule anticancer agents with sgRNA. Briefly, $^1$H and $^{13}$C spectra at room temperature were measured at 400 and at 100 MHz, respectively, using a Bruker NMR spectrometer (Bruker Corporation, Billerica, Mass.). MS measurements were performed on a Quattro Premier XE system equipped with an electrospray interface (ESI-MS; Waters, Milford, Mass.) and with a matrix-assisted laser-desorption ionization and time-of-flight MS (MALDI/TOF MS) machine (Bruker model MicroFlex). Dynamic light scattering (DLS) and zeta potential measurements of nanoparticle suspensions were conducted using on a Zetasizer Nano ZS90; transmission electron microscope (TEM) images of the same suspensions were obtained with a JEOL-1100 Transmission Electronic Microscope at 200 kV and with negative staining. The critical micelle concentrations (CMCs) of various nanoparticle suspensions were determined by the Nile red assay. UV-vis and fluorescence measurements were performed for Cy5.5-labeled mRNA loading and release from nanoparticles as well as to quantify levels within treated cellular populations, using an Infinite® M200 Pro microplate reader (Tecan Systems, Inc., CA, USA). Graphite furnace atomic absorption spectroscopy (GFAAS) measurements were conducted to determine Pt levels in cells as well as in excised tissue samples, using an AAnalyst 600 GFAAS instrument (Perkin Elmer, Waltham, Mass.). Inductively coupled plasma mass spectroscopy (ICP-MS; ICP-MS 7900 instrument, Agilent Technologies, CA, USA) was performed for quantification of trace Pt levels and to determine the amounts of intracellular Pt-DNA adducts in cancer cells.

Nanoparticle fabrication: mPEG-b-PZLL-b-PASP(DET) was synthesized de novo. $^1$H-NMR spectroscopy measurements provided the structure of the final construct as mPEG114-b-PZLL$_{25}$-b-PASP$_{30}$(DET); the subscript denotes the degree of polymerization of each individual monomer in a given block; and, this triblock copolymer is hereafter abbreviated as "P". Aqueous dispersion of P resulted in the generation of a mono-disperse nanoparticle (NP) suspension. For chemical coupling to P, Pt(IV) (26 mg) was first dissolved in dry DMF (10 mL); EDC (19 mg) and NHS (12 mg) were subsequently added; and, the mixture was stirred for 30 min. A solution of water (0.5 mL) and P (100 mg) was then mixed with N,N-Diisopropylethylamine (DIEA) (10 µL) and stirred for 12 h at 4° C. Afterwards, the mixtures was dialyzed against milli-Q water for 72 h and at 4° C. to obtain Pt(IV)-conjugated nanoparticles (NP(Pt(IV)). Note, P was also modified by conjugation to various fluorophores, including Cy7.5-NHS, Cy5.5-NHS or iFluor™ 405-NHS, that were added to aqueous suspensions of either NP or NP(Pt(IV)) at a 1:10 mass ratio; the reaction mixtures were stirred for 12 h followed by dialysis against milli-Q water for 3 additional days and at 4° C.

For electrostatic complexation of various RNA species, NP or NP(Pt(IV)) suspensions were diluted to different final concentrations. Equal volume solutions containing the various mRNA (e.g. Cas9, Cy5.5-Cas9 or Cy5-EGFP) and sgRNA species (e.g. SMAD4, sg1, sg2, sg3, VIM, ESR1, or scramble) in RNase free water were then mixed with these nanoparticle suspensions. The N/P ratios at which the polymer and RNA species were combined varied from 8 to 16. The formed complexes were allowed to stand at room temperature for 30 min to generate the RNA-bound nanoparticles (e.g. NP(Cas9,sgRNA) and NP(Pt(IV);Cas9, sgRNA). The complexation of RNA to the nanoparticles was verified through a gel retardation assay and the rates of release of both RNA and Pt(IV) species were measured in different in situ environments (vide supra). Electrostatic complexation of Cy5-EGFP or Cy5.5-Cas9 resulted in labeled nanoparticles in which the mRNA species could be independently monitored by in vitro and/or in vivo fluorescence imaging. To generate coated nanoparticles with neutral surface charge for in vivo applications, a concentrated solution of mPEG-b-poly(glutamic acid) (mPEG-b-PGA) was added to the platinum-conjugated and/or RNA-complexed nanoparticles at a molar ratio of 1:1 mPEG-b-PGA to P. The sizes of the resultant nanoparticles (e.g. CNP(Pt(IV)) and CNP(PT(IV);Cas9,sg1)) were verified by TEM and DLS; neutralization of their surface charge was further confirmed (i.e. the neutral charge of CNP(Pt(IV)) as compared to the cationic charge of NP(Pt(IV))).

Preparation and characterization of Pt(IV)-loaded and/or RNA-complexed nanoparticles: Detailed descriptions of nanoparticle fabrication, verification of RNA complexation, and evaluation of the rates of release of both RNA and Pt(IV) species in different in situ environments may be found elsewhere in this specification).

Animal Handling: All animal studies were performed under protocols approved by the MIT CAC (0615-069-1) and by the Massachusetts General Hospital IACUC (2009N000117).

Toxicity (MTD) study: BALB/c mice at 4-6 weeks old were purchased from Taconic Bioscience and were administered one of the following treatments by IP injection: cisplatin (Pt(II); at either 1.75 or 3.5 mg/kg of Pt), core-shell nanoparticles that conjugated Pt(IV) alone (CNP(Pt(IV); at 1.75 mg/kg of Pt), or with core-shell nanoparticles that conjugated Pt(IV) and electrostatically complexed Cas9 mRNA and BCL-2 sgRNA (CNP(Pt(IV);Cas9;sg1; at 1.75 mg/kg of Pt, 2.5 mg/kg of Cas9 mRNA, and 1.25 mg/kg of sg1). The body weight of each animal was monitored every other day starting with the day of injection (Day 0). At the end of the study, mice were sacrificed and blood was collected via cardiac puncture for serum chemistries and complete blood counts. The major tissues and organs from each animal were also collected, fixed with 4% formalin, and stained with H&E.

Establishment of the PDX model: C.B-17/Icr-SCID/Sed mice were purchased from Charles River and bred at MGH. They were implanted with primary cells obtained from a patient with "platinum-resistant" and advanced-stage HGSOC after lentiviral transduction of firefly luciferase (10 million cells/animal; 0.5 mL PBS; IP injection). Tumor growth was monitored by BLI.

Biodistribution study: Once the BLI radiant efficiency of their PDX tumors reached $>1\times10^7$ photons/s/cm$^2$/sr, mice were grouped into cohorts with similar mean radiant efficiency values (n=3 mice per group). The animals were subsequently administered core-shell nanoparticles that were conjugated to Cy7.5 and electrostatically complexed with Cy5-labeled EGFP mRNA (CNP(Cy7.5,Pt(IV);Cy5-EGFP mRNA; at 1.75 mg/kg of Pt and 35 µg Cy5 EGFP per mice by IP injection). Whole animal fluorescence imaging was conducted by gating on Cy7.5- and Cy5-based emission signals, which were used to determine the location of the nanoparticles (Cy7.5) and mRNA species (Cy5) with respect to the tumors (BLI). To verify the in vivo stability of the core shell nanoparticles, mice were also treated with nanoparticles in which the core polymer was labeled with Cy5.5 and the shell polymer was conjugated to Cy7.5 (CNP(Cy7.5, Cy5.5,Pt(IV)). At 24 h after IP administration, the mice were injected with 225 mg/kg of d-luciferin (Promega) and anaesthetized 10 min later before BLI imaging, using the IVIS instrument (Caliper LS; auto exposition mode). Imaging was also performed after laparotomy upon animal sacrifice. The following imaging parameter were utilized: Cy5 ($\lambda_{ex}$=640 nm; $\lambda_{end\text{-}em}$=680 nm) along with Cy7.5 ($\lambda_{ex}$=745 nm; $\lambda_{end\text{-}em}$=840 nm); or Cy5.5 ($\lambda_{ex}$=640 nm; $\lambda_{end\text{-}em}$=680 nm) along with Cy7.5 ($\lambda_{ex}$=740 nm; $\lambda_{end\text{-}em}$=820 nm). For mice treated with CNP(Cy7.5,Cy5.5,Pt(IV)), computed tomography (CT) imaging was also conducted in vivo, after sacrifice, and upon organ collection. Half of each of the excised organs was subject to HNO3/H2O2 digestion followed by ICP-MS to quantify the content of Pt per mass tissue.

Pharmacodynamics study: Once the BLI radiant efficiency of their PDX tumors reached $>1\times10^7$ photons/s/cm$^2$/sr, mice were administered x2 weekly doses one of the following treatments by IP injection: PBS, cisplatin alone (Pt(II); at 1.75 mg/kg of Pt), or Pt(II) along with core-shell nanoparticles that complexed Cas9 mRNA and BCL-2 sgRNA (at 1.75 mg/kg of Pt, 2.5 mg/kg of Cas9 mRNA, and 1.25 mg/kg of sg1); additional treatment groups included core-shell nanoparticles that were conjugated to Pt(IV) alone (CNP(Pt(IV); at 1.75 mg/kg of Pt) or that were further complexed with Cas9 mRNA and BCL-2 sgRNA (CNP(Pt(IV);Cas9,sg1; at 1.75 mg/kg of Pt, 2.5 mg/kg of Cas9 mRNA, and 1.25 mg/kg of sg1). 72 h after receiving the second dose, the mice were sacrificed and their tumors were harvested. The tumors were sectioned for confocal imaging after IF staining for cleaved Caspase-3; WB was conducted for BCL-2 levels with respect to that of GAPDH (product of a house-keeping gene; control); and next-generation sequencing was performed to determine the numbers of indels within the BCL-2 gene of each treated tumor. The sequences of the primers used for PCR amplification of the BCL-2 locus were as follows—Forward: 5'-CTGGGGCGA-GAGGTGCCGTTG-3' (SEQ ID NO: 9); Reverse: 5'-CTCGGCGAAGTCGCGGCGGTAGC-3' (SEQ ID NO: 10).

Tumor growth inhibition: Once the BLI radiant efficiency of their PDX tumors reached $>1\times10^7$ photons/s/cm2/sr, mice were grouped into cohorts with similar mean radiant efficiency values (n=5 mice per group) and were administered x4 weekly doses one of the following treatments by IP injection: PBS, cisplatin alone (Pt(II); at 1.75 mg/kg of Pt), or Pt(II) along with core-shell nanoparticles that complexed Cas9 mRNA and BCL-2 sgRNA (at 1.75 mg/kg of Pt, 2.5 mg/kg of Cas9 mRNA, and 1.25 mg/kg of sg1); additional treatment groups included core-shell nanoparticles that were conjugated to Pt(IV) alone (CNP(Pt(IV); at 1.75 mg/kg of Pt) or that were further complexed with Cas9 mRNA and BCL-2 sgRNA (CNP(Pt(IV);Cas9,sg1; at 1.75 mg/kg of Pt, 2.5 mg/kg of Cas9 mRNA, and 1.25 mg/kg of sg1). Mice were monitored twice per week for toxicity (i.e. weight change and by behavioral inventory); and, their tumor burden was monitored weekly by BLI using the IVIS instrument. Once animals reached the designated study endpoint (>15% loss in body-weight and/or moribund status), they were sacrificed; their tumors were collected and weighed; and, their major organs were harvested for H&E staining.

Results

Circumventing Platinum Resistance Through In Vivo Delivery of a Platinum(IV) Prodrug and RNA Components for CRISPR/Cas9-Mediated Silencing of BCL-2

Having validated synergistic activity in established cell lines, we next sought to determine whether combined delivery of platinum-based anticancer agents with CRISRP/Cas9 machinery aimed at silencing BCL-2 could be utilized to overcome resistance in heavily treated human tumors. For our model system, we utilized primary cells obtained from a patient with "platinum-resistant" HGSOC. In vitro delivery of nanoparticles that contained Pt(IV), Cas9 mRNA and sgRNA against BCL-2 (sg1) effectively silenced BCL-2 expression and potentiated the activity of the platinum-based agent (FIGS. 62A and 62B). A PDX model of advanced ovarian cancer was then established in C.B-17/Icr-SCID/Sed mice via IP dissemination of the primary cells after lentiviral based transfection of firefly luciferase, enabling bioluminescence imaging (BLI) to track tumor growth and metastasis; core-shell nanoparticles (CNPs) conjugated with Cy7.5 and containing Cy5-labeled mRNA confirmed co-localization of both species within peritoneal tumor implants after IP administration (FIG. 62C). CT imaging of the same mice detected high platinum (Pt) contrast within the tumors, corresponding to the nanoparticle-conjugated Pt(IV) species (FIG. 62D). I fluorescence and CT imaging of excised organs confirmed that the nanoparticles (Cy7.5), mRNA (Cy5) and Pt(IV) (enhanced Pt contrast on CT) were distributed predominantly within the peritoneal tumor implants (FIG. 62E). Confocal microscopy of tumor sections demonstrated a predominance of mRNA-containing nanoparticles within the periphery as opposed to the core of the tumors (FIG. 62F).

To address concerns over potential toxicities imparted by nanoparticles containing Pt(IV) alone or in conjunction with Cas9 mRNA and sgRNA against BCL-2, single dose toxicity studies in immunocompetent BALB/c mice were undertaken. The mice demonstrated no changes in their daily weights over a two-week period; and, terminal blood draws for serology studies confirmed no nephrotoxicity, hepatotoxicity, nor myelosuppression from nanoparticles administered at up to 1.75 mg/kg of Pt per mouse and with or without Cas9 mRNA (2.5 mg/kg) and BCL-2 sgRNA (1.25 mg/kg). Pathologic examination of tissue sections after H&E staining showed no signs of gross toxicity or microarchitectural distortion in any organ and in every mouse (n=3 mice/group). Pharmacodynamic studies were undertaken in which various nanoparticle and control formulations were administered at this equivalent dose level of Pt and/or Cas9 mRNA/sgRNA and in two weekly IP injections into the PDX model. The mice were sacrificed at 72 h after the second injection; immunofluorescence for cleaved Caspase 3 was conducted on excised tumors; and, the results confirmed that the highest levels of cleaved Caspase 3 were found in the periphery of tumors from mice that were treated with core-shell nanoparticles containing Pt(IV), Cas9 mRNA, and BCL-2 sgRNA (i.e. CNP(Pt(IV);Cas9,sg1)) (FIG. 62G). WB of lysates from the same tumors confirmed suppression of BCL-2 levels in the periphery of the tumors (FIG. 62H); and, next-generation sequencing showed effective cleavage of the BCL-2 gene in the same tumor locations and only after nanoparticle delivery of all three components (FIG. 62I).

Finally, a preliminary therapeutic efficacy study was conducted in the PDX model in which mice were treated with PBS (negative control), free cisplatin (Pt(II)), core-shell nanoparticles containing only Pt(IV) (CNP(Pt(IV)), combinations of free cisplatin and core-shell nanoparticles complexed with Cas9 mRNA and BCL-2 sgRNA (Pt(II)+CNP (Cas9,sg1)), or core-shell nanoparticles that contained Pt(IV), Cas9 mRNA, and BCl-2 sgRNA on the same delivery vehicle (CNP(Pt(IV);Cas9,sg1)). Tumor growth was monitored by BLI; the animals received the first of four weekly injections when the radiant efficiency of their tumors reached $1\times10^7$ photons/s/cm$^2$/sr, which was the level that enabled accurate quantitative comparisons of luminescence signals; and, the study was concluded when animals were moribund or exhibited >15% loss in body weight. The results confirmed that core-shell nanoparticles that delivered Pt(IV), Cas9 mRNA and BCL-2 sgRNA maximally inhibited tumor growth (FIG. 62J) and significantly prolonged survival (FIG. 62K). Measurements of tumors excised upon sacrifice confirmed statistically significant reductions in tumor weights from animals that had received this treatment and as compared to all other experimental groups (FIG. 62L). Gross and pathologic examination of excised organs confirmed that these mice, nevertheless, died from complications of metastatic disease.

Example 14—IP Delivery of Pt(IV) Amphiphiles Encapsulating Drugs or Imaging Agents A platinum(IV) amphiphile that spontaneously assembles into nanoparticles with a PEG surface and that can trap drugs and/or imaging agents (e.g. IRDye1061) in its lipid cavity was synthesized. The nanoparticles were self-assembled from a novel amphiphilic platinum(IV) prodrug comprised of cisplatin, a PEG head group, and a lipid tail. The PEG and lipid are off the axial positions of the cisplatin (FIG. 67) and covert the parent platinum(II) agent into a platinum(IV) prodrug that is only activated intracellular due to high reducing conditions that exist within cancer cells (higher intracellular concentrations of glutathione and ascorbic acid). A uniform suspension of polymeric micelles was formed after dispersion of an organic solution containing the amphiphilic platinum(IV) prodrug (in methylene chloride or THF) into a larger volume of aqueous solution followed by removal of the organic agent. Co-encapsulation of a water-insoluble drug (such as taxol, the PARP inhibitor BMNB673, and/or the NIR-II imaging agent IRdye1061) was achieved by dissolving it in the same organic solution as the amphiphile; upon dispersion of the organic solution into water, polymeric micelles were formed form the platinum(IV) amphiphile that trapped the drug and/or imaging agent within its water-insoluble cavity. Reduction of the platinum(IV) to the active platinum(II) agent within cells not only released the free platinum drug but also disintegrated the micelles, allowing for release of the water-insoluble drugs and/or imaging agents that were contained in the lipid cavities of the micelles.

The nanoparticles were introduced via IP injection into nude mice that had been orthotopically xenografted with SKOV3 cells (an established ovarian cancer cell line) (FIG. 68).

In vivo biodistribution data showed co-localization of the nanoparticles with peritoneal tumors in OVCAR8-bearing nude mice after IP injection.

Example 15—Early Tumor Detection Afforded by In Vivo Imaging of Near-Infrared II Fluorescence Materials and Methods Chemicals and Reagents. Methoxy-terminated poly(ethylene oxide)-block-poly(ε-caprolactone) ($PEO_{5k}$-$PCL_{16k}$) and functionalized α-amino- and ω-hydroxyl terminated poly(ethylene oxide)-block-poly(ε-caprolactone) (amino-terminated $PEO_{6k}$-$PCL_{16k}$) were purchased from Polymer Source (Montreal, Canada). Lanthanide salts, including ytterbium (III) nitrate pentahydrate, erbium (III) nitrate pentahydrate, and thulium (III) nitrate pentahydrate were obtained from Sigma-Aldrich (St. Louis, Mo.); holmium (III) nitrate pentahydrate was purchased from Alfa Aesar (Ward Hill, Mass.). DiR (1,1'-dioctadecyl-3,3,3',3'-tetramethylindotricarbocyanine iodide) and DiL (1,1'-dioctadecyl-3,3,3',3'-tetramethylindocarbocyanine perchlorate) were purchased from Life Technologies (Carlsbad, Calif.). D-luciferin potassium salt (substrate for luciferase bioluminescence imaging) was obtained from PerkinElmer (Waltham, Mass.). Other chemicals, including folic acid, oleic acid, sodium fluoride, and sodium hydroxide, as well as organic solvents, including cyclohexane, ethanol and tetrahydrofuran, were purchased from Sigma-Aldrich (St. Louis, Mo.).

Preparation of Oleic Acid-coated LNPs. LNPs were synthesized, following a previously reported procedure with minor modifications. X. Wang, et al., Nature 2005, 437, 121; Z. Chen, et al., J Am ChemSoc 2008, 130, 3023. Briefly, oleic acid (20 mL), NaOH (1.2 g), dH2O (9 mL), and ethanol (10 mL) were first combined under continuous stirring. Aqueous solutions containing $Y(NO3)3$ (0.5 M), $Yb(NO3)3$ (0.2 M), and either $Er(NO3)3$ (0.2 M) (with and without $Tm(NO3)3$ (0.2 M)) or $Ho(NO3)3$ (0.2 M) were then individually prepared, added to the oleic acid solution, and stirred for 10 min at room temperature (RT). NaF (4 mL) was then added drop-wise. Upon clearing, the suspension was transferred into a Teflon-lined autoclave (100 mL) and placed in a 200° C. oven for 8 h to generate oleic acid-coated LNPs. After completion of the reaction, LNPs were precipitated by the addition of cyclohexane/ethanol and washed to remove excess reactants. They were then re-suspended in tetrahydrofuran (THF) for further encapsulation by PEO-b-PCL polymers (vide infra).

Protocol Optimization to Generate Aqueous Suspensions of Core-shell Nanoparticles. Diblock copolymers of PEO-b-PCL were added to LNP suspensions in THF, which were subsequently dispersed in larger aqueous volumes (e.g. 200 μL of THF added to 4 mL of water) by high frequency sonication using a probe sonicator (Q500 sonicator; Qsonicator, Newtown, Conn.). THF was then removed by centrifugation filtration (Amicon centrifugal unit, EMD Millipore, Billerica, Mass.; MWCO=100 kDa). The relative concentrations of core-shell nanoparticles in aqueous suspensions were determined by comparing the peak intensities of UC and DC emission from core LNPs as a function of sonication power (FIG. 38A), the initial polymer to LNP mass ratio (FIG. 38B), and the amounts of LNPs in the original THF solution (FIG. 38C). Given the seemingly equivalent results obtained with different sonication powers, application of 24 watts (30% amplitude) for a fixed duration of 2 min was thereby adopted for the generation of all subsequent core-shell nanoparticle formulations. For a fixed amount of LNPs, a polymer to LNP ratio of 1:1 resulted in maximal encapsulation within core-shell nanoparticles. Finally, a linear correlation between the concentrations of LNPs in the original THF suspensions (for a fixed polymer-to-LNP ratio of 1:1) and the final aqueous concentrations of core-shell nanoparticles was observed.

Standard Preparation Protocol for Fabricating Core-shell Nanoparticles. PEO-b-PCL diblock copolymer (200 μL of a 2 mM solution), LNPs (8 mg) and DiR (10 μL of a 1 mM solution) were combined in THF (1:1:1.25E-3 polymer:LNPs:DiR by weight) and added to dH2O (4 mL) under agitation (continuous sonication for 2 min at a 30% power amplitude (24 watts; Q500 sonicator; Qsonicator, Newtown, Conn.)). THF was removed and the core-shell nanoparticles were purified by 3 cycles of washing (1×PBS) followed by centrifugation filtration at 3000 rpm for 10 min (Amicon centrifugal unit, EMD Millipore, Billerica, Mass.; MWCO=100 kDa); the final suspension was reconstituted in sterile 1×PBS and placed in a bath sonicator for an additional 30 min (to ensure full particle dispersion). The suspension was further passaged serially through a sterile syringe filter equipped with an immobilized 0.45 μm cellulose acetate membrane (VWR International; Radnor, Pa.) prior to in vitro and in vivo experimentation.

Additional Processing Steps to Achieve Homogenous Suspensions of Core-shell Nanoparticles. To isolate core-shell nanoparticles from the mixed suspensions that also included PEO-b-PCL (shell) nanoparticles, an additional processing step was added after syringe filtration (FIG. 44), whereby the suspensions were subject to centrifugation at 3000 rpm (845×g) for 60 min; shell nanoparticles remained suspended in the supernatant and were discarded. The pellet, which contained a pure population of core-shell nanoparticles, was subsequently re-suspended in a sterile aqueous solution (e.g. 0.4 mL of 1×PBS). Approximately 75% of the LNPs were recovered after this additional processing step, which was determined by measuring the relative fluorescence intensities of the visible UC emission bands of the recovered particles and by comparing them to the original suspension.

Compositional Analysis of Core-Shell Nanoparticles. Suspensions of core-shell nanoparticles were generated following the standard preparation protocol (vide supra). Aqueous suspensions were subsequently characterized by using UV-Vis spectrophotometry (DU800; Beckman Coulter UV-Vis spectrophotometer, Brea, Calif.) and fluorescence spectroscopy (FluoroMax spectrofluorometer; Horiba Jobin Yvon, Edison, N.J.). Corrected absorbance values for DiR were calculated through baseline subtraction of nanoparticle light scattering, which was measured using analogous formulations that did not contain DiR. The nanoparticles suspensions were then lyophilized to weigh the dry pellet (containing PEO-b-PCL polymer, LNPs and DiR), subsequently dissolved in THF, and centrifuged to collect the precipitates (i.e., residual LNPs). The suspensions were again subject to UV-Vis spectrophotometry to calculate the concentrations of DiR, using its known extinction coefficients in THF and by following Beer's Law. DiR extinction coefficients in core-shell nanoparticles were then obtained by normalizing aqueous spectra to these calculated concentrations. LNP concentrations in aqueous suspensions were similarly determined via analogous methodologies but by employing fluorescence standard curves, which were generated after 980 nm excitation of known concentrations of oleic acid-coated LNPs in THF. Finally, the relative amounts of polymer in each nanoparticle formulation were determined after lyophilizing a fixed volume of aqueous suspension, weighing the pellet, and subtracting the calculated amounts of DiR and LNP. The final compositions of each core-shell nanoparticle formulation are summarized in FIG. 43.

In Situ and In Vitro Nanoparticle Characterization. Size and zeta potential measurements of nanoparticle suspensions were conducted using a Malvern Nano-ZS90 Zetasizer (Malvern Instruments, Worcestershire, UK). Particles sizes and morphologies were further visualized by cryo-TEM (JEOL 2100F Transmission Electron Microscope; Peaboy, Mass.). LUC$^+$/RFP$^{neg}$ OVCAR-8 cells were treated with core-shell nanoparticles for different periods of time and the cellular uptake of nanoparticles was then quantified by flow cytometry (FACSCalibur; BD Biosciences, Singapore; $\lambda_{ex}$=488 nm and $\lambda_{em}$=585 nm (or 650 nm), gating on DiL signals with a threshold of 10,000 cells). For in vitro confocal microscopy experiments, LUC$^+$/RFP$^+$ OVCAR-8 cells were grown on glass substrates and then incubated with untargeted (Er/PEOPCL) or FR-targeted core-shell nanoparticles (Er/Folate-PEO-PCL) for different periods of time. The cells were subsequently fixed using 4% paraformaldehyde (in PBS) for 10 min and at 37° C., washed with PBS, and imaged using a confocal microscope (Olympus FV1000 Multiphoton Laser Scanning Confocal Microscope; Tokyo, Japan; $\lambda_{ex}$=980 nm) to visualize UC-Er and RFP simultaneously.

Lentiviral Labeling of Ovarian Cancer Cells. Firefly luciferase-labeled OVCAR-8 cells (LUC$^+$/RFP$^{neg}$ OVCAR-8) were used as previously reported. D. Ghosh, et al. Proceedings of the National Academy of Sciences of the United States of America 2014, 111, 13948. Firefly luciferase and RFP dual-labeled OVCAR-8 cells (LUC$^+$/RFP$^+$ OVCAR-8) were generated by lentiviral vector mediated transduction through a similar procedure as previously reported. W. Wei, et al. Cancer biology & therapy 2013, 14, 164. In brief, cDNA coding lentiviral constructs EF.CMV.RFP (17619), pLenti CMV Puro LUC (17477) and corresponding lentiviral packaging plasmids psPAX2 (12260) and pMD2.G(12259) were purchased from Addgene (catalogue number in parenthesis) (Cambridge, Mass.). Replication incompetent lentiviral particles were generated by co-transfection of 293FT cells with Lipofectamine 2000. Viral supernatants were harvested at 48 h and at 72 h after transfection, combined and filtered through a 0.45-µm PVDF filter (GE Healthcare Life Sciences; Pittsburgh, Pa.), titrated with 293FT cells (using RFP and a puromycin selection marker, respectively), and stored at −80° C. OVCAR-8 ovarian cancer cells were first infected with luciferase-expressing lentivirus at an approximate multiplicity of infection (MOI) of 2 in the presence of polybrene (8 µg/mL); infected cells were subsequently selected with puromycin (1 µg/mL) for 2 weeks. A second infection of RFP-expressing lentivirus was then performed at an approximate MOI of 5 to achieve maximum transduction efficacy. Stably infected cells were maintained in medium containing puromycin (1 µg/mL) and the percentage of RFP positive cells was routinely checked by FACS to ensure >95% positivity.

Synthesis of FA-conjugated PEO-b-PCL Diblock Copolymer. FA (50 mg), 1-ethyl-3-(3-dimethylaminopropyl)-carbodiimide (EDC; 44 mg), and N-hydroxysuccinimide (NETS; 15 mg) were dissolved in dimethyl sulfoxide (DMSO) and stirred overnight. Amino-terminated PEO$_{6k}$-PCL$_{16k}$ (500 mg) and triethanolamine (TEA; 4 µL) were then added and stirred for an additional 12 h. The mixture was dialyzed against DMSO (SnakeSkin Dialysis Tubing, 22 mm dry diameter×10.7 m; MWCO=3,500; Thermo Scientific, Rockford, Ill.) for 48 h to remove the unreacted reagents. The final FA-conjugated PEO-b-PCL product was purified by precipitation in excess ether and confirmed via NMR spectroscopy (FIG. 48).

Cell Viability Studies. LUC$^+$/RFP$^{neg}$ OVCAR-8 cells in RPMI 1640 media (supplemented with 10% fetal bovine serum+1% of a 10,000 units/mL Penicillin-Streptomycin solution; Life Technologies, Grand Island, N.Y.) were plated in a 96-well microplate (PerkinElmer, Waltham, Mass.) at a density of 5000 cells/well and allowed to adhere overnight. Media were removed and suspensions of untargeted (DiR-Er/PEO-PCL) or FR-targeted core-shell nanoparticles (DiREr/Folate-PEO-PCL) in 1:9 v/v PBS:media were then added to different final concentrations in separate wells (n=6 technical replicates per condition). PBS (at 1:9 v/v media) was used as a negative control treatment. After 72 h of incubation, cells were washed with fresh media (×3) and with PBS solution (×3) to remove excessive particles; MTT and solubilization reagents were then added. The suspension absorbance at 570 nm was read using a Tecan plate reader; ABS at 650 nm served as the reference. Cell viability was calculated by dividing the net absorbance obtained from cells exposed to each treatment and compared to that of untreated cells.

Mouse Handling and Nanoparticle Administration. OVCAR-8 human ovarian cancer cells that expressed LUC and RFP were constructed as previously described (vide supra). LUC and RFP expression were assayed and confirmed using a plate reader (Infinite 200 PRO; Tecan group Ltd., Switzerland) and an IVIS Spectrum Bioluminescent and Fluorescent Imaging System (PerkinElmer; Akron, Ohio). To establish an orthotopic xenograft model of human ovarian cancer, LUC$^+$/RFP$^+$ OVCAR-8 cells (200 µL of a suspension of 10$^7$ cells/mL; i.e., 2 million cells) were implanted into female athymic nude mice (NCRNU-F, Taconic Biosciences; Hudson, N.Y.) by IP injection. Tumor growth was monitored weekly by imaging bioluminescence and RFP signals emanating from the animals, using the IVIS imaging instrument. For bioluminescence measurements, luciferin (200 µL of a 15 mg/mL solution in PBS) was administered to each animal by IP injection; after 10 min, mice were imaged both for bioluminescence and RFP signals ($\lambda_{ex}$=535 nm; $\lambda_{em}$=600 nm). For comparative imaging studies at different optical wavelengths (e.g. FIGS. 32 and 33), suspensions of core-shell nanoparticles were introduced into tumor-bearing mice by IP injection (e.g. 200 µL of a suspension containing DiR-Er/PEO-PCL, which was comprised of PEO-b-PCL (2.8 mg), NaYF4:Yb,Er,Tm-based LNPs (0.9 mg), and DiR (1.3 µg)).

For co-administration of two different core-shell nanoparticles to the same mouse, the formulations were simultaneous introduced by either IP or IV tail injection (e.g. 200 µL of a suspension containing both the untargeted nanoparticle formulation (DiR-Er/PEO-PCL), which was comprised of PEO-b-PCL polymer (7.5 mg), NaYF4:Yb,Er-based LNPs (0.4 mg), and DiR (7.8 µg), as well as the FR-targeted nanoparticle construct (DiR-Ho/Folate-PEOPCL), which consisted of FA-conjugated PEO-b-PCL (1.3 mg) and NaYF4:Yb,Ho-based LNPs (2.4 mg). Prior to animal administration, all suspensions were filtered sterilized (0.45 µm cellulose acetate filter, VWR International; Radnor, Pa.). Prior to nanoparticle injection and for all subsequent imaging analyses, mice were anesthetized using isoflurane (2.5% in 02 at 2 L/min). For pharmacokinetic determination, animals were phlebotomized at various time points after nanoparticle administration (15 µL per blood draw), using quartz microcapillary tubes (Sutter Instrument; Novato, Calif.). The tubes were then imaged to measure changes in DiR and LNP emission intensities (vide infra), which were converted to concentrations using predetermined fluorescence standard curves.

Statistical Analysis. Data are presented as the mean±the standard deviation of the mean (SD). 4 mice were used (at a minimum) for each comparison arm unless otherwise indicated. Student's t-test was conducted using GraphPad software (San Diego, USA). A p value of <0.05 was considered statistically significant. Pearson's correlation coefficient (r) between two variables was calculated using OriginLab (Northampton, Mass.).

Tissue Phantom Experiments. Two weeks after implantation of LUC$^+$/RFP$^+$ OVCAR-8 ovarian cancer cells, a mouse was administered untargeted core-shell nanoparticles (DiREr, Tm/PEO-PCL) via IP injection. 72 h later, luciferin (200 µL of 15 mg/mL solution in PBS) was administered (IP) to the same mouse. After 5 minutes, the mouse was sacrificed and the largest tumor implant, which was deposited on the pancreas of the animal, was isolated. This tumor deposit was then placed at different depths (5, 10, or 20 mm) beneath a BioMimic phantom with optical properties that matched that of the human breast (reference wavelength 780 nm, $m_a$ 0.03 cm$^{-1}$, $m_s'$ 9 cm$^{-1}$; INO Inc., Quebec, CA). Imaging of the tumor deposit at different depths beneath the phantom commenced in an analogous fashion to that employed for in vivo imaging, using the IVIS system (to detect LUC, RFP, and NIR-I DC (DiR) signals) as well as by employing the custom-designed imaging instrument (to detect NIR-I UC (UC-Er, Tm) and NIR-II DC emission (DC-Er) from the core-shell nanoparticles). A signal-to-noise ratio (SNR) of greater than 3 was used as the minimum threshold of detection for each optical reporter, using the same parameters that were adopted for in vivo imaging.

Tissue Immunostaining. Upon conclusion of the in vivo imaging experiments (i.e. 72 h after administration of core-shell nanoparticles), mice were euthanized (using CO2 followed by cervical dislocation); their organs were immediately dissected, immersed in a 4% paraformaldehyde (PFA)/PBS solution, and left on a shaker (overnight at 4° C.). The organs were subsequently washed with PBS (x3) followed by immersion in 30% sucrose/PBS (overnight at 4° C.). The samples were then placed in Tissue-Tek embedding media, stored at −80° C., and subsequently sectioned using a cryo-stat (Histology Core Facility in the Koch Institute at MIT). For immunostaining, tissue sections were first washed to remove excessive sucrose and then immersed in blocking buffer (PBS+0.3% Triton X-100+10% v/v normal donkey serum) for 60 min at room temperature (RT). Primary mouse anti-macrophage antibody (F4/80) was incubated with the tissue sections overnight at 4° C. The samples were subsequently washed and incubated with a FITC-labeled rat anti-mouse secondary antibody (overnight at 4° C.). The slide sections were then washed with PBS, mounted using Vectashield media, and stored at 4° C. prior to imaging (multiphoton confocal microscopy).

Confocal Microscopy of Tissue Sections. Core-shell nanoparticles in histological sections of excised tissues were imaged with a 25x, 1.05 NA objective using an Olympus FV1000MP multiphoton microscope equipped with a Spectra Physics Mai Tai Deepsee Tai-Sapphire laser. Collagen 1, imaged by Second Harmonic Generated (SHG) polarized light, tissue autofluorescence and mRFP were imaged at a wavelength of 840 nm with a laser power of 15 mW and were captured on PMTs with emission filters of 425/30, 525/45 and 607/70 nm, respectively. Nanoparticles were imaged at a wavelength of 980 nm with a laser power of 18 mW and were captured on a PMT with an emission filter of 525/45 nm.

In Vivo and Ex Vivo Imaging of Core-Shell Nanoparticles. In vivo and ex vivo imaging of cell intrinsic reporters (LUC and RFP), as well as imaging of DiR emission from core-shell nanoparticles in whole mice, their excised organs, and in blood (microcapillary tubes), were conducted using an IVIS Spectrum-bioluminescent and Fluorescent Imaging System (PerkinElmer; Akron, Ohio; note, for imaging of DiR, $\lambda_{ex}$=710 nm; $\lambda_{em}$=800 nm). NIR-I and NIR-II emission from the same particles was concurrently imaged using a custom designed instrument, which was equipped with 808 nm and 980 nm lasers diodes (CNI Laser; China), a silicon camera for bright-field images (Hamamatsu, ORCA-Flash4.0 LT; Japan), and a liquid nitrogen-cooled InGaAs camera for NIR-II fluorescence imaging (256×320 pixel array, detection range: 800-1700 nm; Princeton Instruments, OMA:V 2D; Acton, Mass.). In front of the InGaAs detector, an NIR camera lens was attached (SWIR-2, Navitar; Rochester, N.Y.). Two long-pass emission filters with a cut-off wavelength of 1400 nm (Thorlabs; Newton, N.J.) and two band-pass filters (1575±25 nm; Thorlabs) were also employed. In front of the silicon detector, a second camera lens was attached (MVL25M1, Navitar). Two short-pass filters with a cut-off wavelength of 900 nm (Thorlabs) and two notch filters (980±40 nm; Edmund Optics, Barrington, N.J.) were also utilized.

For excitation of LNPs, an optical fiber coupled to the 980 nm laser diode (CNI Laser) was used and a laser line filter centered at 980 nm (Edmund Optics) was mounted in front of the laser to remove any unwanted excitation light. The actual fluence (energy density) of the mouse during in vivo imaging was ~100 mW/cm$^2$ and the acquisition time was 0.1~1 s. For the contrast images, white light illumination was utilized. Custom designed software (generated using Visual Basic and LabView; National Instruments, Austin, Tex.) was used to control the lasers and the cameras during imaging. Protective eyewear was utilized during image acquisition. Co-registration of bright-field and fluorescence images, as well as subsequent image processing, were performed using custom-designed algorithms (Matlab; MathWorks, Natick, Mass.). Quantification of fluorescence intensities for biodistribution and pharmacokinetic analyses were conducted using ImageJ software (NIH).

Results

Synthesis and Characterization of Core-Shell Nanoparticles. Oleic acid-coated LNPs comprised of NaYF$_4$, and which were doped with Yb and either Er or Ho with and without Tm, were prepared. The formation of core-shell nanoparticles comprised of polymer-wrapped LNPs occurred immediately after aqueous dispersion of a THF solution of oleic acid-coated LNPs, DiR, and PEO-b-PCL polymer (FIG. 37). The relative hydrophobic nature of DiR and the LNPs drove their segregation into the hydrophobic PCL compartment of the assembled nanoparticles. The hydrophilic PEO corona enabled aqueous dissolution of the nanocomposite and stabilized its core-shell structure. Optimization of sonication power and the initial mass ratio of polymer-to-LNP established a reproducible protocol for generating core-shell nanoparticles (see FIG. 38). Core-shell nanoparticles were further engineered to incorporate the organic NIR-I fluorophore DiR within their PCL shells (FIG. 39). Three imaging constructs were preferentially utilized in this study: untargeted (DiR-Er,Tm/PEO-PCL and DiR-Er/PEO-PCL) as well as FR-targeted core-shell nanoparticles (DiR-Ho/Folate-PEO-PCL), representing DiR-encapsulated PEO$_{5k}$-PCL$_{16k}$-coated NaYF4:Yb,Er,Tm—, PEO$_{5k}$-PCL$_{16k}$-coated NaYF4:Yb,Er—, and FA-conjugated PEO$_{6k}$-PCL$_{16k}$-coated NaYF4:Yb,Ho-based LNPs, respectively.

FIG. 31A illustrates the structure of the core-shell nanoparticle, wherein the PEO-PCL shell is shown as a yellow micelle, the LNPs as blue cubes, and the organic fluorophore DiR as red dots. The structures of the actual nanocomposites were verified by cryo-TEM and the core-shell particles were found to be approximately 60-90 nm in diameter (FIG. 31B); note, the core LNPs were each ~20 nm in size. Each core-shell nanoparticle formulation (DiREr, Tm/PEO-PCL, DiR-Er/PEO-PCL, and DiR-Ho/Folate-PEO-PCL) was further characterized by dynamic light scattering (DLS) in order to measure its average hydrodynamic diameter and its polydispersity index (PDI) in suspension; its average surface charge was also determined through zeta potential measurements (FIGS. 40-42).

These physicochemical properties as well as the synthetic yield and composition of all components in each formulation are summarized in FIG. 43. For each core-shell nanoparticle, the optical properties of each of its emissive components were independently measured to verify their presence in the final aqueous suspension (e.g. FIG. 40E). When excited at 700 nm, an emissive signal that peaked at 778 nm was generated that corresponded to the NIR-I DC emission of DiR; exciting the same formulation at 980 nm, however, resulted in simultaneous UC (visible and NIR-I) and DC (NIR-II) emission from DiR-Er,Tm/PEOPCL (FIG. 40E), DiR-Er/PEO-PCL (FIG. 41E), and DiR-Ho/Folate-PEO-PCL (FIG. 42E). Additional processing enabled isolation of homogeneous populations of core-shell nanoparticles from suspensions that included PEO-b-PCL (shell) nanoparticles (see FIG. 44); but, this was not deemed necessary as all core-shell nanoparticle formulations demonstrated analogous material (size, charge, concentration) and optical properties (absorbance and fluorescence intensities), enabling accurate imaging comparisons between different formulations.

980 nm excitation of core LNPs generated fluorescence bands in the visible range, consistent with a well-known process of UC energy transfer, as well as simultaneous DC emission with a peak at 1566 nm and 1162 nm for Er- and Ho-based LNPs, respectively. For core-shell nanoparticles that contained NaYF4:Yb,Er,Tm-based LNPs, the presence of Tm$^{3+}$ generated another major NIR-I UC peak at 800 nm; other peaks from this composition were similar to those of core-shell nanoparticles that incorporated NaYF4:Yb,Er-based LNPs. Notably, the fluorescent intensity of the LNP's UC emission process scaled with the (power) while that of its DC emission increased linearly with laser power (FIG. 45); similar power-dependent emission phenomena have previously aided in the in vivo detection of NIR-I UC signals from LNP formulations.

In addition to the emission of these extrinsic reporters, bioluminescence due to the luciferaseluciferin reaction and RFP fluorescence upon 535 nm excitation are also included in FIG. 31C, generating a spectral comparison of all reporters that were subsequently utilized for in vivo and ex vivo imaging (vide infra). Prior to embarking on comparisons of in vivo imaging with different reporters, we examined the photostability of each of the emissive components within the core-shell nanoparticles. Nanoparticle suspensions were exposed to continuous laser irradiation for 1 h; UC or DC fluorescence of LNPs that were either suspended in organic solvent or incorporated in aqueous suspensions of core-shell nanoparticles were found to retain >98% of their initial intensities at the end of the study (FIG. 31D). Compared to free DiR in THF, whose fluorescence decreased by over 30% after 1 h of continuous excitation, DiR that was incorporated within the PCL shell of the nanoparticles maintained 88% of its initial emission intensity under the same conditions, exhibiting improved photoresistance in this polymeric environment.

Imaging Fidelity and Sensitivity of Visible, NIR-I, and NIR-II Optical Reporters. We next compared the accuracy of in vivo imaging afforded by detection of cell intrinsic reporters (LUC and RFP) as compared to NIR-I vs. NIR-II emissive signals generated from our core-shell nanoparticles. LUC$^+$/RFP$^+$ OVCAR-8 cells were implanted into nude mice via intraperitoneal (IP) injection, establishing a disseminated cell line xenograft model of ovarian cancer. Peritoneal tumor implants were allowed to develop over a period of two weeks (4 mice); imaging then commenced at 72 h after IP injection of untargeted core-shell nanoparticles (DiR-Er,Tm/PEO-PCL) (FIG. 32A); note, this time delay between nanoparticle injection and imaging allowed for systemic diffusion and in vivo tumor accumulation. Each mouse was imaged using different luminescence and fluorescence detection systems. Optical imaging of intrinsic LUC and RFP signals ($\lambda_{ex}/\lambda_{em}$=535/600 nm), as well as NIR-I DC emission from DiR ($\lambda_{ex}/\lambda_{em}$=710/800), was conducted using an IVIS imaging system equipped with white light excitation and appropriate filters for fluorescence detection; note: luciferase bioimaging commenced 10 min after IP injection of luciferin and did not utilize excitation or emission filters. Imaging of NIR-I UC ($\lambda_{ex}/\lambda_{em}$=980/800 nm) and NIR-II DC emission ($\lambda_{ex}/\lambda_{em}$=980/1175 nm or 980/1575 nm) was conducted using a custom-designed small-animal imaging instrument.

From the in vivo images, it was clear that the LUC and RFP signals co-localized with one another; imaging of RFP fluorescence, however, offered better visualization of individual tumor deposits and detected additional implants that were not visualized by bioluminescence imaging. Notably, imaging of NIR-I DC signals from DiR demonstrated poor association of nanoparticle and tumor biodistribution; imaging of UC-emission (NIR-I) from core LNPs did, however, correlate with the detection of intrinsic reporters for a tumor deposit in the left upper quadrant of each animal. Imaging of DC emission (NIR-II) from core LNPs demonstrated numerous tumor deposits, many of which corresponded with the same tumor sites that were detected by LUC and RFP imaging; but, it did also highlight other potential implants that were not otherwise visualized.

Upon completion of in vivo imaging, mice were sacrificed and major organs were extracted in order to compare in vivo and ex vivo images of tumor locations and numbers as well as those of the nanoparticles and their relative biodistribution. Ex vivo imaging of RFP signals in whole organs demonstrated tumor implants on the serosal surfaces of the ovaries (bilaterally), pancreas, duodenum, liver, spleen, stomach, and intestines (FIG. 32A), which matched the known patterns of peritoneal dissemination for human epithelial ovarian cancers; notably, the ex vivo correlation between RFP and LUC signals was poor, which was attributed to the short half-life of the luciferin/luciferase reaction and the time between in vivo substrate injection, animal sacrifice, and ex vivo imaging. As such, the relative RFP signal intensity in each excised organ was used as a baseline to compare the fidelity of in vivo and ex vivo imaging results that were obtained with other fluorescent channels. Ex vivo imaging of NIR-I DC signals from DiR, again, correlated poorly to most areas with RFP fluorescence; detection of DiR emission did, however, correctly identify two tumor deposits on the duodenum and pancreas that were seen with RFP imaging. In contrast, ex vivo imaging of NIR-I UC emission of core LNPs provided a better correlation with the biodistribution of RFP signals; NIR-II DC emission from the same particles, however, showed a nearly identical pattern of distribution to that of RFP.

Confocal microscopy of excised tumor sections confirmed co-localization of RFP (tumor) and UC-emission (nanoparticle), demonstrating that the nanoparticles accumulated both in the perivascular spaces of large tumor deposits as well as in a punctuate distribution pattern that was consistent with uptake in individual infiltrating tumor cells (FIGS. 32B and 46); notably, there was an absence of nanoparticle uptake in normal healthy tissues, including those of the reticulo-endothelial system (i.e. the liver and spleen), after this IP route of administration. When comparing these ex vivo imaging results with those obtained by in vivo imaging of RFP, it was evident that increased contrast sensitivity and the identification of greater numbers of individual tumor deposits were afforded by in vivo imaging of core-shell nanoparticles at NIR-II wavelengths (FIGS. 33A and 47A). Further, there were superior correlations between the relative in vivo and ex vivo signal intensities, as well as the tissue distribution patterns of tumor deposits, obtained by detection of NIR-II emissive signals as compared to imaging with all other optical reporters.

To compare the utility of each intrinsic and extrinsic reporter for early tumor detection, we next conducted in vivo imaging studies of mice at 1-week post-IP implantation of LUC$^+$/RFP$^+$ OVCAR-8 cells (FIG. 47B). By contrasting in vivo bioluminescence images to those obtained by both in vivo and ex vivo fluorescence imaging of RFP, it became clear that bioluminescence imaging greatly exaggerated tumor sizes, especially for low volumes of disease and at depth. Again, there was a poor correlation between either in vivo and ex vivo imaging of NIR-I DC emission from DiR with respect to RFP; but, there was a nearly identical correlation between the intensity and distribution of NIR-II DC emissive signals from core-shell nanoparticles with those of RFP fluorescence in the same organs. When assessing in vivo images obtained with different fluorescent channels, it was obvious that imaging of NIR-II DC emission from core-shell nanoparticles identified smaller and more numerous tumor deposits than could be seen by detection of RFP (FIGS. 33B and 47C); in vivo imaging of NIR-II DC emission from core-shell nanoparticles further afforded improved detection of individual tumor deposits as compared to in vivo imaging with all other reporters.

In addition to in vivo and ex vivo imaging experiments with mice, we examined the maximal depths of tissue penetration for emissive signals generated from each optical reporter used in our studies. A tumor implant was isolated from the pancreas of our ovarian cancer mouse model, placed in a sample holder, and positioned at different depths beneath a tissue-like phantom comprised of a synthetic polymer that exhibited optical properties for light absorption and scattering that mimicked those of the human breast. The maximum depth of issue penetration for each optical reporter was denoted as the depth (i.e. thickness of phantom applied above the sample chamber) at which the signal-to-noise ratio (SNR) for detection decreased to 3. Analogous to the results obtained with in vivo imaging, the maximum depth of tissue penetration for each reporter correlated strongly with its increasing wavelength of emission (FIG. 33C); NIR-II DC emissive signals from core-shell nanoparticles were detectable at the deepest depths, penetrating a 20 mm-thick phantom.

Engineering Tumor Cell Uptake via FR Targeting. Flow cytometric analysis demonstrated high expression levels of FR on OVCAR-8 cells (FIG. 34A). To generate an FR-targeted core-shell nanoparticle, we conjugated FA to amino-terminated PEO-b-PCL via EDC/NHS chemistry. Integration of NMR peaks assigned to PEO (3.52 ppm) and FA (6.63, 7.6, and 8.653 ppm) verified the presence of 1:1 molar ratio of FA to PEO-b-PCL in the purified reaction product (FIG. 48). DiR-Ho/Folate-PEO-PCL denoted FR-targeted nanoparticles that were comprised of a core of NaYF4:Yb,Ho-based LNPs and a shell made up of a 1:9 molar ratio of FA-conjugated PEO$_{6k}$-PCL$_{16k}$ to methoxy-PEO$_{5k}$-PCL$_{16k}$, which further incorporated DiR. The material and optical properties of these FR-targeted nanoparticles (DiR-Ho/Folate-PEO-PCL) were measured and summarized in FIG. 42 and FIG. 43. For in vitro experiments (vide infra), two other untargeted (DiL/PEO-PCL) and FR-targeted core-shell nanoparticles (DiL/Folate-PEO-PCL) were constructed that incorporated the DiR-related fluorophore DiL ($\lambda_{em\ max}$=575 nm).

We next verified the utility of FR-targeting to increase the accumulation of core-shell nanoparticles within LUC$^+$/RF-P$^{neg}$ OVCAR-8 cells grown in culture. The cells were incubated with either untargeted (DiL/PEO-PCL) or FR-targeted core-shell nanoparticles (DiL/Folate PEO-PCL) for different time periods and washed; cellular accumulation was determined by flow cytometry, gating on DiL signals (FIG. 34B). For both formulations, tumor cell accumulation increased over time but at a rate that was decidedly faster for the FR-targeted nanoparticles; indeed, by 6 h after incubation a marked increase in cellular accrual was already evident for FR-targeted (DiL/Folate-PEO-PCL) as compared to untargeted nanoparticles (DiL/PEO-PCL; FIG. 34C). This result was further corroborated by cellular imaging of LUC$^+$/RFP$^+$ OVCAR-8 cells that confirmed an increased uptake of FR-targeted nanoparticles (Er/Folate-PEO-PCL) with respect to untargeted nanoparticles (Er/PEO-PCL) after 6 h, visualizing visible RFP signals (red) and UC fluorescence emission of core LNPs (green) by multiphoton confocal microscopy (FIG. 34D). Cytotoxicity analyses of LUC$^+$/RFP$^+$ OVCAR-8 cells were also conducted at 72 h after incubation with various concentrations of either FR-targeted or untargeted core-shell nanoparticles. Cell viability was measured, which demonstrated a concentration-dependent toxicity for both formulations (FIG. 49); the relatively enhanced cytotoxicity of FR-targeted nanoparticles was attributed to greater intracellular concentrations mediated by enhanced uptake. Notably, neither nanoparticle formulation demonstrated significant in vitro toxicity to OVCAR8 cells at concentrations that could be expected after in vivo administration (i.e. <1 mg/mL). As such, the aforementioned nanoparticles were unlikely to affect the fidelity of in vivo imaging of cell intrinsic reporters (LUC and RFP), which were dependent upon preserved cellular viability.

The Route of Administration and the Role of FR-targeting on In vivo Tumor Accumulation of Core-shell Nanoparticles. LUC$^+$/RFP$^+$ OVCAR-8 tumor cells were xenotransplanted into nude mice via intraperitoneal dissemination and allowed to grow for 2 weeks. Untargeted (DiR-Er/PEO-PCL) and FR-targeted core-shell nanoparticles (DiRHo/Folate-PEO-PCL) were then introduced by either IP (4 mice) or IV injection (4 mice). Simultaneous injection of both untargeted and FR-targeted nanoparticles into the same animal enabled ready comparisons of the effects of FR-targeting on the accuracy of tumor detection, the spatial contrast, and the maximal SNR that could be achieved via in vivo optical imaging with each emissive agent. FIG. 35A (upper row) shows in vivo images of a single mouse at various time points after simultaneous IP administration of both nanoparticle formulations. Gross comparisons of the ex vivo images of excised organs taken at the time of animal sacrifice, which occurred 72 h after nanoparticle administration, again demonstrated a high correlation between RFP signals and the DC-emission of either the untargeted (Er) or FR-targeted nanoparticles (Ho).

Tumor deposits were easily visualized by all modalities (i.e. ex vivo RFP imaging or detection of NIR-II DC emission from Er and Ho) and were again found on the serosal surfaces of the ovaries (bilaterally), pancreas, duodenum, liver, spleen, stomach, and intestines. Ex vivo fluorescence signals from each excised organ were taken after animal sacrifice and were normalized to the intensity value obtained from the largest tumor deposit, which was on the pancreas of each animal; these normalized intensity values were then used to determine the relative biodistribution patterns for untargeted and FR-targeted core-shell nanoparticles after IP administration (FIG. 35B). A close association was evident between the relative distribution of the RFP fluorescence and the NIR-II DC emission from both untargeted (Er) and FR-targeted nanoparticles (Ho).

From in vivo images taken longitudinally, it was apparent that a stable signal distribution occurred for both the untargeted and FR-targeted nanoparticles at 10 h after IP administration (FIGS. 50A and 50B); both formulations were able to better visualize individual tumor deposits and to detect increased numbers of implants as compared to in vivo imaging of RFP. Pharmacokinetic analyses were simultaneous conducted by taking small volumes (typically 15 µL) blood draws at time points that corresponded to the in vivo images; measurements of NIR-II DC emission from Er (core LNPs) and NIR-I DC emission from DiR (in the PCL shell) enabled determination of the relative concentrations of each species in blood over time. Emission intensities were normalized to their highest values, yielding a half-life of clearance ($t_{1/2}$) of 12.5+0.5 h (based on the NIR-II DC emission of Er) and 11.9+0.2 h (based on NIR-I DC emission of DiR) for untargeted nanoparticles (FIG. 50C). As such, monitoring of each optical channel yielded nearly identical blood clearance rates (p=0.9704; Student's t-test), establishing the in vivo stability of the core-shell structure after IP administration of the nanoparticles (FIG. 35C, black circles).

Alternatively, IV administration of both untargeted and FR-targeted nanoparticles demonstrated a different distribution pattern to that which was seen after IP injection. FIG. 35A (lower row) shows in vivo images of a single mouse at various time points after simultaneous IV administration of both formulations. Again, there was an apparent correlation between the in vivo images obtained by detection of each core-shell nanoparticle over time, demonstrating a stable biodistribution pattern at 10 h after IV injection (FIG. 50D). Examination of ex vivo images taken of excised organs at the time of sacrifice, which, again, occurred at 72 h after injection, demonstrated a decreased correlation between the relative tissue distribution patterns of untargeted and FR-targeted nanoparticles introduced via this route (FIGS. 35D and 50E); additionally, the biodistribution pattern for either nanoparticle did not seem to correspond with tumor locations visualized by in vivo or ex vivo imaging of RFP. The pharmacokinetics measurements based on NIR-II DC emission of Er and NIR-I DC emission of DiR were again similar after IV administration, demonstrating a t½=11.4+0.6 h (FIG. 35C, red triangles, and 50F).

In order to accurately compare biodistribution patterns, we next sought to numerically correlate the relative intensities obtained by ex vivo imaging of NIR-II DC emission with those of RFP signals from harvested organs after IP administration of untargeted vs. FR-targeted core-shell nanoparticles. The results are depicted in FIG. 35E, which contains diagonal plots that adopt the same fluorescence biodistribution patterns that are shown in FIG. 35B. Each off-diagonal plot represents the correlation of a pair of fluorescent reporters, consisting of a linear-fit (red line), a value for the Pearson's correlation coefficient (r), and an adjusted $R^2$ value. It was evident that the correlation between the RFP signal and either the NIR-II DC emission of untargeted (DC-Er) or FR-targeted core-shell nanoparticles (DC-Ho) was very high: the distribution patterns of NIR-II signals from each nanoparticle formulation demonstrated an r>0.96 with $R^2$>0.90 when compared to RFP. The correlation coefficient between RFP and DiR was, however, very poor (r=0.42, $R^2$<0.10), demonstrating the inherent inaccuracies that result from identification of tumors by monitoring of NIR-I DC emission of DiR from these same particles (FIG. 50G).

Additionally, the correlation between untargeted and FR-targeted core-shell nanoparticles was nearly perfect with an r>0.99 and $R^2$>0.99, demonstrating an identical pattern of tissue biodistribution (FIGS. 35E and 50G). Histologic sections were made of excised tissues from separate animals that were similarly implanted with LUC$^+$/RFP$^+$ OVCAR-8 cells and imaged with either untargeted (Er/PEO-PCL; Figure S46 or FR-targeted core shell nanoparticles (Er/Folate-PEO-PCL) at 72 h after IP administration (FIG. 51). When visualized via confocal microscopy, the untargeted and FR-targeted nanoparticles demonstrated identical patterns of tumor-specific accumulation with no evidence of healthy tissue uptake. Immunofluorescence was also performed for tumor-derived macrophages using FITC-conjugated F4/80 (green); tumor cells were detected by RFP emission (red) and core-shell nanoparticles were identified from their visible UC-emission (blue; pseudo-color). Multifocal confocal microscopy, again, demonstrated nanoparticle uptake by OVCAR-8 tumor cells (magenta) irrespective of FR-targeting (FIGS. 35F and 35G, respectively). Taken together, these data supported that no further advantages in tumor targeting were afforded by conjugation of FA to nanoparticles introduced by IP administration.

Notably, enumeration of the ex vivo tissue distribution patterns for untargeted (Er) and FR-targeted core-shell nanoparticles (Ho) after IV administration revealed that they correlated poorly with those of the tumor deposits (RFP), yielding an r=0.20 ($R^2$<0.1), 0.16 ($R^2$<0.1), and 0.26 ($R^2$<0.1) for the association of RFP with DiR, DC-Er and DC-Ho signals, respectively (data not shown). Both untargeted and FR-targeted nanoparticles demonstrated a pattern of predominantly liver and splenic accumulation, corresponding to organs of known reticuloendothelial cell activity and nanoparticle uptake. These results were confirmed by fluorescence imaging of histologic tissue sections (FIGS. 52 and 53). On closer examination, the association between the signals from untargeted (Er) and FR-targeted nanoparticles (Ho) was also lower after IV administration, yielding an r=0.8 ($R^2$=0.6); this was attributed to a relatively larger but variable degree of lung accumulation for FR-targeted core-shell nanoparticles. Immunostaining demonstrated the presence of tumor-associated macrophages (green) near LUC$^+$/RFP$^+$ OVCAR-8 tumor cells (red); the intratumoral distributions of both untargeted (Er/PEO-PCL) and FR-targeted nanoparticles (Er/Folate-PEO-PCL; blue), however, did not clearly indicate a particular cellular tropism (FIG. 54).

Early Detection of Tumor Deposits at 1 week after Implantation. Nude mice were xenotransplanted with LUC+/RFP+ OVCAR-8 cells and untargeted core-shell nanoparticles (DiR-Er/PEO-PCL) were administered by IP injection at 1 week after tumor cell implantation. Animals were again imaged over a period of 72 h and organs were excised to compare the relative intensities and tissue distributions of NIR-I DC signals from DiR, NIR-II DC fluorescence from core LNPs (Er) and RFP (FIG. 36). Comparisons of ex vivo images, again, readily demonstrated a strong correlation between NIR-II DC emissive signals (Er) and RFP localization; in vivo imaging confirmed the superiority of monitoring of NIR-II emission to detect numerous early tumor deposits within these animals, demonstrating increased sensitivity and improved spatial contrast as compared to imaging of RFP (FIG. 36A).

For each reporter, the fluorescence intensities from various organs were, again, normalized to that of the largest tumor deposit, which was in the pancreas of each animal (FIG. 36B). A correlation matrix was similarly obtained by comparing the distribution patterns of all three emissive signals (RFP, DiR and Er) and was used to further quantify the ability of each extrinsic reporter to detect early tumor deposits, which were delineated by RFP fluorescence (FIG. 36C). Correlation of RFP signals with NIR-I DC emission from DiR was particularly poor ($r=0.20$, $R^2<0.10$); NIR-II DC emission from Er also demonstrated a weaker correlation with RFP fluorescence in excised organs from these 1-week old xenotransplants ($r>0.80$, $R^2>0.60$), especially when compared to results obtained at two weeks after tumor cell implantation ($r>0.96$, $R^2>0.92$). Notably, the intensity of RFP fluorescence was much weaker in these early tumor deposits, which correlated to a decreased SNR when imaging with this intrinsic reporter. As a result, in vivo and ex vivo optical imaging of RFP fluorescence in excised organs demonstrated a diminished ability to correctly identify tumor implants that were confirmed by multiphoton confocal microscopy of RFP fluorescence in histologic sections. Notably, these microscopic tumor deposits corresponded to organs that demonstrated high NIR-II DC emission on ex vivo imaging; NIR-II signals from these same organs were also visualized by in vivo imaging, demonstrating the improved detection sensitivity that was afford by utilizing NIR-II fluorescence as compared to that of RFP in order to identify early tumor deposits within these animals.

Discussion

Intrinsic reporters such as RFP and LUC have been commonly utilized to visualize tumors, to follow their growth, and to monitor their therapeutic responses in whole-animal imaging studies. In vivo bioluminescence imaging, however, has been constrained by: 1) the short lifetime of the enzyme-substrate reaction, which has necessitated re-dosing and which has decreased the frequency at which longitudinal studies may be conducted; 2) non-uniform diffusion of the luciferin substrate and its inaccessibility to necrotic portions of a tumor; and, 3) substantial light scattering at depth, which has resulted in inaccurate estimations of tumor volumes. Conversely, in vivo RFP imaging has obviated many of these aforementioned limitations; but, the absolute magnitude of the RFP signal has not correlated with tumor burden due to nonlinear optical scattering and biological absorbance, which have further hindered the accuracy of tumor detection with increasing depth. As in vivo optical imaging with various NIR-I and NIR-II emissive agents has been proposed to circumvent these challenges, we undertook a comparative study to establish the fidelity of the in vivo imaging results obtained by detection of each of these intrinsic and extrinsic reporters.

Oleic acid-modified LNPs were coated with amphiphilic diblock copolymers of PEO-b-PCL, through optimization of an aqueous dispersion method. These core-shell nanoparticles further encapsulated the organic fluorophore DiR in their PCL shells. As a result, the particles generated visible, NIR-I (DC and UC), and NIR-II (DC) emissive signals, facilitating correlative whole animal and tissue-level experiments. Two weeks after peritoneal dissemination of LUC+/RFP+ OVCAR-8 cells in nude mice, ex vivo imaging confirmed a nearly perfect association between biodistribution of peritoneal tumor implants (RFP) with that of the core-shell nanoparticles (NIR-II DC) that were introduced by IP administration. Notably, both ex vivo and in vivo imaging of NIR-II DC emissive signals demonstrated superior sensitivity and improved spatial resolution as compared to detection of either NIR-I DC or UC fluorescence from the same particles. Moreover, in vivo imaging of NIR-II emission uniquely enabled the visualization of individual tumor deposits, detecting all microscopically-confirmed tumors and at substantially deeper depths of tissue penetration than could be obtained by monitoring of NIR-I fluorescence or that of the cell intrinsic reporters. These advantages further enabled the earlier detection of tumors, which were imaged at 1 week after implantation; in vivo imaging of NIR-II fluorescence again proved superior at identifying all tumor locations, visualizing numerous minute deposits that were not otherwise identified.

Although core-shell nanoparticles were highly localized to in vivo tumor locations after IP administration, we also explored the role of a tumor-targeting agent to further improve the SNR for in vivo imaging. The FR has been shown to be a highly expressed and validated target for clinical ovarian cancer therapy; and, conjugation of the small molecule FA to various imaging agents has previously enabled accurate detection of epithelial ovarian cancers in both preclinical and clinical studies. Here, FR-targeted core-shell nanoparticles were generated from FA-conjugated PEO-b-PCL polymers; their materials and optical properties were validated; and, their enhanced in vitro uptake by FR-expressing OVCAR-8 cells was observed by flow cytometry and by confocal microscopy.

In vivo optical imaging of two separate nanoparticles with spectrally unique NIR-II emissive signatures enabled independent tracking of each formulation within a single animal after simultaneous administration. When introduced by IP injection at 2 weeks after tumor cell implantation, the biodistribution of FR-targeted core-shell nanoparticles was found to be identical to that of their untargeted counterparts, which showed a nearly perfect correlation with tumor locations. Indeed, in vivo imaging of NIR-II DC emission confirmed that IP injection of untargeted core-shell nanoparticles was sufficient to enable preferential uptake in tumor tissues even at 1 week after tumor cell implantation, demonstrating increased sensitivity and improved spatial contrast as compared to utilizing intrinsic RFP signals to identify these early stage tumors. Notably, there was a poor correlation between the relative tissue biodistribution of untargeted and FR-targeted core-shell nanoparticles after IV injection, demonstrating no discernable tumor-specific targeting or intratumoral cellular tropism. As such, while FA conjugation to nanoparticles definitively aided in vitro tumor cell uptake, the results presented here indicate that no further advantages for in vivo tumor targeting were achieved.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicant reserves the right to physically incorporate into this application any and all materials and information from any such articles, patents, patent applications, or other physical and electronic documents.

EQUIVALENTS

The inventions have been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The inventions are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of embodiments of the invention. Further, each of the narrower species and subgeneric groupings falling within the generic disclosure also form parts of the inventions. This includes the generic description of embodiments of the invention with a proviso or negative limitation removing any subject matter from the genus, regardless of whether or not the excised material is specifically recited herein.

We claim:

1. A particle comprising a core and a diblock copolymer non-covalently associated with the core, wherein the diblock copolymer comprises:
   (i) a first block comprising a plurality of first monomers, wherein each first monomer is selected from the group consisting of ethylene glycol, propylene glycol, vinyl alcohol, acrylic acid, methacrylic acid, methyl acrylate, methyl methacrylate, ethyl acrylate, ethyl methacrylate, hydroxyethyl methacrylate, 2,3-dihydroxypropyl methacrylate, vinyl pyrrolidone, and dextrin;
   (ii) a second block comprising a plurality of second monomers, wherein each second monomer is 6-hydroxycaproic acid; the core comprises an imaging agent, wherein the imaging agent is a lanthanide;
   the size of the particle, as determined by DLS, is about 20 nm to about 300 nm; and
   the particle does not comprise a targeting agent.

2. The particle of claim 1, wherein each first monomer is selected from the group consisting of ethylene glycol and propylene glycol.

3. The particle of claim 1, wherein each first monomer is ethylene glycol.

4. A method of imaging cancer in a human subject in need thereof comprising
   administering by intraperitoneal injection or infusion to the intraperitoneal cavity a composition comprising a plurality of particles of claim 1 and an aqueous pharmaceutically acceptable carrier; and
   obtaining an image of the cancer,
   the cancer is a cancer that forms a peritoneal implant on the serosal surface of an organ of the peritoneal cavity.

5. The method of claim 4, wherein the composition does not comprise a targeting agent.

6. The method of claim 4, wherein the cancer is a cancer that spreads by peritoneal carcinomatosis.

7. The method of claim 4, wherein the cancer is ovarian, gastric, appendiceal, liver, pancreatic, colorectal, uterine, lobular breast, cervical, or primary peritoneal cancer.

8. The method of claim 4, wherein the cancer is endometrial cancer, abdominal methothelioma, or a soft tissue sarcoma.

9. The particle of claim 1, wherein the particle is from about 60 nm to about 90 nm in diameter.

10. The particle of claim 1, wherein the particle further comprises oleic acid non-covalently associated with the core.

11. The particle of claim 1, wherein the particle further comprises an organic fluorophore non-covalently associated with the diblock copolymer.

12. The particle of claim 11, wherein the organic fluorophore is a lipophilic carbocyanine dye.

13. The particle of claim 11, wherein the organic fluorophore is 1,1'-dioctadecyl-3,3,3',3'-tetramethylindotricarbocyanine iodide (DiR) or 1,1'-dioctadecyl-3,3,3',3'-tetramethylindocarbocyanine perchlorate (DiL).

14. The particle of claim 1, wherein each first monomer is ethylene glycol and the particle further comprises oleic acid non-covalently associated with the core.

15. The method of claim 4, wherein the cancer is ovarian.

16. A plurality of particles of claim 1.

* * * * *

SEQUENCE LISTING

```
<160> NUMBER OF SEQ ID NOS: 10

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggguaagugu ccuacugaag u                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uguggaugac ugaguaccug a                                              21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<223> OTHER INFORMATION: Description of Combined DNA/RNA Molecule:
      Synthetic oligonucleotide

<400> SEQUENCE: 3
ucagguacuc agucauccac att                                            23
```

```
<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
uguggaugac ugaguaccug att                                           23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgcacctga cgcccttcac c                                             21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cacatgaccc caccgaactc aaaga                                         25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttcaccacca tggagaaggc                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggcatggact gtggtcatga                                               20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctggggcgag aggtgccgtt g                                             21
```

```
<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctcggcgaag tcgcggcggt agc                                              23
```